US008859620B2

(12) United States Patent
Mobashery et al.

(10) Patent No.: US 8,859,620 B2
(45) Date of Patent: Oct. 14, 2014

(54) PHTHALANILATE COMPOUNDS AND METHODS OF USE

(75) Inventors: Shahriar Mobashery, Granger, IN (US); Dusan Hesek, Mishawaka, IN (US); Mayland Chang, Granger, IN (US)

(73) Assignee: University of Notre Dame du Lac, Notre Dame, IN (US)

(*) Notice: Subject to any disclaimer, the term of this patent is extended or adjusted under 35 U.S.C. 154(b) by 0 days.

(21) Appl. No.: 13/393,436

(22) PCT Filed: Aug. 31, 2010

(86) PCT No.: PCT/US2010/047322
§ 371 (c)(1),
(2), (4) Date: May 16, 2012

(87) PCT Pub. No.: WO2011/026107
PCT Pub. Date: Mar. 3, 2011

(65) Prior Publication Data
US 2012/0232150 A1    Sep. 13, 2012

Related U.S. Application Data

(60) Provisional application No. 61/238,549, filed on Aug. 31, 2009.

(51) Int. Cl.
*A61K 31/195*    (2006.01)
*A01N 37/12*     (2006.01)
(Continued)

(52) U.S. Cl.
CPC ............ *C07C 233/75* (2013.01); *C07C 233/66* (2013.01); *C07D 295/108* (2013.01); *C07C 233/26* (2013.01); *C07C 235/16* (2013.01);
(Continued)

(58) Field of Classification Search
None
See application file for complete search history.

(56) References Cited

U.S. PATENT DOCUMENTS 6,583,119 B2    6/2003    Haesslein et al.
6,846,953 B1    1/2005    Bryans et al.
(Continued)

FOREIGN PATENT DOCUMENTS

DE    3220883 C2    12/1983
EP    0043487 A1    6/1981
(Continued)

OTHER PUBLICATIONS

Dauengauer, Thermogravimetric Analysis of Complexes of Compounds Serving As Models of Polyamic Acids With Amic Solvents, Journal of Thermal Analysis, 1983, 28, pp. 317-324.*

(Continued)

*Primary Examiner* — San-Ming Hui
*Assistant Examiner* — Andrew Lee
(74) *Attorney, Agent, or Firm* — Haukaas Fish PLLC; Michael H. Haukaas, Esq.

(57) ABSTRACT

The invention provides antimicrobial compounds and compositions, and methods of using them. The compounds and compositions include, for example, a compound of any one of Formulas I-X. The invention further provides methods of preparing the compounds, and useful intermediates for their preparation. The compounds can possess highly specific and selective activity, such as antibacterial activity and/or enzymatic inhibitory activity. Accordingly, the compounds and compositions can be used to treat bacterial infections, or to inhibit or kill bacteria, either in vitro or in vivo.

21 Claims, 17 Drawing Sheets

(51) Int. Cl.
   A01N 37/44     (2006.01)
   C07C 233/66    (2006.01)
   C07D 295/108   (2006.01)
   C07C 233/26    (2006.01)
   C07C 235/16    (2006.01)
   C07D 339/08    (2006.01)
   C07D 295/135   (2006.01)
   C07C 233/59    (2006.01)
   C07D 213/75    (2006.01)
   C07C 233/75    (2006.01)
   C07D 495/04    (2006.01)
   C07C 271/58    (2006.01)
   C07C 233/60    (2006.01)
   C07C 333/08    (2006.01)
   C07D 209/46    (2006.01)
   C07C 233/15    (2006.01)
   C07C 233/73    (2006.01)
   C07C 233/81    (2006.01)
   C07D 501/34    (2006.01)
   C07C 327/48    (2006.01)

(52) U.S. Cl.
   CPC ......... *C07D 339/08* (2013.01); *C07D 295/135* (2013.01); *C07C 233/59* (2013.01); *C07D 213/75* (2013.01); *C07C 2101/08* (2013.01); *C07C 307/52* (2013.01); *C07D 495/04* (2013.01); *C07C 271/58* (2013.01); *C07C 233/60* (2013.01); *C07C 2101/02* (2013.01); *C07C 333/08* (2013.01); *C07D 209/46* (2013.01); *C07C 233/15* (2013.01); *C07C 233/73* (2013.01); *C07C 233/81* (2013.01); *C07D 501/34* (2013.01); *C07C 327/48* (2013.01); *C70C 233/69* (2013.01); *C07C 2101/14* (2013.01)
   USPC .......................................... 514/562; 514/563

(56) References Cited

U.S. PATENT DOCUMENTS

| 7,141,573 | B2 | 11/2006 | Hanson et al. |
| 7,259,167 | B2 | 8/2007 | Nichols et al. |
| 7,314,888 | B1 | 1/2008 | Chaki et al. |
| 2006/0281810 | A1 | 12/2006 | Dehmlow et al. |

FOREIGN PATENT DOCUMENTS

| EP | 0043488 A1 | 1/1982 |
| JP | 50-116640 A2 | 9/1975 |
| JP | 10259176 A2 | 9/1998 |
| WO | WO2009082398 A1 | 7/2009 |

OTHER PUBLICATIONS

International Search Report and Written Opinion for priority application PCT/US2010/047322 filed Aug. 31, 2010 published as WO 2011/026107 A1.

Dolzhenko, A.V., et al., Synthesis and Biological Activity of Substituted Tetrachlorophthalic Acid Monoamides; Translated from Khimiko-Farmatsevticheskii Zhurnal, vol. 39, No. 8, pp. 16-18, Aug. 2005. English version pp. 409-412. Translated Apr. 9, 2004.

Fuda, Cosimo, et al., Mechanistic Basis for the Action of New Cephalosporin Antibiotics Effective Against Methicillin- and Vancomycin-resistant *Staphylococcus aureus*, Journal of Biological Chemistry Apr. 14, 2006, vol. 281, No. 15, pp. 10035-10041, Apr. 14, 2006 The American Society for Biochemistry and Molecular Biology, Inc. USA.

Georgopapadakou, Nafsika H., Penicillin-Binding Proteins in Bacteria, The Squibb Institute for Medical Research, Princeton, NJ, Antimicrobial Agents and Chemotherapy, Jul. 1980, vol. 18, No. 1, pp. 148-157, 0066-4804/80/07/0148/10$02.00/0.

Haddad, Jalal, et al., Design of Novel Antibiotics that Bind to the Ribosomal Acyltransfer Site, Journal of the American Chemical Society, 2002, 124 (13), pp. 3229-3237, DOI 10.1021/ja011695m, downloaded from http://pubs.acs.org on Dec. 23, 2008.

Huang, Wanzhi, et al., A Broad-spectrum Peptide Inhibitor of β-lactamase Identified Using Phage Display and Peptide Arrays; Protein Engineering, vol. 16, No. 11, pp. 853-860, 2003, DOI: 10-1093/protein/gzg108.

Jacobs, L., Gastrointestinal Allergy, Remissions in Chronic Eczema Following Administration of Phthalanilic Acid, Journal of the Medical Association of Georgia, vol. 39, Issue 10 (1950) pp. 405-408.

Kishida, Hiroyuki, et al., Crystal Structure of Penicillin Binding Protein 4 (dacB) from *Escherichia coli*, both in the Native Form and Covalently Linked to Various Antibiotics, Biochemistry, 2006, vol. 45, pp. 783-792, (2006) American Chemical Society 10.1021/bi051533t.

Leevy, W. Matthew, et al., Optical Imaging of Bacterial Infection in Living Mice Using a Fluorescent Near-Infrared Molecular Probe, Journal of the American Chemical Society 2006, 128 (51), pp. 16476-16477, DOI 10.1021/ja0665592, downloaded from http://pubs.acs.org on Dec. 23, 2008.

Mycobacterium Tuberculosis, Wikipedia, 4 pgs., Retrieved from the Internet <URL: http://en.wikipedia.org/wiki/Mycobacterium_tuberculosis>, Retrieved on Dec. 23, 2008.

Filipescu, Gabriela et al., Morphological and Biochemical Characteristics in the Experimentally Treated Rats with Indigenous Synthetical Products Used as Pesticides, Romanian Journal of Morphology and Embryology, vol. 37, Issue 1-2, 1991, pp. 49-54, ISSN 1220-0522.

White, G.A, Substituted 2-Methylbenzanilides and Structurally Related Carboxamides: Inhibition of Complex II Activity in Mitochondria from a Wild-Strain and a Carboxin-Resistant Mutant Strain of *Ustilago maydis*, Pesticide Biochemistry and Physiology 34, pp. 255-276 (1989).

* cited by examiner

PHTHALANILATE COMPOUNDS AND METHODS OF USE

RELATED APPLICATIONS

This application is a national stage filing under 35 U.S.C. §371 of PCT/US2010/047322, filed Aug. 31, 2010, which claims priority under 35 U.S.C. §119(e) to U.S. Provisional Patent Application No. 61/238,549, filed Aug. 31, 2009, which applications are incorporated herein by reference.

GOVERNMENT INTEREST STATEMENT

This invention was made with government support under Grant No. GM061629 awarded by the National Institutes of Health. The United States Government has certain rights in the invention.

BACKGROUND OF INVENTION

Penicillin-binding proteins (PBPs) are a group of enzymes involved in assembly of the cell wall in both gram negative and gram positive bacteria. They are characterized by their affinity for and binding of penicillin. There are a large number of PBPs, usually several in each organism, and are found as both membrane bound and cytoplasmic proteins.

*Staphylococcus aureus* (SA), a gram positive bacterium, has been linked to several pathologies. Treatment and management of this disease and other bacterial infections is increasingly difficult due, at least in part, to the emergence of antibiotic-resistant bacterial strains, for example, methicillin-resistant *Staphylococcus aureus* (MRSA) and vancomycin-resistant methicillin-resistant *Staphylococcus aureus*.

*S. aureus* normally produces four penicillin-binding proteins (PBPs), which are know to be susceptible to modifications by β-lactam antibiotics, which can lead to bacterial death. The product of the gene mecA from MRSA is another penicillin-binding protein (PBP), designated PBP2a. Unfortunately, PBP2a has been found to be resistant to the action of the vast majority of commercially available β-lactam antibiotics. Furthermore, PBP2a is capable of taking over the functions of the other PBPs of *S. aureus* in the face of the challenge by β-lactam antibiotics.

Accordingly, new compounds and compositions are needed that are capable of inhibiting bacteria, such as antibiotic-resistant bacterial strains. New compounds and compositions that can be used to treat bacterial infections are also needed. Additionally, a model for screening and identifying anti-bacterial agents against evolving new bacterial strains would aid researchers in treating infectious diseases, such as those caused by antibiotic resistant strains of bacteria.

SUMMARY OF INVENTION

The invention provides compounds and compositions capable of inhibiting or killing bacteria, such as antibiotic-resistant bacteria, including vancomycin-resistant bacteria, and/or treating a bacterial infection. Methods for screening and identifying active compounds are also provided. Thus, the invention provides compositions that include an active ingredient, which can be an antibiotic or combination of antibiotic agents, effective to inhibit a microorganism such as a bacterium and/or an antibiotic-resistant organism, such as MRSA. The active agents can also be effective for treating or inhibiting penicillin-binding proteins (PBPs). The active agents can be one or more compounds of Formulas I-X.

Accordingly, the invention provides a compound of Formula I:

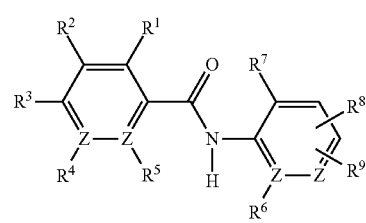

wherein
each Z is independently C, CH, N, or N-oxide;
$R^1$ is -L-R wherein L is —$CO_2$— or a direct bond, and R is H, 1-imidazolyl, —($C_1$-$C_4$)alkenyl, or —($C_1$-$C_8$)alkyl-N(($C_1$-$C_4$)alkyl)$_2$;
$R^2$ is H, halo, or nitro;
$R^3$ is H, halo, or nitro;
$R^4$ is H, halo, nitro, —X-aryl, or absent;
$R^5$ is H, halo, nitro, —X-aryl, or absent;
$R^6$ is H, halo, nitro, —X-aryl, or absent;
$R^7$ is H, halo, nitro, —X-aryl, or absent;
$R^8$ is H, halo, or —X-aryl;
$R^9$ is H, aryl, —(OCH$_2$CH$_2$)$_n$—($C_1$-$C_6$)alkyl wherein n is 1-10, —Y-aryl, —Y—CH$_2$-aryl, —Y—($C_1$-$C_{10}$)alkyl,
each X is independently O, NH, or a direct bond;
each Y is independently O, NH, S, SO$_2$, CH$_2$, carbonyl, or a direct bond;
wherein $R^4$, $R^5$, $R^6$, or $R^7$ is absent when the Z to which it is attached is CH, N, or N-oxide; and
wherein any alkyl or aryl is optionally substituted with one or more alkyl, alkoxy, aryl, hydroxy, halo, amino, nitro, cyano, alkylsulfonamide, —NH—CO$_2$-aryl, trifluoromethyl, or trifluoromethoxy groups, or a combination thereof;
or a pharmaceutically acceptable salt, solvate, prodrug, or a metabolite thereof. As would be recognized by one of skill in the art, several compounds of formula II-X are also compounds of Formula I. Additionally, several specific examples of compounds of Formula I are illustrated in FIGS. 1-17, as well as specific examples of compounds of Formulas II-X.

The invention also provides a compound of the Formula II:

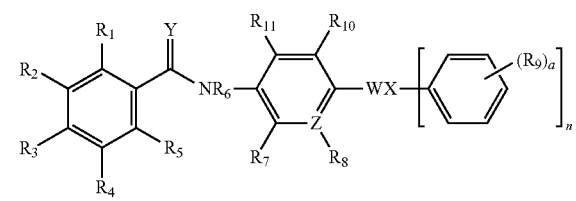

wherein
W is hydrogen or oxygen;
X is absent or ($C_1$-$C_{24}$)alkylene;
Y is oxygen or sulfur;
Z is carbon or nitrogen, provided that when Z is nitrogen, $R_8$ is absent;
$R_1$ is carboxylic acid, ($C_1$-$C_{10}$)alkyl ester, —NR'$_2$ where each R' is independently H or ($C_1$-$C_{10}$)alkyl;
$R_2$ is hydrogen or halogen;
$R_3$ is hydrogen, halogen, or —CONH($C_6$-$C_{30}$)aryl;

$R_4$ and $R_5$ are each independently hydrogen, halogen, or nitro;

$R_6$, $R_7$, and $R_{11}$ are each independently hydrogen;

$R_8$ and $R_9$ are each independently absent or hydrogen;

$R_{10}$ is hydrogen, halogen, or —O($C_6$-$C_{30}$)aryl;

any ($C_1$-$C_{24}$)alkylene or ($C_6$-$C_{30}$)aryl can be optionally substituted on carbon with one or more oxy, hydroxyl, halogen, ($C_6$-$C_{30}$)aryl, nitro, cyano, ($C_1$-$C_6$)alkoxy, or trifluoromethyl groups or any combination thereof, and optionally substituted on carbon with one or more oxo, imino, or thio groups;

a is 0, 1, or 2; and n is 0 or 1;

or a pharmaceutically acceptable salt, a prodrug, or a metabolite thereof.

In one embodiment, W is hydrogen or oxygen; X is absent, —$CH_2$—, or —$CH(CH_3)$—; Y is oxygen or sulfur; Z is carbon or nitrogen; $R_1$ is —$CO_2H$; $R_2$ is hydrogen, fluorine, chlorine, or bromine; $R_3$ is hydrogen, fluorine, chlorine, bromine, or —CONH-(2-methoxy-4-nitro)phenyl; $R_4$ and $R_5$ are each independently hydrogen, fluorine, chlorine, bromine, or nitro; $R_6$, $R_7$, and $R_{11}$ are each independently hydrogen; $R_8$ and $R_9$ are each independently absent or hydrogen; $R_{10}$ is hydrogen, chlorine, or —O-phenyl; a is 0, 1, or 2; and n is 0 or 1.

In certain embodiments, the compound of Formula II can include, for example, compound 222, 239, 251, 253, 268, 277-3, 278-2, 296, 364, 365, 381, 382, 385, 386, 387, 388, 389, 390, 393, 412, 414, 413, 414, 417, 418, 419, 420, or 422, which are illustrated in Table 10.

The invention also provides a compound of the Formula III:

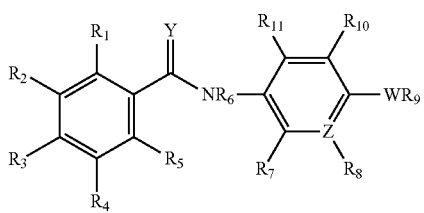

(III)

wherein

W is absent, oxygen, ($C_1$-$C_{24}$)alkylene, or carbonyl;

Y is oxygen or sulfur;

Z is carbon or nitrogen, provided that when Z is nitrogen, $R_8$ is absent or oxygen;

$R_1$ is carboxylic acid, thiocarboxylic acid, or a salt thereof;

$R_2$ is hydrogen, halogen, or nitro;

$R_3$ and $R_4$ are each independently hydrogen, halogen, or ($C_1$-$C_{24}$)alkyl;

$R_5$ is hydrogen or halogen;

$R_6$ is hydrogen or ($C_1$-$C_{24}$)alkyl;

$R_7$ is hydrogen or halogen;

$R_8$ is absent, hydrogen, or oxygen;

$R_9$ is hydrogen, halogen, ($C_1$-$C_{24}$)alkyl, —O($C_1$-$C_{24}$)alkyl, or ($C_1$-$C_{24}$)alkylene($C_1$-$C_{24}$)cycloalkyl;

$R_{10}$ is hydrogen, cyano, halogen, halo($C_1$-$C_{24}$)alkyl, ($C_1$-$C_{24}$)alkylhydroxyl, or ($C_1$-$C_{24}$)alkyl;

$R_{10}$, $R_{11}$, and the atoms in between form a fused ($C_6$-$C_{30}$)aryl;

any ($C_1$-$C_{24}$)alkyl, ($C_1$-$C_{24}$)alkylene, ($C_6$-$C_{30}$)aryl, or ($C_1$-$C_{24}$)cycloalkyl can be optionally substituted on carbon with one or more oxy, hydroxyl, halogen, ($C_6$-$C_{30}$)aryl, nitro, cyano, ($C_1$-$C_6$)alkoxy, or trifluoromethyl groups or any combination thereof, and optionally exchanged on carbon with one or more oxo, imino, or thio groups;

$R_{11}$ is hydrogen;

or a pharmaceutically acceptable salt, a prodrug, or a metabolite thereof.

In one embodiment, W is absent, oxygen, —$CH_2$—, or carbonyl; Y is oxygen or sulfur; Z is carbon or nitrogen; $R_1$ is —$CO_2H$, —$CS_2H$, —$CO_2Na$, or —COSH; $R_2$ is hydrogen, fluorine, chlorine, bromine, or nitro; $R_3$ and $R_4$ are each independently hydrogen, fluorine, chlorine, bromine, or methyl; $R_5$ is hydrogen, fluorine, chlorine, or bromine; $R_6$ is hydrogen or methyl; $R_7$ is hydrogen or chlorine; $R_8$ is absent, hydrogen, or oxygen; $R_9$ is hydrogen, chlorine, —$(CH_2)_7CH_3$, —$(CH_2)_9CH_3$, —$(CH_2)_{15}CH_3$, —$O(CH_2)_3CH_3$, —$CH_2CH(OH)CH_2OCH_2$(Cyclopropyl); or —$CH_2CH(OH)CH_2$—O—$(CH_2)_3CH_3$; $R_{10}$ is hydrogen, cyano, chlorine, trifluoromethyl, —$CH_2OH$, or methyl; $R_{10}$, $R_{11}$, and the atoms in between form a fused 3-hydroxyphenyl; and $R_{11}$ is hydrogen.

In certain embodiments, the compound of Formula III can include, for example, compound 44, 46, 85, 86, 89, 92, 93, 196, 201, 223, 232, 252, 254, 256, 257, 262, 265, 270, 271, 274, 279-2, 280-2, 281-2, 288, 289, 290, 291, 300, 301, 302, 303, 305, 307, 316, 318, 319, 329, 333, 334, 343, 344, 345, 346, 355, 358, 360, which are illustrated in Table 10.

The invention also provides a compound of Formula IV:

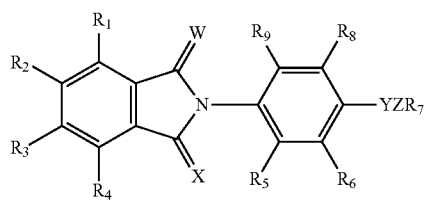

(IV)

wherein

W is oxygen or sulfur;

X is sulfur;

Y is oxygen;

Z is absent or ($C_1$-$C_{24}$)alkylene;

$R_1$, $R_2$, $R_3$, and $R_4$ are each independently halogen;

$R_5$, $R_6$, and $R_9$ are each independently hydrogen;

$R_7$ is ($C_1$-$C_{24}$)alkyl or ($C_6$-$C_{30}$)aryl;

any ($C_1$-$C_{24}$)alkyl, ($C_1$-$C_{24}$)alkylene, or ($C_6$-$C_{30}$)aryl can be optionally substituted on carbon with one or more oxy, hydroxyl, halogen, ($C_6$-$C_{30}$)aryl, nitro, cyano, ($C_1$-$C_6$) alkoxy, or trifluoromethyl groups or any combination thereof, and optionally exchanged on carbon with one or more oxo, imino, or thio groups;

$R_8$ is hydrogen or halogen;

or a pharmaceutically acceptable salt, a prodrug, or a metabolite thereof.

In one embodiment, W is oxygen or sulfur; X is sulfur; Y is oxygen; Z is absent or —$CH_2$—; $R_1$, $R_2$, $R_3$, and $R_4$ are each independently chlorine or bromine; $R_5$, $R_6$, and $R_9$ are each independently hydrogen; $R_7$ is -phenyl or —$(CH_2)_7CH_3$; and $R_8$ is hydrogen or chlorine.

In certain embodiments, the compound of Formula IV can include, for example, compound 277-2, 280-1, 281-1, or 380-1, which are illustrated in Table 10.

The invention provides a compound of Formula V:

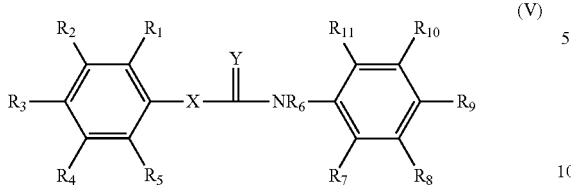

wherein
X is oxygen or sulfur;
$R_1$ is carboxylic acid;
$R_2$, $R_3$, $R_4$, $R_5$, $R_6$, $R_7$, $R_9$, $R_{10}$, and $R_{11}$ are each independently hydrogen;
$R_9$ is $(C_1-C_{24})$alkoxycarbonyl; or a pharmaceutically acceptable salt, a prodrug, or a metabolite thereof.

In one embodiment, X is oxygen or sulfur; $R_1$ is —$CO_2H$; $R_2$, $R_3$, $R_4$, $R_5$, $R_6$, $R_7$, $R_8$, $R_{10}$, and $R_{11}$ are each independently hydrogen; and $R_9$ is —$COO(CH_2)_3CH_3$.

In certain embodiments, the compound of Formula V can include, for example, compound 323 or 324, which are illustrated in Table 10.

The invention also provides a compound of Formula VI:

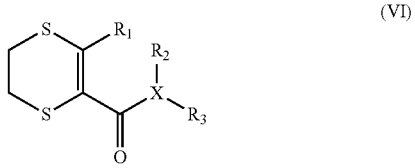

wherein
X is nitrogen, methoxy, amino, or hydroxyl;
$R_1$ is carboxylic acid or a salt thereof, or $R_1$ and $R_2$ and the atom in between form carbonyl;
$R_2$ is absent, hydrogen, or $(C_1-C_{24})$alkyl, or $(C_1-C_{24})$alkylenehydroxyl;
$R_3$ is absent, $(C_1-C_{24})$alkyl, $(C_1-C_{24})$alkylene, $(C_1-C_{24})$alkylene$(C_6-C_{30})$aryl, $(C_3-C_{30})$heterocyclyl, or $(C_6-C_{30})$aryl;
any $(C_1-C_{24})$alkyl, $(C_1-C_{24})$alkylene, $(C_3-C_{30})$heterocyclyl or $(C_6-C_{30})$aryl can be optionally substituted on carbon with one or more oxy, hydroxyl, halogen, $(C_6-C_{30})$aryl, nitro, cyano, oxo, $(C_1-C_{24})$alkoxycarbonyl, $(C_1-C_{24})$alkoxycarbonyl, —$CO_2H$, $SO_3Na$, $CO_2Na$, $(C_1-C_6)$alkoxy, or trifluoromethyl groups or any combination thereof, and optionally exchanged on carbon with one or more oxo, imino, or thio groups;
or a pharmaceutically acceptable salt, a prodrug, or a metabolite thereof.

In one embodiment, X is nitrogen, methoxy, amino, or hydroxyl; $R_1$ is —$CO_2H$, —$CO_2Na$, or $R_1$ and $R_2$ and the atom in between form carbonyl; $R_2$ is absent, hydrogen, methyl, or —$(CH_2)_2OH$; and $R_3$ is absent, —$C(CH_2OH)CH_2CH_3$, —$C(CH_2OH)CHOH$-phenyl, —$CH_2CHOHCH_3$, —$C(CH_2OH)CHOHCH_3$, -(3-chloro-4-(3-trifluoromethylphenyl)benzyl, —$CH(CH_3)CHOH$-phenyl, —$CH(CH_3)$-phenyl, —$C(CH_2OH)CHOH$-(4-nitrophenyl), —$(CH_2)_3SO_3Na$, —$C(CO_2H)CH_2$-(4-nitrophenyl), 3-(acetoxymethyl)-7-methyl-8-oxo-5-thia-1-azabicyclo[4.2.0]oct-2-ene-2-carboxylic acid, or —$C(CO_2Na)CH_2$-(4-nitrophenyl).

In certain embodiments, the compound of Formula VI can include, for example, compound 119, 120, 121, 122, 126, 127, 128, 129, 133, 134, 135, 136, 138, 139, 140, 141, 142, 143, 144, 145, 146, or 427, which are illustrated in Table 10.

The invention also provides a compound of Formula VII:

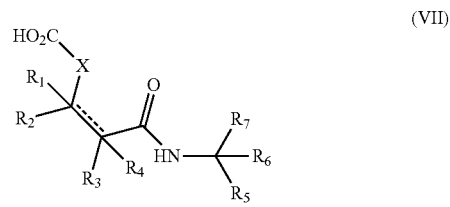

wherein
X is absent or $(C_1-C_2)$alkylene;
- - - is an optional bond;
$R_1$ is absent, hydrogen;
$R_2$ is hydrogen, $(C_6-C_{14})$arylcarbonyloxy; or
$R_1$ and $R_2$ and the atom in between form a $(C_1-C_{24})$cycloalkyl;
$R_3$ is hydrogen or phenyl, or
$R_2$, $R_3$, and the atoms in between form a $(C_1-C_{24})$cycloalkyl, or phenyl, or $(C_6-C_{14})$aryloxycarbonyl;
$R_4$ is absent or hydrogen;
$R_5$ is $(C_1-C_8)$alkyl;
$R_6$ is hydrogen;
$R_7$ is hydroxy$(C_1-C_8)$alkyl; or
$R_5$, $R_6$, $R_7$, and the atom in between form a $(C_6-C_{14})$aryl or $(C_3-C_{14})$heterocyclyl$(C_6-C_{14})$aryl; and
any alkylene, alkyl, aryl, cycloalkyl, heterocyclyl, or heteroaryl is optionally substituted on carbon with one or more oxy, hydroxyl, halo, $(C_6-C_{14})$aryl, $(C_6-C_{14})$aryl$(C_1-C_8)$alkoxy, nitro, cyano, $(C_1-C_6)$alkoxy, or trifluoromethyl groups or any combination thereof, and optionally exchanged on carbon with one or more oxo, imino, or thio groups;
or a pharmaceutically acceptable salt, a prodrug, or a metabolite thereof.

In one embodiment, X is absent or —$CH_2$-; $R_1$ is absent, hydrogen, or $R_1$ and $R_2$ and the atom in between form a cyclopentyl; $R_2$ is hydrogen, —OCO-phenyl, or $R_2$, $R_3$, and the atoms in between form a 3-methylcyclohexyl, 4-methylcyclohexyl, a cyclohexyl, 1-cyclopentyl, or $R_3$ is hydrogen, phenyl, or —OCO-phenyl; $R_4$ is absent or hydrogen; $R_5$ is —$CH_2CH_3$ or $R_5$, $R_6$, $R_7$, and the atom in between form a –3-trifluoromethyl-4-chlorophenyl, -4-(N-morpholino)phenyl, or -3-chloro-4-(O-benzyl)phenyl; $R_6$ is hydrogen; and $R_7$ is —$CH_2OH$.

In certain embodiments, the compound of Formula VII can include, for example, compound 94, 95, 96, 97, 100, 158, 243, 246, or 253, which are illustrated in Table 10.

The invention provides a compound of Formula VIII:

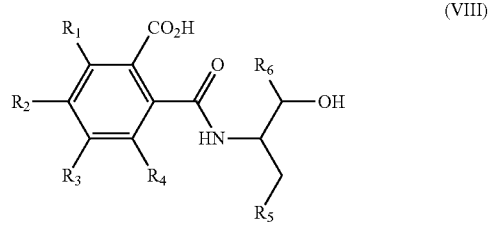

wherein
$R_1$, $R_2$, $R_3$, and $R_4$ are each independently halogen;
$R_5$ is hydroxyl or $(C_1-C_{24})$alkyl;
$R_6$ is hydrogen or $(C_6-C_{30})$aryl;

any ($C_1$-$C_{24}$)alkyl or ($C_6$-$C_{30}$)aryl can be optionally substituted on carbon with one or more oxy, hydroxyl, halogen, ($C_6$-$C_{30}$)aryl, nitro, cyano, ($C_1$-$C_6$)alkoxy, or trifluoromethyl groups or any combination thereof, and optionally exchanged on carbon with one or more oxo, imino, or thio groups;

or a pharmaceutically acceptable salt, a prodrug, or a metabolite thereof.

In one embodiment, $R_1$, $R_2$, $R_3$, and $R_4$ are each independently chlorine or bromine; $R_5$ is hydroxyl or methyl, and $R_6$ is hydrogen or 4-nitrophenyl.

In certain embodiments, the compound of Formula VIII can include, for example, compound 217, 238, or 267, which are illustrated in Table 10.

The invention provides a compound of Formula IX:

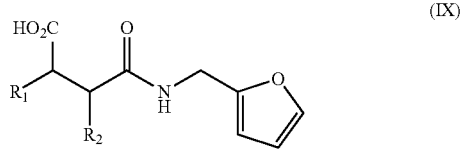

wherein $R_1$ and $R_2$ are each independently ($C_6$-$C_{14}$)arylcarbonyloxy or ($C_1$-$C_{24}$)alkylcarbonyloxy; or $R_1$ and $R_2$ together form a benzene ring, optionally substituted with one or two carboxy groups; and any ($C_1$-$C_{24}$)alkoxycarbonyl or ($C_6$-$C_{30}$)aryl is optionally substituted on carbon with one or more oxo, hydroxyl, halogen, ($C_6$-$C_{30}$)aryl, nitro, cyano, ($C_1$-$C_6$)alkoxy, or trifluoromethyl groups or any combination thereof, and optionally exchanged on carbon with one or more oxo, imino, or thio groups; or a pharmaceutically acceptable salt, a prodrug, or a metabolite thereof.

In one embodiment, $R_1$ and $R_2$ are each independently —OBz or —OAc. In another embodiment, the compound of Formula IX is compound 108, 109, 110, or 111, which are illustrated in Table 10.

The invention provides a compound of Formula X:

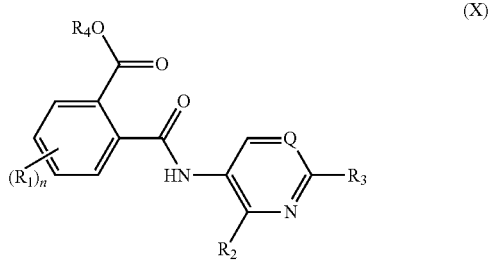

wherein each $R_1$ is independently H, F, Cl, Br, or I, and n is 1, 2, 3, or 4;

Q is N or CH;

$R_2$ and $R_3$ are independently —$NH_2$, —N(alkyl)$_2$, N-imidazolyl, or —O-phenyl;

$R_4$ is H or —O—($CH_2$)$_m$—$R_5$ wherein m is 1, 2, 3, or 4;

$R_5$ is —$NH_2$, —NH(alkyl), —N(alkyl)$_2$, or —$N^+$(alkyl)(benzyl)$X^-$ wherein X is a pharmaceutically acceptable anion;

any alkyl or phenyl of $R_2$ and any alkyl or benzyl of $R_5$ is optionally substituted on carbon with one or more oxo, hydroxyl, halogen, ($C_1$-$C_8$)alkyl, ($C_6$-$C_{14}$)aryl, nitro, cyano, ($C_1$-$C_8$)alkoxy, trifluoromethyl, or trifluoromethoxy groups or any combination thereof, and optionally exchanged on carbon with one or more oxo, imino, or thio groups;

or a pharmaceutically acceptable salt, a prodrug, or a metabolite thereof.

In one embodiment, the compound of Formula X is a compound illustrated in FIG. 18 or FIG. 19.

The invention yet further provides a pharmaceutical composition comprising one or more compounds of Formulas I-X; and a pharmaceutically acceptable diluent, excipient, or carrier. Examples of the compounds of Formulas II-X are illustrated in Table 10 below. Specific suitable examples include, but are not limited to, compound 271, 277-2, 277-3, 278-2, 279-2, 280-1, 280-2, 281-2, 290, 300, 301, 382, 385, 386, 390, 413, 414, 419, 420, and 422.

In other embodiments, the invention provides a method of treating an animal inflicted with a bacterial infection by administering to an animal in need of such treatment an effective amount of a compound of any one of Formulas I-X. In various embodiments, the compound can be in the form of a composition, as described herein.

The invention also provides a method of killing or inhibiting a bacteria comprising contacting the bacteria with an effective amount of a compound of any one of Formulas I-X. In one embodiment, the contacting is in vitro. In one embodiment, the contacting is in vivo. The bacteria can be a gram positive bacteria or a gram negative bacteria. Examples of the bacteria include, but are not limited to, *S. aureus, Enterococcus faecalis, Pseudomonas aeruginosa, Klebsiella pneumonia* and *Proteus mirabilis*, as well as vancomycin-resistant methicillin-resistant *Staphylococcus aureus*.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

DETAILED DESCRIPTION OF THE INVENTION

Figure 1:
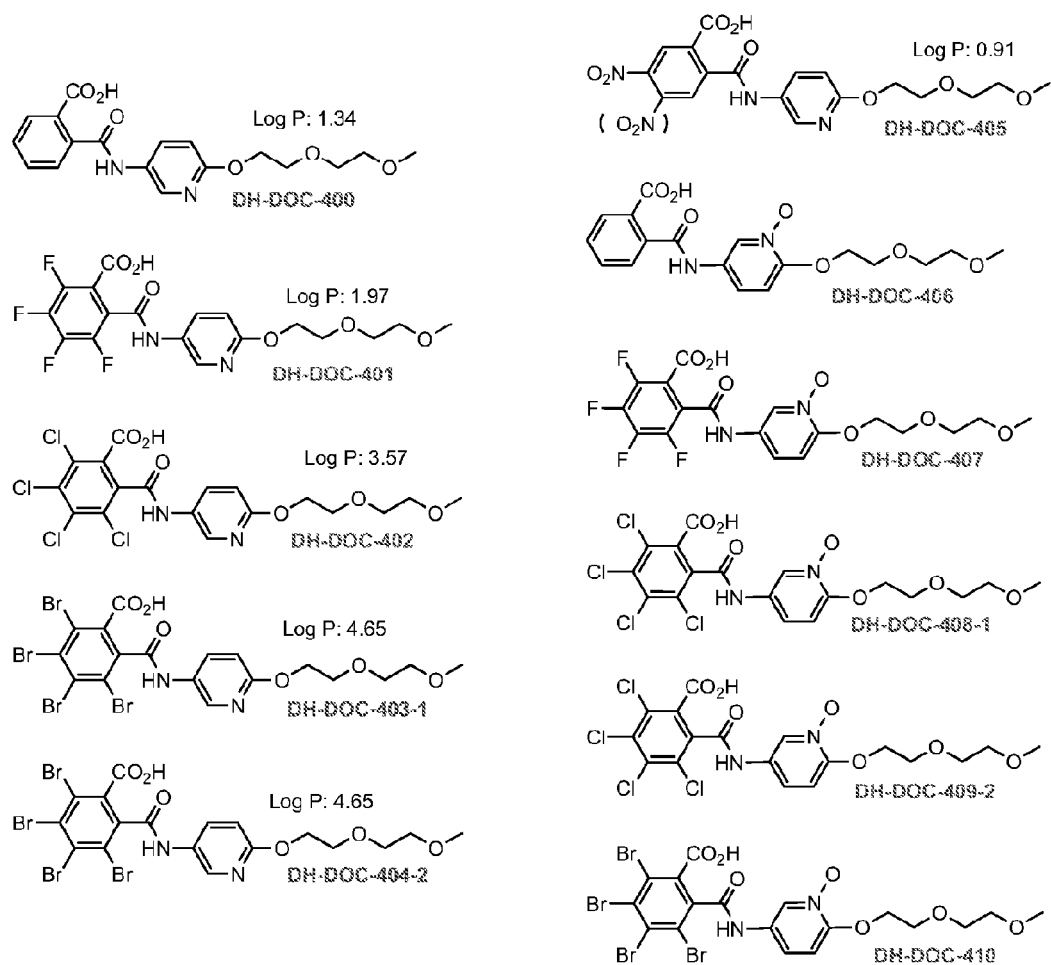
FIGS. 1-16 illustrate certain specific compounds of Formula I, according to various embodiments of the invention.
Figure 2:
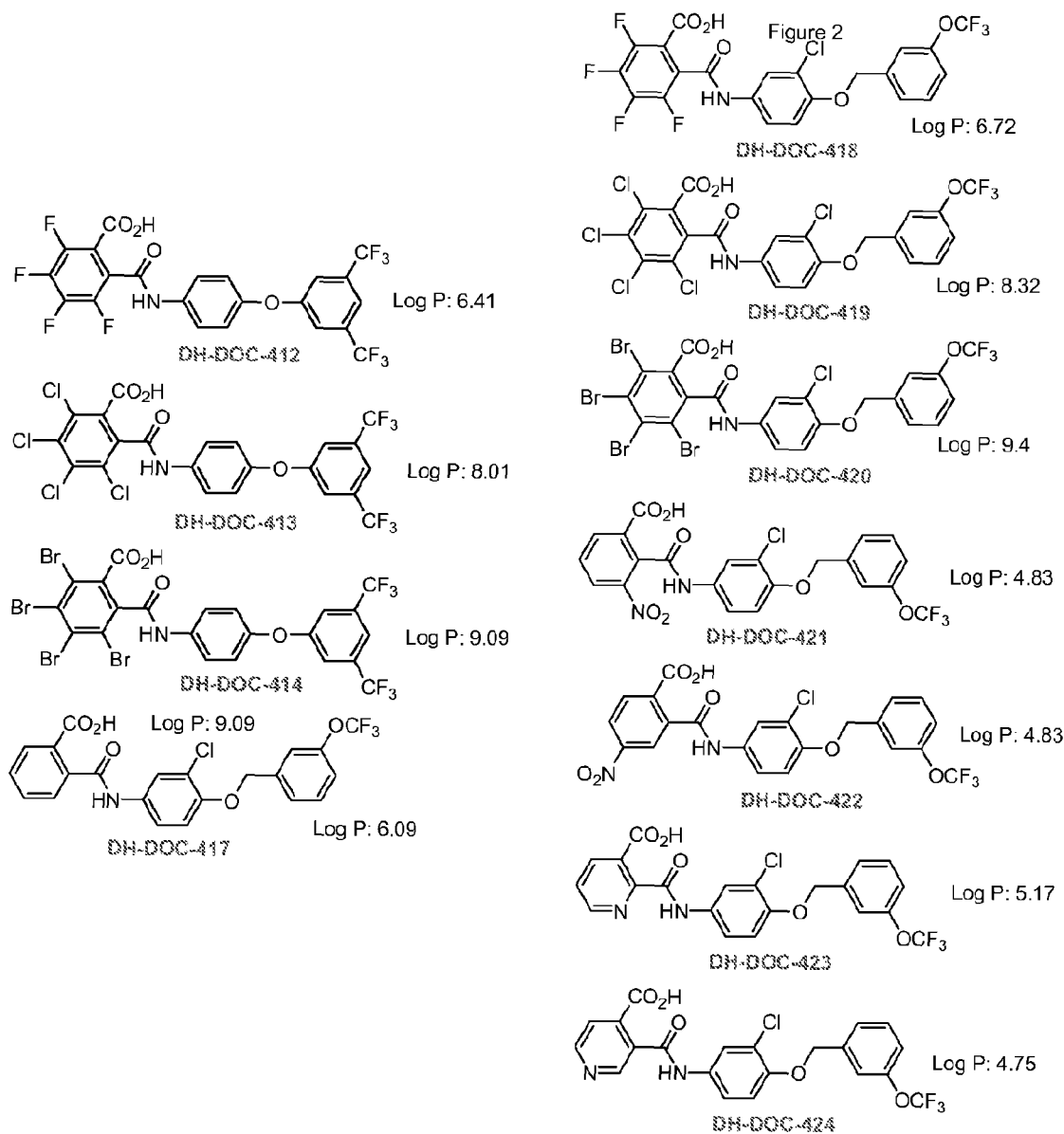
Figure 3:
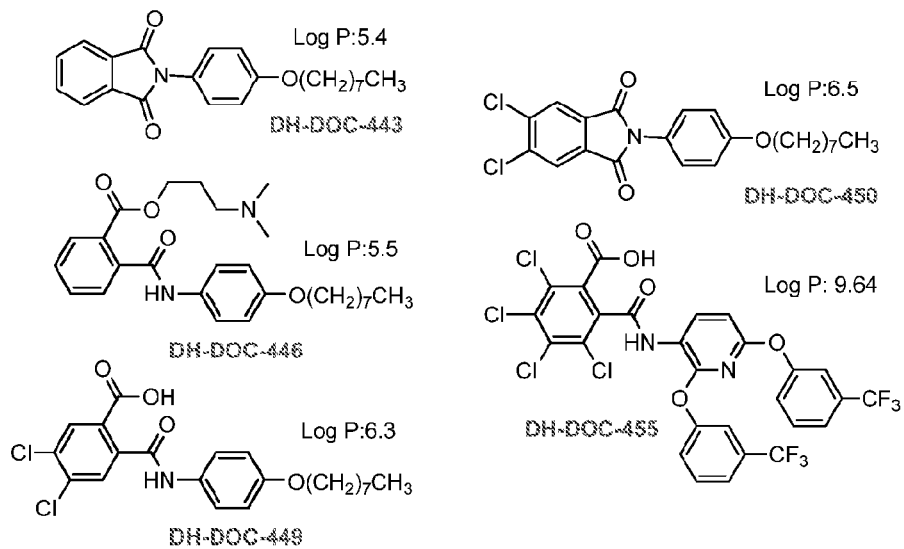
Figure 4:
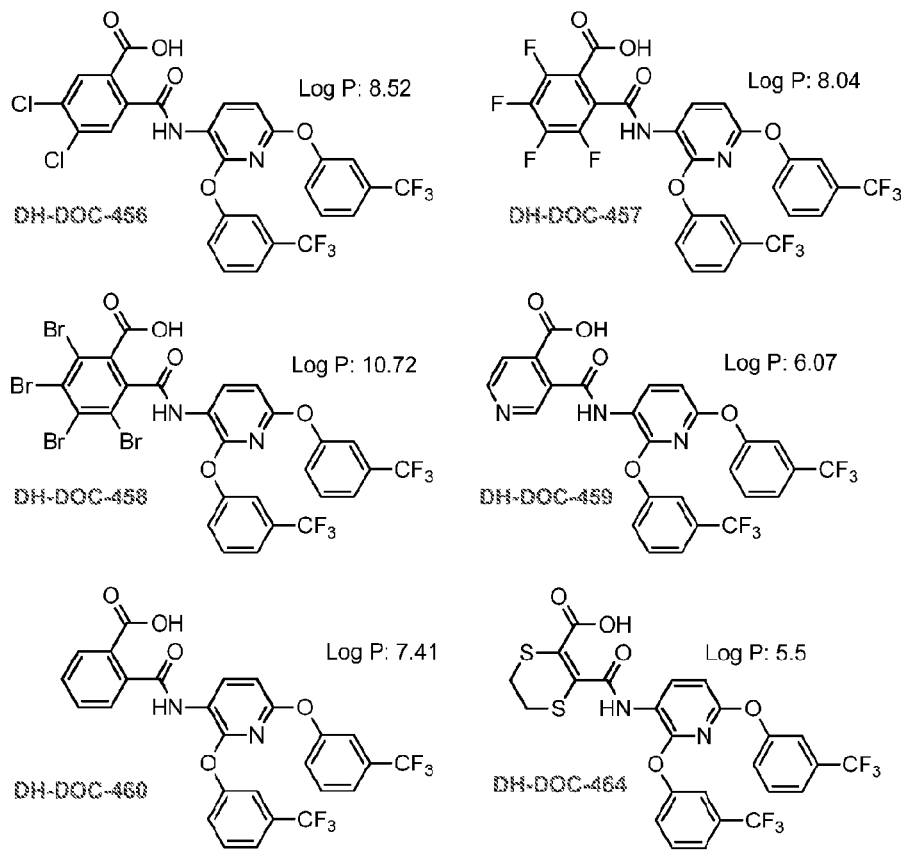
Figure 5:
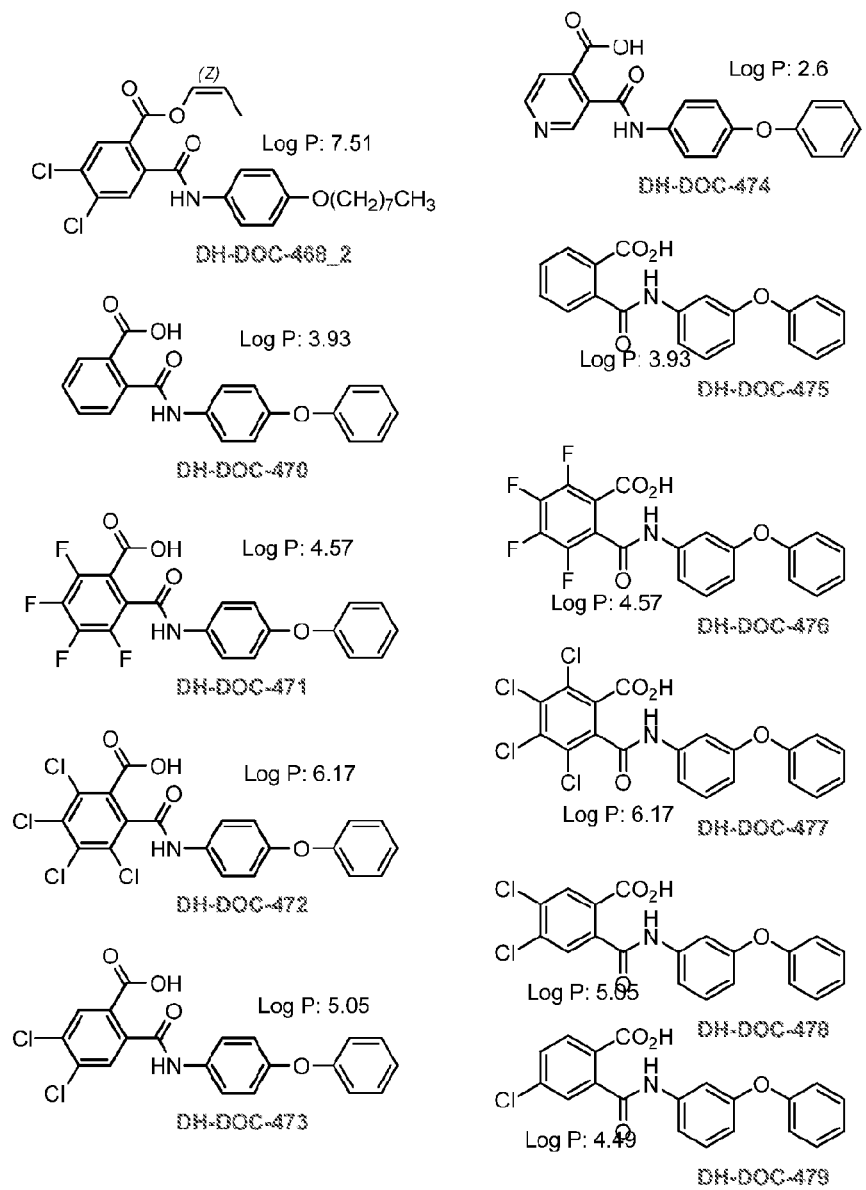
Figure 6:
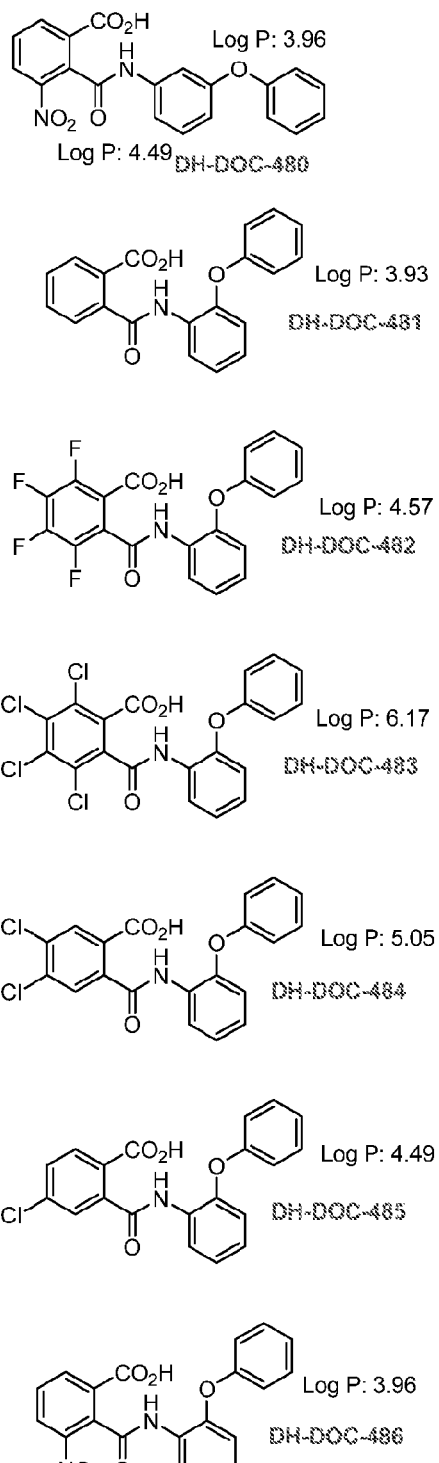
Figure 6:
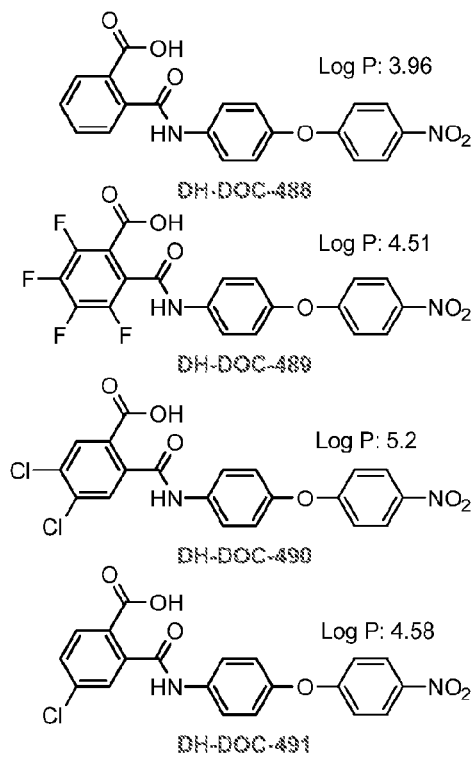
Figure 7:
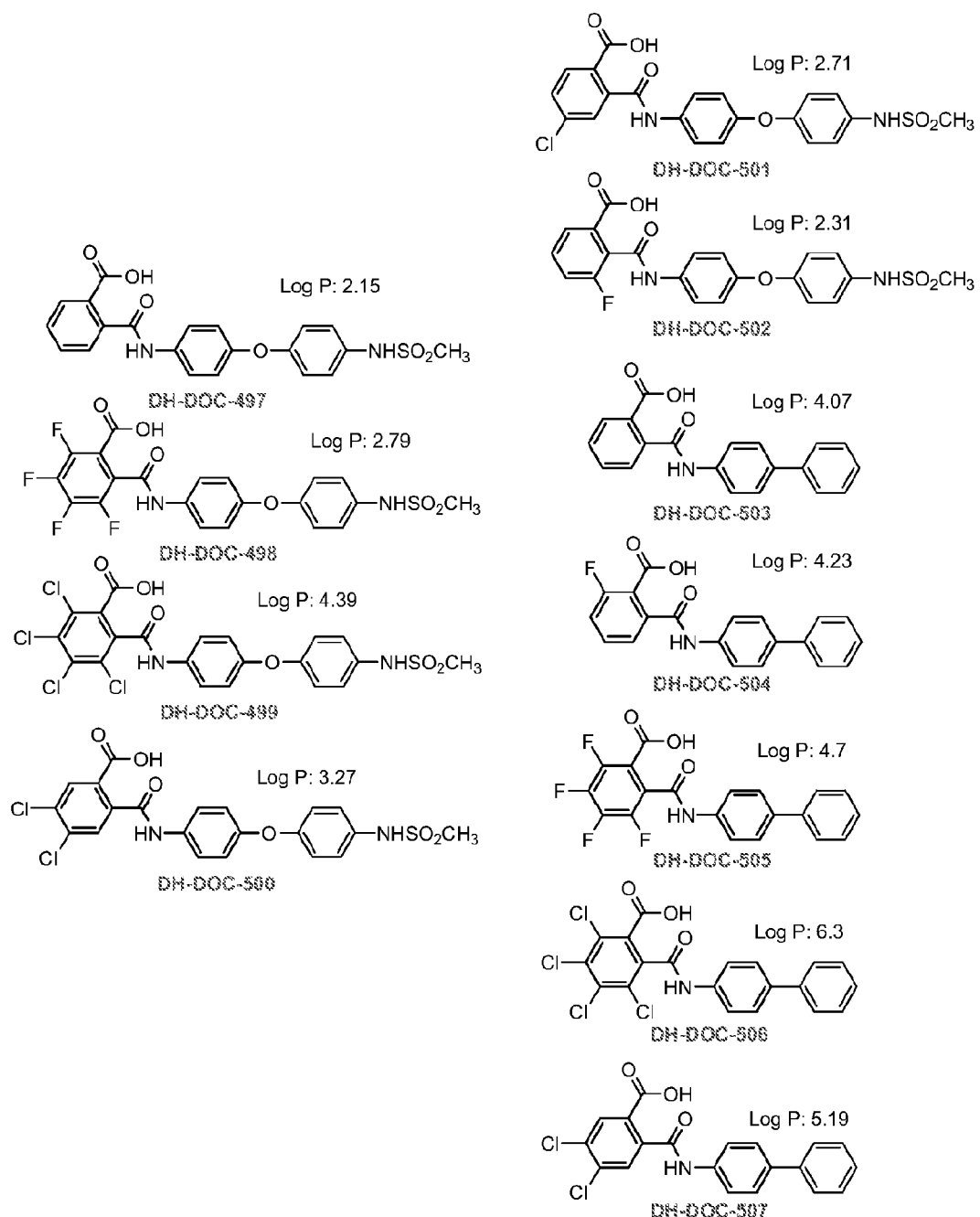
Figure 8:
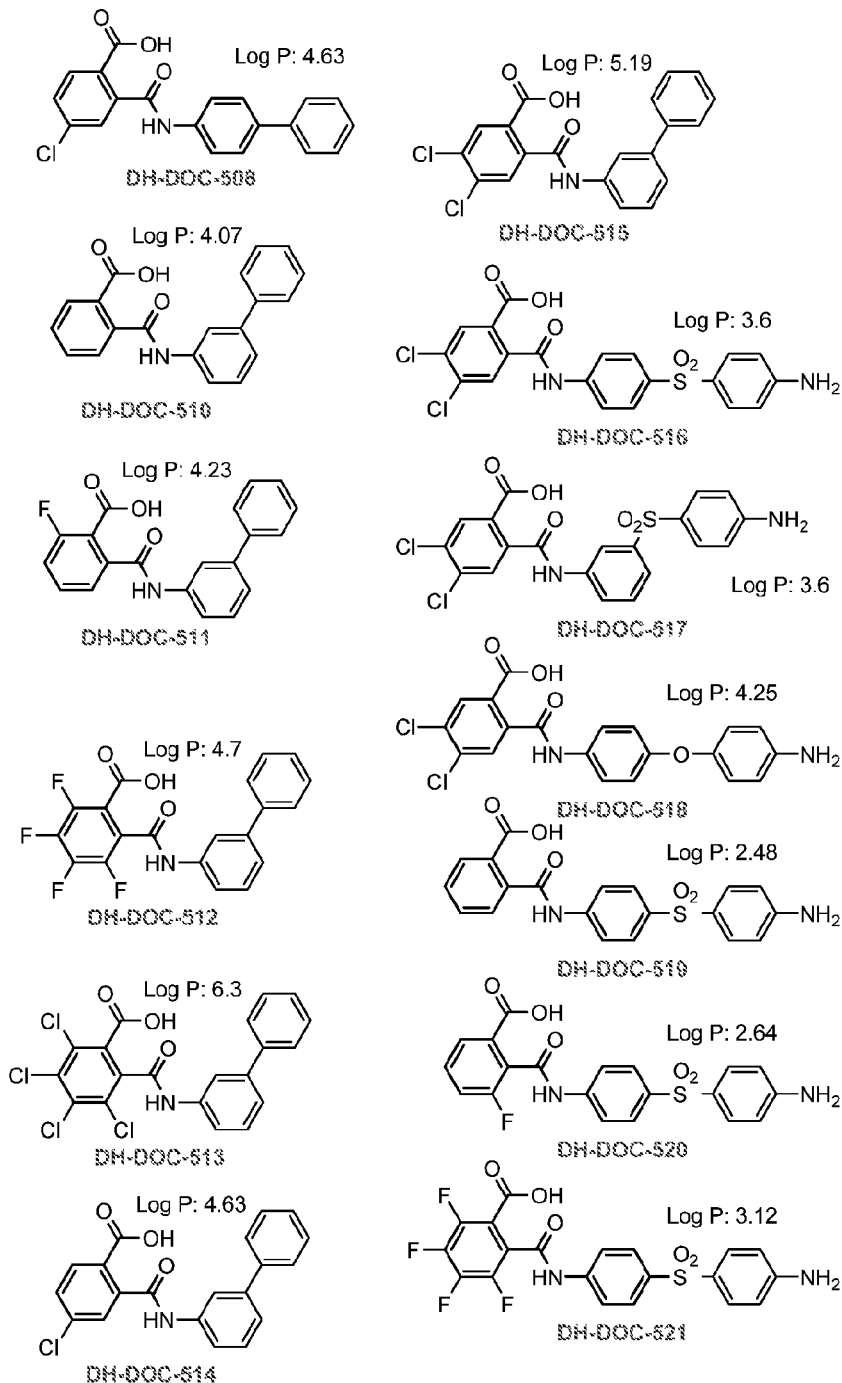
Figure 9:
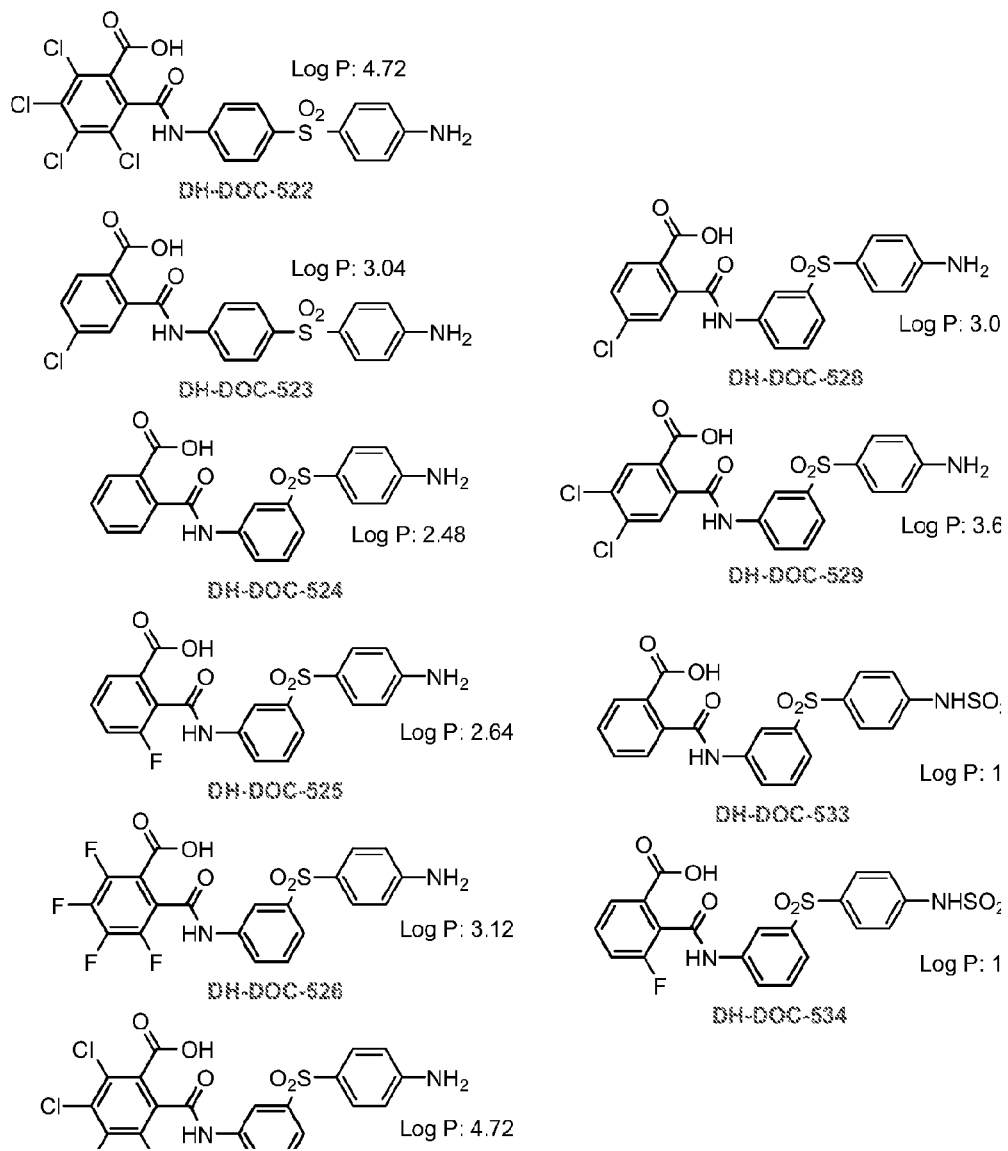
Figure 10:
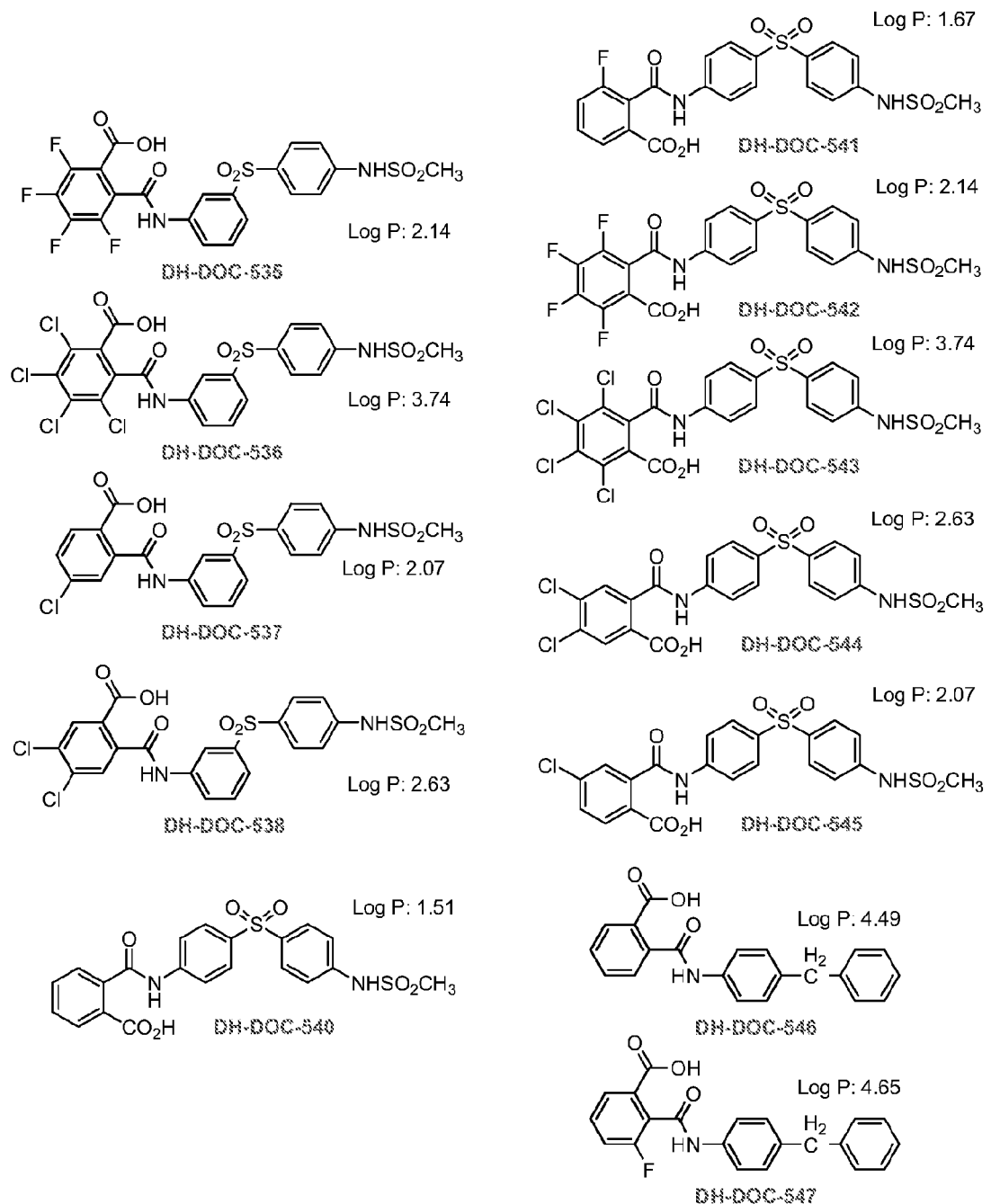
Figure 11:
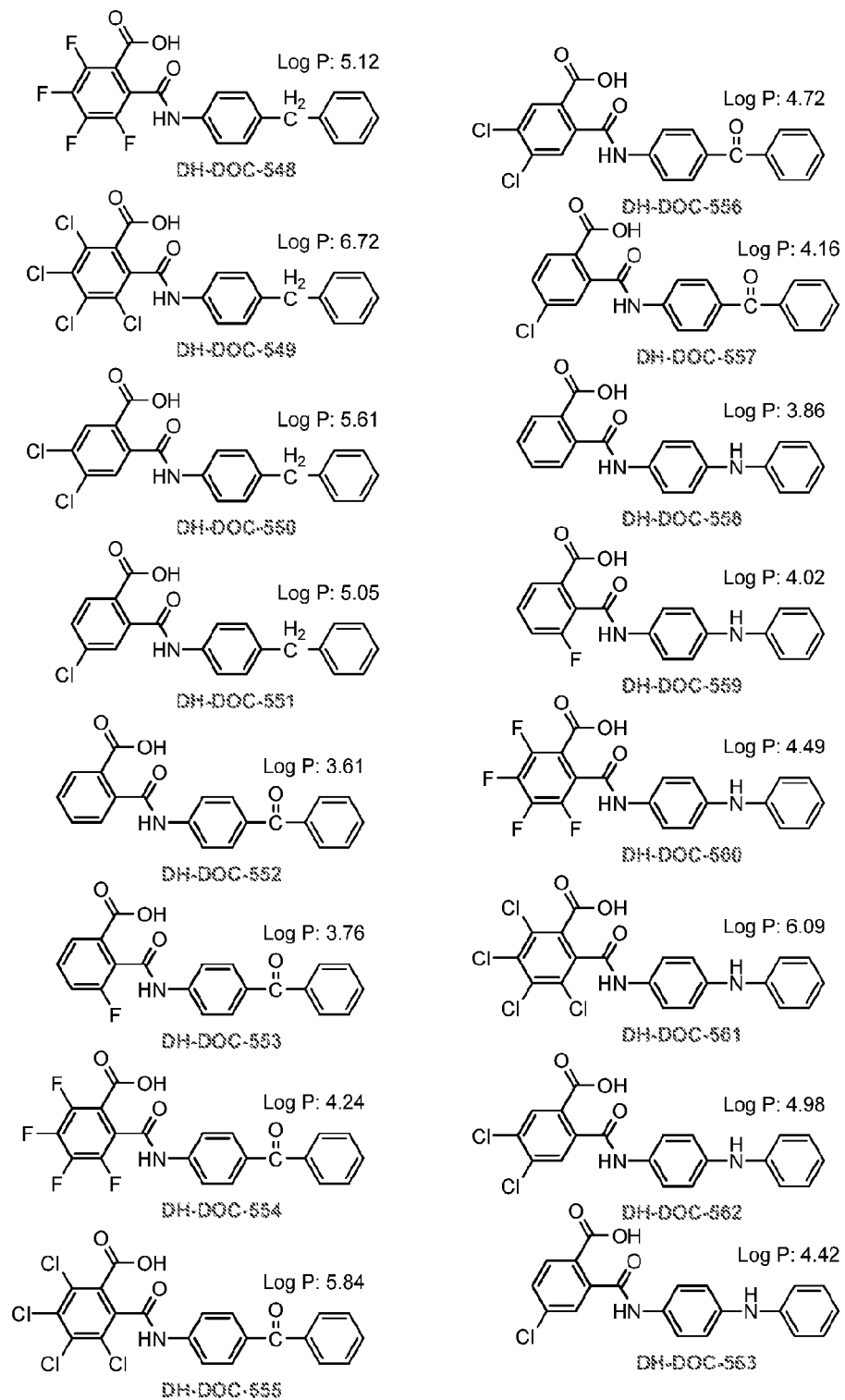
Figure 12:
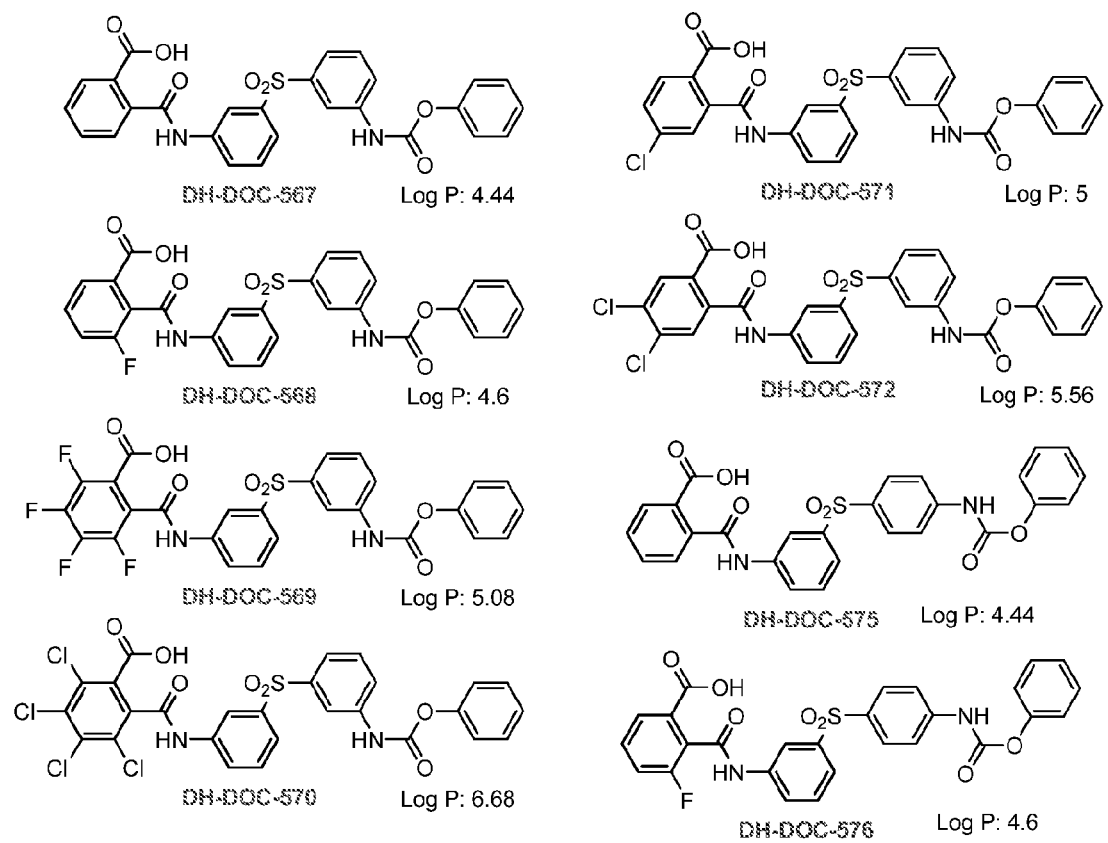
Figure 13:
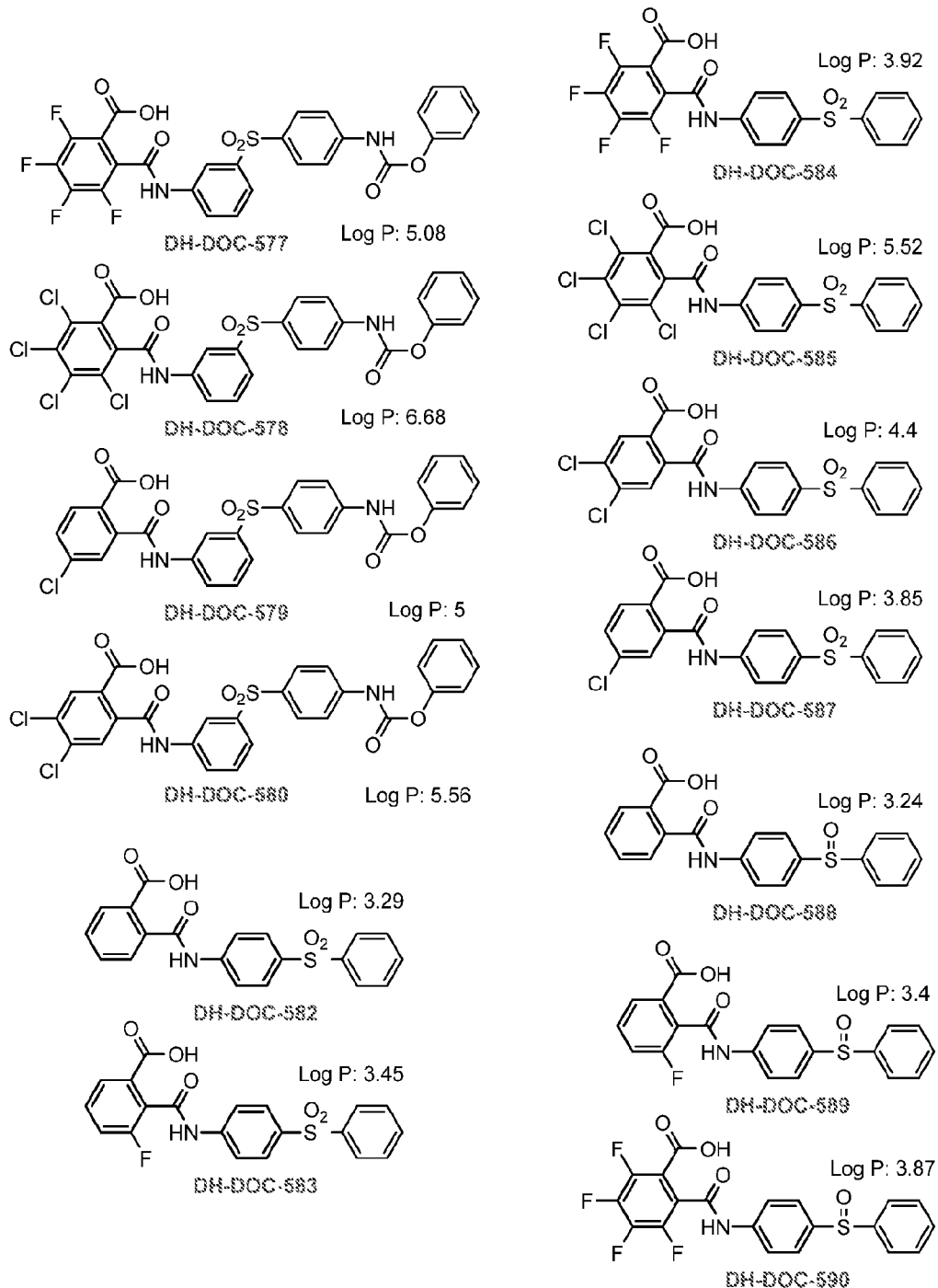
Figure 14:
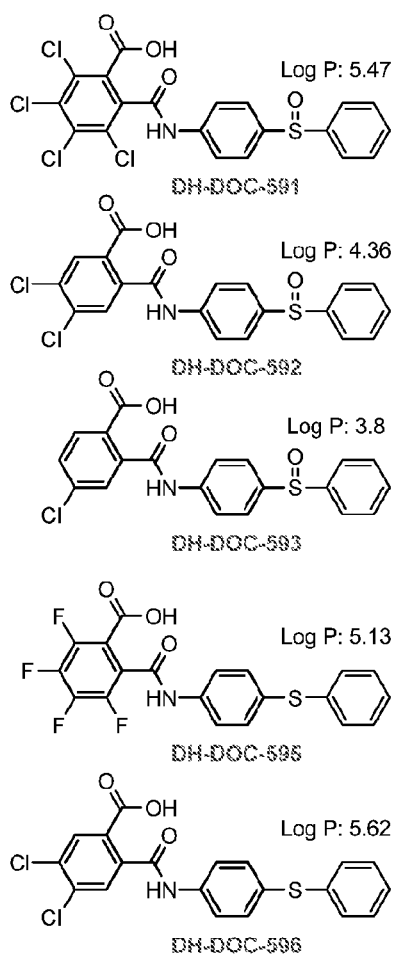
Figure 14:
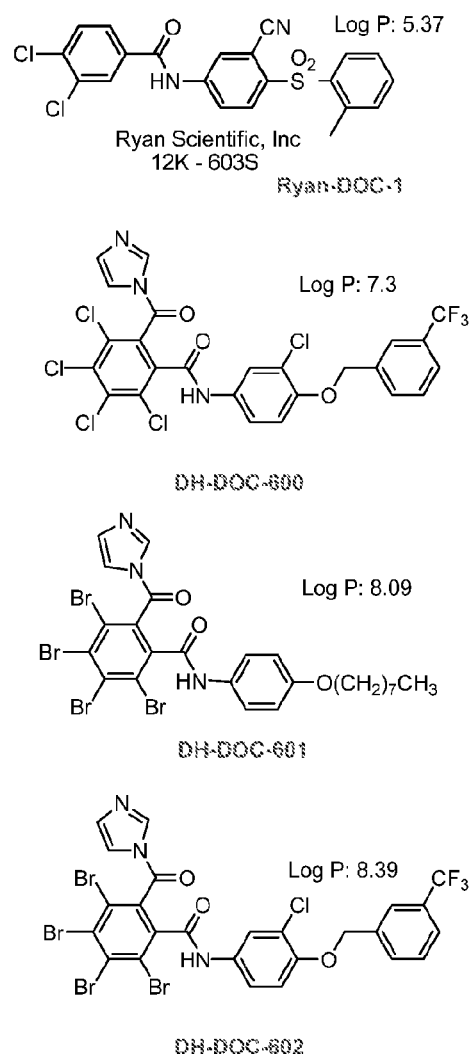
Figure 15:
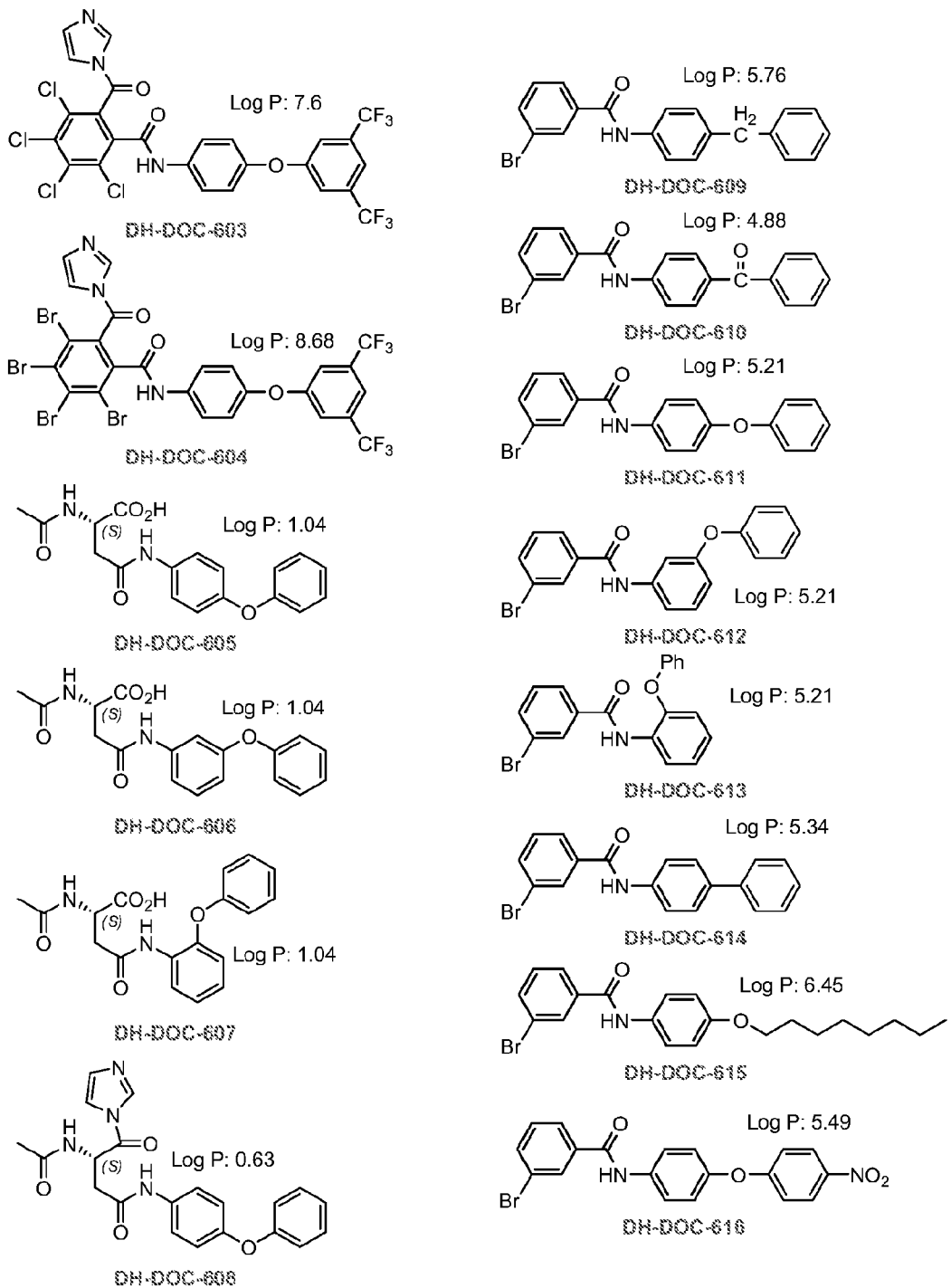
Figure 16:
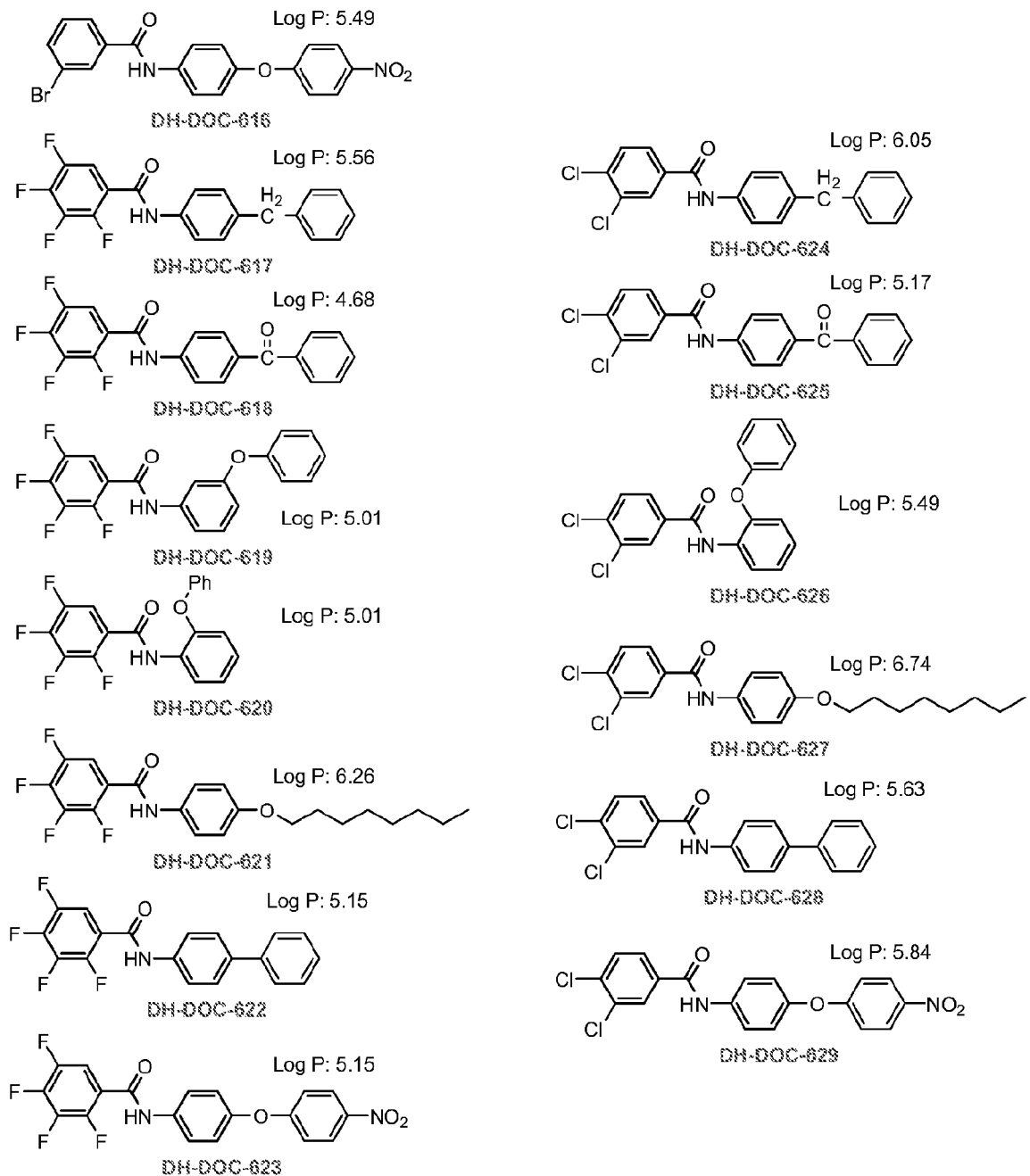

One of ordinary skill in the art would readily appreciate that the pharmaceutical formulations and methods described herein can be prepared and practiced by applying known procedures in the pharmaceutical arts. These include, for example, unless otherwise indicated, conventional techniques of pharmaceutical sciences including pharmaceutical dosage form design, drug development, pharmacology, of organic chemistry, and polymer sciences. See generally, for example, *Remington: The Science and Practice of Pharmacy*, 21$^{st}$ edition, Lippincott, Williams & Wilkins (2005).

DEFINITIONS

Before the invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

References in the specification to "one embodiment", "an embodiment", "an example embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect such aspect, feature, structure, moiety, or characteristic in connection with other embodiments, whether or not explicitly described. Reference to a compound of Formulas I-X refers to a compound of any one of Formulas I, II, III, IV, V, VI, VII, VIII, IX, or X; or a combination of any two or more of such formulas. In some embodiments, only a subset of Formulas I-X may be included in the subject matter of interest.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third New International Dictionary*, Merriam-Webster Inc., Springfield, Mass., 1993, *The American Heritage Dictionary of the English Language*, Houghton Mifflin, Boston Mass., 1981, and *Hawley's Condensed Chemical Dictionary*, 14$^{th}$ edition, Wiley Europe, 2002.

The following explanations of certain terms are meant to be illustrative rather than exhaustive. These terms have their ordinary meanings given by usage in the art and in addition include the following explanations.

The term "about" can refer to a variation of 5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment. In addition, unless indicated otherwise herein, a recited range (e.g., weight percents or carbon groups) includes each specific value, integer, decimal, or identity within the range.

As used herein, the term "and/or" refers to any one of the items, any combination of the items, or all of the items with which this term is associated.

As used herein, the singular forms "a," "an," and "the" include plural reference unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

Specific and preferred values listed below for radicals, substituents, and ranges, are for illustration only; they do not exclude other defined values or other values within defined ranges for the radicals and substituents.

The term "acyl" group refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen atom, the group is a "formyl" group, an acyl group as the term is defined herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "adjuvant" refers to an agent that may affect any of (1) the rate of release of the drug; (2) the stability of the drug; (3) the solubility of the drug; or (4) physicochemical characteristics of the core itself, including compactness, pH, etc. However, an adjuvant does not include those ingredients that affect the release rate by providing an osmotic pressure or ion gradient. In one aspect, adjuvants may include solubilizing agents, solubility decreasing agents, and dispersing agents.

The term "amino" refers to —NH$_2$. The amino group can be optionally substituted as defined herein for the term "substituted." The term "alkylamino" refers to —NR$_2$, wherein at least one R is alkyl and the second R is alkyl or hydrogen. The term "acylamino" refers to N(R)C(=O)R, wherein each R is independently hydrogen, alkyl, or aryl.

The terms "amide" (or "amido") refer to C- and N-amide groups, i.e., —C(O)NR$_2$, and —NRC(O)R groups, respectively. Amide groups therefore include but are not limited to carbamoyl groups (—C(O)NH$_2$) and formamide groups (—NHC(O)H).

The term "alkanoyl" or "alkylcarbonyl" refers to —C(=O)R, wherein R is an alkyl group as previously defined.

The term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(=O)OR (or "COOR"), wherein R is an alkyl group as previously defined.

The term "alkyl" refers to a $C_1$-$C_{18}$ hydrocarbon containing normal, secondary, tertiary or cyclic carbon atoms. Examples are methyl, ethyl, 1-propyl, 2-propyl, 1-butyl, 2-methyl-1 propyl(iso-butyl, —CH$_2$CH(CH$_3$)$_2$), 2-butyl(sec-butyl, —CH(CH$_3$)CH$_2$CH$_3$), 2-methyl-2-propyl(tert-butyl, —C(CH$_3$)$_3$), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl. The alkyl can be a monovalent hydrocarbon radical, as described and exemplified above, or it can be a divalent hydrocarbon radical (i.e., alkylene).

The alkyl can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl or hydroxy. The alkyl can optionally be interrupted with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)—), carboxylato (—OC(=O)—), imino (C=NH), sulfinyl (SO) or sulfonyl(SO$_2$). Additionally, the alkyl can optionally be at least partially unsaturated, thereby providing an alkenyl.

The term "alkenyl" refers to a $C_2$-$C_{18}$ hydrocarbon containing normal, secondary, tertiary or cyclic carbon atoms with at least one site of unsaturation, i.e., a carbon-carbon, sp$^2$ double bond. Examples include, but are not limited to: ethylene or vinyl (—CH=CH$_2$), allyl (—CH$_2$CH=CH$_2$), cyclopentenyl (—O$_5$H$_7$), and 5-hexenyl (—CH$_2$CH$_2$CH$_2$CH$_2$CH=CH$_2$). The alkenyl can be a movalent hydrocarbon radical, as described and exemplified above, or it can be a divalent hydrocarbon radical (i.e., alkenylene).

The alkenyl can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl or hydroxy. Additionally, the alkenyl can optionally be interrupted with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) or sulfonyl(SO$_2$).

The term "alkylene" refers to a saturated, branched or straight chain or cyclic hydrocarbon radical of 1-18 carbon atoms, and having two monovalent radical centers derived by the removal of two hydrogen atoms from the same or different carbon atoms of a parent alkane. Typical alkylene radicals include, but are not limited to: methylene (—CH$_2$—) 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), and the like.

The alkylene can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl or hydroxy. Additionally, the alkylene can optionally be interrupted with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) or sulfonyl(SO$_2$). Moreover, the alkylene can optionally be at least partially unsaturated, thereby providing an alkenylene.

The term "alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethenylene (—CH=CH—).

The alkenylene can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, NR$^x$R$^y$ and/or COOR$^x$, wherein each R$^x$ and R$^y$ are independently H, alkyl, alkenyl, aryl, heteroaryl, heterocycle, cycloalkyl or hydroxy. Additionally, The alkenylene can optionally be interrupted with one or more non-peroxide oxy (—O—), thio (—S—), imino (—N(H)—), methylene dioxy (—OCH$_2$O—), carbonyl carboxy (—C(=O)O—), carbonyldioxy (—OC(=O)O—), carboxylato (—OC(=O)—), imine (C=NH), sulfinyl (SO) or sulfonyl (SO$_2$).

The term "alkoxy" refers to the group alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The alkoxy can optionally be substituted with one or more halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The term "antimicrobial" refers to a molecular entity that is effective as a therapeutic agent or as a protective agent against an infection by a microorganism, which could be a bacterium, a protozoan, a fungus, a virus, or another pathogenic living organism. In many embodiments, the compounds described herein have antimicrobial activity. An antimicrobial may be an antibiotic, effective against bacteria, including aminoglycoside antibiotics such as gentamicin or streptomycin, a cephalosporin such as cephalexin or cephtriaxone, a carbacephem such as loracarbef, a glycopeptide such as vancomycin, a macrolide such as erythromycin, a penicillin such as amoxicillin or ampicillin, a polypeptide such as bacitracin or polymyxin B, a quinolone such as ciprofloxacin, a tetracycline such as oxytetracycline, a sulfonamide, or any other medically approved agent for treatment of bacterial infections. Alternatively the antimicrobial may be an antifungal agent such as ketoconazole, miconazole or amphotericin B, or an antiviral agent such as acyclovir or AZT.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like. The aryl can optionally be a divalent radical, thereby providing an arylene.

The aryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

The term "binder" refers to a pharmacologically inert substance, which is suitable for human consumption and serves to hold the constituents of a tablet together after compression forming of the tablet has occurred.

The term "carbocycle" refers to a saturated, unsaturated or aromatic ring having 3 to 8 carbon atoms as a monocycle, 7 to 12 carbon atoms as a bicycle, and up to about 30 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "carboxy" or "carboxyl" refers to —$CO_2H$.

All chiral, diastereomeric, racemica forms of a structure are intended, unless the specific stereochemistry or isomeric form is specifically indicated. Compounds used in the invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

The term "chemically feasible" refers to a bonding arrangement or a compound where the generally understood rules of organic structure are not violated; for example a structure within a definition of a claim that would contain in certain situations a pentavalent carbon atom that would not exist in nature would be understood to not be within the claim.

When a substituent is specified to be an atom or atoms of specified identity, "or a bond", a configuration is referred to when the substituent is "a bond" that the groups that are immediately adjacent to the specified substituent are directly connected to each other by a chemically feasible bonding configuration.

The phrase "compounds of the invention" refer to compounds of Formulas I-X, and pharmaceutically acceptable enantiomers, diastereomers, salts, or solvates thereof. Similarly, references to intermediates, are meant to embrace their salts or solvates where the context so permits.

The term "contacting" refers to the act of touching, making contact, or of bringing to immediate or close proximity, including at the molecular level, for example, to bring about a chemical reaction, physical change, or biological interaction, e.g., in a solution or other reaction mixture, or in a biological assay.

The term "cycloalkyl" refers to cyclic alkyl groups of from 3 to about 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The cycloalkyl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The cycloalkyl can optionally be at least partially unsaturated, thereby providing a cycloalkenyl. Additionally, the cycloalkyl can optionally be a divalent radical, thereby providing a cycloalkylene.

The term "derivative" of a compound refers to a chemically modified compound wherein the chemical modification takes place at one or more functional groups of the compound and/or on an aromatic, alicyclic, or heterocyclic structures, when present. The derivative however is expected to retain the pharmacological activity of the compound from which it is derived.

The term "diluent" refers to a pharmacologically inert substance that is nevertheless suitable for human consumption that serves as an excipient in the inventive dosage form. A diluent serves to dilute the API in the inventive dosage form, such that tablets of a typical size can be prepared incorporating a wide range of actual doses of the API.

The term "disintegrant" refers to substance that assists in dissolution of the dosage form after oral ingestion. It is believed to assist in hydration and to avoid the formation of gels in the stomach of the patient as the tablet dissolves, thus assisting in the release of the API into the gastric juices so that it can be absorbed into the bloodstream.

The term "dispersing agent" refers to an agent that facilitates the formation of a dispersion of one or more internal phases in a continuous phase. Examples of such dispersions include suspensions and emulsions, wherein the continuous phase may be water, for example, and the internal phase is a solid or a water-immiscible liquid, respectively. Thus, dispersing agents may include suspending agents and emulsifying agents.

The term "dosage form" refers to a physical and chemical composition of an active pharmaceutical ingredient (API) that is adapted for administration to a patient in need thereof. The inventive dosage form is a tablet. By a tablet is meant a relatively hard, compact object, suitable for oral ingestion, prepared by compression of a powder including an active pharmaceutical ingredient and, usually, excipients.

The term "drug" refers to a therapeutic agent or a diagnostic agent and includes any substance, other than food, used in the prevention, diagnosis, alleviation, treatment, or cure of a disease. *Stedman's Medical Dictionary*, 25$^{th}$ Edition (1990). The drug can include any substance disclosed in at least one of: *The Merck Index*, 13$^{th}$ Edition, 1998, published by Merck & Co., Rahway, N.J.; Pei-Show Juo, *Concise Dictionary of Biomedicine and Molecular Biology*, (1996); *U.S. Pharmacopeia Dictionary*, 2000 Edition; and Physician's Desk Reference, 2001 Edition.

The term "an effective amount" refers to an amount sufficient to effect beneficial or desired results. An effective amount can be administered in one or more administrations, applications, or dosages. Determination of an effective amount for a given administration is well within the ordinary skill in the pharmaceutical arts.

The terms "ethylenically unsaturated group" or "olefinically unsaturated group" are employed herein in a broad sense and is intended to encompass any groups containing at least one C=C group. Exemplary ethylenically unsaturated groups include without limitation acryloyl, methacryloyl, allyl, vinyl, styrenyl, or other C=C containing groups.

The term "excipient" refers to an ingredient of the dosage form that is not medicinally active, but serves to dilute the API, assist in dispersion of the tablet in the patient's stomach, bind the tablet together, and serve other functions like stabilizing the API against decomposition.

The term "glidant" refers to a substance that assists in maintaining favorable powder flow properties of the powder materials that are compressed to form the inventive tablet.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted. The heteroaryl can optionally be a divalent radical, thereby providing a heteroarylene.

Examples of heteroaryl groups include, but are not limited to, 2H-pyrrolyl, 3H-indolyl, 4H-quinolizinyl, 4nH-carbazolyl, acridinyl, benzo[b]thienyl, benzothiazolyl, β-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl, or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The heteroaryl can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

The term "heterocycle" or "heterocyclyl" refers to a saturated or partially unsaturated ring system, containing at least one heteroatom selected from the group oxygen, nitrogen, and sulfur, and optionally substituted with alkyl, or C(=O) $OR^b$, wherein $R^b$ is hydrogen or alkyl. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine. The heterocycle can optionally be a divalent radical, thereby providing a heterocyclene.

The heterocycle can optionally be substituted with one or more alkyl, alkenyl, alkoxy, halo, haloalkyl, hydroxy, hydroxyalkyl, aryl, heteroaryl, heterocycle, cycloalkyl, alkanoyl, alkoxycarbonyl, amino, imino, alkylamino, acylamino, nitro, trifluoromethyl, trifluoromethoxy, carboxy, carboxyalkyl, keto, thioxo, alkylthio, alkylsulfinyl, alkylsulfonyl, cyano, acetamido, acetoxy, acetyl, benzamido, benzenesulfinyl, benzenesulfonamido, benzenesulfonyl, benzenesulfonylamino, benzoyl, benzoylamino, benzoyloxy, benzyl, benzyloxy, benzyloxycarbonyl, benzylthio, carbamoyl, carbamate, isocyannato, sulfamoyl, sulfinamoyl, sulfino, sulfo, sulfoamino, thiosulfo, $NR^xR^y$ and/or $COOR^x$, wherein each $R^x$ and $R^y$ are independently H, alkyl, alkenyl, aryl, heteroaryl, heterocycle, cycloalkyl, or hydroxy.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "hydrate" refers to the complex where the solvent molecule is water.

The term "include," "for example," "such as," and the like are used illustratively and are not intended to limit the present invention.

The terms "individual," "host," "subject," and "patient" are used interchangeably, and refer to a mammal, including, but not limited to, primates, including simians and humans.

The term "inhibitor" refers to an agent that inhibits the growth of microbes, such as bacteria. Examples of inhibitors include the compounds described herein.

The term "keto" refers to (C=O). The term "oxo" refers to =O.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in an claim of the disclosed subject matter, the total number will be determined as set forth above.

The term "infection" refers to the invasion of the host by germs that reproduce and multiply, causing disease by local cell injury, release of poisons, or germ-antibody reaction in the cells. The infection can be in a mammal (e.g., human).

The term "lubricant" refers to a substance that is useful in the tablet compression process, serving to lubricate metal parts of the tablet die.

The term "mammal" refers to any of a class of warm-blooded higher vertebrates that nourish their young with milk secreted by mammary glands and have skin usually more or less covered with hair, and non-exclusively includes humans and non-human primates, their children, including neonates and adolescents, both male and female, livestock species, such as horses, cattle, sheep, and goats, and research and domestic species, including dogs, cats, mice, rats, guinea pigs, and rabbits.

The term "metabolite" refers to any compound of Formulas I-X produced in vivo or in vitro from the parent drug (compound), or its prodrug.

The term "microbe" refers to an organism that is too small to be seen by the naked human eye. As used herein, the term "microbe" refers to a bacterium, a fungus, an archaea, or a protist.

The term "molecular weight" refers to a weight-average molecular weight, as is well known in the art.

The terms "optional" or "optionally" mean that the subsequently described event or condition may but need not occur, and that the description includes instances where the event or condition occurs and instances in which it does not. For example, "optionally substituted" means that the named substituent may be present but need not be present in a specific embodiment, and the description includes situations where the named substituent is included and situations where the named substituent is not included.

The term "patient" refers to a warm-blooded animal, and preferably a mammal, for example, a cat, dog, horse, cow, pig, mouse, rat, or primate, including a human.

The term "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio. Several pharmaceutically acceptable ingredients are known in the art and official publications such as *The United States Pharmacoepia* describe the analytical criteria to assess the pharmaceutical acceptability of numerous ingredients of interest.

The term "pharmaceutically acceptable salts" refers to ionic compounds, wherein a parent non-ionic compound is modified by making acid or base salts thereof. Examples of pharmaceutically acceptable salts include, mineral or organic acid salts of basic residues such as amines; alkali or organic salts of acidic residues such as carboxylic acids; and the like. The pharmaceutically acceptable salts include conventional non-toxic salts and quaternary ammonium salts of the parent compound formed, for example, from non-toxic inorganic or organic acids. Non-toxic salts can include those derived from inorganic acids such as hydrochloric, hydrobromic, hydroiodic, sulfuric, sulfamic, phosphoric, nitric and the like. Salts prepared from organic acids can include those such as acetic, 2-acetoxybenzoic, ascorbic, behenic, benzenesulfonic, benzoic, citric, ethanesulfonic, ethane disulfonic, formic, fumaric, gentisinic, glucaronic, gluconic, glutamic, glycolic, hydroxymaleic, isethionic, isonicotinic, lactic, maleic, malic, mesylate or methanesulfonic, oxalic, pamoic (1,1'-methylene-bis-(2-hydroxy-3-naphthoate)), pantothenic, phenylacetic, propionic, salicylic, sulfanilic, toluenesulfonic, stearic, succinic, tartaric, bitartaric, and the like. Certain compounds can form pharmaceutically acceptable salts with various amino acids. For a review on pharmaceutically acceptable salts, see, e.g., Berge et al., *J. Pharm. Sci.* 1977, 66(1), 1-19, which is incorporated herein by reference.

The pharmaceutically acceptable salts of the compounds described herein can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of many suitable salts are found in *Remington: The Science and Practice of Pharmacy*, 21$^{st}$ edition, Lippincott, Williams & Wilkins, (2005).

It will be appreciated by those skilled in the art that compounds useful in the disclosed subject matter having a chiral center may exist in and be isolated in optically active and racemic forms. Some compounds may exhibit polymorphism. It is to be understood that the presently disclosed subject matter encompasses any racemic, optically-active, polymorphic, or stereoisomeric form, or mixtures thereof, of a compound of the presently disclosed subject matter, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-HCV activity using the standard tests described herein, or using other similar tests which are well known in the art.

One diastereomer of a compound disclosed herein may display superior activity compared with the other. When required, separation of the racemic material can be achieved by HPLC using a chiral column or by a resolution using a resolving agent such as camphonic chloride as in Tucker et al., *J. Med. Chem.*, 37, 2437 (1994). A chiral compound described herein may also be directly synthesized using a chiral catalyst or a chiral ligand, e.g., Huffman et al., *J. Org. Chem.*, 60:1590 (1995).

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "prevent," "preventative," "prevention," "protect," and "protection" refer to medical procedures that keep the malcondition from occurring in the first place. The terms mean that there is no or a lessened development of disease or disorder where none had previously occurred, or no further disorder or disease development if there had already been development of the disorder or disease.

The term "prodrug" refers to any pharmaceutically acceptable form of a compound of Formulas I-X, which, upon administration to a patient, provides a compound of any one of Formulas I-X. Pharmaceutically acceptable prodrugs refer to a compound that is metabolized, for example hydrolyzed or oxidized, in the host to form a compound of any one of Formulas I-X. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The prodrug can be readily prepared from the compounds of Formulas I-X using methods known in the art. See, e.g., See Notari, R. E., "Theory and Practice of Prodrug Kinetics," *Methods in Enzymology*, 112:309 323 (1985); Bodor, N., "Novel Approaches in Prodrug Design," *Drugs of the Future*, 6(3):165 182 (1981); and Bundgaard, H., "Design of Prodrugs: Bioreversible-Derivatives for Various Functional Groups and Chemical Entities," in *Design of Prodrugs* (H. Bundgaard, ed.), Elsevier, N.Y. (1985); *Burger's Medicinal Chemistry and Drug Chemistry*, Fifth Ed., Vol. 1, pp. 172 178, 949 982 (1995).

The prodrug may be prepared with the objective(s) of improved chemical stability, improved patient acceptance and compliance, improved bioavailability, prolonged duration of action, improved organ selectivity (including improved brain penetrance), improved formulation (e.g., increased hydrosolubility), and/or decreased side effects (e.g., toxicity). See e.g., T. Higuchi and V. Stella, "Prodrugs as Novel Delivery Systems", Vol. 14 of the A.C.S. Symposium Series; Bioreversible Carriers in Drug Design, ed. Edward B. Roche, American Pharmaceutical Association and Pergamon Press, (1987). Prodrugs include, but are not limited to, compounds derived from compounds of Formulas I-X, wherein a hydroxy, amine or sulfhydryl groups, if present, are bonded to any group that, when administered to the subject, cleaves to form the free hydroxyl, amino or sulfhydryl group, respectively. Selected examples include, but are not limited to, biohydrolyzable amides and biohydrolyzable esters and biohydrolyzable carbamates, carbonates, acetate, formate and benzoate derivatives of alcohol and amine functional groups.

The term "protecting group" refers to any group which, when bound to a hydroxyl, nitrogen, or other heteroatom prevents undesired reactions from occurring at this group and which can be removed by conventional chemical or enzymatic steps to reestablish the original group. The particular removable protecting group employed is typically not critical. Some removable protecting groups include conventional substituents such as, for example, allyl, benzyl, acetyl, chloroacetyl, thiobenzyl, benzylidine, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a functionality and later selectively removed either by chemical or enzymatic methods in mild conditions compatible with the nature of the product.

A large number of protecting groups and corresponding chemical cleavage reactions are described in *Protective Groups in Organic Synthesis*, Theodora W. Greene (John Wiley & Sons, Inc., New York, 1991, ISBN 0-471-62301-6) ("Greene", which is incorporated herein by reference in its entirety). Included therein are hydroxyl and nitrogen protecting groups, for example, amide-forming groups. In particular, see Chapter 1, Protecting Groups: An Overview, pages 1-20, Chapter 2, Hydroxyl Protecting Groups, pages 21-94, Chapter 4, Carboxyl Protecting Groups, pages 118-154, and Chapter 5, Carbonyl Protecting Groups, pages 155-184. See also Kocienski, Philip J; *Protecting Groups* (Georg Thieme Verlag Stuttgart, New York, 1994), which is incorporated herein by reference in its entirety.

The term "solvate" refers to a complex of variable stoichiometry formed by a solute (e.g., a compound of a formula described herein, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent.

The term "stereoisomer" refers to a compound made up of the same atoms bonded by the same bonds but having different three-dimensional structures, which are not interchangeable.

The term "solubility" refers to the extent to which a solute dissolves in a solvent, wherein the solute and "solvent" may be of the same or of different physical state. Thus, a solution of a solid or a liquid in any "solvent" such as a solid, liquid or gas is within the scope of this term. Solubility can be expressed in many ways, such as: weight/volume (grams/mL); molality (number of moles of solute/1000 grams of solvent); mol fraction (fraction of the total number of moles present which are mole of one component); mol % (mol fraction.times.100); normality (number of gram equivalent weights of solute dissolved in 1000 mL of solution); % by weight (% w/w); % weight in volume (% w/v); % by volume (% v/v). Solubility can also be described by terms such as: very soluble (less than 1 part of solvent per 1 part of solute); freely soluble (from 1 to 10 parts of solvent per 1 part of solute); soluble (from 10 to 30 parts of solvent per 1 part of solute); sparingly soluble (from 30 to 100 parts of solvent for 1 part of solute); slightly soluble (from 100 to 1000 parts of solvent for 1 part of solute); very slightly soluble (from 1000 to 10,000 parts of solvent for 1 part of solute); and practically insoluble, or insoluble (more than 10,000 parts of solvent for 1 part of solute). For further elaboration, see Remington, supra, Chapter 16, which is incorporated by reference.

The terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

The term "substituted" is intended to indicate that one or more (e.g., 1, 2, 3, 4, 5, or 6; in some embodiments 1, 2, or 3; and in other embodiments 1 or 2) hydrogens on the group indicated in the expression using "substituted" is replaced with one or more of a selection from the indicated group(s) or with a suitable group known to those of skill in the art, provided that the indicated atom's normal valency is not exceeded, and that the substitution results in a stable compound. As would be readily understood by one skilled in the art, when a substituent is keto (=O) or thioxo (=S), or the like, then two hydrogen atoms on the substituted atom are replaced. One or more substituents recited above can be excluded from a formula or specific embodiment.

The term "therapeutic agent" refers any agent which serves to repair damage to a living organism to heal the organism, to cure a malcondition, to combat an infection by a microorganism or a virus, to assist the body of the living mammal to return to a healthy state.

The term "therapeutic composition" refers to an admixture with an organic or inorganic carrier or excipient, and can be compounded, for example, with the usual non-toxic, pharmaceutically acceptable carriers for tablets, pellets, capsules, suppositories, solutions, emulsions, suspensions, or other form suitable for use.

The term "therapeutically effective amount" is intended to include an amount of a compound described herein, or an amount of the combination of compounds described herein, e.g., to treat or prevent the disease or disorder, or to treat the symptoms of the disease or disorder, in a host. The combination of compounds is preferably a synergistic combination. Synergy, as described for example by Chou and Talalay, Adv. Enzyme Regul., 22:27 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

The terms "therapy," and "therapeutic" refer to either "treatment" or "prevention," thus, agents that either treat damage or prevent damage are "therapeutic."

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes both medical, therapeutic, and/or prophylactic administration, as appropriate.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

In various embodiments, the compound or set of compounds, such as are used in the inventive methods, can be any one of any of the combinations and/or sub-combinations of the embodiments recited herein.

Asymmetric carbon atoms may be present in the compounds described. All such isomers, including diastereomers and enantiomers, as well as the mixtures thereof, are intended to be included in the scope of the recited compound. In certain cases, compounds can exist in tautomeric forms. All tautomeric forms are intended to be included in the scope. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated. Thus, reference herein to a compound includes all of the aforementioned isomeric forms unless the context clearly dictates otherwise.

Various forms are included in the embodiments, including polymorphs, solvates, hydrates, conformers, salts, and prodrug derivatives. A polymorph is a composition having the same chemical formula, but a different structure. A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts can be prepared by reacting the appropriate base or acid with a stoichiometric equivalent of a compound. A prodrug is a compound that undergoes biotransformation (chemical conversion) before exhibiting its pharmacological effects. For example, a prodrug can thus be viewed as a drug containing specialized protective groups used in a transient manner to alter or to eliminate undesirable properties in the parent molecule. Thus, reference herein to a compound includes all of the aforementioned forms unless the context clearly dictates otherwise.

Concentrations, amounts, etc., of various components are often presented in a range format throughout this disclosure. The description in range format is merely for convenience and brevity and should not be construed as an inflexible limitation on the scope of the claimed invention. Accordingly, the description of a range should be considered to have specifically disclosed all the possible subranges as well as individual numerical values within that range. For example, description of a range such as 1% to 8% should be considered to have specifically disclosed subranges such as 1% to 7%, 2% to 8%, 2% to 6%, 3% to 6%, 4% to 8%, 3% to 8% etc., as well as individual numbers within that range, such as, 2%, 5%, 7% etc. This construction applies regardless of the breadth of the range and in all contexts throughout this disclosure.

COMPOUNDS OF THE INVENTION

Compounds of the invention include compounds of the Formulas described herein, which can be used for treating, inhibiting, or killing bacteria, or for treatment of associated conditions. These compounds are further defined in Tables 1-9 below.

Table 1. Compounds of Formula II.

Compound 382 includes: W is oxygen; X is —CH(CH3)-; Y is oxygen; R6 is hydrogen; Z is carbon; R7 is hydrogen; R1 is —CO2H; R8 is hydrogen; R2 is bromine; R9 is hydrogen; R3 is bromine; R10 is chlorine; R4 is bromine; R11 is hydrogen; R5 is bromine; a is 1, n is 1.

Compound 385 includes: W is oxygen; X is —CH2-; Y is oxygen; R6 is hydrogen; Z is carbon; R7 is hydrogen; R1 is —CO$_2$H; R8 is hydrogen; R2 is chlorine; R9 is 2-methyl; R3 is chlorine; R10 is chlorine; R4 is chlorine; R11 is hydrogen; R5 is chlorine; a is 1, n is 1.

Compound 386 includes: W is oxygen; X is —CH2-; Y is oxygen; R6 is hydrogen; Z is carbon; R7 is hydrogen; R1 is —CO2H; R8 is hydrogen; R2 is bromine; R9 is 2-methyl; R3 is bromine; R10 is chlorine; R4 is bromine; R11 is hydrogen; R5 is bromine; a is 1, n is 1.

Compound 390 includes: W is oxygen; R5 is bromine; X is —CH2-; R6 is hydrogen; Y is oxygen; R7 is hydrogen; Z is carbon; R8 is hydrogen; R1 is —CO2H; R9 is 3-trifluoromethyl; R2 is bromine; R10 is chlorine; R3 is bromine; R11 is hydrogen; R4 is bromine; a is 1, n is 1.

Compound 413 includes: W is oxygen; R5 is chlorine; X is absent; R6 is hydrogen; Y is oxygen; R7 is hydrogen; Z is carbon; R8 is hydrogen; R1 is —CO2H; R9 is 3,5-di(trifluoromethyl); R2 is chlorine; R10 is hydrogen; R3 is chlorine; R11 is hydrogen; R4 is chlorine; a is 2, n is 1.

Compound 414 includes: W is oxygen; R5 is bromine; X is absent; R6 is hydrogen; Y is oxygen; R7 is hydrogen; Z is carbon; R8 is hydrogen; R1 is —CO2H; R9 is 3,5-di(trifluoromethyl); R2 is bromine; R10 is hydrogen; R3 is bromine; R11 is hydrogen; R4 is bromine; a is 2, n is 1.

Compound 418 includes: W is oxygen; R5 is fluorine; X is —CH2-; R6 is hydrogen; Y is oxygen; R7 is hydrogen; Z is carbon; R8 is hydrogen; R1 is —CO2H; R9 is 3-O-trifluoromethoxy; R2 is fluorine; R10 is chlorine; R3 is fluorine; R11 is hydrogen; R4 is fluorine; a is 1, n is 1.

Compound 419 includes: W is oxygen; R5 is chlorine; X is —CH2-; R6 is hydrogen; Y is oxygen; R7 is hydrogen; Z is carbon; R8 is hydrogen; R1 is —CO2H; R9 is 3-O-trifluoromethoxy; R2 is chlorine; R10 is chlorine; R3 is chlorine; R11 is hydrogen; R4 is chlorine; a is 1, n is 1.

Compound 420 includes: W is oxygen; R5 is bromine; X is —CH2-; R6 is hydrogen; Y is oxygen; R7 is hydrogen; Z is carbon; R8 is hydrogen; R1 is —CO2H; R9 is 3-O-trifluoromethoxy; R2 is bromine; R10 is chlorine; R3 is bromine; R11 is hydrogen; R4 is bromine; a is 1, n is 1.

Compound 422 includes: W is oxygen; R5 is hydrogen; X is —CH2-; R6 is hydrogen; Y is oxygen; R7 is hydrogen; Z is carbon; R8 is hydrogen; R1 is —CO2H; R9 is 3-O-trifluoromethoxy; R2 is hydrogen; R10 is chlorine; R3 is hydrogen; R11 is hydrogen; R4 is —NO2; a is 1, n is 1.

Compound 222 includes: W is oxygen; R5 is bromine; X is absent; R6 is hydrogen; Y is oxygen; R7 is hydrogen; Z is carbon; R8 is hydrogen; R1 is —CO2H; R9 is hydrogen; R2 is bromine; R10 is hydrogen; R3 is bromine; R11 is hydrogen; R4 is bromine; a is 1, n is 1.

Compound 239 includes: W is oxygen; R5 is bromine; X is absent; R6 is hydrogen; Y is oxygen; R7 is hydrogen; Z is carbon; R8 is hydrogen; R1 is —CO2H; R9 is hydrogen; R2 is bromine; R10 is chlorine; R3 is bromine; R11 is hydrogen; R4 is bromine; a is 1, n is 1.

Compound 277-3 includes: W is oxygen; R5 is chlorine; X is —CH2-; R6 is hydrogen; Y is sulfur; R7 is hydrogen; Z is carbon; R8 is hydrogen; R1 is —CO2H; R9 is hydrogen; R2 is chlorine; R10 is chlorine; R3 is chlorine; R11 is hydrogen; R4 is chlorine; a is 1, n is 1.

Compound 278-2 includes: W is oxygen; R5 is bromine; X is —CH2-; R6 is hydrogen; Y is sulfur; R7 is hydrogen; Z is carbon; R8 is hydrogen; R1 is —CO2H; R9 is hydrogen; R2 is bromine; R10 is chlorine; R3 is bromine; R11 is hydrogen; R4 is bromine; a is 1, n is 1.

Compound 422 includes: W is oxygen; R5 is hydrogen; X is —CH2-; R6 is hydrogen; Y is oxygen; R7 is hydrogen; Z is carbon; R8 is hydrogen; R1 is —CO2H; R9 is 3-O-trifluoromethoxy; R2 is hydrogen; R10 is chlorine; R3 is hydrogen; R11 is hydrogen; R4 is —NO2; a is 1, n is 1.

Compound 381 includes: W is oxygen; R5 is chlorine; X is —CH(CH3)-; R6 is hydrogen; Y is oxygen; R7 is hydrogen; Z is carbon; R8 is hydrogen; R1 is —CO2H; R9 is hydrogen; R2 is chlorine; R10 is chlorine; R3 is chlorine; R11 is hydrogen; R4 is chlorine; a is 1, n is 1.

Compound 382 includes: W is oxygen; R5 is bromine; X is —CH(CH3)-; R6 is hydrogen; Y is oxygen; R7 is hydrogen; Z is carbon; R8 is hydrogen; R1 is —CO2H; R9 is hydrogen; R2 is bromine; R10 is chlorine; R3 is bromine; R11 is hydrogen; R4 is bromine; a is 1, n is 1.

Compound 385 includes: W is oxygen; R5 is chlorine; X is —CH2-; R6 is hydrogen; Y is oxygen; R7 is hydrogen; Z is carbon; R8 is hydrogen; R1 is —CO2H; R9 is 2-methyl; R2 is chlorine; R10 is chlorine; R3 is chlorine; R11 is hydrogen; R4 is chlorine; a is 1, n is 1.

Compound 420 includes: W is oxygen; R5 is bromine; X is —CH2-; R6 is hydrogen; Y is oxygen; R7 is hydrogen; Z is carbon; R8 is hydrogen; R1 is —CO2H; R9 is 3-O-trifluoromethoxy; R2 is bromine; R10 is chlorine; R3 is bromine; R11 is hydrogen; R4 is bromine; a is 1, n is 1.

Compound 419 includes: W is oxygen; R5 is chlorine; X is —CH2-; R6 is hydrogen; Y is oxygen; R7 is hydrogen; Z is carbon; R8 is hydrogen; R1 is —CO2H; R9 is 3-O-trifluoromethoxy; R2 is chlorine; R10 is chlorine; R3 is chlorine; R11 is hydrogen; R4 is chlorine; a is 1, n is 1.

Compound 414 includes: W is oxygen; R5 is bromine; X is absent; R6 is hydrogen; Y is oxygen; R7 is hydrogen; Z is carbon; R8 is hydrogen; R1 is —CO2H; R9 is 3,5-di(trifluoromethyl); R2 is bromine; R10 is hydrogen; R3 is bromine; R11 is hydrogen; R4 is bromine; a is 2, n is 1.

Compound 413 includes: W is oxygen; R5 is chlorine; X is absent; R6 is hydrogen; Y is oxygen; R7 is hydrogen; Z is carbon; R8 is hydrogen; R1 is —CO2H; R9 is 3,5-di(trifluoromethyl); R2 is chlorine; R10 is hydrogen; R3 is chlorine; R11 is hydrogen; R4 is chlorine; a is 2, n is 1.

Compound 393 includes: W is oxygen; R5 is —NO2; X is —CH2-; R6 is hydrogen; Y is oxygen; R7 is hydrogen; Z is carbon; R8 is hydrogen; R1 is —CO2H; R9 is 3-trifluoromethyl; R2 is hydrogen; R10 is chlorine; R3 is hydrogen; R11 is hydrogen; R4 is hydrogen; a is 1, n is 1.

Compound No 390 includes: W is oxygen; R5 is bromine; X is —CH2-; R6 is hydrogen; Y is oxygen; R7 is hydrogen; Z is carbon; R8 is hydrogen; R1 is —CO2H; R9 is 3-trifluoromethyl; R2 is bromine; R10 is chlorine; R3 is bromine; R11 is hydrogen; R4 is bromine; a is 1, n is 1.

Compound 389 includes: W is oxygen; R5 is chlorine; X is —CH2-; R6 is hydrogen; Y is oxygen; R7 is hydrogen; Z is carbon; R8 is hydrogen; R1 is —CO$_2$H; R9 is 3-trifluoromethyl; R2 is chlorine; R10 is chlorine; R3 is chlorine; R11 is hydrogen; R4 is chlorine; a is 1, n is 1.

Compound 386 includes: W is oxygen; R5 is bromine; X is —CH2-; R6 is hydrogen; Y is oxygen; R7 is hydrogen; Z is carbon; R8 is hydrogen; R1 is —CO2H; R9 is 2-methyl; R2 is bromine; R10 is chlorine; R3 is bromine; R11 is hydrogen; R4 is bromine; a is 1, n is 1.

Compound 268 includes: W is hydrogen; R5 is chlorine; X is absent; R6 is hydrogen; Y is oxygen; R7 is hydrogen; Z is carbon; R8 is hydrogen; R1 is —CO2H; R9 is absent; R2 is chlorine; R10 is —O-phenyl; R3 is chlorine; R11 is hydrogen; R4 is chlorine; A is 0, n is 0.

Compound 253 includes: W is oxygen; R5 is chlorine; X is —CH2-; R6 is hydrogen; Y is oxygen; R7 is hydrogen; Z is carbon; R8 is hydrogen; R1 is —CO2H; R9 is hydrogen; R2 is chlorine; R10 is chlorine; R3 is chlorine; R11 is hydrogen; R4 is chlorine; a is 1, n is 1.

Compound No 278-2 includes: W is oxygen; R5 is bromine; X is —CH2-; R6 is hydrogen; Y is sulfur; R7 is hydrogen; Z is carbon; R8 is hydrogen; R1 is —CO2H; R9 is hydrogen; R2 is bromine; R10 is chlorine;

R3 is bromine; R11 is hydrogen; R4 is bromine; a is 1, n is 1.

Compound 277-3 includes: W is oxygen; R5 is chlorine; X is —CH2-; R6 is hydrogen; Y is sulfur; R7 is hydrogen; Z is carbon; R8 is hydrogen; R1 is —CO2H; R9 is hydrogen; R2 is chlorine; R10 is chlorine; R3 is chlorine; R11 is hydrogen; R4 is chlorine; a is 1, n is 1.

Compound 268 includes: W is hydrogen; R5 is chlorine; X is absent; R6 is hydrogen; Y is oxygen; R7 is hydrogen; Z is carbon; R8 is hydrogen; R1 is —CO2H; R9 is absent; R2 is chlorine; R10 is —O-phenyl; R3 is chlorine; R11 is hydrogen; R4 is chlorine; A is 0, n is 0.

Compound DHD-251 includes: W is oxygen; R5 is fluorine; X is —CH2-; R6 is hydrogen; Y is oxygen; R7 is hydrogen; Z is carbon; R8 is hydrogen; R1 is —CO2H; R9 is hydrogen; R2 is fluorine; R10 is chlorine; R3 is fluorine; R11 is hydrogen; R4 is fluorine; a is 1, n is 1.

Compound 387 includes: W is oxygen; R5 is hydrogen; X is —CH2-; R6 is hydrogen; Y is oxygen; R7 is hydrogen; Z is carbon; R8 is hydrogen; R1 is —CO2H; R9 is 3-trifluoromethyl; R2 is hydrogen; R10 is chlorine; R3 is hydrogen; R11 is hydrogen; R4 is hydrogen; a is 1, n is 1.

Compound 412 includes: W is oxygen; R5 is fluorine; X is absent; R6 is hydrogen; Y is oxygen; R7 is hydrogen; Z is carbon; R8 is hydrogen; R1 is —CO2H; R9 is 3,5-di(trifluoromethyl); R2 is fluorine; R10 is hydrogen; R3 is fluorine; R11 is hydrogen; R4 is fluorine; a is 2, n is 1.

Compound 296 includes: W is oxygen; R5 is hydrogen; X is —CH2-; R6 is hydrogen; Y is oxygen; R7 is hydrogen; Z is carbon; R8 is hydrogen; R1 is —CO2H; R9 is hydrogen; R2 is hydrogen; R10 is chlorine; R3 is —CONH-(2-methoxy-4-nitro)phenyl; R11 is hydrogen; R4 is hydrogen; a is 1, n is 1.

Compound 253 includes: W is oxygen; R5 is chlorine; X is —CH2-; R6 is hydrogen; Y is oxygen; R7 is hydrogen; Z is carbon; R8 is hydrogen; R1 is —CO2H; R9 is hydrogen; R2 is chlorine; R10 is chlorine; R3 is chlorine; R11 is hydrogen; R4 is chlorine; a is 1, n is 1.

Compound No 418 includes: W is oxygen; R5 is fluorine; X is —CH2-; R6 is hydrogen; Y is oxygen; R7 is hydrogen; Z is carbon; R8 is hydrogen; R1 is —CO2H; R9 is 3-trifluoromethoxy; R2 is fluorine; R10 is chlorine; R3 is fluorine; R11 is hydrogen; R4 is fluorine; a is 1, n is 1.

Compound 417 includes: W is oxygen; R5 is hydrogen; X is —CH2-; R6 is hydrogen; Y is oxygen; R7 is hydrogen; Z is carbon; R8 is hydrogen; R1 is —CO2H; R9 is 3-trifluoromethoxy; R2 is hydrogen; R10 is chlorine; R3 is hydrogen; R11 is hydrogen; R4 is hydrogen; a is 1, n is 1.

Compound 412 includes: W is oxygen; R5 is fluorine; X is absent; R6 is hydrogen; Y is oxygen; R7 is hydrogen; Z is carbon; R8 is hydrogen; R1 is —CO2H; R9 is 3,5-di(trifluoromethyl); R2 is fluorine; R10 is hydrogen; R3 is fluorine; R11 is hydrogen; R4 is fluorine; a is 2, n is 1.

Compound 388 includes: W is oxygen; R5 is fluorine; X is —CH2-; R6 is hydrogen; Y is oxygen; R7 is hydrogen; Z is carbon; R8 is hydrogen; R1 is —CO2H; R9 is 3-trifluoromethyl; R2 is fluorine; R10 is chlorine; R3 is fluorine; R11 is hydrogen; R4 is fluorine; a is 1, n is 1.

Compound 365 includes: W is oxygen; R5 is bromine; X is —CH2-; R6 is hydrogen; Y is oxygen; R7 is hydrogen; Z is nitrogen; R8 is absent; R1 is —CO2H; R9 is hydrogen; R2 is bromine; R10 is hydrogen; R3 is bromine; R11 is hydrogen; R4 is bromine; a is 1, n is 1.

Compound 364 includes: W is oxygen; R5 is chlorine; X is —CH2-; R6 is hydrogen; Y is oxygen; R7 is hydrogen; Z is nitrogen; R8 is absent; R1 is —CO2H; R9 is hydrogen; R2 is fluorine; R10 is hydrogen; R3 is chlorine; R11 is hydrogen; R4 is chlorine; a is 1, n is 1.

Compound 387 includes: W is oxygen; R5 is hydrogen; X is —CH2-; R6 is hydrogen; Y is oxygen; R7 is hydrogen; Z is carbon; R8 is hydrogen; R1 is —CO2H; R9 is 3-trifluoromethyl; R2 is hydrogen; R10 is chlorine; R3 is hydrogen; R11 is hydrogen; R4 is hydrogen; a is 1, n is 1.

Table 2. Compounds of Formula III.

Compound 319 includes: W is oxygen; R5 is fluorine; Y is oxygen; R6 is methyl; Z is carbon; R7 is hydrogen; R1 is —CO2H; R8 is hydrogen; R2 is fluorine; R9 is —(CH2)$_9$CH3; R3 is fluorine; R10 is hydrogen; R4 is fluorine; R11 is hydrogen.

Compound 329 includes: W is oxygen; R5 is bromine; Y is oxygen; R6 is hydrogen; Z is carbon; R7 is hydrogen; R1 is —CO2H; R8 is hydrogen; R2 is bromine; R9 is —(CH2)$_9$CH3; R3 is bromine; R7 is hydrogen; R4 is bromine; R8 is hydrogen.

Compound 271 includes: W is oxygen; R5 is fluorine; Y is oxygen; R6 is hydrogen; Z is carbon; R7 is hydrogen; R1 is —CO2H; R8 is hydrogen; R2 is fluorine; R9 is —(CH2)$_7$CH3; R3 is fluorine; R10 is hydrogen; R4 is fluorine; R11 is hydrogen.

Compound 279-2 includes: W is oxygen; R5 is hydrogen; Y is sulfur; R6 is hydrogen; Z is carbon; R7 is hydrogen; R1 is —CO2H; R8 is hydrogen; R2 is hydrogen; R9 is —(CH2)$_7$CH3; R3 is hydrogen; R10 is hydrogen; R4 is hydrogen; R11 is hydrogen.

Compound 280-2 includes: W is oxygen; R5 is chlorine; Y is sulfur; R6 is hydrogen; Z is carbon; R7 is hydrogen; R1 is —CS2H; R8 is hydrogen; R2 is chlorine; R9 is —(CH2)₇CH3; R3 is chlorine; R10 is hydrogen; R4 is chlorine; R11 is hydrogen.

Compound 201 includes: W is absent; R5 is bromine; Y is oxygen; R6 is hydrogen; Z is carbon; R7 is hydrogen; R1 is —CO2Na; R8 is hydrogen; R2 is bromine; R9 is hydrogen; R3 is bromine; R10 is cyano; R4 is bromine; R11 is hydrogen.

Compound 281-2 includes: W is oxygen; R5 is bromine; Y is sulfur; R6 is hydrogen; Z is carbon; R7 is hydrogen; R1 is —COSH; R8 is hydrogen; R2 is bromine; R9 is —(CH2)₇CH3; R3 is bromine; R10 is hydrogen; R4 is bromine; R11 is hydrogen.

Compound 289 includes: W is oxygen; R5 is fluorine; Y is oxygen; R6 is hydrogen; Z is carbon; R7 is hydrogen; R1 is —CO2H; R8 is hydrogen; R2 is fluorine; R9 is —(CH2)15CH3; R3 is fluorine; R10 is hydrogen; R4 is fluorine; R11 is hydrogen.

Compound 290 includes; W is oxygen; R5 is chlorine; Y is oxygen; R6 is hydrogen; Z is carbon; R7 is hydrogen; R1 is —CO2H; R8 is hydrogen; R2 is chlorine; R9 is —(CH2)15CH3; R3 is chlorine; R10 is hydrogen; R4 is chlorine; R11 is hydrogen.

Compound 300 includes: W is oxygen; R5 is hydrogen; Y is oxygen; R6 is hydrogen; Z is carbon; R7 is hydrogen; R1 is —CO2H; R8 is hydrogen; R2 is hydrogen; R9 is —(CH2)₇CH3; R3 is hydrogen; R10 is chlorine; R4 is hydrogen; R11 is hydrogen.

Compound 301 includes: W is oxygen; R5 is hydrogen; Y is oxygen; R6 is hydrogen; Z is carbon; R7 is hydrogen; R1 is —CO2H; R8 is hydrogen; R2 is hydrogen; R9 is —(CH2)₇CH3; R3 is hydrogen; R10 is chlorine; R4 is hydrogen.

Compound 302 includes: W is oxygen; R5 is chlorine; Y is oxygen; R6 is hydrogen; Z is carbon; R7 is hydrogen; R1 is —CO2H; R8 is hydrogen; R2 is chlorine; R9 is —(CH2)₇CH3; R3 is chlorine; R10 is chlorine; R4 is chlorine; R11 is hydrogen.

Compound 318 includes: W is oxygen; R5 is hydrogen; Y is oxygen; R6 is methyl; Z is carbon; R7 is hydrogen; R1 is —CO2H; R8 is hydrogen; R2 is hydrogen; R9 is —(CH2)₉CH3; R3 is hydrogen; R10 is hydrogen; R4 is hydrogen; R11 is hydrogen.

Compound 303 includes: W is oxygen; R5 is bromine; Y is oxygen; R6 is hydrogen; Z is carbon; R7 is hydrogen; R1 is —CO2H; R8 is hydrogen; R2 is bromine; R9 is —(CH2)₇CH3; R3 is bromine; R10 is chlorine; R4 is bromine; R11 is hydrogen.

Compound 302 includes: W is oxygen; R5 is chlorine; Y is oxygen; R6 is hydrogen; Z is carbon; R7 is hydrogen; R1 is —CO2H; R8 is hydrogen; R2 is chlorine; R9 is —(CH2)₇CH3; R3 is chlorine; R10 is chlorine; R4 is chlorine; R11 is hydrogen.

Compound 346 includes: W is oxygen; R5 is bromine; Y is oxygen; R6 is hydrogen; Z is nitrogen; R7 is hydrogen; R1 is —CO2H; R8 is absent; R2 is bromine; R9 is —(CH2)₇CH3; R3 is bromine; R10 is hydrogen; R4 is bromine; R11 is hydrogen.

Compound 355 includes; W is oxygen; R5 is chlorine; Y is oxygen; R6 is hydrogen; Z is carbon; R7 is hydrogen; R1 is —CO2H; R8 is hydrogen; R2 is chlorine; R9 is —CH2CH(OH)CH2OCH2-(cyclopropyl); R3 is chlorine; R10 is chlorine; R4 is chlorine; R11 is hydrogen.

Compound 358 includes: W is oxygen; R5 is chlorine; Y is oxygen; R6 is hydrogen; Z is nitrogen; R7 is hydrogen; R1 is —CO2H; R8 is oxygen; R2 is chlorine; R9 is —(CH2)₇CH3; R3 is chlorine; R10 is hydrogen; R4 is chlorine; R11 is hydrogen.

Compound 360 includes: W is oxygen; R5 is bromine; Y is oxygen; R6 is hydrogen; Z is carbon; R6 is hydrogen; R1 is —CO2H; R7 is hydrogen; R2 is bromine; R9 is —(CH2)₇CH3; R3 is bromine; R10 is hydrogen; R4 is bromine; R11 is hydrogen.

Compound 223 includes: W is —CH2-; R5 is bromine; Y is oxygen; R6 is hydrogen; Z is carbon; R7 is hydrogen; R1 is —CO2H; R8 is hydrogen; R2 is bromine; R9 is —OH; R3 is bromine; R10 is hydrogen; R4 is bromine; R11 is hydrogen.

Compound 201 includes: W is absent; R5 is bromine; Y is oxygen; R6 is hydrogen; Z is carbon; R7 is hydrogen; R1 is —CO2Na; R8 is hydrogen; R2 is bromine; R9 is hydrogen; R3 is bromine; R10 is cyano; R4 is bromine; R11 is hydrogen.

Compound 89 includes: W is absent; R5 is bromine; Y is oxygen; R6 is hydrogen; Z is carbon; R7 is hydrogen; R1 is —CO2H; R8 is hydrogen; R2 is bromine; R9 is chlorine; R3 is bromine; R10 is trifluoromethyl; R4 is bromine; R11 is hydrogen.

Compound 270 includes: W is oxygen; R5 is hydrogen; Y is oxygen; R6 is hydrogen; Z is carbon; R7 is hydrogen; R1 is —CO2H; R8 is hydrogen; R2 is hydrogen; R9 is —(CH2)₇CH3; R3 is hydrogen; R10 is hydrogen; R4 is hydrogen; R11 is hydrogen.

Compound 265 includes: W is oxygen; R5 is chlorine; Y is oxygen; R6 is hydrogen; Z is carbon; R7 is hydrogen; R1 is —CO2H; R8 is hydrogen; R2 is chlorine; R9 is —(CH2)₇CH3; R3 is chlorine; R10 is hydrogen; R4 is chlorine; R11 is hydrogen.

Compound 252 includes: W is absent; R5 is bromine; Y is oxygen; R6 is hydrogen; Z is carbon; R7 is hydrogen; R1 is —CO2Na; R8 is hydrogen; R2 is bromine; R9 is —OH; R3 is bromine; R10 is chlorine; R4 is bromine; R11 is hydrogen.

Compound 345 includes: W is oxygen; R5 is chlorine; Y is oxygen; R6 is hydrogen; Z is nitrogen; R7 is hydrogen; R1 is —CO2H; R8 is absent; R2 is chlorine; R9 is —(CH2)₇CH3; R3 is chlorine; R10 is hydrogen; R4 is chlorine; R11 is hydrogen.

Compound 307 includes: W is oxygen; R5 is bromine; Y is oxygen; R6 is methyl; Z is carbon; R7 is hydrogen; R1 is —CO2H; R8 is hydrogen; R2 is bromine; R9 is —(CH2)₇CH3; R3 is bromine; R10 is hydrogen; R4 is bromine; R11 is hydrogen.

Compound 301 includes: W is oxygen; R5 is fluorine; Y is oxygen; R6 is hydrogen; Z is carbon; R7 is hydrogen; R1 is —CO2H; R8 is hydrogen; R2 is fluorine; R9 is —(CH2)₇CH3; R3 is fluorine; R10 is chlorine; R4 is fluorine; R11 is hydrogen.

Compound 300 includes: W is oxygen; R5 is hydrogen; Y is oxygen; R6 is hydrogen; Z is carbon; R7 is hydrogen; R1 is —CO2H; R8 is hydrogen; R2 is hydrogen; R9 is —(CH2)7CH3; R3 is hydrogen; R10 is chlorine; R4 is hydrogen; R11 is hydrogen.

Compound 291 includes: W is oxygen; R5 is bromine; Y is oxygen; R6 is hydrogen; Z is carbon; R7 is hydrogen; R1 is —CO2H; R8 is hydrogen; R2 is bromine; R9 is —(CH2)15CH3; R3 is bromine; R10 is hydrogen; R4 is bromine; R11 is hydrogen.

Compound 290 includes: W is oxygen; R5 is chlorine; Y is oxygen; R6 is hydrogen; Z is carbon; R7 is hydrogen; R1 is —CO2H; R8 is hydrogen; R2 is chlorine; R9 is —(CH2)15CH3; R3 is chlorine; R10 is hydrogen; R4 is chlorine; R11 is hydrogen.

Compound 280-2 includes: W is oxygen; R5 is chlorine; Y is sulfur; R6 is hydrogen; Z is carbon; R7 is hydrogen; R1 is —CS2H; R8 is hydrogen; R2 is chlorine; R9 is —(CH2)₇CH3; R3 is chlorine; R10 is hydrogen; R4 is chlorine; R11 is hydrogen.

Compound 279-2 includes: W is oxygen; R5 is hydrogen; Y is sulfur; R6 is hydrogen; Z is carbon; R7 is hydrogen; R1 is —CO2H; R8 is hydrogen; R2 is hydrogen; R9 is —(CH2)$_7$CH3; R3 is hydrogen; R10 is hydrogen; R4 is hydrogen; R11 is hydrogen.

Compound 274 includes: W is oxygen; R5 is bromine; Y is oxygen; R6 is hydrogen; Z is carbon; R7 is hydrogen; R1 is —CO2H; R8 is hydrogen; R2 is bromine; R9 is —(CH2)7CH3; R3 is bromine; R10 is hydrogen; R4 is bromine; R11 is hydrogen.

Compound 271 includes: W is oxygen; R5 is fluorine; Y is oxygen; R6 is hydrogen; Z is carbon; R7 is hydrogen; R1 is —CO2H; R8 is hydrogen; R2 is fluorine; R9 is —(CH2)$_7$CH3; R3 is fluorine; R10 is hydrogen; R4 is fluorine; R11 is hydrogen.

Compound 333 includes: W is carbonyl; R5 is chlorine; Y is oxygen; R6 is hydrogen; Z is carbon; R7 is hydrogen; R1 is —CO2H; R8 is hydrogen; R2 is chlorine; R9 is —O(CH2)3CH3; R3 is chlorine; R10 is hydrogen; R4 is chlorine; R11 is hydrogen.

Compound 307 includes: W is oxygen; R5 is bromine; Y is oxygen; R6 is methyl; Z is carbon; R7 is hydrogen; R1 is —CO2H; R8 is hydrogen; R2 is bromine; R9 is —(CH2)7CH3; R3 is bromine; R10 is hydrogen; R4 is bromine; R11 is hydrogen.

Compound 288 includes: W is oxygen; R5 is hydrogen; Y is oxygen; R6 is hydrogen; Z is carbon; R7 is hydrogen; R1 is —CO2H; R8 is hydrogen; R2 is hydrogen; R9 is —(CH2)15CH3; R3 is hydrogen; R10 is hydrogen; R4 is hydrogen; R11 is hydrogen.

Compound 86 includes: W is absent; R5 is hydrogen; Y is oxygen; R6 is hydrogen; Z is carbon; R7 is hydrogen; R1 is —CO2H; R8 is hydrogen; R2 is —NO2; R9 is chlorine; R3 is hydrogen; R10 is trifluoromethyl; R4 is hydrogen; R11 is hydrogen.

Compound 262 includes: W is absent; R5 is chlorine; Y is oxygen; R6 is hydrogen; Z is carbon; R7 is hydrogen; R1 is —CO2H; R8 is hydrogen; R2 is chlorine; R9 is hydrogen; R3 is chlorine; R10 is —CH2OH; R4 is chlorine; R11 is hydrogen.

Compound 85 includes: W is absent; R5 is hydrogen; Y is oxygen; R6 is hydrogen; Z is carbon; R7 is chlorine; R1 is —CO2H; R8 is hydrogen; R2 is —NO2; R9 is hydrogen; R3 is hydrogen; R10 is trifluoromethyl; R4 is hydrogen; R11 is hydrogen.

Compound 257 includes: W is absent; R5 is chlorine; Y is oxygen; R6 is hydrogen; Z is carbon; R7 is hydrogen; R1 is —CO2H; R8 is hydrogen; R2 is chlorine; R9 is chlorine; R3 is chlorine; R10 is methyl; R4 is chlorine; R11 is hydrogen.

Compound 346 includes: W is oxygen; R5 is bromine; Y is oxygen; R6 is hydrogen; Z is nitrogen; R7 is hydrogen; R1 is —CO2H; R8 is absent; R2 is bromine; R9 is —(CH2)7CH3; R3 is bromine; R10 is hydrogen; R4 is bromine; R11 is hydrogen.

Compound 316 includes: W is oxygen; R5 is bromine; Y is oxygen; R6 is methyl; Z is carbon; R7 is hydrogen; R1 is —CO2H; R8 is hydrogen; R2 is bromine; R9 is —(CH2)9CH3; R3 is bromine; R10 is hydrogen; R4 is bromine; R11 is hydrogen.

Compound 291 includes: W is oxygen; R5 is bromine; Y is oxygen; R6 is hydrogen; Z is carbon; R7 is hydrogen; R1 is —CO2H; R8 is hydrogen; R2 is bromine; R9 is —(CH2)15CH3; R3 is bromine; R10 is hydrogen; R4 is bromine; R11 is hydrogen.

Compound 270 includes: W is oxygen; R5 is hydrogen; Y is oxygen; R6 is hydrogen; Z is carbon; R7 is hydrogen; R1 is —CO2H; R8 is hydrogen; R2 is hydrogen; R9 is —(CH2)$_7$CH3; R3 is hydrogen; R10 is hydrogen; R4 is hydrogen; R11 is hydrogen.

Compound 356 includes: W is oxygen; R5 is bromine; Y is oxygen; R6 is hydrogen; Z is carbon; R7 is hydrogen; R1 is —CO2H; R8 is hydrogen; R2 is bromine; R9 is —CH2CH(OH)CH$_2$OCH2-(cyclopropyl); R3 is bromine; R10 is chlorine; R4 is bromine; R11 is hydrogen.

Compound 305 includes: W is oxygen; R5 is fluorine; Y is oxygen; R6 is methyl; Z is carbon; R7 is hydrogen; R1 is —CO2H; R8 is hydrogen; R2 is fluorine; R9 is —(CH2)7CH3; R3 is fluorine; R10 is hydrogen; R4 is fluorine; R11 is hydrogen.

Compound 254 includes: W is —CH2-; R5 is chlorine; Y is oxygen; R6 is hydrogen; Z is carbon; R7 is hydrogen; R1 is —CO2H; R8 is hydrogen; R2 is chlorine; R9 is —OH; R3 is chlorine; R10 is hydrogen; R4 is chlorine; R11 is hydrogen.

Compound 196 includes: W is absent; R5 is bromine; Y is oxygen; R6 is hydrogen; Z is carbon; R7 is hydrogen; R1 is —CO2H; R8 is hydrogen; R2 is bromine; R9 is hydrogen; R3 is bromine; R10 is trifluoromethyl; R4 is bromine; R11 is hydrogen.

Compound 93 includes: W is absent; R5 is hydrogen; Y is oxygen; R6 is hydrogen; Z is carbon; R7 is hydrogen; R1 is —CO2H; R8 is hydrogen; R2 is hydrogen; R9 is chlorine; R3 is hydrogen; R10 is trifluoromethyl; R4 is methyl; R11 is hydrogen.

Compound 92 includes: W is absent; R5 is hydrogen; Y is oxygen; R6 is hydrogen; Z is carbon; R7 is hydrogen; R1 is —CO2H; R8 is hydrogen; R2 is hydrogen; R9 is chlorine; R3 is methyl; R10 is trifluoromethyl; R4 is hydrogen; R11 is hydrogen.

Compound 86 includes: W is absent; R5 is hydrogen; Y is oxygen; R6 is hydrogen; Z is carbon; R7 is hydrogen; R1 is —CO2H; R8 is hydrogen; R2 is —NO2; R9 is chlorine; R3 is hydrogen; R10 is trifluoromethyl; R4 is hydrogen; R11 is hydrogen.

Compound 350 includes: W is oxygen; R5 is chlorine; Y is oxygen; R6 is hydrogen; Z is carbon; R7 is hydrogen; R1 is —CO2H; R8 is hydrogen; R2 is chlorine; R9 is —CH2CH(OH)CH2-O—(CH2)3CH3; R3 is chlorine; R10 is chlorine; R4 is chlorine; R11 is hydrogen.

Compound 344 includes: W is oxygen; R5 is fluorine; Y is oxygen; R6 is hydrogen; Z is nitrogen; R7 is hydrogen; R1 is —CO2H; R8 is absent; R2 is fluorine; R9 is —(CH2)7CH3; R3 is fluorine; R10 is hydrogen; R4 is fluorine; R11 is hydrogen.

Compound 343 includes: W is oxygen; R5 is hydrogen; Y is oxygen; R6 is hydrogen; Z is nitrogen; R7 is hydrogen; R1 is —CO2H; R8 is absent; R2 is hydrogen; R9 is —(CH2)7CH3; R3 is hydrogen; R10 is hydrogen; R4 is hydrogen; R11 is hydrogen.

Compound 334 includes: W is carbonyl; R5 is bromine; Y is oxygen; R6 is hydrogen; Z is carbon; R7 is hydrogen; R1 is —CO2H; R8 is hydrogen; R2 is bromine; R9 is —O(CH2)3CH3; R3 is bromine; R10 is hydrogen; R4 is bromine; R11 is hydrogen.

Compound 288 includes: W is oxygen; R5 is hydrogen; Y is oxygen; R6 is hydrogen; Z is carbon; R7 is hydrogen; R1 is —CO2H; R8 is hydrogen; R2 is hydrogen; R9 is —(CH2)15CH3; R3 is hydrogen; R10 is hydrogen; R4 is hydrogen; R11 is hydrogen.

Compound 232 includes: W is absent; R5 is bromine; Y is oxygen; R6 is hydrogen; Z is carbon; R7 is hydrogen; R1 is —CO2H; R8 is hydrogen; R2 is bromine; R9 is chlorine; R3 is bromine; R10 is methyl; R4 is bromine; R11 is hydrogen.

Compound 47 includes: W is absent; R5 is hydrogen; Y is oxygen; R6 is hydrogen; Z is carbon; R7 is hydrogen; R1 is —CO2H; R8 is hydrogen; R2 is hydrogen; R9 is hydrogen; R3 is hydrogen; R10, R11, and the atoms in between form a fused 3-hydroxyphenyl; R4 is hydrogen.

Compound 44 includes: W is absent; R5 is hydrogen; Y is oxygen; R6 is hydrogen; Z is carbon; R7 is hydrogen; R1 is —CO2H; R8 is hydrogen; R2 is hydrogen; R9 is chlorine; R3 is hydrogen; R10 is trifluoromethyl; R4 is hydrogen; R11 is hydrogen.

Table 3. Compounds of Formula IV.

Compound 277-2 includes: W is sulfur; X is sulfur; Y is oxygen; Z is —CH2-; R1 is chlorine; R6 is hydrogen; R2 is chlorine; R7 is -phenyl; R3 is chlorine; R8 is chlorine; R4 is chlorine; R9 is hydrogen; R5 is hydrogen.

Compound 280-1 includes: W is oxygen; X is sulfur; Y is oxygen; Z is absent; R1 is chlorine; R6 is hydrogen; R2 is chlorine; R7 is —(CH2)7CH3; R3 is chlorine; R8 is hydrogen; R4 is chlorine; R9 is hydrogen; R5 is hydrogen.

Compound 281-1 includes: W is oxygen; X is sulfur; Y is oxygen; Z is absent; R1 is bromine; R6 is hydrogen; R2 is bromine; R7 is —(CH2)7CH3; R3 is bromine; R8 is hydrogen; R4 is bromine; R9 is hydrogen; R5 is hydrogen.

Compound 280-1 includes: W is oxygen; X is sulfur; Y is oxygen; Z is absent; R1 is chlorine; R6 is hydrogen; R2 is chlorine; R7 is —(CH2)7CH3; R3 is chlorine; R8 is hydrogen; R4 is chlorine; R9 is hydrogen; R5 is hydrogen.

Compound 277-2 includes: W is sulfur; X is sulfur; Y is oxygen; Z is —CH2-; R1 is chlorine; R6 is hydrogen; R2 is chlorine; R7 is -phenyl; R3 is chlorine; R8 is chlorine; R4 is chlorine; R9 is hydrogen; R5 is hydrogen.

Table 4. Compounds of Formula V.

Compound 323 includes: X is oxygen; $R_6$ is hydrogen; Y is oxygen; $R_7$ is hydrogen; $R_1$ is —CO$_2$H; $R_8$ is hydrogen; $R_2$ is hydrogen; $R_9$ is —COO(CH$_2$)$_3$CH$_3$; $R_3$ is hydrogen; $R_{10}$ is hydrogen; $R_4$ is hydrogen; $R_{11}$ is hydrogen; $R_5$ is hydrogen.

Compound 324 includes: X is sulfur; $R_6$ is hydrogen; Y is oxygen; $R_7$ is hydrogen; $R_1$ is —CO$_2$H; $R_8$ is hydrogen; $R_2$ is hydrogen; $R_9$ is —COO(CH$_2$)$_3$CH$_3$; $R_3$ is hydrogen; $R_{10}$ is hydrogen; $R_4$ is hydrogen; $R_{11}$ is hydrogen; $R_5$ is hydrogen.

Table 5. Compounds of Formula VI.

Compound 126 includes: X is nitrogen; $R_2$ is hydrogen; $R_1$ is —CO$_2$H; $R_3$ is —C(CH$_2$OH)CH$_2$CH$_3$.

Compound 127 includes: X is nitrogen; $R_2$ is hydrogen; $R_1$ is —CO$_2$H; $R_3$ is —C(CH$_2$OH)CHOH-phenyl.

Compound 118 includes: X is nitrogen; $R_2$ is hydrogen; $R_1$ is —CO$_2$H; $R_3$ is 3-(acetoxymethyl)-7-methyl-8-oxo-5-thia-1-azabicyclo[4.2.0]oct-2-ene-2-carboxylic acid.

Compound 138 includes: X is nitrogen; $R_3$ is —C(CH$_2$OH)CHOH-phenyl; $R_1$ and $R_2$ together form carbonyl.

Compound 119 includes: X is methoxy; $R_2$ is absent; $R_1$ is —CO$_2$H; $R_3$ is absent.

Compound 120 includes: X is amino; $R_2$ is absent; $R_1$ is —CO$_2$H; $R_3$ is absent.

Compound 121 includes: X is hydroxyl; $R_2$ is absent; $R_1$ is —CO$_2$H; $R_3$ is absent.

Compound 123 includes: X is nitrogen; $R_2$ is hydrogen; $R_1$ is —CO$_2$H; $R_3$ is —CH$_2$CHOHCH$_3$. Compound 128 includes: X is nitrogen; $R_2$ is hydrogen; $R_1$ is —CO$_2$H; $R_3$ is —C(CH$_2$OH)CHOH-phenyl.

Compound 129 includes: X is nitrogen; $R_2$ is hydrogen; $R_1$ is —CO$_2$Na; $R_3$ is —C(CH$_2$OH)CHOHCH$_3$.

Compound 140 includes: X is nitrogen; $R_3$ is —C(CH$_2$OH)CHOH-(4-nitrophenyl); $R_1$ and $R_2$ together form carbonyl.

Compound 427 includes: X is nitrogen; $R_2$ is hydrogen; $R_1$ is —CO$_2$H; $R_3$ is —(3-chloro-4-(3-trifluoromethylphenyl)benzyl).

Compound 133 includes: X is nitrogen; $R_2$ is methyl; $R_1$ is —CO$_2$H; $R_3$ is —CH(CH$_3$)CHOH-phenyl.

Compound 134 includes: X is nitrogen; $R_2$ is —(CH$_2$)$_2$OH; $R_1$ is —CO$_2$H; $R_3$ is —CH(CH$_3$)-phenyl.

Compound 135 includes: X is nitrogen; $R_2$ is methyl; $R_1$ is —CO$_2$H; $R_3$ is —CH(CH$_3$)CHOH-phenyl.

Compound 136 includes: X is nitrogen; $R_2$ is —(CH$_2$)$_2$OH; $R_1$ is —CO$_2$H; $R_3$ is —CH(CH$_3$)-phenyl.

Compound 138 includes: X is nitrogen; $R_3$ is —C(CH$_2$OH)CHOH-phenyl; $R_1$ and $R_2$ together form carbonyl.

Compound 139 includes: X is nitrogen; $R_2$ is hydrogen; $R_1$ is —CO$_2$H; $R_3$ is —C(CH$_2$OH)CHOH-(4-nitrophenyl).

Compound 140 includes: X is nitrogen; $R_3$ is —C(CH$_2$OH)CHOH-(4-nitrophenyl); $R_1$ and $R_2$ together form carbonyl.

Compound 141 includes: X is nitrogen; $R_2$ is hydrogen; $R_1$ is —CO$_2$Na; $R_3$ is —(CH$_2$)$_3$SO$_3$Na.

Compound 142 includes: X is nitrogen; $R_3$ is —(CH$_2$)$_3$SO$_3$Na; $R_1$ and $R_2$ together form carbonyl.

Compound 143 includes: X is nitrogen; $R_2$ is hydrogen; $R_1$ is —CO$_2$Na; $R_3$ is —C(CH$_2$OH)CHOH-(4-nitrophenyl).

Compound 144 includes: X is nitrogen; $R_3$ is —C(CH$_2$OH)CHOH-(4-nitrophenyl); $R_1$ and $R_2$ together form carbonyl.

Compound 145 includes: X is nitrogen; $R_3$ is —C(CO$_2$H)CH$_2$-(4-nitrophenyl); $R_1$ and $R_2$ together form carbonyl; and Compound 146 includes: X is nitrogen; $R_2$ is hydrogen; $R_1$ is —CO$_2$Na; $R_3$ is —C(CO$_2$Na)CH$_2$-(4-hydroxyphenyl).

Table 6. Compounds of Formula VII.

Compound 95 includes: X is absent; $R_4$ is hydrogen; $R_1$ is hydrogen; $R_5$, $R_6$, $R_7$, and the atom in between form a –3-trifluoromethyl-4-chlorophenyl; $R_2$, $R_3$, and the atoms in between form a 3-methylcyclohexyl.

Compound 96 includes: X is absent; $R_4$ is hydrogen; $R_1$ is hydrogen; $R_5$, $R_6$, $R_7$, and the atom in between form a –3-trifluoromethyl-4-chlorophenyl; $R_2$, $R_3$, and the atoms in between form a 4-methylcyclohexyl.

Compound 94 includes: X is absent; $R_4$ is hydrogen; $R_1$ is hydrogen; $R_5$, $R_6$, $R_7$, and the atom in between form a –3-trifluoromethyl-4-chlorophenyl; $R_2$, $R_3$, and the atoms in between form a cyclohexyl.

Compound 100 includes: X is absent; $R_3$ is phenyl; $R_1$ is hydrogen; $R_4$ is absent; $R_2$ is hydrogen; $R_5$, $R_6$, $R_7$, and the atom in between form a –3-trifluoromethyl-4-chlorophenyl.

Compound 253 includes: X is absent; $R_3$ is hydrogen; $R_1$ is absent; $R_4$ is absent; $R_2$ is hydrogen; $R_5$, $R_6$, $R_7$, and the atom in between form a –4-(N-morpholino)phenyl.

Compound 243 includes: X is —CH$_2$-; $R_4$ is hydrogen; $R_2$, $R_3$, and the atoms in between form a 1-cyclopentyl; $R_5$, $R_6$, $R_7$, and the atom in between form a –3-chloro-4-(O-benzyl)phenyl; $R_3$ is hydrogen.

Compound 246 includes: X is —CH$_2$-; $R_4$ is hydrogen; $R_1$ and $R_2$ together form a cyclopentyl group; $R_5$, $R_6$, $R_7$, and the atom in between form a –3-trifluoromethyl-4-chlorophenyl; $R_3$ is hydrogen.

Compound 97 includes: X is absent; $R_3$ is —OCO-phenyl; $R_1$ is hydrogen; $R_4$ is hydrogen; $R_2$ is —OCO-phenyl; $R_5$, $R_6$, $R_7$, and the atom in between form a –3-trifluoromethyl-4-chlorophenyl.

Compound 158 includes: X is absent; $R_5$ is —CH$_2$CH$_3$; $R_1$ is hydrogen; $R_6$ is hydrogen; $R_2$, $R_3$, and the atoms in between form a 3-methylcyclohexyl; $R_7$ is —CH$_2$OH; $R_4$ is hydrogen.

Table 7. Compounds of Formula VIII.

Compound 217 includes: $R_1$ is bromine; $R_4$ is bromine; $R_2$ is bromine; $R_5$ is methyl; $R_3$ is bromine; $R_6$ is hydrogen.

Compound 267 includes: $R_1$ is chlorine; $R_4$ is chlorine; $R_2$ is chlorine; $R_5$ is hydroxyl; $R_3$ is chlorine; $R_6$ is 4-nitrophenyl.

Compound 238 includes: $R_1$ is bromine; $R_4$ is bromine; $R_2$ is bromine; $R_5$ is hydroxyl; $R_3$ is bromine; $R_6$ is 4-nitrophenyl.

Table 8. Compounds of Formula IX.

Compound 108 includes: $R_1$ is —OCO-phenyl; $R_2$ is —OCO-phenyl. Compound 109 includes: $R_1$ is —OCOCH$_3$; $R_2$ is —OCOCH$_3$. Compound 110 includes $R_1$ and $R_2$ together form a benzene ring that is substituted with carboxy (—CO$_2$H). Compound III includes: $R_1$ and $R_2$ together form a benzene ring that is substituted with carboxy.

Table 9. Compounds of Formula X.

Figure 17:
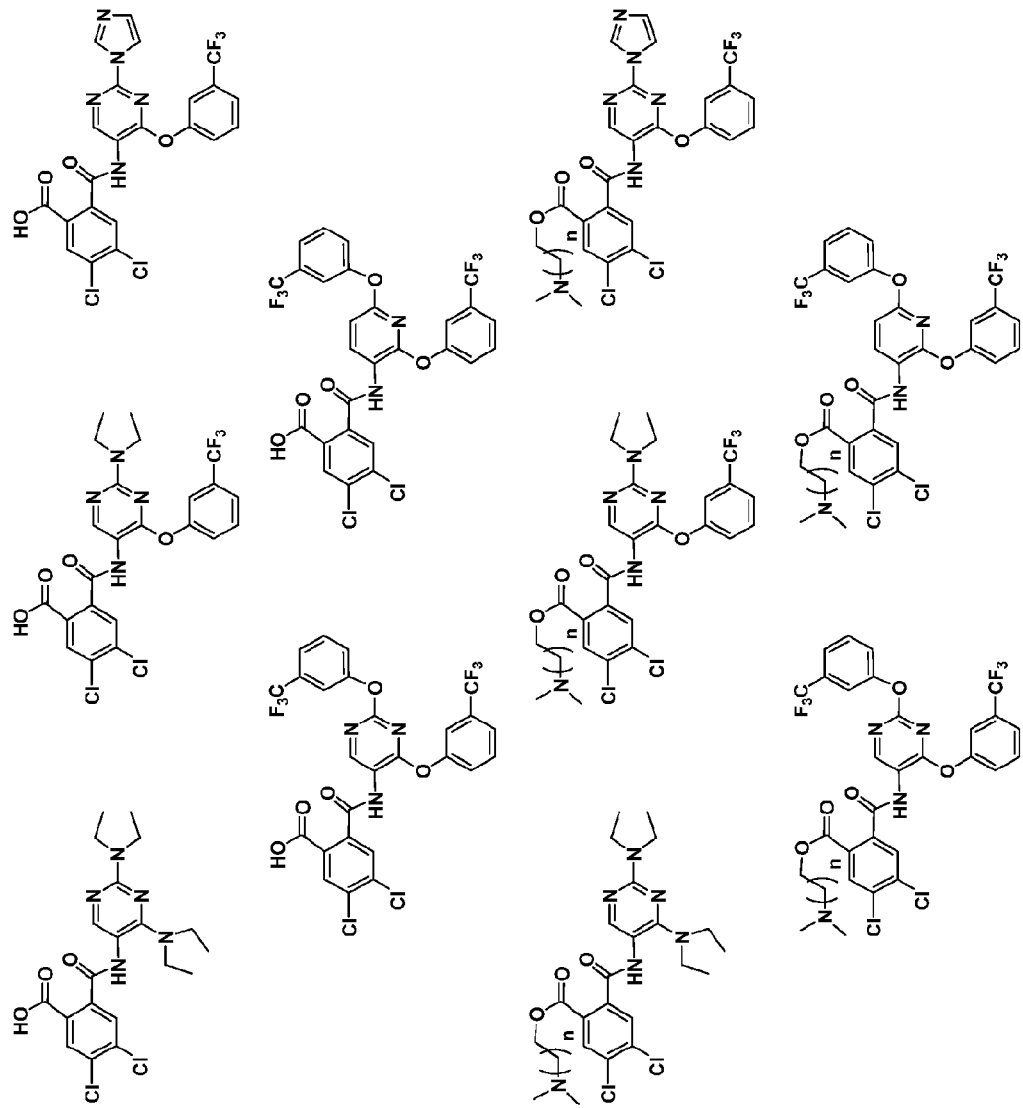
FIG. 17 illustrates certain compounds of Formula X, where n is 1, 2, 3, or 4, according to various embodiments.
Figure 18:
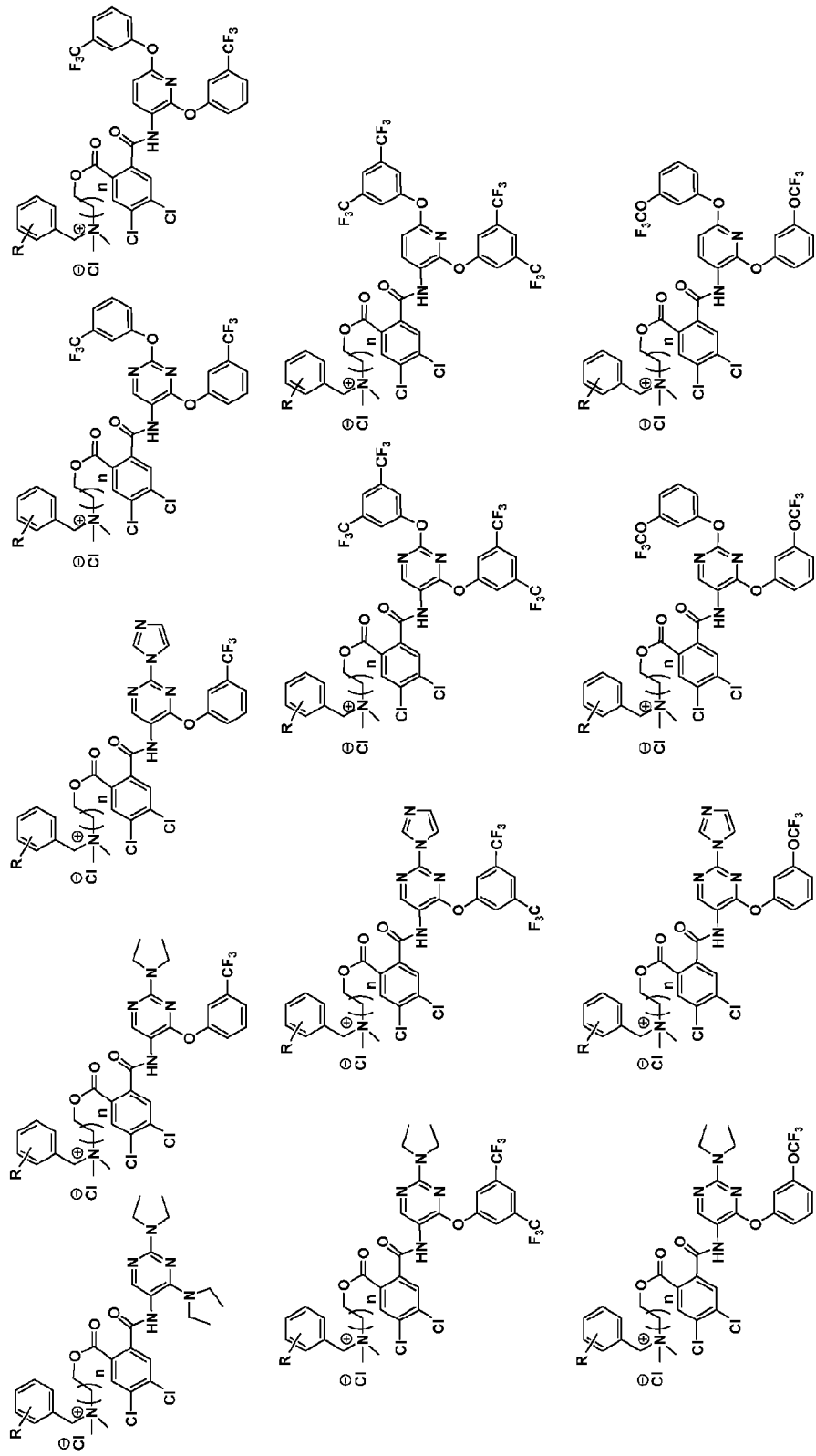
FIG. 18 illustrates certain compounds of Formula X, where n is 1, 2, 3, or 4, and R is hydroxy, halo, ($C_1$-$C_8$)alkyl, ($C_6$-$C_{14}$)aryl, nitro, cyano, ($C_1$-$C_8$)alkoxy, trifluoromethyl, or trifluoromethoxy, according to various embodiments. The counterion $Cl^-$ may also be other halo anions, or other suitable pharmaceutically acceptable anions known in the art.

Compounds of Formula X include the compounds illustrated in FIGS. 17 and 18, where n is 1, 2, 3, or 4, and R is hydroxy, halo, $(C_1-C_8)$alkyl, $(C_6-C_{14})$aryl, nitro, cyano, $(C_1-C_8)$alkoxy, trifluoromethyl, or trifluoromethoxy, according to various embodiments.

Tables 1-9 above recite certain specific values for various compounds of Formulas II-X. In some embodiments, a variable "R" (e.g., $R_1$, $R_2$, $R_3$, $R_4$, $R_5$, $R_6$, $R_7$, $R_8$, $R_9$, $R_{10}$, $R_{11}$, $R_{12}$, and the like), "W", "X", "Y", or "Z" that is used in connection with one compound or formula may be used in connection with any other formula described herein to provide other compounds of the invention. For example, in some embodiments, one specific halo group can be any halo group, or it can be exchanged for another specific halo group.

In addition to the exchange of various specific groups described above, organic moieties of the formulas may be optionally substituted with 1, 2, 3, 4, or 5 substituents, as would be readily recognized by one skilled in the art of synthetic organic chemistry. Accordingly, in some embodiments, an alkyl, cycloalkyl, aryl, heteroaryl, or cycloalkyl group of a formula described herein can optionally be substituted with one or more (e.g., 1-5, 1-4, 1-3, 1-2, or 1) substituents. Suitable substituents of a substituted group can include alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acetylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, cyano, as well as —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR—S(=O)$_2$O$^-$, —S(=O)$_2$OH, —S(=O)$_2$R, —OS(=O)$_2$OR, —S(=O)$_2$NR, —S(=O)R, —OP(=O)(OR$_2$), —P(=O)(OR$_2$), —P(=O)(O$^-$)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, and/or —C(NR)NRR, where each X is independently halo (F, Cl, Br, or I); and each R is independently H, alkyl, aryl, heteroaryl, heterocycle, a protecting group or prodrug moiety. In some embodiments, specific substituents can be excluded from a particular formula as well.

Methods of Using the Compounds Described Herein:

The invention provides compositions that include an active ingredient (e.g., a compound as described herein) capable of inhibiting microorganisms such as bacteria, particularly vancomycin-resistant bacteria. The invention also provides methods for screening and identifying these active ingredients.

In one embodiment, the method for screening and identifying an antibacterial compound comprises selecting agents having affinity for one or more penicillin-binding proteins (PBPs) present on the surface of bacteria. For example, such PBPs are found on a class of bacteria known in the phylum, *Firmicutes*. By way of example, member bacteria within this phylum include *Bacillus* (such as *Bacillus anthracis*), *Listeria*, *Staphylococcus* (such as *Staphylococcus aureus*), *Streptococcus*, *Enterococcus*, *Clostridium*, and *Mycobacterium* (such as *Mycobacterium tuberculosis*).

The invention thus provides a method for selecting compounds that are capable of binding, and therefore, inhibiting, bacterial species linked to disease, and thereby inhibit and or eliminate bacterial infection. Among other advantages, the methods provide a technique for identifying specific antibacterial compounds and classes of compounds that bind to strains of bacteria that have become resistant to conventional pharmaceutical agents.

Several functional assays have been used in the present screening and selection methods, including in vitro screening methods that demonstrate the activity of the compound against vancomycin-resistant, methicillin resistant *Staphylococcus aureus*. Since PBPs are related to other proteins of interest in bacteria, the methodology is versatile in screening for additional activities. These activities include inhibiting β-lactamase enzymes. β-Lactamases are responsible for bacterial resistance to β-lactam antibiotics. For example, β-lactamases can destroy the activity of β-lactam antibiotics such as penicillins and cephalosporins, etc. If these deleterious enzymes are inhibited, β-lactam antibiotics can be used for treatment of bacterial strains that harbor β-lactamases. There are four classes of β-lactamases. Class B is zinc-dependent. Classes A, C and D are serine-dependent. Representative members of class A, C, and D β-lactamases are TEM-1, P99 and OXA-10 enzymes, respectively. As described in the Examples below, compounds of the invention inhibit these enzymes.

As discussed above, PBP 2a is a factor in converting a standard *S. aureus* strain into the problematic MRSA. Furthermore, MRSA is also able to produce its own class A β-lactamase. Both production of the β-lactamase and PBP 2a are inducible events, mediated by the protein B1aR (and the related MecR). The surface domain of B1aR is the β-lactam sensor domain and is related structurally to β-lactamases and PBPs. Assays for inhibition of B1aR and PBP2a are described herein. These and other assays have been employed to select the most promising of candidates from a library of chemical compounds.

The invention thus provides compounds and compositions that are effective to inhibit antibiotic-resistant organisms, such as MRSA. The compounds and compositions, in some embodiments, can also inhibit penicillin-binding proteins (PBPs). In some embodiments, the compositions include one or more compounds, such as one or more compounds of the Formulas described herein.

A screening method for identifying antibiotics having affinity to bacteria is also disclosed. In some embodiments the method employs as an active agent a compound of one of the Formulas described herein. Upon selection of a candidate compound from a chemical library of compounds, the selection being based on chemical structure similarity to one of the chemical core structure of Formulas I-X, the compound is assessed for activity in one or more functional assays that assess biological inhibitory activity for a microorganism, such as a bacterial organism. By way of example, such biological inhibitory activity may be assessed though the use of a TEM assay, P99 assay, OXA10 assay, B1aR assay or PBP2 assay, as described herein and/or as can be carried out by techniques well known to those of skill in the art.

Compounds of the invention can be formulated into suitable pharmaceutical compositions for administration to subjects, such as humans, for example, in a biologically compatible form for administration in vivo. Accordingly, in certain embodiments, a pharmaceutical composition is provided that includes compounds as described herein, admixed with a suitable diluent or carrier. Suitable diluents or carriers include saline or aqueous dextrose, for example, a 5% aqueous dextrose solution. Such formulations can be prepared so that they are isotonic with human fluids, such as blood, or various tissue environments. In certain embodiments, it may also be desirable to prepare hypertonic or hypotonic preparations. In other embodiments, the composition can be prepared and used for in vitro experimentation, for example, in various screens and diagnostic procedures.

Methods for preparing pharmaceutically acceptable compositions are well known in the art. The compositions containing a compound as described herein and a pharmaceutically acceptable vehicle. Suitable vehicles are described, for example, in Remington's Pharmaceutical Sciences (2003, 20$^{th}$ Ed.), in The United States Pharmacopeia The National Formulary (USP 24 NF 19) published in 1999, and in the Handbook of Pharmaceutical Additives (compiled by Michael and Irene Ash, Gower Publishing Limited, Aldershot, England (1995)). On this basis, the compositions include, albeit not exclusively, solutions of the compounds in association with one or more pharmaceutically acceptable vehicles or diluents, as well as buffered solutions with a suitable pH that are iso-osmotic with physiological fluids. In this regard, reference can be made to U.S. Pat. No. 5,843,456 (Paoletti et al.).

The compounds described herein can be administered to a subject in a variety of forms depending on the route of administration selected, as is readily understood by those of skill in the art. The compounds can be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, intrasternal, transepithelial, nasal, intrapulmonary, intrathecal, rectal and infusion modes of administration. Parenteral administration may be carried out by continuous infusion over a selected period of time.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents can also be useful.

A compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like. Solutions of a compound can be prepared in water suitably mixed with suitable excipients. Under ordinary conditions of storage and use, these preparations may contain a preservative, for example, to prevent the growth of microorganisms.

The pharmaceutical forms suitable for injectable use include sterile aqueous solutions or dispersion and sterile powders for the extemporaneous preparation of sterile injectable solutions or dispersions. The formulation should be sterile and should be fluid to the extent that the solution or dispersion can be administered via syringe.

The compositions described herein can be administered to an animal alone or in combination with pharmaceutically acceptable carriers, as noted above, the proportion of which is determined by the solubility and chemical nature of the compound, chosen route of administration and standard pharmaceutical practice. In an embodiment, the pharmaceutical compositions are administered in a convenient manner such as by direct application to the infected site, e.g. by injection (subcutaneous, intravenous, parenteral, etc.). In case of respiratory infections, it may be desirable to administer the compounds of the invention and compositions comprising same, through known techniques in the art, for example by inhalation. Depending on the route of administration (e.g., injection, oral, or inhalation, etc.), the pharmaceutical compositions or compounds or biologically active agents in the compounds of the invention may be coated in a material to protect the compounds or agents from the action of enzymes, acids, and other natural conditions that may inactivate certain properties of the composition or its encapsulated agent.

In addition to pharmaceutical compositions, compositions for non-pharmaceutical purposes are also included within the scope of the invention. Such non-pharmaceutical purposes may include the preparation of diagnostic or research tools. In one embodiment, the compounds can be labeled with labels known in the art, such as florescent or radio-labels, or the like.

The dosage of the compounds of the invention can vary depending on many factors such as the pharmacodynamic properties of the compound, the rate of release of the agent from the delivery composition, the mode of administration, the age, health and weight of the recipient, the nature and extent of the symptoms, the frequency of the treatment and the type of concurrent treatment, if any, and the clearance rate of the agent and/or compound in the subject to be treated.

For example, in some embodiments, a dose of a compound formulation equivalent to about 1 mg mL$^{-1}$ to about 100 mg mL$^{-1}$ can be administered to a patient. In certain other embodiments, the compound formulation includes about 2-20, about 5-15, or about 10 mg mL$^{-1}$. The specific doses of the compounds administered according to this invention to obtain therapeutic and/or prophylactic effects will, of course, be determined by the particular circumstances surrounding the case, including, for example, the compounds administered, the route of administration, the condition being treated and the individual being treated. A typical daily dose (administered in single or in divided doses) can contain a dosage level of from about 0.01 mg/kg to about 150 mg/kg of body weight of an active therapeutic agent described herein. In some embodiments, about 5-10, about 10-20, about 20-40, about 25-50, about 50-75, about 75-100, or about 100-150 150 mg/kg of body weight of a therapeutic agent are provided in a dose. In other embodiments, about 5, 10, 15, 20, 25, 30, 40, 50, 60, 70, 75, 80, 90, 100, 110, 120, 125, 140, or 150 mg/kg of body weight of a therapeutic agent are delivered in a dose. Often times, daily doses generally will be from about 0.05 mg/kg to about 20 mg/kg and ideally from about 0.1 mg/kg to about 10 mg/kg.

The compounds can be used alone or in combination with other agents that treat the same and/or another condition, disease or disorder. In another embodiment, where either or both the compound or biologically active agent is labeled, one can conduct in vivo or in vitro studies for determining optimal dose ranges and drug loading concentrations for the specific condition.

Other compounds and techniques well known to those of skill in the art that can be used in conjunction with the compounds and methods described herein include those described in U.S. Pat. Nos. 7,314,888, 7,259,167, 7,141,573, 6,846,953, and 6,583,119.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Preparation of Various Compounds of the Invention

Compound numbers refer to the corresponding chemical structures illustrated at the end of this Example. Compounds described herein may be prepared by the methods analogous to those illustrated below in Scheme 14-1 and by following general procedures.

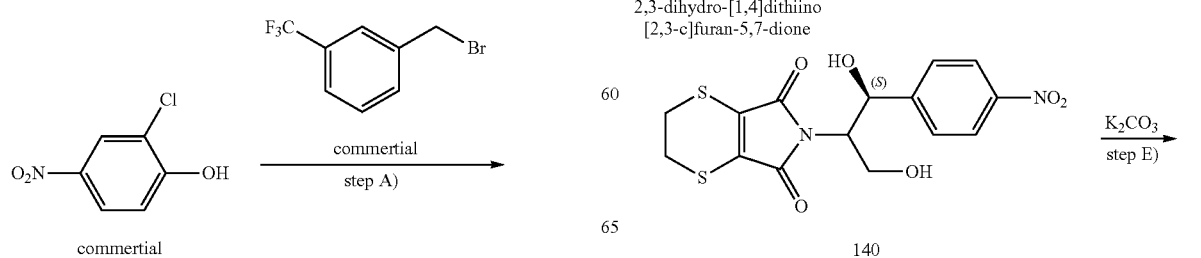

-continued

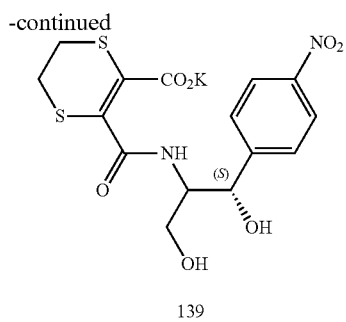

139

General Procedure for Coupling Reactions:

Step A. To a stirred solution of 2-chloro-4-nitrophenol, (17.3 grams, 0.10 mol) and NaH (60% in oil, 5 grams, 0.125 mol) in THF (200 mL) and DMF (30 mL) was added alkyl bromide (0.11 mol). The reaction was stirred for 2 hours at 45° C. under argon. The resultant mixture was concentrated to give an oily residue, which was carefully diluted with water, and extracted three times with dichloromethane (50 mL). The organic layer was washed with 0.1 M hydrochloric acid (HCl), then successively with water, and brine, and dried over anhydrous sodium sulfate. The resulting organic layer was filtered, and concentrated in vacuo to afford a crude material, which was purified via flash chromatography using either silica (230-400 mesh), or activated neutral alumina (Aldrich, Brockmann 1, 150 mesh), eluting with solvent systems individually developed for each compound.

Compound 372.

To a stirred solution of 2-chloro-4-nitrophenol (17.3 grams, 0.10 mol) and NaH (60% in oil, 5 grams, 0.125 mol) in THF (200 mL) and DMF (30 mL) is added (3-trifluoromethyl)benzyl bromide (17 mL) at room temperature (r.t.). The reaction mixture is stirred for 2 hours at 45° C. under argon. The resulted mixture is concentrated to give an oily residue, which is dissolved in dichloromethane (50 mL), washed successively with 10 mL each of water, 0.1 M hydrochloric acid (HCl), water, saturated sodium hydrogen carbonate solution and brine, and dried over anhydrous sodium sulfate. Sample was isolated by column chromatography using silica gel ($CH_2Cl_2/Et_2O$=1:3) in 86% yield. $^1$H NMR (300 MHz, DMSO-d6) δ ppm 5.49 (s, 2H), 7.49 (d, J=9.1 Hz, 1H), 7.66-7.79 (m, 2H), 7.79-7.84 (m, 1H), 7.89 (s, 1H), 8.27 (dd, J=9.1, 2.7 Hz, 1H), 8.32-8.36 (m, 1H). $^{13}$C NMR (75 MHz, DMSO-d6) δ ppm 70.1, 113.8, 122.1, 124.1, 124.1, 124.6, 125.0, 125.4, 129.8, 131.6, 137.1, 141.0, 158.6.

General Procedure for the Reductions:

Step B) Using $SnCl_2$. A solution of the starting nitro derivative (e.g., compound 372, 1.3 mmol), and stannous chloride dihydrate (1.1 grams, 4.4 mmol) in EtOH (15 mL) was heated at 70° C. for 2-4 hours. The solvent was removed under reduced pressure and the residue diluted with 20-30% aqueous NaOH. The aqueous layer was extracted with organic solvents. The organic extract were washed with saturated aqueous NaCl, dried ($MgSO_4$), filtered, and concentrated under reduced pressure to afford a corresponding crude amino derivative, which was further purified by column chromatography or introduced into the next reaction step without further purification.

Step B) Using Pd/C—$H_2$. A stirred solution of nitro compound (0.1 mol) in MeOH (400 mL), was cautiously treated with Pd/C (10%, 2 grams), and then kept under an atmosphere of hydrogen with continued stirring at room temperature overnight. The mixture was diluted with MeOH (200 mL) and filtered through a layer of Celite, and the Celite pad was washed with MeOH. The volatiles were evaporated in vacuo to afford a corresponding amino derivative, which was introduced into the next reaction step without further purification.

Compound 378.

A homogenous solution of derivative 372 (24 grams, 0.072 mol) and stannous chloride dihydrate (53 grams, 0.24 mol) in EtOH (400 mL) was heated at 70° C. for 1 hour. The solvent was removed under reduced pressure and the residue diluted with 20-30% aqueous NaOH to raise the pH to about 9. The aqueous layer was extracted with $CH_2Cl_2$. The combined organic extracts were washed with saturated aq. NaCl, dried ($MgSO_4$), filtered, and concentrated under reduced pressure to afford a crude material, which was further purified by silica gel column chromatography ($CH_2Cl_2$/n-Hexane=6:1) to afford compound 378 in 79% yield. 1H NMR (500 MHz, $CDCl_3$) δ ppm 3.48 (s, 2H), 5.06 (s, 2H), 6.50 (dd, J=8.7, 2.7 Hz, 1H), 6.72-6.81 (m, 2H), 7.47-7.51 (m, 1H), 7.58 (d, J=7.7 Hz, 1H), 7.65 (d, J=7.7 Hz, 1H), 7.74 (s, 1H). $^{13}$C NMR (126 MHz, $CDCl_3$) δ ppm 71.6, 114.3, 117.1, 117.1, 123.1, 124.0, 124.0, 124.0, 124.1, 124.5, 124.7, 124.7, 124.7, 124.8, 125.3, 128.9, 129.1, 130.6, 130.9, 138.2, 141.9, 146.7.

General Procedure for Coupling Terminal Amines and Phthalic Anhydrides:

Step C. A round-bottom flask was charged with substituted phthalic anhydrides (1 equiv), aryl- or alkyl amine (1.05-1.10 equiv), THF and dry triethylamine (0.1 equiv). For some sequences, DMF was used as a cosolvent due to poor solubility of the reactants. The concentrations of the reactions varied from 0.3 to 0.1 M depending on the solubility of the reactants. The flask was then evacuated and backfilled with nitrogen, sealed with a cap, and stirred at 30° C. for 1-12 hours. The disappearance of starting materials may be monitored by Thin Layer Chromatography. After completion, the solvent was removed and the reaction mixture was purified by flash column chromatography.

Compound 390.

To a solution of compound 378 (3.17 grams, 0.010 mol) in THF (80 mL), $Et_3N$ (0.1 mL) was added a solution of 3,4,5,6-tetrabromophthalic anhydride (5.0 grams, 0.011 mol) dissolved in dry DMF (3D mL). The reaction mixture was flushed with nitrogen, and the reaction vessel was closed, and stirred at 30° C. for 6 hours. The organic solvents were evaporated. The residue was chromatographed on silica gel ($CH_2Cl_2$/MeOH, 5:1) as eluent and was further purified by recrystallization from a mixture of $CH_3CN/H_2O$ to give 390 as yellowish powder in 76% yield. $^1$H NMR (500 MHz, DMSO-d6) δ ppm 5.31 (s, 2H), 7.27 (d, J=8.7 Hz, 1H), 7.43 (dd, J=8.9, 1.4 Hz, 1H), 7.64-7.73 (m, 2H), 7.77 (d, J=6.9 Hz, 1H), 7.80-7.86 (m, 2H), 10.77 (s, 1H). $^{13}$C NMR (126 MHz, DMSO-d6) δ ppm 69.9, 115.4, 116.3, 119.9, 121.6, 122.1, 123.4, 124.3, 125.2, 130.1, 130.8, 131.8, 133.0, 138.1, 138.6, 150.4, 166.3.

The Substituted 2,3-Dihydro[1,4]dithiino Phthalimides were Prepared by the Following General Method.

Step D). 2,3-Dihydro[1,4]dithiino[2,3-c]furan-5,7-dione (1.88 grams, 0.01 mol) and (1S,2S)-2-amino-1-(4-nitrophenyl)propane-1,3-diol (2.10 grams, 0.01 mol) were added to DMF (10 mL). The mixture was heated with stirring to 60° C. for 1 hour. At this point the majority of the starting material had been converted into the 2,3-dihydro[1,4]dithiino phthalimide derivative 140. The reaction mixture was then evaporated and the crude product poured into water to remove any remaining DMF. The resulting material was further purified by column chromatography to give 140 in high yield. $^1$H NMR (500 MHz, DMSO-d6) δ ppm 3.00-3.10 (m, 1H), 3.41 (s, 4H), 3.80 (td, J=10.8, 5.7 Hz, 1H), 4.06 (td, J=9.9, 4.2 Hz, 1H), 4.82 (t, J=5.9 Hz, 1H), 4.99 (dd, J=9.5, 4.3 Hz, 1H), 5.95

(d, J=4.4 Hz, 1H), 7.65 (d, J=8.6 Hz, 2H), 8.24 (d, J=8.6 Hz, 2H). $^{13}$C NMR (126 MHz, DMSO-d6) δ ppm 25.2, 26.0, 57.5, 60.2, 67.0, 69.2, 95.4, 123.6, 128.1, 147.1, 150.4, 167.1.

The Substituted 2,3-Dihydro[1,4]dithiino Carbamoyl Derivatives were Prepared by the Following General Method Step E) A solution of previously synthesized imide derivative 140 (2.45 grams, 0.01 mol) was treated with 2 equiv of $K_2CO_3$ in 50% EtOH (100 mL) at room temperature. With continued stirring, the resultant solution was allowed to warm to 30° C., and stirred for 4-5 hours to complete disappearance of the starting material. After filtration a few drops of diluted aqueous HCl were added before the solvents were removed in vacuo and the residue was chromatographed ($CH_2Cl_2$/MeOH, 4:1) to give 2.9 grams (68%) of the corresponding potassium 3-((1S,2S)-1,3-dihydroxy-1-(4-nitrophenyl)propane-2-ylcarbamoyl)-5,6-dihydro-1,4-dithiine-2-carboxylate (Compound 139) as a yellow solid. $^1$H NMR (500 MHz, $CD_3OD$) δ ppm 3.12-3.20 (m, 4H), 3.63-3.69 (m, 1H), 3.69-3.76 (m, 1H), 4.12 (dd, J=9.9, 5.8 Hz, 1H), 5.05 (d, J=3.5 Hz, 1H), 7.66 (d, J=8.6 Hz, 2H), 8.17 (d, J=8.6 Hz, 2H). In a similar fashion, the following compounds were prepared.

Compound 7. $^1$H NMR (300 MHz, $CD_3OD$) δ ppm 4.55 (s, 2H), 7.17-7.27 (m, 1H), 7.43-7.57 (m, 5H), 7.69-7.76 (m, 1H), 7.82 (d, J=6.7 Hz, 1H), 8.40 (d, J=4.3 Hz, 1H).

Compound 8. $^1$H NMR (400 MHz, DMSO-d6) δ ppm 7.42 (d, J=7.3 Hz, 1H), 7.54-7.61 (m, 3H), 7.64-7.70 (m, 1H), 7.84-7.93 (m, 2H), 8.22 (s, 1H), 10.69 (s, 1H), 13.14 (s, 1H).

Compound 11. $^1$H NMR (300 MHz, $CDCl_3$) δ ppm 1.76-1.86 (m, 4H), 3.09 (t, J=6.4 Hz, 2H), 3.53 (t, J=6.7 Hz, 2H), 7.18 (d, J=6.1 Hz, 1H), 7.98 (d, J=7.3 Hz, 1H).

Compound 19. $^1$H NMR (400 MHz, $CDCl_3$) δ ppm 1.21 (t, J=6.9 Hz, 3H), 1.28 (t, J=7.3 Hz, 3H), 3.45-3.51 (m, 4H), 6.38 (d, J=13.0 Hz, 1H), 6.61 (d, J=13.0 Hz, 1H).

Compound 20. $^1$H NMR (400 MHz, DMSO-d6) δ ppm 6.31 (d, J=11.4 Hz, 1H), 6.48 (d, J=12.2 Hz, 1H), 7.72 (d, J=8.9 Hz, 2H), 7.90 (d, J=8.1 Hz, 2H), 10.60 (s, 1H), 12.84 (s, 1H).

Compound 21. $^1$H NMR (400 MHz, DMSO-d6) δ ppm 2.84 (s, 2H), 3.01 (s, 2H), 3.17 (s, 3H), 3.71 (s, 2H), 6.85 (d, J=3.2 Hz, 3H), 6.89-6.97 (m, 3H), 7.31 (d, J=7.3 Hz, 1H), 7.51 (t, J=6.9 Hz, 1H), 7.63 (t, J=6.9 Hz, 1H), 7.92 (d, J=6.5 Hz, 1H).

Compound 22. $^1$H NMR (400 MHz, DMSO-d6) δ ppm 1.05 (t, J=7.3 Hz, 7H), 3.23-3.33 (m, 5H), 6.65 (d, J=8.9 Hz, 2H), 7.45-7.56 (m, 5H).

Compound 23. $^1$H NMR (400 MHz, DMSO-d6) δ ppm 7.57 (d, J=4.1 Hz, 1H), 7.59-7.67 (m, 3H), 7.67-7.74 (m, 3H), 7.91 (d, J=7.3 Hz, 1H), 8.38 (d, J=8.1 Hz, 1H), 8.73 (d, J=7.3 Hz, 1H), 8.83 (d, J=4.1 Hz, 1H), 10.15 (s, 1H).

Compound 24. $^1$H NMR (400 MHz, DMSO-d6) δ ppm 7.62 (t, J=6.9 Hz, 2H), 7.70 (t, J=7.7 Hz, 1H), 7.79 (s, 1H), 7.93 (d, J=7.3 Hz, 1H), 8.35 (s, 2H), 10.99 (s, 1H), 13.20 (s, 1H).

Compound 25. $^1$H NMR (400 MHz, DMSO-d6) δ ppm 3.66 (s, 3H), 3.76 (s, 4H), 6.36 (d, J=8.1 Hz, 1H), 6.52 (s, 1H), 6.73 (d, J=8.9 Hz, 1H), 7.55 (d, J=3.2 Hz, 2H), 7.78 (s, 1H), 7.80 (d, J=5.7 Hz, 2H).

Compound 26. $^1$H NMR (400 MHz, DMSO-d6) δ ppm 4.11 (dd, J=17.4, 5.3 Hz, 5H), 6.13-6.21 (m, 2H), 6.57 (d, J=8.1 Hz, 1H), 7.50-7.58 (m, 1H), 7.70-7.76 (m, 2H).

Compound 27. $^1$H NMR (400 MHz, DMSO-d6) δ ppm 7.26-7.37 (m, 1H), 7.43 (dt, J=14.6, 7.3 Hz, 3H), 7.57 (t, J=6.9 Hz, 1H), 7.66 (t, J=6.9 Hz, 1H), 7.89 (d, J=8.1 Hz, 2H), 10.23 (s, 1H), 13.08 (s, 1H).

Compound 28. $^1$H NMR (400 MHz, DMSO-d6) δ ppm 7.16 (t, J=7.3 Hz, 1H), 7.54-7.66 (m, 4H), 7.72 (s, 1H), 7.84 (t, J=6.5 Hz, 2H), 8.32 (s, 1H), 8.59 (d, J=7.3 Hz, 1H), 12.21 (s, 1H).

Compound 29. $^1$H NMR (400 MHz, DMSO-d6) δ ppm 1.30 (s, 1H), 1.30-1.39 (m, 6H), 4.01 (d, J=6.5 Hz, 5H), 7.50-7.61 (m, 8H), 7.78 (d, J=7.3 Hz, 1H), 7.95 (d, J=7.3 Hz, 2H).

Compound 30. $^1$H NMR (400 MHz, DMSO-d6) δ ppm 6.90 (t, J=8.5 Hz, 1H), 7.37 (td, J=15.8, 8.1 Hz, 2H), 7.52-7.61 (m, 2H), 7.62-7.71 (m, 2H), 7.89 (d, J=8.1 Hz, 1H), 10.55 (s, 1H), 13.10 (s, 1H).

Compound 32. $^1$H NMR (400 MHz, DMSO-d6) δ ppm 1.05 (t, J=6.9 Hz, 6H), 3.24-3.32 (m, 4H), 6.26-6.31 (m, 1H), 6.46-6.52 (m, 1H), 6.63 (d, J=9.7 Hz, 2H), 7.43 (d, J=8.9 Hz, 2H), 10.51 (s, 1H).

Compound 33. $^1$H NMR (400 MHz, DMSO-d6) δ ppm 6.40 (d, J=12.2 Hz, 1H), 6.84 (d, J=12.2 Hz, 1H), 7.56-7.66 (m, 2H), 7.69-7.74 (m, 1H), 8.41 (d, J=8.1 Hz, 1H), 8.64 (d, J=7.3 Hz, 1H), 8.92 (s, 1H), 10.58 (s, 1H).

Compound 34. $^1$H NMR (400 MHz, DMSO-d6) δ ppm 6.33-6.41 (m, 1H), 6.46-6.54 (m, 1H), 7.72 (s, 1H), 8.24-8.29 (m, 2H), 10.89 (s, 1H).

Compound 35. $^1$H NMR (400 MHz, DMSO-d6) δ ppm 3.74 (s, 4H), 3.81 (s, 3H), 6.31 (d, J=12.2 Hz, 1H), 6.48-6.53 (m, 1H), 6.63 (s, 2H), 7.72 (d, J=8.9 Hz, 1H), 9.91 (s, 1H).

Compound 36. $^1$H NMR (400 MHz, DMSO-d6) δ ppm 4.19 (s, 4H), 6.27 (d, J=12.2 Hz, 1H), 6.41 (d, J=12.2 Hz, 1H), 6.79 (d, J=8.9 Hz, 1H), 6.99 (d, J=8.9 Hz, 1H), 7.24 (s, 1H), 10.29 (s, 1H).

Compound 37. $^1$H NMR (400 MHz, DMSO-d6) δ ppm 6.36 (d, J=12.2 Hz, 1H), 6.49 (d, J=12.2 Hz, 1H), 7.74 (s, 1H), 8.25 (s, 3H), 10.89 (s, 1H).

Compound 38. $^1$H NMR (400 MHz, DMSO-d6) δ ppm 6.25 (d, J=12.2 Hz, 1H), 6.53 (d, J=11.4 Hz, 1H), 7.15 (t, J=7.7 Hz, 1H), 7.50 (t, J=7.7 Hz, 1H), 7.74 (s, 1H), 7.80 (d, J=7.3 Hz, 1H), 8.28 (s, 1H), 8.43 (d, J=8.1 Hz, 1H), 11.91 (s, 1H), 12.95 (s, 1H).

Compound 39. $^1$H NMR (400 MHz, DMSO-d6) δ ppm 1.29-1.38 (m, 8H), 3.96-4.06 (m, 6H), 7.50-7.60 (m, 4H), 7.89 (s, 1H), 7.93 (d, J=7.3 Hz, 3H).

Compound 40. $^1$H NMR (400 MHz, DMSO-d6) δ ppm 6.30 (d, J=12.2 Hz, 1H), 6.42-6.49 (m, 1H), 6.87-6.93 (m, 1H), 7.28-7.37 (m, 2H), 7.59 (d, J=12.2 Hz, 1H), 10.49 (s, 1H), 12.91 (s, 1H).

Compound 41. $^1$H NMR (400 MHz, DMSO-d6) δ ppm 1.66-1.76 (m, 4H), 2.67-2.77 (m, 4H), 6.94 (d, J=7.3 Hz, 1H), 7.09 (t, J=7.7 Hz, 1H), 7.27 (d, J=8.1 Hz, 1H), 7.52-7.58 (m, 2H), 7.61-7.69 (m, 2H), 7.86 (d, J=8.1 Hz, 1H), 9.60 (s, 1H).

Compound 42. $^1$H NMR (400 MHz, DMSO-d6) δ ppm 6.22 (s, 2H), 7.06 (s, 2H), 7.33-7.42 (m, 4H), 7.53 (t, J=7.3 Hz, 1H), 7.61 (t, J=7.3 Hz, 1H), 7.66 (d, J=7.3 Hz, 1H), 7.85 (d, J=7.3 Hz, 1H), 9.83 (s, 1H).

Compound 43. $^1$H NMR (400 MHz, DMSO-d6) δ ppm 3.04 (d, J=4.9 Hz, 4H), 3.66-3.76 (m, 4H), 6.90 (d, J=8.9 Hz, 2H).

7.50-7.57 (m, 4H), 7.61 (d, J=7.3 Hz, 1H), 7.85 (d, J=7.3 Hz, 1H), 10.11 (s, 1H).

Compound 404. $^1$H NMR (400 MHz, DMSO-d6) δ ppm 7.58 (dd, J=12.2, 7.3 Hz, 2H), 7.63-7.71 (m, 2H), 7.91 (d, J=8.1 Hz, 2H), 8.29 (s, 1H), 10.77 (s, 1H).

Compound 45. $^1$H NMR (400 MHz, DMSO-d6) δ ppm 7.53-7.61 (m, 4H), 7.67 (t, J=7.3 Hz, 1H), 7.90 (t, J=6.5 Hz, 2H), 8.17 (s, 1H), 10.69 (s, 1H).

Compound 46. $^1$H NMR (300 MHz, DMSO-d6) δ ppm 7.53-7.61 (m, 3H), 7.63-7.69 (m, 2H), 7.76 (d, J=8.5 Hz, 1H), 7.91 (d, J=7.9 Hz, 1H), 8.13 (s, 1H), 10.26 (s, 1H).

Compound 47. ¹H NMR (400 MHz, DMSO-d6) δ ppm 6.65 (d, J=6.5 Hz, 1H), 6.95-7.06 (m, 4H), 7.23 (s, 1H), 7.53-7.62 (m, 4H), 7.69 (d, J=3.2 Hz, 3H).

Compound 48. ¹H NMR (400 MHz, DMSO-d6) δ ppm 7.44 (t, J=7.7 Hz, 2H), 7.53-7.60 (m, 3H), 7.65 (t, J=6.9 Hz, 2H), 7.86 (dd, J=12.2, 8.1 Hz, 2H), 8.37 (s, 1H), 10.50 (s, 1H).

Compound 50. ¹H NMR (400 MHz, DMSO-d6) δ ppm 3.61 (s, 3H), 3.66 (s, 3H), 6.19 (d, J=8.1 Hz, 1H), 6.36 (s, 1H), 6.69 (d, J=8.1 Hz, 1H), 7.54 (d, J=3.2 Hz, 2H), 7.56 (s, 1H), 7.73 (s, 1H), 7.74 (d, J=5.7 Hz, 1H).

Compound 51. ¹H NMR (400 MHz, DMSO-d6) δ ppm 1.69 (d, J=5.7 Hz, 4H), 2.55-2.64 (m, 2H), 2.67-2.75 (m, 2H), 6.28 (d, J=12.2 Hz, 1H), 6.57 (d, J=13.0 Hz, 1H), 6.93 (d, J=8.1 Hz, 1H), 7.06 (t, J=7.7 Hz, 1H), 7.21 (d, J=7.3 Hz, 1H), 9.82 (s, 1H).

Compound 52. ¹H NMR (400 MHz, DMSO-d6) δ ppm 6.20-6.29 (m, 3H), 6.46 (d, J=12.2 Hz, 1H), 6.97 (s, 2H), 7.31-7.39 (m, 3H), 7.64 (d, J=6.5 Hz, 1H), 9.96 (s, 1H).

Compound 53. ¹H NMR (400 MHz, DMSO-d6) δ ppm 3.00-3.07 (m, 4H), 3.65-3.74 (m, 4H), 6.29 (d, J=12.2 Hz, 1H), 6.43-6.49 (m, 1H), 6.90 (d, J=8.9 Hz, 2H), 7.49 (d, J=8.9 Hz, 2H), 10.42 (s, 1H).

Compound 54. ¹H NMR (400 MHz, DMSO-d6) δ ppm 6.30-6.37 (m, 1H), 6.46 (d, J=12.2 Hz, 1H), 7.64 (d, J=8.9 Hz, 1H), 7.83 (d, J=8.1 Hz, 1H), 8.19 (s, 1H), 10.68 (s, 1H), 12.89 (s, 1H).

Compound 55. ¹H NMR (400 MHz, DMSO-d6) δ ppm 6.32 (d, J=12.2 Hz, 1H), 6.44-6.51 (m, 1H), 7.51-7.56 (m, 2H), 7.79 (d, J=4.1 Hz, 1H), 8.09 (s, 1H), 10.61 (s, 1H).

Compound 56. ¹H NMR (400 MHz, DMSO-d6) δ ppm 6.38 (d, J=12.2 Hz, 1H), 6.63 (d, J=12.2 Hz, 1H), 7.49 (d, J=8.9 Hz, 1H), 7.70 (d, J=8.1 Hz, 1H), 8.24 (s, 1H), 10.25 (s, 1H).

Compound 57. ¹H NMR (400 MHz, DMSO-d6) δ ppm 6.39 (d, J=12.2 Hz, 1H), 6.70 (d, J=12.2 Hz, 1H), 7.12 (d, J=8.9 Hz, 1H), 7.22-7.32 (m, 2H), 7.57 (d, J=7.3 Hz, 1H), 7.68 (d, J=8.1 Hz, 1H), 7.79 (d, J=8.1 Hz, 1H), 9.84 (s, 1H), 10.42 (s, 1H).

Compound 58. ¹H NMR (400 MHz, DMSO-d6) δ ppm 6.30 (d, J=11.4 Hz, 1H), 6.43-6.50 (m, 2H), 7.43 (t, J=8.1 Hz, 1H), 7.65 (d, J=8.1 Hz, 1H), 7.81 (d, J=8.1 Hz, 1H), 8.26 (s, 1H), 10.51 (s, 1H).

Compound 59. ¹H NMR (400 MHz, DMSO-d6) δ ppm 3.17 (d, J=4.9 Hz, 4H), 3.44 (s, 2H), 3.58 (s, 2H), 5.99 (d, J=12.2 Hz, 1H), 6.70 (d, J=12.2 Hz, 1H), 6.80 (d, J=8.1 Hz, 1H), 6.89 (d, J=8.1 Hz, 1H), 6.95 (s, 1H), 7.21 (t, J=8.1 Hz, 1H).

Compound 60. ¹H NMR (400 MHz, DMSO-d6) δ ppm 3.71 (d, J=3.2 Hz, 7H), 6.28-6.34 (m, 1H), 6.40-6.48 (m, 1H), 6.90 (d, J=8.9 Hz, 1H), 7.12 (d, J=8.1 Hz, 1H), 7.32 (s, 1H), 10.36 (s, 1H).

Compound 81. ¹H NMR (500 MHz, DMSO-d6) δ ppm 1.05 (t, J=7.1 Hz, 7H), 3.29 (q, J=7.1 Hz, 5H), 6.59-6.66 (m, 2H), 7.44-7.51 (m, 3H), 7.89 (d, J=8.1 Hz, 1H), 7.97 (d, J=7.6 Hz, 1H).

Compound 82. ¹H NMR (400 MHz, DMSO-d6) δ ppm 7.83 (s, 1H), 7.88 (t, J=8.1 Hz, 1H), 8.22 (s, 2H), 8.34 (d, J=8.1 Hz, 1H), 8.42 (d, J=8.1 Hz, 1H), 11.31 (s, 1H).

Compound 83. ¹H NMR (400 MHz, DMSO-d6) δ ppm 3.75 (s, 6H), 6.54 (d, J=8.9 Hz, 1H), 6.60 (s, 1H), 7.74 (t, J=8.1 Hz, 1H), 7.90 (d, J=8.9 Hz, 1H), 8.20 (d, J=8.1 Hz, 1H), 8.27 (d, J=8.1 Hz, 1H), 9.78 (s, 1H).

Compound 84. ¹H NMR (400 MHz, DMSO-d6) δ ppm 7.25 (t, J=7.3 Hz, 1H), 7.37-7.46 (m, 2H), 7.81 (t, J=7.7 Hz, 1H), 8.18 (d, J=8.1 Hz, 1H), 8.28 (d, J=7.3 Hz, 1H), 8.35 (d, J=8.1 Hz, 1H), 10.48 (s, 1H).

Compound 86. ¹H NMR (400 MHz, DMSO-d6) δ ppm 7.70 (d, J=8.9 Hz, 1H), 7.78-7.84 (m, 1H), 7.84-7.88 (m, 1H), 8.18 (s, 1H), 8.32 (d, J=8.1 Hz, 1H), 8.38 (d, J=8.1 Hz, 1H), 11.07 (s, 1H).

Compound 87. ¹H NMR (500 MHz, DMSO-d6) δ ppm 7.61 (d, J=8.1 Hz, 1H), 7.69 (d, J=7.6 Hz, 1H), 7.78 (d, J=8.6 Hz, 1H), 8.14 (s, 1H), 8.20 (d, J=8.1 Hz, 1H), 8.44 (s, 1H), 10.42 (s, 1H).

Compound 89. ¹H NMR (500 MHz, DMSO-d6) δ ppm 7.64 (d, J=7.8 Hz, 1H), 7.80 (d, J=8.4 Hz, 1H), 7.94 (s, 1H), 8.10 (br. s., 1H), 10.77 (s, 1H).

Compound 92/93. ¹H NMR (500 MHz, DMSO-d6) δ ppm 2.42 (d, J=6.2 Hz, 3H), 7.34-7.44 (m, 1H), 7.48 (s, 1H), 7.60 (d, J=8.4 Hz, 1H), 7.78 (d, J=8.4 Hz, 1H), 7.84 (d, J=7.8 Hz, 1H), 8.15 (br. s, 1H), 10.19-10.31 (m, 1H).

Compound 94. ¹H NMR (500 MHz, DMSO-d6) δ ppm 1.33 (dd, J=8.8, 3.8 Hz, 1H), 1.39-1.54 (m, 2H), 1.54-1.67 (m, 1H), 1.67-1.82 (m, 2H), 1.95-2.13 (m, 2H), 2.60-2.78 (m, 1H), 3.09 (d, J=4.8 Hz, 1H), 7.50 (dd, J=8.4, 2.0 Hz, 1H), 7.72 (d, J=8.4 Hz, 1H), 8.08 (d, J=1.6 Hz, 1H), 9.55 (s, 1H).

Compound 95/96. ¹H NMR (500 MHz, DMSO-d6) δ ppm 0.83-0.96 (m, 3H), 1.45 (dd, J=6.4, 3.4 Hz, 1H), 1.49-1.67 (m, 2H), 1.77-1.96 (m, 2H), 1.96-2.13 (m, 1H), 2.56-2.78 (m, 1H), 3.10-3.24 (m, 1H), 7.50 (dd, J=8.5, 2.3 Hz, 1H), 7.73 (d, J=8.4 Hz, 1H), 8.12 (s, 1H), 9.38 (s, 1H).

Compound 97. ¹H NMR (300 MHz, DMSO-d6) δ ppm 3.71 (s, 1H), 5.88 (s, 2H), 7.61 (t, J=7.5 Hz, 5H), 7.74 (t, J=7.2 Hz, 3H), 7.89-8.12 (m, 4H), 13.93 (br. s, 1H)

Compound 100. ¹H NMR (500 MHz, DMSO-d6) δ ppm 7.02 (s, 1H), 7.48-7.52 (m, 3H), 7.54-7.59 (m, 2H), 7.77-7.80 (m, 1H), 8.45 (d, J=1.6 Hz, 1H), 10.06 (s, 1H).

Compound 108. ¹H NMR (500 MHz, DMSO-d6) δ ppm 4.22-4.37 (m, 2H), 5.87 (dd, J=19.9, 2.8 Hz, 2H), 6.09 (d, J=2.6 Hz, 1H), 6.18 (dd, J=3.1, 1.9 Hz, 1H), 7.58 (dt, J=11.3, 7.8 Hz, 4H), 7.72 (t, J=7.5 Hz, 2H), 7.97-8.09 (m, 4H), 9.01 (t, J=5.8 Hz, 1H).

Compound 111. ¹H NMR (500 MHz, DMSO-d6) δ ppm 4.43 (d, J=5.6 Hz, 3H), 6.32-6.36 (m, 1H), 6.41 (dd, J=3.2, 1.8 Hz, 1H), 7.56-7.62 (m, 1H), 7.84 (d, J=8.2 Hz, 1H), 7.95 (d, J=1.8 Hz, 1H), 8.05 (dd, J=8.0, 1.8 Hz, 1H), 9.01 (t, J=5.7 Hz, 1H).

Compound 114. ¹H NMR (500 MHz, DMSO-d6) δ ppm 2.94 (d, J=6.6 Hz, 3H), 3.18 (d, J=14.2 Hz, 4H), 7.18 (s, 1H), 7.43 (s, 1H Compound 118. ¹H NMR (500 MHz, DMSO-d6) δ ppm 2.01 (s, 3H), 3.23 (d, J=16.9 Hz, 1H), 3.36-3.48 (m, 6H), 4.85 (d, J=12.2 Hz, 1H), 4.98-5.06 (m, 2H), 5.61 (d, J=4.8 Hz, 1H).

Compound 119. ¹H NMR (400 MHz, DMSO-d6) δ ppm 2.96 (s, 4H), 4.07 (s, 4H).

Compound 120. ¹H NMR (400 MHz, DMSO-d6) δ ppm 3.43 (s, 4H).

Compound 121. ¹H NMR (400 MHz, DMSO-d6) δ ppm 3.02 (s, 4H).

Compound 123. ¹H NMR (400 MHz, D₂O) δ ppm 1.12 (d, J=6.5 Hz, 2H), 1.19 (d, J=6.5 Hz, 2H), 2.84 (dd, J=13.0, 9.7 Hz, 1H), 3.00-3.10 (m, 1H), 3.13-3.24 (m, 4H), 3.90-3.95 (m, 1H), 3.99 (d, J=6.5 Hz, 1H).

Compound 124. ¹H NMR (400 MHz, D₂O) δ ppm 1.15 (d, J=6.5 Hz, 3H), 3.18-3.27 (m, 7H), 3.91-4.00 (m, 2H).

Compound 125. ¹H NMR (300 MHz, CDCl₃) δ ppm 0.95 (ddd, J=15.6, 7.6, 7.3 Hz, 4H), 1.39-1.54 (m, 1H), 1.67 (dt, J=14.7, 7.3 Hz, 1H), 3.49-3.64 (m, 2H), 3.69-3.79 (m, 2H), 3.81-3.92 (m, 1H).

Compound 126a. ¹H NMR (400 MHz, D₂O) δ ppm 0.93 (t, J=7.7 Hz, 3H), 1.45 (dd, J=16.2, 7.3 Hz, 1H), 1.57 1.67 (m, 1H), 3.20-3.29 (m, 4H), 3.55-3.60 (m, 1H), 3.62-3.68 (m, 1H), 3.75-3.83 (m, 1H).

Compound 127. ¹H NMR (500 MHz, D₂O) δ ppm 3.03-3.10 (m, 3H), 3.40 (dd, J=11.6, 7.1 Hz, 1H), 3.50 (dd, J=11.6, 5.1 Hz, 1H), 3.98-4.03 (m, 1H), 4.76 (d, J=5.6 Hz, 1H), 7.21-7.26 (m, 1H), 7.26-7.30 (m, 5H).

Compound 128. ¹H NMR (400 MHz, D₂O) δ ppm 3.17 (d, J=8.9 Hz, 3H), 3.20 (s, 1H), 3.46-3.54 (m, 1H), 3.54-3.64 (m, 1H), 4.06-4.15 (m, 1H), 4.86 (d, J=5.7 Hz, 1H), 7.29-7.36 (m, 1H), 7.36-7.41 (m, 4H).

Compound 129. ¹H NMR (300 MHz, DMSO-d6) δ ppm 0.95-1.08 (m, 3H), 3.04 (s, 1H), 3.10-3.28 (m, 2H), 3.28-3.46 (m, 2H), 3.50 (br. s, 1H), 3.66 (br. s, 1H), Compound 130. ¹H NMR (400 MHz, CD₃OD) δ ppm 1.26 (d, J=5.7 Hz, 4H), 2.99-3.07 (m, 1H), 3.19 (s, 2H), 3.63-3.72 (m, 2H), 3.80 (dd, J=11.8, 3.6 Hz, 1H), 3.84-3.91 (m, 1H).

Compound 133. ¹H NMR (500 MHz, D₂O) δ ppm 0.92 (d, J=6.6 Hz, 3H), 2.05 (s, 2H), 2.59 (s, 3H), 3.00-3.07 (m, 3H), 4.50 (d, J=9.1 Hz, 1H), 7.22 (s, 1H), 7.24-7.32 (m, 5H).

Compound 134. ¹H NMR (300 MHz, CDCl₃) δ ppm 1.56 (d, J=6.7 Hz, 2H), 3.01-3.15 (m, 5H), 3.58-3.68 (m, 5H), 4.07-4.18 (m, 3H), 7.22-7.35 (m, 3H).

Compound 135. ¹H NMR (500 MHz, CDCl₃) δ ppm 0.99 (d, J=7.1 Hz, 2H), 1.19 (t, J=7.3 Hz, 2H), 2.94-3.03 (m, 3H), 3.09-3.18 (m, 3H), 7.15-7.21 (m, 1H), 7.22-7.27 (m, 3H), 7.29-7.36 (m, 2H).

Compound 136. ¹H NMR (500 MHz, CDCl₃) δ ppm 1.74 (d, J=7.1 Hz, 3H), 3.16-3.19 (m, 2H), 3.20-3.24 (m, 2H), 3.44 (s, 1H), 3.70 (s, 2H), 3.79-3.84 (m, 2H), 7.34 (t, J=7.3 Hz, 1H), 7.40 (t, J=7.6 Hz, 2H), 7.51 (d, J=7.6 Hz, 2H).

Compound 138. ¹H NMR (500 MHz, ACETONE-d6) δ ppm 1.76-1.82 (m, 3H), 2.05 (qd, J=2.2, 2.0 Hz, 1H), 3.62 (t, J=6.8 Hz, 3H), 3.95-4.03 (m, 1H), 4.37 (ddd, J=13.4, 4.8, 4.6 Hz, 1H), 5.24-5.29 (m, 1H), 7.74 (d, J=8.6 Hz, 2H), 8.25-8.28 (m, 2H).

Compound 139. ¹H NMR (500 MHz, CD₃OD) δ ppm 3.12-3.20 (m, 4H), 3.63-3.69 (m, 1H), 3.69-3.76 (m, 1H), 4.12 (dd, J=9.9, 5.8 Hz, 1H), 5.05 (d, J=3.5 Hz, 1H), 7.66 (d, J=8.6 Hz, 2H), 8.17 (d, J=8.6 Hz, 2H).

Compound 140. ¹H NMR (500 MHz, DMSO-d6) δ ppm 3.00-3.10 (m, 1H), 3.41 (s, 4H), 3.80 (td, J=10.8, 5.7 Hz, 1H), 4.06 (td, J=9.9, 4.2 Hz, 1H), 4.82 (t, J=5.9 Hz, 1H), 4.99 (dd, J=9.5, 4.3 Hz, 1H), 5.95 (d, J=4.4 Hz, 1H), 7.65 (d, J=8.6 Hz, 2H), 8.24 (d, J=8.6 Hz, 2H). ¹³C NMR (126 MHz, DMSO-d6) δ ppm 25.2, 26.0, 57.5, 60.2, 67.0, 69.2, 95.4, 123.6, 128.1, 147.1, 150.4, 167.1

Compound 141. ¹H NMR (400 MHz, D₂O) δ ppm 1.89-1.99 (m, 2H), 2.88-2.97 (m, 2H), 3.17-3.26 (m, 4H), 3.28-3.32 (m, 1H).

Compound 142. ¹H NMR (500 MHz, D₂O) δ ppm 1.12 (t, J=7.3 Hz, 9H), 1.82-1.88 (m, 2H), 2.72-2.77 (m, 2H), 3.05 (q, J=7.1 Hz, 6H), 3.22 (s, 4H), 3.47 (t, J=6.8 Hz, 2H)

Compound 143. ¹H NMR (400 MHz, D₂O) δ ppm 3.09-3.18 (m, 5H), 3.60-3.66 (m, 1H), 3.68-3.75 (m, 1H), 4.09-4.15 (m, 1H), 5.09 (d, J=4.1 Hz, 1H), 7.57 (d, J=8.9 Hz, 2H), 8.18 (d, J=8.9 Hz, 2H).

Compound 145. ¹H NMR (400 MHz, CD₃OD) δ ppm 1.29 (t, J=7.3 Hz, 2H), 3.14-3.25 (m, 4H), 4.83 (dd, J=12.2, 4.9 Hz, 1H), 6.65 (d, J=8.1 Hz, 1H), 6.93 (d, J=8.1 Hz, 2H).

Compound 153. ¹H NMR (300 MHz, CDCl₃) δ ppm 0.88-1.01 (m, 9H), 1.01-1.31 (m, 2H), 1.33-1.73 (m, 3H), 1.73-2.08 (m, 4H), 2.23-2.57 (m, 2H), 2.95-3.25 (m, 4H), 6.25 (d, J=6.0 Hz, 1H).

Compound 158. ¹H NMR (500 MHz, CDCl₃) δ ppm 0.90-0.99 (m, 15H), 1.55-1.64 (m, 5H), 1.77-1.87 (m, 3H).

Compound 165. ¹H NMR (500 MHz, CDCl₃) δ ppm 0.96 (d, J=6.4 Hz, 2H), 1.01-1.17 (m, 4H), 1.47-1.60 (m, 1H), 1.60-1.84 (m, 3H), 1.86-2.10 (m, 2H), 2.22-2.41 (m, 1H), 2.48-2.68 (m, 1H), 7.16 (dd, J=8.9, 2.5 Hz, 1H), 7.28 (d, J=4.9 Hz, 1H), 8.04 (s, 1H), 8.28-8.50 (m, 1H).

Compound 166. ¹H NMR (500 MHz, DMSO-d6) δ ppm 3.64 (s, 3H), 3.69 (s, 3H), 6.20 (dd, J=8.4, 2.5 Hz, 1H), 6.38 (d, J=2.5 Hz, 1H), 6.70 (d, J=8.4 Hz, 1H), 6.93 (d, J=8.9 Hz, 1H), 10.65 (s, 1H).

Compound 167. ¹H NMR (500 MHz, CDCl₃) δ ppm 7.42 (d, J=8.4 Hz, 1H), 7.77 (dd, J=8.7, 2.2 Hz, 1H), 7.94 (d, J=2.5 Hz, 1H).

Compound 168. ¹H NMR (500 MHz, CDCl₃) δ ppm 7.01-7.14 (m, 1H), 7.32-7.38 (m, 1H), 7.41 (t, J=7.9 Hz, 1H), 7.81 (d, J=7.9 Hz, 1H), 8.00 (s, 1H), 10.07 (s, 1H).

Compound 169. ¹H NMR (500 MHz, DMSO-d6) δ ppm 6.49-6.64 (m, 1H), 6.75-6.95 (m, 1H), 7.22 (t, J=8.9 Hz, 1H), 7.65 (dd, J=8.9, 4.9 Hz, 1H).

Compound 172. ¹H NMR (500 MHz, CDCl₃) δ ppm 1.14-1.37 (m, 3H), 1.37-1.59 (m, 2H), 1.62-1.71 (m, 1H), 1.71-1.91 (m, 2H), 1.98-2.06 (m, 1H), 2.10 (d, J=9.9 Hz, 1H), 7.92 (br. s, 1H).

Compound 173. ¹H NMR (500 MHz, DMSO-d6) δ ppm 0.87 (d, J=6.4 Hz, 2H), 0.90-1.12 (m, 2H), 1.40-1.64 (m, 2H), 1.68-1.77 (m, 1H), 1.77-1.97 (m, 2H), 1.97-2.08 (m, 1H), 2.64-2.87 (m, 1H), 2.99-3.20 (m, 1H), 7.65-7.77 (m, 2H), 8.29 (d, J=8.4 Hz, 1H), 9.09 (d, J=3.0 Hz, 1H), 11.05 (br. s, 1H), 12.09 (br. s, 1H).

Compound 174. ¹H NMR (500 MHz, DMSO-d6) δ ppm 0.78-1.01 (m, 3H), 1.07-1.31 (m, 1H), 1.36-1.60 (m, 3H), 1.62-1.75 (m, 1H), 1.75-1.94 (m, 2H), 2.00 (dd, J=13.4, 3.0 Hz, 1H), 2.56-2.75 (m, 1H), 7.06 (dd, J=6.9, 4.9 Hz, 1H), 7.74 (t, J=7.9 Hz, 1H), 8.03 (d, J=8.4 Hz, 1H), 8.29 (d, J=3.0 Hz, 1H), 10.03-10.16 (m, 1H), 11.97 (br. s, 1H).

Compound 175. ¹H NMR (500 MHz, DMSO-d6) δ ppm 0.82-1.02 (m, 4H), 1.35-1.53 (m, 1H), 1.53-1.68 (m, 2H), 1.72 (dd, J=12.6, 2.7 Hz, 1H), 1.76-1.89 (m, 1H), 2.00 (d, J=13.4 Hz, 1H), 2.16 (d, J=9.9 Hz, 7H), 2.94-3.17 (m, 1H), 7.01 (d, J=8.4 Hz, 1H), 7.27 (d, J=7.9 Hz, 1H), 7.38 (br. s, 1H), 9.38 (d, J=4.0 Hz, 1H), 11.93 (br. s, 1H).

Compound 176. ¹H NMR (500 MHz, DMSO-d6) δ ppm 0.79-1.02 (m, 6H), 1.41-1.65 (m, 3H), 1.77-1.96 (m, 3H), 2.01 (d, J=12.9 Hz, 1H), 3.06 (d, J=4.5 Hz, 1H), 7.08 (d, J=8.9 Hz, 2H), 7.41 (d, J=8.4 Hz, 1H), 7.77 (br. s, 1H), 9.53 (d, J=5.9 Hz, 1H), 11.98 (br. s, 1H).

Compound 177. ¹H NMR (500 MHz, DMSO-d6) δ ppm 0.80-1.04 (m, 4H), 1.48 (d, J=2.0 Hz, 2H), 1.53-1.77 (m, 3H), 1.85 (dd, J=16.6, 13.1 Hz, 1H), 1.94-2.08 (m, 1H), 3.04-3.16 (m, 1H), 6.92-7.06 (m, 3H), 7.09 (t, J=7.4 Hz, 1H), 7.36 (t, J=7.9 Hz, 2H), 7.60 (d, J=8.9 Hz, 2H), 9.57 (d, J=4.0 Hz, 1H), 11.98 (br. s, 1H).

Compound 178. ¹H NMR (500 MHz, DMSO-d6) δ ppm 0.79-1.03 (m, 4H), 1.13 (d, J=12.9 Hz, 1H), 1.41-1.52 (m, 1H), 1.53-1.68 (m, 2H), 1.80-1.91 (m, 1H), 1.91-2.07 (m, 2H), 2.99-3.11 (m, 1H), 4.43 (br. s, 2H), 5.09 (br. s, 1H), 7.23 (m, 2H), 7.55 (m, 2H), 9.50 (s, 1H), 11.97 (br. s, 1H).

Compound 179. ¹H NMR (500 MHz, DMSO-d6) δ ppm 0.78-0.97 (m, 4H), 1.58 (d, J=12.4 Hz, 2H), 1.77-1.94 (m, 2H), 2.01 (d, J=13.4 Hz, 1H), 2.30 (s, 4H), 2.93-3.12 (m, 1H), 7.28-7.41 (m, 1H), 7.46 (d, J=8.9 Hz, 1H), 7.53-7.73 (m, 1H), 9.60 (d, J=6.9 Hz, 1H), 11.97 (br. s, 1H).

Compound 180. ¹H NMR (500 MHz, DMSO-d6) δ ppm 0.80-0.97 (m, 5H), 1.26 (d, J=5.9 Hz, 8H), 1.59 (s, 2H), 2.00 (d, J=2.0 Hz, 3H), 3.05 (br. s, 1H), 4.41-4.62 (m, 1H), 6.56 (dd, J=7.9, 2.5 Hz, 1H), 7.00-7.22 (m, 2H), 9.48 (d, J=3.5 Hz, 1H), 11.95 (s, 1H).

Compound 181. ¹H NMR (500 MHz, DMSO-d6) δ ppm 0.79-1.02 (m, 6H), 1.12-1.25 (m, 6H), 1.48 (br. s, 1H), 1.53-1.76 (m, 2H), 1.76-1.94 (m, 1H), 1.94-2.09 (m, 1H), 2.97-3.10 (m, 1H), 3.13 (s, 1H), 3.17 (s, 1H), 3.94 (dq, J=7.4, 7.3

Hz, 4H), 7.17 (dd, J=8.7, 2.2 Hz, 2H), 7.51 (d, J=8.4 Hz, 2H), 9.52 (d, J=3.5 Hz, 1H), 11.95 (br. s, 1H).

Compound 182. $^1$H NMR (500 MHz, DMSO-d6) δ ppm 0.87 (d, J=4.9 Hz, 3H), 0.90-1.06 (m, 2H), 1.41-1.65 (m, 3H), 1.72 (d, J=10.9 Hz, 1H), 1.79-1.96 (m, 2H), 2.01 (d, J=12.9 Hz, 1H), 3.06 (d, J=4.0 Hz, 1H), 5.16 (s, 2H), 7.17 (d, J=7.4 Hz, 1H), 7.29-7.52 (m, 5H), 7.80 (d, J=2.0 Hz, 1H), 9.54 (d, J=4.5 Hz, 1H), 11.98 (br. s, 1H).

Compound 184. $^1$H NMR (500 MHz, DMSO-d6) δ ppm 0.83-1.06 (m, 6H), 1.06-1.19 (m, 1H), 1.41-1.52 (m, 1H), 1.54-1.69 (m, 2H), 1.77-1.98 (m, 1H), 1.98-2.05 (m, 1H), 3.07 (d, J=4.0 Hz, 1H), 4.46 (br. s, 2H), 6.96 (d, J=7.4 Hz, 1H), 7.21 (t, J=7.7 Hz, 1H), 7.46 (d, J=6.9 Hz, 1H), 7.59 (br. s, 1H), 9.48-9.58 (m, 1H), 11.94 (br. s, 1H).

Compound 185. $^1$H NMR (500 MHz, DMSO-d6) δ ppm 0.79-1.03 (m, 6H), 1.18-1.34 (m, 8H), 1.34-1.51 (m, 4H), 1.53-1.75 (m, 5H), 1.76-1.90 (m, 1H), 1.90-2.11 (m, 2H), 2.94-3.14 (m, 1H), 3.90 (t, J=6.7 Hz, 2H), 6.83 (m, J=8.9 Hz, 2H), 7.45 (m, J=8.9 Hz, 2H), 9.38 (s, 1H), 11.95 (br. s, 1H).

Compound 186. $^1$H NMR (500 MHz, DMSO-d6) δ ppm 0.80-0.97 (m, 5H), 1.48 (br. s, 2H), 1.51-1.67 (m, 2H), 1.79-1.96 (m, 2H), 2.02 (dd, J=13.4, 3.0 Hz, 1H), 2.26 (s, 3H), 2.97-3.18 (m, 1H), 7.24 (d, J=8.4 Hz, 1H), 7.35 (ddd, J=8.2, 2.5, 2.2 Hz, 1H), 7.68-7.87 (m, 1H), 9.62 (d, J=6.4 Hz, 1H), 11.98 (br. s, 1H).

Compound 187. $^1$H NMR (500 MHz, CDCl$_3$) δ ppm 0.85-1.09 (m, 6H), 1.33-1.45 (m, 8H), 1.52 (br. s, 2H), 1.61 (d, J=11.9 Hz, 1H), 1.75 (d, J=12.4 Hz, 1H), 1.91-2.08 (m, 1H), 2.18-2.37 (m, 1H), 3.36 (d, J=13.9 Hz, 1H), 4.59 (ddd, J=12.2, 6.1, 5.9 Hz, 1H), 8.15 (br. s, 1H).

Compound 188. $^1$H NMR (500 MHz, DMSO-d6) δ ppm 0.82-1.03 (m, 4H), 1.48 (br. s, 1H), 1.52-1.76 (m, 2H), 1.81-1.96 (m, 1H), 1.97-2.09 (m, 1H), 2.28 (s, 3H), 2.94-3.16 (m, 1H), 7.30 (d, J=8.9 Hz, 1H), 7.39-7.53 (m, 1H), 7.53-7.71 (m, 1H), 9.59 (d, J=6.9 Hz, 1H), 11.96 (br. s, 1H).

Compound 189. $^1$H NMR (500 MHz, CDCl$_3$) δ ppm 0.86-1.04 (m, 7H), 1.13-1.25 (m, 5H), 1.43-1.66 (m, 4H), 1.84 (br. s, 2H), 1.87-1.99 (m, 1H), 2.35-2.56 (m, 1H), 3.63-3.87 (m, 3H).

Compound 190. $^1$H NMR (500 MHz, DMSO-d6) δ ppm 0.81-0.93 (m, 5H), 0.95-1.05 (m, 5H), 1.34-1.58 (m, 4H), 1.69 (d, J=11.9 Hz, 3H), 1.98 (br. s, 2H), 3.26-3.37 (m, 1H), 3.37-3.44 (m, 1H), 3.54-3.68 (m, 1H), 3.87 (ddd, J=6.2, 3.0, 2.7 Hz, 1H).

Compound 195. $^1$H NMR (500 MHz, DMSO-d6) δ ppm 1.03-1.27 (m, 4H), 1.55 (d, J=11.9 Hz, 1H), 1.59-1.73 (m, 2H), 1.73-1.94 (m, 2H), 8.13 (br. s, 2H).

Compound 196. $^1$H NMR (500 MHz, DMSO-d6) δ ppm 7.20 (t, J=7.9 Hz, 1H), 7.51 (d, J=7.9 Hz, 1H), 7.62 (t, J=7.9 Hz, 1H), 7.76 (d, J=7.9 Hz, 1H), 8.11 (s, 1H), 11.10 (s, 1H).

Compound 199. $^1$H NMR (500 MHz, DMSO-d6) δ ppm 6.57 (dd, J=8.7, 4.7 Hz, 2H), 6.85 (t, J=8.9 Hz, 2H).

Compound 201. $^1$H NMR (500 MHz, DMSO-d6) δ ppm 7.80 (br. s, 2H), 7.92 (br. s, 1H), 7.98 (br. s, 1H).

Compound 202. $^1$H NMR (500 MHz, DMSO-d6) δ ppm 3.64 (s, 3H), 3.68 (s, 4H), 6.23 (dd, J=8.4, 2.5 Hz, 1H), 6.40 (d, J=2.5 Hz, 1H), 6.71 (d, J=8.4 Hz, 1H), 10.65 (br. s, 1H).

Compound 211. $^1$H NMR (500 MHz, DMSO-d6) δ ppm 1.31 (d, J=5.9 Hz, 6H), 4.48-4.67 (m, 1H), 7.50 (s, 1'-1).

Compound 216. $^1$H NMR (500 MHz, DMSO-d6) δ ppm 0.79-0.96 (m, 8H), 1.78 (dd, J=13.4, 6.9 Hz, 1H), 2.52 (d, J=7.4 Hz, 1H), 2.93 (t, J=6.2 Hz, 2H), 8.12 (br. s, 2H).

Compound 218. $^1$H NMR (500 MHz, DMSO-d6) δ ppm 7.61 (d, J=8.4 Hz, 1H), 7.81 (d, J=2.0 Hz, 1H), 7.84 (d, J=8.9 Hz, 1H), 11.08 (s, 1H).

Compound 222. $^1$H NMR (300 MHz, DMSO-d6) δ ppm 6.65 (d, J=8.8 Hz, 2H), 6.74-6.91 (m, 3H), 6.94-7.18 (m, 3H), 7.30 (t, J=8.0 Hz, 1H), 7.37 (t, J=7.6 Hz, 1H), 7.63 (d, J=8.8 Hz, 1H).

Compound 223. $^1$H NMR (300 MHz, DMSO-d6) δ ppm 4.46 (s, 2H), 7.29 (m, J=8.1 Hz, 2H), 7.55 (m, J=8.6 Hz, 2H), 10.64 (s, 1H).

Compound 223Na. $^1$H NMR (500 MHz, DMSO-d6) δ ppm 4.44 (s, 2H), 7.23 (m, J=8.4 Hz, 2H), 7.58 (m, J=8.4 Hz, 2H), 10.34 (s, 1H).

Compound 226. $^1$H NMR (500 MHz, DMSO-d6) δ ppm 1.21 (t, J=6.9 Hz, 6H), 3.31 (s, 2H), 3.36 (s, 2H), 4.00 (qd, J=7.3, 7.2 Hz, 4H), 7.34-7.40 (m, 2H), 7.44 (d, J=6.4 Hz, 2H).

Compound 227. $^1$H NMR (500 MHz, DMSO-d6) δ ppm 5.00 (s, 2H), 6.55 (dd, J=8.7, 2.7 Hz, 1H), 6.93 (d, J=8.9 Hz, 1H), 7.30 (d, J=7.4 Hz, 1H), 7.36 (t, J=7.4 Hz, 2H), 7.38-7.47 (m, 2H).

Compound 232. $^1$H NMR (300 MHz, DMSO-d6) δ ppm 2.16 (s, 3H), 6.41 (d, J=7.5 Hz, 1H), 6.51 (br. s, 1H), 6.99 (d, J=8.3 Hz, 1H).

Compound 236. $^1$H NMR (500 MHz, DMSO-d6) δ ppm 2.65-2.84 (m, 2H), 3.29-3.40 (m, 2H), 3.42-3.54 (m, 2H), 7.13-7.23 (m, 1H), 7.30-7.37 (m, 2H), 8.07 (br. s, 2H), 8.17 (d, J=8.9 Hz, 1H).

Compound 237. $^1$H NMR (500 MHz, DMSO-d6) δ ppm 3.01-3.13 (m, 1H), 3.45 (d, J=11.4 Hz, 2H), 3.94 (t, J=10.9 Hz, 1H), 4.28 (td, J=9.6, 4.0 Hz, 1H), 5.14 (d, J=9.4 Hz, 1H), 7.67-7.76 (m, 3H), 8.27 (d, J=8.4 Hz, 2H).

Compound 238. $^1$H NMR (500 MHz, DMSO-d6) δ ppm 2.90 (s, 1H), 3.07 (dd, J=11.4, 4.0 Hz, 1H), 3.18-3.30 (m, 1H), 3.47 (d, J=3.5 Hz, 1H), 3.95 (t, J=10.9 Hz, 1H), 4.22-4.34 (m, 1H), 5.14 (d, J=9.4 Hz, 1H), 7.68-7.76 (m, 2H), 8.27 (d, J=8.4 Hz, 2H).

Compound 239. $^1$H NMR (500 MHz, DMSO-d6) δ ppm 5.20 (s, 2H), 7.24 (d, J=8.8 Hz, 1H), 7.30-7.37 (m, 1H), 7.37-7.45 (m, 3H), 7.45-7.53 (m, 2H), 7.78 (d, J=2.0 Hz, 1H), 10.74 (s, 1H).

Compound 243. $^1$H NMR (300 MHz, DMSO-d6) δ ppm 1.60 (br. s, 8H), 2.48 (d, J=2.5 Hz, 4H), 5.15 (s, 2H), 7.16 (d, J=9.1 Hz, 1H), 7.27-7.58 (m, 6H), 7.82 (d, J=1.9 Hz, 1H), 9.87 (s, 1H), 11.98 (br. s, 1H).

Compound 246. $^1$H NMR (500 MHz, DMSO-d6) δ ppm 1.54-1.70 (m, 8H), 2.47 (s, 2H), 2.55 (s, 2H), 7.61 (d, J=8.8 Hz, 1H), 7.81 (dd, J=8.8, 2.4 Hz, 1H), 8.19 (d, J=2.4 Hz, 1H), 10.28 (s, 1H), 11.99 (br. s, 1H).

Compound 251. $^1$H NMR (500 MHz, DMSO-d6) δ ppm 5.20 (s, 3H), 7.25 (d, J=9.4 Hz, 1H), 7.33 (t, J=7.2 Hz, 1H), 7.40 (t, J=7.4 Hz, 3H), 7.45-7.47 (m, 2H), 7.80 (d, J=2.5 Hz, 1H), 10.84 (s, 1H).

Compound 252. $^1$H NMR (500 MHz, DMSO-d6) δ ppm 6.96 (d, J=8.4 Hz, 1H), 7.26 (dd, J=8.9, 2.5 Hz, 1H), 7.70 (d, J=2.5 Hz, 1H), 10.11 (br. s, 1H), 10.62 (s, 1H).

Compound 253. $^1$H NMR (500 MHz, DMSO-d6) δ ppm 5.20 (s, 2H), 7.25 (d, J=9.4 Hz, 1H), 7.34 (d, J=6.9 Hz, 1H), 7.40 (t, J=7.4 Hz, 3H), 7.43-7.49 (m, 2H), 7.80 (d, J=2.5 Hz, 1H), 10.84 (s, 1H).

Compound 254. $^1$H NMR (500 MHz, DMSO-d6) δ ppm 4.45 (s, 2H), 7.22 (m, J=8.4 Hz, 2H), 7.53 (m, J=8.4 Hz, 2H), 10.82 (br. s, 1H).

Compound 255. $^1$H NMR (500 MHz, DMSO-d6) δ ppm 7.42 (ddd, J=16.2, 8.0, 7.9 Hz, 2H), 7.83 (d, J=7.9 Hz, 1H), 8.04 (s, 1H), 11.36 (br. s, 1H).

Compound 257. $^1$H NMR (500 MHz, DMSO-d6) δ ppm 2.33 (s, 3H), 7.36-7.51 (m, 2H), 7.63 (d, J=2.5 Hz, 1H), 10.87 (s, 1H).

Compound 258. ¹H NMR (500 MHz, DMSO-d6) δ ppm 7.68-7.78 (m, 1H), 7.83 (dd, J=8.7, 2.2 Hz, 1H), 8.20 (d, J=2.5 Hz, 1H), 11.32 (s, 1H).

Compound 259. ¹H NMR (500 MHz, DMSO-d6) δ ppm 2.99-3.04 (m, 4H), 7.00 (d, J=9.4 Hz, 1H), 7.31 (t, J=8.2 Hz, 1H), 7.40 (d, J=8.4 Hz, 1H), 7.54 (s, 1H), 9.86 (s, 1H), 10.87 (s, 1H).

Compound 261. ¹H NMR (500 MHz, DMSO-d6) δ ppm 6.93 (d, J=6.4 Hz, 1H), 7.23 (br. s, 1H), 7.73 (br. s, 1H), 10.80 (br. s, 1H).

Compound 262. ¹H NMR (500 MHz, DMSO-d6) δ ppm 4.49 (s, 2H), 7.06 (d, J=7.4 Hz, 1H), 7.22 (t, J=7.9 Hz, 1H), 7.40 (d, J=7.9 Hz, 1H), 7.70 (s, 1H), 10.90 (s, 1H).

Compound 263. ¹H NMR (500 MHz, DMSO-d6) δ ppm 1.19 (t, J=6.9 Hz, 6H), 3.18 (s, 1H), 3.22 (s, 1H), 3.96 (quin, J=7.4 Hz, 4H), 7.26 (dd, J=8.4, 2.5 Hz, 2H), 7.54 (d, J=8.4 Hz, 2H), 10.77 (s, 1H).

Compound 264. ¹H NMR (500 MHz, DMSO-d6) δ ppm 3.74 (d, J=2.5 Hz, 7H), 6.94 (d, J=8.4 Hz, 1H), 7.11 (d, J=2.5 Hz, 1H), 7.31 (d, J=2.5 Hz, 1H), 10.63 (s, 1H).

Compound 265. ¹H NMR (500 MHz, DMSO-d6) δ ppm 0.81-0.91 (m, 3H), 1.15-1.36 (m, 9H), 1.36-1.51 (m, 2H), 1.60-1.76 (m, 2H), 3.90 (t, J=6.7 Hz, 2H), 6.83 (m, J=8.9 Hz, 2H), 7.53 (m, J=8.9 Hz, 2H), 10.47 (br. s, 1H).

Compound 267. ¹H NMR (500 MHz, DMSO-d6) δ ppm 4.25 (d, J=6.9 Hz, 1H), 4.32-4.44 (m, 1H), 4.49 (dd, J=8.2, 4.2 Hz, 1H), 5.22 (br. s, 1H), 7.73 (d, J=8.9 Hz, 2H), 8.07 (d, J=8.9 Hz, 2H), 8.49 (d, J=8.9 Hz, 1H).

Compound 268. ¹H NMR (500 MHz, DMSO-d6) δ ppm 6.69-6.79 (m, 1H), 7.05 (d, J=7.9 Hz, 2H), 7.16 (t, J=7.2 Hz, 1H), 7.23-7.32 (m, 2H), 7.40 (t, J=8.2 Hz, 2H), 10.92 (br. s, 1H).

Compound 269. ¹H NMR (300 MHz, DMSO-d6) δ ppm 7.76-7.88 (m, 2H), 7.88-8.08 (m, 2H).

Compound 270. ¹H NMR (500 MHz, DMSO-d6) δ ppm 0.82-0.93 (m, 3H), 1.19-1.37 (m, 8H), 1.37-1.52 (m, 2H), 1.59-1.80 (m, 2H), 3.94 (t, J=6.4 Hz, 2H), 6.90 (d, J=8.9 Hz, 2H), 7.47-7.68 (m, 5H), 7.87 (d, J=7.9 Hz, 1H), 10.19 (s, 1H), 13.02 (br. s, 1H).

Compound 271. ¹H NMR (500 MHz, DMSO-d6) δ ppm 0.74-0.95 (m, 3H), 1.18-1.35 (m, 9H), 1.35-1.54 (m, 2H), 1.60-1.82 (m, 2H), 3.92 (t, J=6.4 Hz, 2H), 6.89 (m, J=8.9 Hz, 2H), 7.51 (m, J=8.9 Hz, 2H), 10.63 (s, 1H).

Compound 272. ¹H NMR (500 MHz, DMSO-d6) δ ppm 5.20 (s, 2H), 7.22 (d, J=8.9 Hz, 1H), 7.31-7.38 (m, 1H), 7.42 (t, J=7.7 Hz, 3H), 7.46-7.54 (m, 4H), 7.54-7.65 (m, 3H), 7.84 (d, J=7.4 Hz, 1H), 7.92 (d, J=2.5 Hz, 1H).

Compound 273. ¹H NMR (500 MHz, DMSO-d6) δ ppm 7.85 (d, J=8.9 Hz, 2H), 8.11 (d, J=8.4 Hz, 2H), 11.40 (br. s, 1H).

Compound 274. ¹H NMR (500 MHz, DMSO-d6) δ ppm 0.80-0.96 (m, 3H), 1.20-1.35 (m, 9H), 1.35-1.52 (m, 2H), 1.59-1.80 (m, 2H), 3.90 (t, J=6.4 Hz, 2H), 6.82 (d, J=8.9 Hz, 2H), 7.54 (m, J=8.9 Hz, 2H), 10.40 (br. s, 1H). ¹³C NMR (126 MHz, DMSO-d6) δ ppm 14.5, 22.5, 26.0, 29.2, 29.3, 31.8, 68.3, 115.7, 123.4, 126.4, 127.9, 135.5, 155.4, 157.2.

Compound 275. ¹H NMR (500 MHz, DMSO-d6) δ ppm 0.92 (t, J=7.1 Hz, 3H), 1.23-1.46 (m, 4H), 1.62-1.82 (m, 2H), 3.95 (t, J=6.5 Hz, 2H), 6.92 (d, J=9.2 Hz, 2H), 7.49-7.59 (m, 2H), 7.59-7.71 (m, 3H), 7.90 (d, J=7.8 Hz, 1H), 10.22 (s, 1H).

Compound 277-1. ¹H NMR (500 MHz, CDCl₃) δ ppm 5.18 (s, 2H), 6.98-7.06 (m, 1H), 7.17-7.24 (m, 2H), 7.32 (d, J=7.2 Hz, 1H), 7.34-7.40 (m, 2H), 7.42-7.48 (m, 2H).

Compound 277-2. ¹H NMR (500 MHz, DMSO-d6) δ ppm 5.26 (s, 2H), 7.10 (dd, J=8.8, 2.6 Hz, 1H), 7.27 (d, J=2.6 Hz, 1H), 7.35-7.40 (m, 2H), 7.40-7.46 (m, 2H), 7.46-7.53 (m, 2H).

Compound 278. ¹H NMR (500 MHz, DMSO-d6) δ ppm 5.16 (br. s, 2H), 7.12 (d, J=8.6 Hz, 1H), 7.33 (d, J=6.8 Hz, 2H), 7.36-7.42 (m, 3H), 7.45 (d, J=7.0 Hz, 2H), 7.91 (br. s, 1H), 10.71 (br. s, 1H).

Compound 279-2. ¹H NMR (500 MHz, METHANOL-d4) δ ppm 0.94 (t, J=6.7 Hz, 3H), 1.26-1.45 (m, 8H), 1.50 (d, J=7.6 Hz, 2H), 1.73-1.86 (m, 2H), 3.98 (t, J=6.4 Hz, 2H), 6.90 (d, J=8.8 Hz, 2H), 7.46-7.70 (m, 5H), 7.87 (d, J=6.8 Hz, 1H).

Compound 280-2. ¹H NMR (500 MHz, METHANOL-d4) δ ppm 0.89 (t, J=6.6 Hz, 3H), 1.24-1.38 (m, 9H), 1.44 (d, J=7.8 Hz, 3H), 1.68-1.79 (m, 2H), 3.92 (t, J=6.4 Hz, 2H), 6.84 (d, J=8.8 Hz, 2H), 7.49 (d, J=8.6 Hz, 2H).

Compound 281. ¹H NMR (500 MHz, DMSO-d6) δ ppm 0.79-0.92 (m, 3H), 1.22-1.35 (m, 8H), 1.41 (d, J=7.6 Hz, 2H), 1.65-1.77 (m, 2H), 3.99 (t, J=6.5 Hz, 2H), 7.06 (m, 4H).

Compound 282. ¹H NMR (300 MHz, CDCl₃) δ ppm 0.78-0.99 (m, 3H), 1.23-1.38 (m, 10H), 1.42 (dd, J=14.6, 6.8 Hz, 2H), 1.68-1.89 (m, 3H), 3.42 (s, 3H), 3.84-3.95 (m, 2H), 6.74 (m, J=9.0 Hz, 2H), 7.29 (m, 2H).

Compound 288. ¹H NMR (300 MHz, acetone-d6) δ ppm 0.78-0.99 (m, 3H), 1.27 (br. s, 23H), 1.40-1.61 (m, 2H), 1.68-1.88 (m, 2H), 1.96-2.13 (m, 2H), 3.96 (t, J=6.6 Hz, 2H), 6.88 (d, J=9.0 Hz, 2H), 7.44-7.77 (m, 4H), 7.92 (d, J=8.1 Hz, 1H).

Compound 289. ¹H NMR (300 MHz, acetone-d6) δ ppm 0.72-0.98 (m, 2H), 1.27 (br. s, 24H), 1.41 (br. s, 2H), 1.42-1.63 (m, 2H), 1.64-1.93 (m, 2H), 1.98-2.21 (m, 1H), 3.96 (t, J=6.6 Hz, 2H), 6.89 (d, J=9.0 Hz, 2H), 7.58 (d, J=9.0 Hz, 2H).

Compound 290. ¹H NMR (300 MHz, DMSO-d6) δ ppm 0.75-0.92 (m, 3H), 1.08-1.47 (m, 25H), 1.66 (br. s, 2H), 3.36 (br. s, 2H), 3.85 (br. s, 2H), 6.75 (m, J=7.9 Hz, 2H), 7.51 (m, J=7.9 Hz, 2H), 10.54 (br. s, 1H).

Compound 291. ¹H NMR (300 MHz, acetone) δ ppm 0.77-0.95 (m, 3H), 1.27 (br. s, 25H), 1.69-1.84 (m, 2H), 1.96-2.10 (m, 3H), 3.97 (t, J=6.6 Hz, 2H), 6.84-6.96 (m, 2H), 7.50-7.66 (m, 2H).

Compound 293. ¹H NMR (300 MHz, acetone) δ ppm 0.80-0.99 (m, 3H), 1.21-1.45 (m, 8H), 1.45-1.63 (m, 2H), 1.79-1.96 (m, 2H), 4.25 (t, J=6.6 Hz, 2H), 7.30 (d, J=9.0 Hz, 1H), 8.12-8.28 (m, 1H).

Compound 295. ¹H NMR (300 MHz, acetone) δ ppm 3.23 (s, 3H), 5.10 (s, 2H), 6.73-6.94 (m, 3H), 7.12 (d, J=9.0 Hz, 2H), 7.21-7.45 (m, 4H).

Compound 297. ¹H NMR (500 MHz, CDCl₃) δ ppm 0.83-0.98 (m, 3H), 1.24-1.43 (m, 8H), 1.43-1.56 (m, 2H), 1.72-1.90 (m, 2H), 3.30 (s, 3H), 3.96 (t, J=6.6 Hz, 2H), 5.18 (br. s, 2H), 6.80-7.00 (m, 2H), 7.16 (br. s, 2H), 7.33 (d, J=13.8 Hz, 4H).

Compound 298. ¹H NMR (300 MHz, CDCl₃) δ ppm 0.75-0.91 (m, 3H), 1.26 (d, J=2.4 Hz, 10H), 1.59-1.83 (m, 2H), 3.82 (t, J=6.3 Hz, 2H), 6.75 (m, J=8.5 Hz, 2H), 7.34 (m, J=8.5 Hz, 2H), 10.19 (br. s, 1H).

Compound 299. ¹H NMR (500 MHz, CDCl₃) δ ppm 0.84-0.95 (m, 3H), 1.28-1.37 (m, 8H), 1.44-1.53 (m, 2H), 1.73-1.85 (m, 2H), 3.47 (br. s, 2H), 3.93 (t, J=6.6 Hz, 2H), 6.53 (dd, J=8.6, 2.8 Hz, 1H), 6.71-6.82 (m, 2H).

Compound 300. ¹H NMR (500 MHz, DMSO-d6) δ ppm 0.84-0.89 (m, 3H), 1.22-1.37 (m, 8H), 1.38-1.47 (m, 2H), 1.67-1.76 (m, 2H), 4.01 (t, J=6.4 Hz, 2H), 7.12 (d, J=9.0 Hz, 1H), 7.49 (dd, J=8.9, 2.5 Hz, 1H), 7.51-7.55 (m, 1H), 7.57 (td, J=7.6, 1.2 Hz, 1H), 7.63-7.68 (m, 1H), 7.79-7.96 (m, 2H), 10.32 (s, 1H).

Compound 301. ¹H NMR (500 MHz, DMSO-d6) δ ppm 0.80-0.92 (m, 3H), 1.19-1.38 (m, 8H), 1.38-1.50 (m, 2H), 1.63-1.81 (m, 2H), 4.03 (t, J=6.4 Hz, 2H), 7.15 (d, J=9.0 Hz, 1H), 7.42 (dd, J=8.9, 2.5 Hz, 1H), 7.78 (d, J=2.4 Hz, 1H), 10.82 (s, 1H).

Compound 302. $^1$H NMR (500 MHz, DMSO-d6) δ ppm 0.85 (td, J=6.9, 1.7 Hz, 3H), 1.16-1.37 (m, 8H), 1.37-1.52 (m, 2H), 1.63-1.84 (m, 3H), 4.03 (t, J=6.4 Hz, 2H), 7.15 (d, J=9.0 Hz, 1H), 7.40 (dd, J=8.8, 2.6 Hz, 1H), 7.76 (d, J=2.4 Hz, 1H), 10.80 (s, 1H).

Compound 303. $^1$H NMR (500 MHz, DMSO-d6) δ ppm 0.78-0.92 (m, 3H), 1.17-1.36 (m, 3H), 1.36-1.52 (m, 2H), 1.62-1.79 (m, 3H), 4.02 (t, J=6.4 Hz, 2H), 7.15 (d, J=9.0 Hz, 1H), 7.39 (dd, J=9.0, 2.4 Hz, 1H), 7.75 (d, J=2.4 Hz, 1H), 10.71 (s, 1H).

Compound 304. $^1$H NMR (500 MHz, DMSO-d6) δ ppm 0.78-0.88 (m, 4H), 1.21-1.28 (m, 9H), 1.31 (d, J=7.2 Hz, 3H), 1.57-1.64 (m, 2H), 3.80 (t, J=6.5 Hz, 2H), 6.70 (d, J=8.8 Hz, 2H), 7.08-7.19 (m, 3H), 7.22-7.31 (m, 1H), 7.35 (dd, J=7.6, 1.2 Hz, 1H), 7.68 (d, J=7.8 Hz, 1H).

Compound 305. $^1$H NMR (500 MHz, DMSO-d6) δ ppm 0.80-0.95 (m, 3H), 1.18-1.28 (m, 10H), 1.28-1.39 (m, 3H), 1.58-1.70 (m, 2H), 3.86 (t, J=6.5 Hz, 2H), 6.81 (m, 2H), 7.25 (m, 2H).

Compound 306. $^1$H NMR (500 MHz, CDCl$_3$) δ ppm 0.86-0.97 (m, 3H), 1.22-1.38 (m, 11H), 1.38-1.51 (m, 3H), 1.68-1.84 (m, 2H), 3.82-3.95 (m, 2H), 6.72 (d, J=8.6 Hz, 1H), 7.29 (d, J=7.8 Hz, 1H), 7.36 (d, J=8.6 Hz, 1H).

Compound 307. $^1$H NMR (500 MHz, CDCl$_3$) δ ppm 0.91 (q, J=6.7 Hz, 3H), 1.23-1.39 (m, 9H), 1.39-1.52 (m, 2H), 1.69-1.85 (m, 2H), 2.98 (s, 1H), 3.91 (t, J=6.6 Hz, 2H), 6.74 (t, J=9.5 Hz, 2H), 7.20 (d, J=8.6 Hz, 1H), 7.27-7.35 (m, 1H), 7.43 (d, 1H).

Compound 308. $^1$H NMR (500 MHz, CDCl$_3$) δ ppm 0.92 (dd, J=4.7, 1.7 Hz, 3H), 1.23-1.42 (m, 9H), 1.46 (d, J=6.0 Hz, 2H), 1.67-1.85 (m, 2H), 2.82 (d, J=5.6 Hz, 3H), 3.91 (td, J=6.6, 2.0 Hz, 2H), 6.53-6.67 (m, 2H), 6.75-6.90 (m, 2H).

Compound 310. $^1$H NMR (500 MHz, CDCl$_3$) δ ppm 0.79-0.95 (m, 3H), 1.17-1.40 (m, 12H), 1.41-1.60 (m, 2H), 1.76-1.93 (m, 2H), 4.04 (t, J=6.5 Hz, 2H), 6.82-6.99 (m, 2H), 8.09-8.25 (m, 2H).

Compound 311. $^1$H NMR (500 MHz, CDCl$_3$) δ ppm 0.81-0.97 (m, 3H), 1.23-1.38 (m, 13H), 1.38-1.50 (m, 2H), 1.67-1.85 (m, 2H), 3.88 (t, J=6.6 Hz, 2H), 6.61-6.71 (m, 2H), 6.71-6.80 (m, 2H).

Compound 312. $^1$H NMR (300 MHz, CDCl$_3$) δ ppm 0.80-0.95 (m, 3H), 1.21-1.43 (m, 13H), 1.43-1.62 (m, 2H), 1.77-2.01 (m, 2H), 4.12 (t, J=6.6 Hz, 2H), 6.96 (d, J=9.0 Hz, 1H), 8.13 (dd, J=9.0, 2.6 Hz, 1H).

Compound 314. $^1$H NMR (300 MHz, CDCl$_3$) δ ppm 0.82-0.99 (m, 3H), 1.20-1.38 (m, 13H), 1.45 (d, J=7.7 Hz, 3H), 1.70-1.89 (m, 2H), 3.29 (s, 3H), 3.95 (t, J=6.6 Hz, 2H), 5.16 (s, 2H), 6.87 (d, J=9.0 Hz, 2H), 7.14 (d, J=8.1 Hz, 2H), 7.31 (br. s, 3H).

Compound 315. $^1$H NMR (300 MHz, CDCl$_3$) δ ppm 0.79-1.01 (m, 3H), 1.29 (br. s, 11H), 1.35-1.53 (m, 4H), 1.68-1.87 (m, 2H), 2.81 (s, 3H), 3.90 (t, J=6.4 Hz, 2H), 6.58 (m, J=9.0 Hz, 2H), 6.81 (m, 2H).

Compound 316. $^1$H NMR (300 MHz, DMSO-d6) δ ppm 0.73-0.89 (m, 3H), 1.10-1.44 (m, 17H), 1.52-1.74 (m, 2H), 3.79 (t, J=6.2 Hz, 2H), 3.92 (t, J=6.4 Hz, 1H), 6.61-6.77 (m, 2H), 6.95 (d, J=9.0 Hz, 1H), 7.41 (d, J=8.6 Hz, 1H).

Compound 317. $^1$H NMR (300 MHz, DMSO-d6) δ ppm 7.38 (d, J=8.1 Hz, 2H), 7.48-7.59 (m, 2H), 7.59-7.67 (m, 2H), 7.71 (d, J=8.6 Hz, 2H), 7.88 (d, J=7.3 Hz, 1H), 10.47 (s, 1H). $^{13}$C NMR (75 MHz, DMSO-d6) δ ppm 121.3, 127.2, 127.9, 128.8, 129.8, 130.0, 132.0, 138.6, 138.8, 167.6, 167.8.

Compound 318. $^1$H NMR (300 MHz, DMSO-d6) δ ppm 0.76-0.93 (m, 6H), 1.23 (br. s, 16H), 1.52-1.72 (m, 4H), 3.80 (t, J=6.4 Hz, 2H), 6.69 (d, J=8.6 Hz, 2H), 7.07-7.20 (m, 2H), 7.20-7.42 (m, 1H).

Compound 319. $^1$H NMR (500 MHz, DMSO-d6) δ ppm 0.82 (t, J=6.7 Hz, 3H), 1.17-1.29 (m, 12H), 1.32 (d, J=8.0 Hz, 2H), 1.57-1.66 (m, 2H), 3.30 (s, 3H), 3.85 (t, J=6.4 Hz, 2H), 6.79 (d, J=9.0 Hz, 2H), 7.23 (d, J=8.6 Hz, 2H).

Compound 324. $^1$H NMR (600 MHz, CDCl$_3$) δ ppm 0.84-0.95 (m, 3H), 1.32-1.44 (m, 2H), 1.65 (dd, J=14.9, 7.1 Hz, 2H), 3.89 (br. s, 1H), 4.14-4.27 (m, 2H), 7.39-7.51 (m, 3H), 7.79-7.93 (m, 2H).

Compound 325. $^1$H NMR (500 MHz, Acetone) δ ppm 1.00 (t, J=7.4 Hz, 3H), 1.44-1.61 (m, 2H), 1.68-1.87 (m, 2H), 4.31 (t, J=6.6 Hz, 3H), 7.11 (td, J=7.6, 1.1 Hz, 1H), 7.62 (ddd, J=8.7, 7.2, 1.6 Hz, 1H), 7.73-7.86 (m, 2H), 7.96-8.05 (m, 2H), 8.11 (dd, J=7.9, 1.7 Hz, 1H), 8.65 (d, J=8.8 Hz, 1H), 9.48 (br. s, 1H), 10.69 (br. s, 1H).

Compound 326. $^1$H NMR (600 MHz, CDCl$_3$) δ ppm 0.95 (t, J=7.3 Hz, 3H), 1.36-1.51 (m, 2H), 1.60-1.77 (m, 2H), 3.27 (s, 3H), 4.24 (t, J=6.6 Hz, 2H), 6.24 (br. s, 1H), 7.21-7.36 (m, 2H), 7.41 (d, J=7.3 Hz, 1H), 7.53 (t, J=7.3 Hz, 1H), 7.68 (t, J=7.6 Hz, 1H), 7.83 (d, J=8.8 Hz, 2H), 8.12 (d, J=7.3 Hz, 1H).

Compound 329. $^1$H NMR (500 MHz, DMSO-d6) δ ppm 0.86 (br. s, 3H), 1.25 (br. s, 13H), 1.65 (br. s, 2H), 3.83 (br. s, 2H), 6.60 (d, J=7.0 Hz, 2H), 6.74 (br. s, 3H)

Compound 331. $^1$H NMR (300 MHz, CDCl$_3$) δ ppm 0.78-1.07 (m, 3H), 1.28-1.55 (m, 2H), 1.58-1.80 (m, 2H), 4.13-4.34 (m, 2H), 7.36-7.58 (m, 3H), 7.65 (d, J=7.7 Hz, 2H), 7.90 (d, J=7.7 Hz, 3H).

Compound 332. $^1$H NMR (300 MHz, CDCl$_3$) δ ppm 0.79-1.05 (m, 3H), 1.26-1.59 (m, 2H), 1.59-1.86 (m, 2H), 4.15-4.35 (m, 2H), 7.63 (d, J=8.6 Hz, 2H), 7.81-8.10 (m, 2H).

Compound 333. $^1$H NMR (300 MHz, CDCl$_3$) δ ppm 0.80-1.00 (m, 3H), 1.31-1.52 (m, 2H), 1.60-1.77 (m, 2H), 3.80 (s, 2H), 4.12-4.34 (m, 2H), 7.61 (m, J=8.6 Hz, 2H), 7.91 (m, J=8.6 Hz, 2H).

Compound 334. $^1$H NMR (300 MHz, CDCl$_3$) δ ppm 0.89 (t, J=7.4 Hz, 3H), 1.30-1.46 (m, 2H), 1.59-1.73 (m, 2H), 3.95 (s, 2H), 4.21 (t, J=6.7 Hz, 2H), 7.59 (m, J=9.1 Hz, 2H), 7.89 (m, J=8.6 Hz, 2H).

Compound 335. $^1$H NMR (300 MHz, CDCl$_3$) δ ppm 2.79 (dd, J=4.8, 2.6 Hz, 2H), 3.36 (dt, J=4.1, 2.9 Hz, 1H), 4.43 (dd, J=11.3, 2.5 Hz, 2H), 6.98 (d, J=9.1 Hz, 1H), 8.07 (dd, J=9.1, 2.8 Hz, 1H), 8.21 (d, J=2.8 Hz, 1H).

Compound 336. $^1$H NMR (600 MHz, CDCl$_3$) δ ppm 0.96 (t, J=7.3 Hz, 3H), 1.39-1.55 (m, 2H), 1.63-1.78 (m, 2H), 3.35 (s, 2H), 4.25 (t, J=6.6 Hz, 4H), 6.65 (d, J=8.3 Hz, 2H), 7.84 (d, J=8.8 Hz, 2H).

Compound 337. $^1$H NMR (300 MHz, CDCl$_3$) δ ppm 0.70-0.93 (m, 7H), 1.29-1.69 (m, 7H), 1.71-1.91 (m, 2H), 2.02-2.21 (m, 1H), 2.35-2.57 (m, 1H), 3.03-3.18 (m, 1H), 3.97 (br. s, 2H), 4.07-4.24 (m, 2H), 7.51 (d, J=7.2 Hz, 2H), 7.85 (d, J=8.1 Hz, 2H).

Compound 338. $^1$H NMR (300 MHz, CDCl$_3$) δ ppm 0.77-0.94 (m, 3H), 1.27 (d, J=7.7 Hz, 8H), 1.33-1.50 (m, 4H), 1.67-1.86 (m, 2H), 4.39 (t, J=6.7 Hz, 2H), 6.78 (d, J=9.1 Hz, 1H), 8.31 (dd, J=9.1, 2.9 Hz, 1H), 9.03 (d, J=2.9 Hz, 1H).

Compound 339. $^1$H NMR (300 MHz, CDCl$_3$) δ ppm 5.53 (s, 2H), 6.92 (d, J=9.1 Hz, 1H), 7.34-7.56 (m, 5H), 8.40 (dd, J=9.1, 2.8 Hz, 1H), 9.13 (d, J=2.5 Hz, 1H).

Compound 340. $^1$H NMR (300 MHz, CDCl$_3$) δ ppm 0.90 (t, J=7.4 Hz, 3H), 1.26-1.46 (m, 2H), 1.48-1.67 (m, 2H), 3.50 (t, J=6.0 Hz, 3H), 3.64 (d, J=4.3 Hz, 3H), 4.13-4.28 (m, 4H), 7.03 (d, J=9.6 Hz, 1H), 8.14 (dd, J=9.1, 2.4 Hz, 1H), 8.28 (d, J=2.4 Hz, 1H).

Compound 341. $^1$H NMR (500 MHz, CDCl$_3$) δ ppm 0.14-0.29 (m, 2H), 0.51-0.63 (m, 2H), 1.00-1.17 (m, 1H), 3.39 (d, J=7.2 Hz, 3H), 3.65-3.77 (m, 3H), 4.19-4.34 (m, 4H), 7.07 (d, J=9.0 Hz, 1H), 8.18 (dd, J=9.3, 2.8 Hz, 1H), 8.32 (d, J=2.8 Hz, 1H).

Compound 342. ¹H NMR (300 MHz, CDCl₃) δ ppm 0.75-0.92 (m, 3H), 1.27 (br. s, 8H), 1.32-1.48 (m, 4H), 1.58-1.86 (m, 3H), 3.78 (br. s, 3H), 4.06-4.27 (m, 2H), 6.50-6.66 (m, 1H), 7.07 (dd, J=8.9, 3.1 Hz, 1H), 7.69 (d, J=2.9 Hz, 1H).

Compound 343. ¹H NMR (300 MHz, DMSO-d6) δ ppm 0.78-0.92 (m, 2H), 1.27 (d, J=3.3 Hz, 9H), 1.59-1.85 (m, 2H), 4.21 (t, J=6.8 Hz, 2H), 6.80 (d, J=8.8 Hz, 1H), 7.49-7.78 (m, 3H), 7.81-8.13 (m, 2H), 8.41 (d, J=2.5 Hz, 1H), 10.32 (s, 1H), 13.00 (br. s, 1H).

Compound 344. ¹H NMR (300 MHz, DMSO-d6) δ ppm 0.75-0.98 (m, 3H), 1.26 (d, J=3.6 Hz, 10H), 1.54-1.87 (m, 2H), 4.21 (t, J=6.6 Hz, 3H), 6.83 (d, J=8.8 Hz, 1H), 7.91 (dd, J=8.8, 2.8 Hz, 1H), 8.35 (d, J=2.8 Hz, 1H), 10.83 (s, 1H).

Compound 345. ¹H NMR (300 MHz, CDCl₃) δ ppm 0.72-0.87 (m, 3H), 1.17-1.32 (m, 9H), 1.36 (d, J=8.3 Hz, 2H), 1.61-1.76 (m, 2H), 4.02 (s, 3H), 4.14 (t, J=6.6 Hz, 2H), 6.69 (d, J=9.1 Hz, 1H), 7.92 (dd, J=9.0, 2.6 Hz, 1H), 8.15 (d, J=2.5 Hz, 1H).

Compound 346. ¹H NMR (300 MHz, DMSO-d6) δ ppm 0.74-0.93 (m, 3H), 1.26 (d, J=3.6 Hz, 11H), 1.56-1.81 (m, 2H), 4.21 (t, J=6.6 Hz, 2H), 6.83 (d, J=8.8 Hz, 1H), 7.88 (dd, J=8.8, 2.8 Hz, 1H), 8.33 (d, J=2.8 Hz, 1H), 10.73 (s, 1H).

Compound 347. ¹H NMR (300 MHz, CDCl₃) δ ppm 0.87-1.00 (m, 3H), 1.28-1.46 (m, 2H), 1.48-1.66 (m, 2H), 3.50 (t, J=6.2 Hz, 3H), 3.58-3.66 (m, 2H), 3.95-4.05 (m, 2H), 4.15 (t, J=5.3 Hz, 1H), 6.58 (dd, J=8.6, 2.9 Hz, 1H), 6.73-6.88 (m, 2H).

Compound 348. ¹H NMR (500 MHz, CDCl₃) δ ppm 0.72-0.93 (m, 3H), 1.21-1.39 (m, 2H), 1.39-1.59 (m, 2H), 3.42 (br. s, 2H), 3.49 (td, J=6.3, 2.1 Hz, 2H), 3.53-3.71 (m, 1H), 3.77 (br. s, 1H), 4.01 (br. s, 1H), 6.47 (br. s, 1H), 7.12 (br. s, 1H), 7.19-7.38 (m, 2H), 7.46 (dd, J=2.5, 1.1 Hz, 2H).

Compound 349. ¹H NMR (300 MHz, DMSO-d6) δ ppm 0.85 (t, J=7.3 Hz, 3H), 1.20-1.39 (m, 2H), 1.39-1.59 (m, 2H), 3.32-3.54 (m, 6H), 3.84-4.10 (m, 4H), 7.17 (d, J=8.8 Hz, 1H), 7.42 (dd, J=9.0, 2.6 Hz, 1H), 7.78 (d, J=2.5 Hz, 1H), 10.83 (s, 1H).

Compound 350. ¹H NMR (300 MHz, DMSO-d6) δ ppm 0.85 (t, J=7.3 Hz, 3H), 1.22-1.36 (m, 2H), 1.41-1.52 (m, 2H), 3.38-3.52 (m, 5H), 3.90-4.05 (m, 4H), 7.17 (d, J=9.1 Hz, 1H), 7.40 (dd, J=8.8, 2.5 Hz, 1H), 10.81 (s, 1H).

Compound 351. ¹H NMR (300 MHz, DMSO-d6) δ ppm 0.85 (t, J=7.2 Hz, 3H), 1.22-1.36 (m, 2H), 1.40-1.53 (m, 2H), 3.36-3.52 (m, 6H), 3.89-4.04 (m, 4H), 7.17 (d, J=8.8 Hz, 1H), 7.34-7.44 (m, 1H).

Compound 352. ¹H NMR (500 MHz, CDCl₃) δ ppm 0.19-0.25 (m, 3H), 0.55 (ddd, J=8.0, 6.1, 4.3 Hz, 3H), 1.04-1.11 (m, 1H), 3.34-3.38 (m, 3H), 3.63-3.70 (m, 3H), 3.99-4.06 (m, 3H), 4.18 (t, J=5.4 Hz, 1H), 6.55 (dd, J=8.8, 2.8 Hz, 1H), 6.83 (d, J=8.8 Hz, 1H).

Compound 355. ¹H NMR (300 MHz, DMSO-d6) δ ppm 0.06-0.19 (m, 3H), 0.36-0.48 (m, 3H), 0.91-1.05 (m, 1H), 3.38 (dd, J=13.9, 6.8 Hz, 2H), 3.42-3.57 (m, J=15.1, 9.9, 4.9, 4.9 Hz, 3H), 3.87-4.01 (m, 3H), 7.08 (d, J=9.1 Hz, 1H), 7.39 (dd, J=9.1, 2.5 Hz, 1H), 7.79-7.85 (m, 1H)

Compound 357. ¹H NMR (300 MHz, DMSO-d6) δ ppm 0.84 (s, 2H), 1.25 (s, 7H), 1.36 (s, 3H), 1.69 (d, J=6.2 Hz, 2H), 4.14 (t, J=6.0 Hz, 2H), 7.40-7.53 (m, 2H), 7.57 (s, 3H), 7.79-7.92 (m, 1H)

Compound 358. ¹H NMR (300 MHz, DMSO-d6) δ ppm 0.77-0.96 (m, 3H), 1.27 (br. s, 9H), 1.40 (br. s, 2H), 1.56-1.91 (m, 2H), 4.30 (br. s, 3H), 7.24 (d, J=9.1 Hz, 1H), 7.34-7.60 (m, 1H)

Compound 359. ¹H NMR (500 MHz, DMSO-d6) δ ppm 0.79-0.94 (m, 3H), 1.17-1.36 (m, 9H), 1.36-1.48 (m, 2H), 1.62-1.81 (m, 2H), 4.19 (t, J=6.6 Hz, 2H), 7.25 (d, J=9.2 Hz, 1H), 7.44 (dd, J=9.2, 2.4 Hz, 1H), 8.65 (d, J=2.4 Hz, 1H), 11.13 (s, 1H)

Compound 360. ¹H NMR (600 MHz, DMSO-d6) δ ppm 0.78-0.92 (m, 3H), 1.16-1.35 (m, 8H), 1.35-1.47 (m, 2H), 1.66-1.83 (m, 2H), 4.17 (t, J=6.5 Hz, 1H), 4.22-4.34 (m, 1H), 7.31-7.42 (m, 1H).

Compound 361. ¹H NMR (300 MHz, CDCl₃) δ ppm 3.50 (s, 2H), 5.33 (s, 2H), 6.28 (d, J=8.0 Hz, 1H), 6.96 (d, J=8.0 Hz, 1H), 7.31-7.45 (m, 3H), 7.45-7.54 (m, 2H).

Compound 362. ¹H NMR (300 MHz, DMSO-d6) δ ppm 5.34 (s, 2H), 6.47 (d, J=8.2 Hz, 1H), 7.29-7.37 (m, 1H), 7.37-7.48 (m, 3H), 7.48-7.60 (m, 2H), 7.60-7.70 (m, 1H), 7.84 (d, J=7.4 Hz, 1H), 8.01 (d, J=8.5 Hz, 1H), 9.48 (s, 1H).

Compound 363. ¹H NMR (500 MHz, CDCl₃) δ ppm 5.28 (s, 2H), 6.36 (d, J=8.5 Hz, 1H), 7.23-7.29 (m, 1H), 7.29-7.35 (m, 2H), 7.35-7.42 (m, 2H), 8.38 (d, J=8.5 Hz, 1H).

Compound 364. ¹H NMR (300 MHz, DMSO-d6) δ ppm 5.34 (s, 2H), 6.48 (d, J=8.5 Hz, 1H), 7.28-7.49 (m, 5H), 8.03 (d, J=8.5 Hz, 1H), 10.04 (s, 1H).

Compound 365. ¹H NMR (500 MHz, CDCl₃) δ ppm 5.28 (s, 2H), 6.34 (d, J=8.3 Hz, 1H), 7.28-7.48 (m, 6H), 8.12 (s, 1H), 8.30 (d, J=8.37 Hz, 1H).

Compound 366. ¹H NMR (300 MHz, DMSO-d6) δ ppm 3.88 (s, 6H), 7.49-7.61 (m, 4H), 7.63-7.71 (m, 2H), 7.82-7.91 (m, 2H), 10.56 (s, 2H).

Compound 368. ¹H NMR (500 MHz, DMSO-d6) δ ppm 4.14 (s, 2H), 7.27 (s, 3H), 7.49-7.57 (m, 2H), 7.69 (d, J=7.7 Hz, 2H), 7.86-7.93 (m, 3H).

Compound 370. ¹H NMR (500 MHz, CDCl₃) δ ppm 1.78 (d, J=6.3 Hz, 3H), 5.50 (d, J=6.3 Hz, 1H), 6.84-6.87 (m, 1H), 7.29-7.35 (m, 1H), 7.39 (d, J=4.3 Hz, 4H), 7.98 (dd, J=9.1, 2.7 Hz, 1H), 8.29 (d, J=2.7 Hz, 1H).

Compound 371. ¹H NMR (500 MHz, CDCl₃) δ ppm 2.43 (s, 3H), 5.26 (s, 2H), 7.11 (d, J=9.1 Hz, 1H), 7.25-7.29 (m, 2H), 7.32 (d, J=6.7 Hz, 1H), 7.46 (d, J=7.1 Hz, 1H), 8.18 (ddd, J=9.0, 2.6, 1.00 Hz, 1H), 8.34 (dd, J=2.5, 0.8 Hz, 1H).

Compound 372. ¹H NMR (300 MHz, DMSO-d6) δ ppm 5.49 (s, 2H), 7.49 (d, J=9.1 Hz, 1H), 7.66-7.79 (m, 2H), 7.79-7.84 (m, 1H), 7.89 (s, 1H), 8.27 (dd, J=9.1, 2.7 Hz, 1H), 8.32-8.36 (m, 1H). ¹³C NMR (75 MHz, DMSO-d6) δ ppm 70.1, 113.8, 122.1, 124.1, 124.1, 124.6, 125.0, 125.4, 129.8, 131.6, 137.1, 141.0, 158.6.

Compound 375. ¹H NMR (500 MHz, CDCl₃) δ ppm 5.27 (s, 2H), 7.04 (d, J=9.1 Hz, 1H), 7.22 (d, J=7.7 Hz, 1H), 7.35 (s, 1H), 7.38-7.43 (m, 1H), 7.46 (t, J=7.7 Hz, 1H), 8.14 (dd, J=8.9, 2.5 Hz, 1H), 8.31 (d, J=2.5 Hz, 1H).

Compound 377. ¹H NMR (600 MHz, DMSO-d6) δ ppm 2.34 (s, 3H), 4.98 (s, 3H), 6.51 (dd, J=8.5, 2.6 Hz, 1H), 6.68 (d, J=2.4 Hz, 1H), 6.97 (d, J=8.7 Hz, 1H), 7.18-7.25 (m, 3H), 7.41 (d, J=7.3 Hz, 1H).

Compound 378. ¹H NMR (500 MHz, CDCl₃) δ ppm 3.48 (s, 2H), 5.06 (s, 2H), 6.50 (dd, J=8.7, 2.7 Hz, 1H), 6.72-6.81 (m, 2H), 7.47-7.51 (m, 1H), 7.58 (d, J=7.7 Hz, 1H), 7.65 (d, J=7.7 Hz, 1H), 7.74 (s, 1H). ¹³C NMR (126 MHz, CDCl₃) δ ppm 71.6, 114.3, 117.1, 117.1, 123.1, 124.0, 124.0, 124.0, 124.1, 124.5, 124.7, 124.7, 124.7, 124.8, 125.3, 128.9, 129.1, 130.6, 130.9, 138.2, 141.9, 146.7.

Compound 379. ¹H NMR (600 MHz, DMSO-d6) δ ppm 1.58 (d, J=6.3 Hz, 3H), 5.58 (d, J=6.8 Hz, 1H), 7.03 (d, J=9.2 Hz, 1H), 7.27 (s, 1H), 7.33-7.37 (m, 3H), 7.42 (d, J=7.3 Hz, 2H), 7.51 (d, J=7.3 Hz, 1H), 7.57 (d, J=6.3 Hz, 1H), 7.63 (d, J=8.7 Hz, 1H), 7.85-7.88 (m, 2H), 10.28 (s, 1H).

Compound 380. ¹H NMR (600 MHz, DMSO-d6) δ ppm 1.58 (d, J=6.3 Hz, 3H), 5.59 (d, J=6.3 Hz, 1H), 7.07 (d, J=8.7 Hz, 1H), 7.28 (td, J=5.7, 2.2 Hz, 2H), 7.36 (t, J=7.5 Hz, 2H), 7.41 (d, J=7.3 Hz, 2H), 7.78 (d, J=2.4 Hz, 1H), 10.79 (s, 1H).

Compound 381. ¹H NMR (600 MHz, DMSO-d6) δ ppm 1.58 (d, J=6.3 Hz, 3H), 5.59 (d, J=6.3 Hz, 1H), 7.06 (d, J=9.2 Hz, 1H), 7.23-7.30 (m, 2H), 7.32-7.39 (m, 3H), 7.41 (d, J=7.3 Hz, 2H), 7.77 (d, J=2.4 Hz, 1H), 10.79 (s, 1H).

Compound 382. ¹H NMR (600 MHz, DMSO-d6) δ ppm 1.58 (d, J=6.3 Hz, 3H), 5.59 (d, J=6.3 Hz, 1H), 7.06 (d, J=9.2 Hz, 1H), 7.23-7.28 (m, 2H), 7.33-7.38 (m, 3H), 7.41 (d, J=7.3 Hz, 2H), 7.76 (d, J=2.4 Hz, 1H), 10.70 (s, 1H).

Compound 383. ¹H NMR (600 MHz, DMSO-d6) δ ppm 2.37 (s, 3H), 5.17 (s, 2H), 7.21-7.27 (m, 3H), 7.29 (d, J=8.7 Hz, 1H), 7.46 (d, J=7.3 Hz, 1H), 7.52-7.56 (m, 2H), 7.58 (t, J=7.0 Hz, 1H), 7.66 (t, J=6.8 Hz, 1H), 7.88-7.91 (m, 2H), 10.36 (s, 1H).

Compound 384. ¹H NMR (600 MHz, DMSO-d6) δ ppm 2.36 (s, 3H), 5.18 (s, 2H), 7.22 (s, 1H), 7.23-7.28 (m, 2H), 7.32 (d, J=9.2 Hz, 1H), 7.43-7.48 (m, 2H), 7.83 (d, J=2.9 Hz, 1H), 10.86 (s, 1H).

Compound 385. ¹H NMR (300 MHz, DMSO-d6) δ ppm 2.35 (s, 3H), 5.18 (s, 2H), 7.20-7.27 (m, 3H), 7.29-7.34 (m, 1H), 7.40-7.47 (m, 2H), 7.80 (d, J=2.2 Hz, 1H), 10.84 (s, 1H).

Compound 386. ¹H NMR (600 MHz, DMSO-d6) δ ppm 5.17 (s, 3H), 7.20-7.27 (m, 4H), 7.31 (d, J=9.2 Hz, 1H), 7.42 (dd, J=9.0, 2.6 Hz, 1H), 7.44 (d, J=7.8 Hz, 1H), 7.78 (d, J=2.4 Hz, 1H), 10.74 (s, 1H).

Compound 387. ¹H NMR (600 MHz, DMSO-d6) δ ppm 5.31 (s, 2H), 7.24 (d, J=9.2 Hz, 1H), 7.51-7.55 (m, 2H), 7.57-7.60 (m, 1H), 7.66 (td, J=7.2, 3.1 Hz, 2H), 7.70-7.74 (m, 1H), 7.78 (d, J=7.8 Hz, 1H), 7.85-7.91 (m, 3H), 10.37 (s, 1H).

Compound 388. ¹H NMR (300 MHz, DMSO-d6) δ ppm 5.32 (s, 2H), 7.27 (d, J=8.8 Hz, 1H), 7.45 (dd, J=8.8, 2.4 Hz, 1H), 7.67 (d, J=7.4 Hz, 1H), 7.69-7.75 (m, 1H), 7.78 (d, J=7.4 Hz, 1H), 7.83 (d, J=2.4 Hz, 1H), 7.85 (s, 1H), 10.86 (s, 1H).

Compound 389. ¹H NMR (500 MHz, DMSO-d6) δ ppm 5.32 (s, 2H), 7.27 (d, J=8.9 Hz, 1H), 7.43 (dd, J=8.8, 2.4 Hz, 1H), 7.67 (d, J=7.5 Hz, 1H), 7.71 (s, 1H), 7.78 (d, J=7.5 Hz, 1H), 7.81 (d, J=2.5 Hz, 1H), 7.85 (s, 1H), 10.85 (s, 1H). ¹³C NMR (75 MHz, DMSO-d6) δ ppm 69.4, 94.3, 114.9, 119.5, 121.2, 121.6, 123.8, 124.6, 124.7, 126.0, 128.7, 129.4, 129.5, 129.6, 131.4, 132.4, 133.4, 135.2, 138.1, 150.1, 161.2, 164.7.

Compound 390. ¹H NMR (500 MHz, DMSO-d6) δ ppm 5.31 (s, 2H), 7.27 (d, J=8.7 Hz, 1H), 7.43 (dd, J=8.9, 1.4 Hz, 1H), 7.64-7.73 (m, 2H), 7.77 (d, J=6.9 Hz, 1H), 7.80-7.86 (m, 2H), 10.77 (s, 1H). ¹³C NMR (126 MHz, DMSO-d6) δ ppm 69.9, 115.4, 116.3, 119.9, 121.6, 122.1, 123.4, 124.3, 125.2, 130.1, 130.8, 131.8, 133.0, 138.1, 138.6, 150.4, 166.3.

Compound 391. ¹H NMR (300 MHz, DMSO-d6) δ ppm 1.58 (d, J=6.0 Hz, 3H), 5.57 (d, J=6.3 Hz, 1H), 7.04 (d, J=8.8 Hz, 1H), 7.18-7.29 (m, 2H), 7.38 (dt, J=15.2, 7.70 Hz, 4H), 7.72-7.85 (m, 2H), 8.23-8.34 (m, 2H), 10.55 (s, 1H).

Compound 392. ¹H NMR (300 MHz, DMSO-d6) δ ppm 5.32 (s, 3H), 6.47 (d, J=8.5 Hz, 1H), 7.30-7.46 (m, 5H), 7.77 (t, J=8.0 Hz, 1H), 8.15 (d, J=8.2 Hz, 1H), 8.20-8.34 (m, 2H), 9.90 (s, 1H).

Compound 393. ¹H NMR (300 MHz, DMSO-d6) δ ppm 5.30 (s, 2H), 7.25 (d, J=9.1 Hz, 1H), 7.32-7.43 (m, 1H), 7.63-7.73 (m, 2H), 7.75-7.86 (m, 4H), 8.24-8.36 (m, 2H), 10.62 (s, 1H).

Compound 400. ¹H NMR (300 MHz, DMSO-d6) δ ppm 3.39-3.51 (m, 2H) 3.51-3.62 (m, 2H) 3.64-3.85 (m, 2H) 4.24-4.44 (m, 2H) 6.83 (d, J=8.8 Hz, 1H) 7.45-7.72 (m, 3H) 7.72-8.09 (m, 2H) 8.41 (d, J=2.2 Hz, 1H) 10.33 (s, 1H) 13.06 (br. s, 1H). ¹³C NMR (DMSO-d6) δ ppm 58.1, 64.9, 68.8, 69.7, 71.3, 110.3, 127.8, 129.6, 130.0, 130.5, 131.7, 131.7, 137.8, 138.5, 159.2, 167.4.

Compound 401. ¹H NMR (300 MHz, DMSO-d6) δ ppm 3.22 (s, 3H) 3.38-3.50 (m, 2H) 3.51-3.61 (m, 2H) 3.64-3.85 (m, 2H) 4.13-4.50 (m, 2H) 6.87 (d, J=8.8 Hz, 1H) 7.91 (dd, J=8.8, 2.7 Hz, 1H) 8.36 (d, J=2.4 Hz, 1H) 10.84 (s, 1H).

Compound 402. ¹H NMR (300 MHz, DMSO-d6) δ ppm 3.23 (s, 2H) 3.36-3.52 (m, 2H) 3.52-3.64 (m, 2H) 3.64-3.87 (m, 2H) 4.26-4.44 (m, 2H) 6.87 (d, J=8.8 Hz, 1H) 7.89 (dd, J=8.9, 2.6 Hz, 1H) 8.34 (d, J=2.4 Hz, 1H) 10.83 (s, 1H).

Compound 404. ¹H NMR (300 MHz, DMSO-d6) δ ppm 3.32-3.51 (m, 3H) 3.51-3.64 (m, 3H) 3.66-3.87 (m, 3H) 4.13-4.47 (m, 2H) 6.86 (d, J=8.8 Hz, 1H) 7.88 (dd, J=8.9, 2.35 Hz, 1H) 8.33 (d, J=2.2 Hz, 1H) 10.74 (s, 1H).

Compound 405. ¹H NMR (300 MHz, DMSO-d6) δ ppm 3.38-3.51 (m, 4H) 3.51-3.64 (m, 2H) 3.66-3.85 (m, 2H) 4.24-4.45 (m, 2H) 6.86 (d, J=9.3 Hz, 1H) 7.90-8.02 (m, 2H) 8.37-8.52 (m, 2H) 10.58 (d, J=14.6 Hz, 2H).

Compound 406. ¹H NMR (500 MHz, DMSO-d6) δ ppm 3.34 (br. s, 2H) 3.45 (dd, J=5.5, 3.7 Hz, 2H) 3.59 (dd, J=5.4, 3.8 Hz, 2H) 3.67-3.86 (m, 2H) 4.22-4.39 (m, 2H) 7.21 (d, J=9.1 Hz, 1H) 7.46 (dd, J=8.9, 2.3 Hz, 1H) 7.52-7.65 (m, 3H) 7.67 (dd, J=7.4, 1.10 Hz, 1H) 7.91 (d, J=6.9 Hz, 1H) 8.72 (d, J=2.3 Hz, 1H) 10.56 (s, 1H).

Compound 407. ¹H NMR (500 MHz, DMSO-d6) δ ppm 3.24 (s, 3H) 3.44 (br. s, 2H) 3.58 (br. s, 2H) 3.75 (br. s, 2H) 4.34 (br. s, 2H) 7.25 (d, J=8.9 Hz, 1H) 7.41 (br. s, 1H) 8.65 (br. s, 1H) 11.10 (s, 1H).

Compound 412. ¹H NMR (500 MHz, DMSO-d6) δ ppm 7.23 (d, J=8.9 Hz, 2H) 7.62 (s, 2H) 7.73 (d, J=8.7 Hz, 2H) 7.84 (s, 1H) 10.96 (s, 1H).

Compound 413. ¹H NMR (500 MHz, DMSO-d6) δ ppm 7.23 (m, J=8.6 Hz, 2H) 7.62 (s, 2H) 7.72 (m, J=8.6 Hz, 2H) 7.84 (s, 1H), 10.95 (s, 1H). ¹³C NMR (126 MHz, DMSO-d6) δ ppm 118.5, 121.1, 122.0, 122.3, 124.4, 129.2, 129.9, 132.3, 132.6, 133.8, 133.8, 135.8, 136.0, 151.1, 159.2, 161.7, 165.2.

Compound 414. ¹H NMR (500 MHz, DMSO-d6) δ ppm 7.21 (d, J=9.5 Hz, 2H) 7.58 (s, 2H) 7.70 (d, J=7.9 Hz, 2H) 7.81 (s, 1H) 10.87 (s, 1H). ¹³C NMR (126 MHz, DMSO-d6) δ ppm 67.5, 121.1, 122.0, 122.2, 123.4, 124.4, 130.7, 132.3, 132.6, 136.0, 137.0, 138.2, 151.0, 159.2, 163.2, 166.4.

Compound 415. ¹H NMR (300 MHz, CDCl₃) δ ppm 3.70 (br. s, 2H) 6.71-6.83 (m, 2H) 6.86-6.98 (m, 2H), 7.35 (s, 2H) 7.53 (s, 1H).

Compound 416. ¹H NMR (300 MHz, CDCl₃) δ ppm 5.55 (s, 2H) 6.95 (d, J=9.1 Hz, 1H) 7.48-7.58 (m, 1H) 7.66-7.75 (m, 1H) 7.79 (s, 1H) 8.43 (dd, J=9.1, 2.7 Hz, 1H) 9.10 (d, J=2.7 Hz, 1H). ¹³C NMR (75 MHz, CDCl₃) δ ppm 67.6, 111.5, 112.8, 118.4, 129.4, 131.4, 131.8, 132.2, 134.3, 137.6, 144.6.

Compound 417. ¹H NMR (500 MHz, DMSO-d6) δ ppm 5.26 (s, 2H), 7.23 (d, J=8.8 Hz, 1H), 7.34 (d, J=7.2 Hz, 1H), 7.46-7.63 (m, 7H), 7.66 (t, J=7.5 Hz, 1H), 7.85-7.95 (m, 2H), 10.37 (s, 1H).

Compound 418. ¹H NMR (500 MHz, DMSO-d6) δ ppm 5.27 (s, 2H) 7.26 (d, J=8.9 Hz, 1H) 7.34 (d, J=7.5 Hz, 1H) 7.39-7.61 (m, 5H) 7.83 (d, J=2.5 Hz, 1H) 10.87 (s, 1H).

Compound 419. ¹H NMR (500 MHz, DMSO-d6) δ ppm 5.27 (s, 2H) 7.26 (d, J=8.9 Hz, 1H) 7.34 (d, J=7.7 Hz, 1H) 7.38-7.62 (m, 5H) 7.82 (d, J=1.9 Hz, 1H) 10.86 (s, 1H).

Compound 420. ¹H NMR (500 MHz, DMSO-d6) δ ppm 5.27 (s, 2H) 7.25 (d, J=8.9 Hz, 1H) 7.33 (d, J=7.7 Hz, 1H) 7.44 (dd, J=8.8, 2.2 Hz, 1H) 7.49 (d, J=9.3 Hz, 2H) 7.52-7.59 (m, 1H) 7.83 (d, J=2.1 Hz, 1H) 10.79 (s, 1H). ¹³C NMR (126 MHz, DMSO-d6) δ ppm 54.9, 69.3, 119.5, 121.2, 121.6, 122.9, 126.2, 130.3, 130.5, 132.5, 139.5, 148.5, 150.0, 162.6, 166.9.

Compound 421. ¹H NMR (500 MHz, DMSO-d6) δ ppm 5.27 (s, 2H) 7.24 (d, J=8.9 Hz, 1H) 7.31-7.44 (m, 2H) 7.47-7.61 (m, 3H) 7.79-7.88 (m, 2H) 8.29 (d, J=7.7 Hz, 1H) 8.35 (d, J=8.1 Hz, 1H) 10.64 (s, 1H).

Compound 422. ¹H NMR (500 MHz, DMSO-d6) δ ppm 5.27 (s, 2H) 7.21-7.31 (m, 1H) 7.34 (d, J=7.7 Hz, 1H) 7.44-7.54 (m, 4H) 7.56 (t, J=7.7 Hz, 1H) 7.77-7.94 (m, 2H) 8.35-8.45 (m, 3H). ¹³C NMR (126 MHz, CDCl₃) δ ppm 56.0, 69.5, 111.1, 111.6, 111.9, 121.5, 128.3, 134.1, 144.8, 149.2, 149.4, 166.9, 166.9.

Compound 423. ¹H NMR (500 MHz, DMSO-d6) δ ppm 5.27 (s, 2H) 7.25 (d, J=8.9 Hz, 1H) 7.34 (d, J=7.7 Hz, 1H) 7.48-7.69 (m, 5H) 8.00 (d, J=2.5 Hz, 1H) 8.18-8.26 (m, 1H) 8.72-8.79 (m, 1H).

Compound 424. 10.66 (s, 1H). ¹H NMR (500 MHz, DMSO-d6) δ ppm 5.27 (br. s, 2H) 7.25 (d, J=8.7 Hz, 1H) 7.34 (br. s, 1H) 7.41-7.58 (m, 5H) 7.60 (d, J=3.9 Hz, 2H) 7.88 (br. s, 1H) 8.85 (d, J=16.9 Hz, 2H) 10.55 (br. s, 1H).

Compound 425. ¹H NMR (500 MHz, CDCl₃) δ ppm 3.88-3.96 (m, 7H), 5.44 (s, 2H), 6.89 (d, J=2.0 Hz, 1H), 7.02 (d, J=1.8 Hz, 1H), 7.05 (dd, J=8.2, 2.0 Hz, 1H), 8.37 (dd, J=9.1, 2.9 Hz, 1H), 9.11 (d, J=2.8 Hz, 1H). ¹³C NMR (126 MHz, CDCl₃) δ ppm 56.0, 69.5, 111.1, 111.6, 111.9, 121.5, 128.3, 134.1, 144.8, 149.2, 149.4, 166.9.

Compound 427. ¹H NMR (500 MHz, DMSO-d6) δ ppm 3.12 (s, 4H) 5.28 (s, 2H) 7.20 (d, J=8.9 Hz, 1H) 7.39 (dd, J=8.8, 2.2 Hz, 1H) 7.66 (d, J=7.7 Hz, 1H) 7.70 (s, 1H) 7.76-7.79 (m, 1H) 7.79-7.89 (m, 2H).

Specific compounds of the invention include the following structures and their pharmaceutical salts.

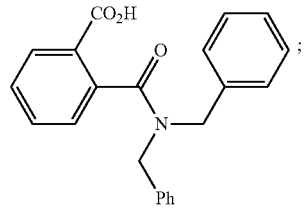

1

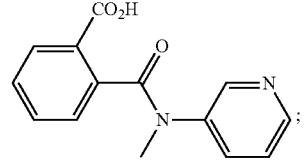

2

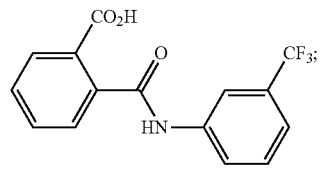

3

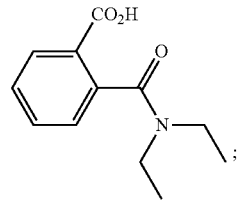

4

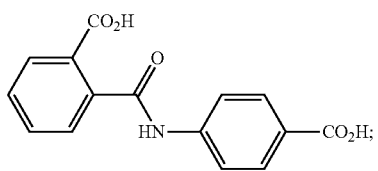

5

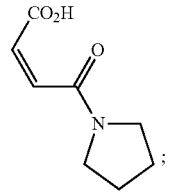

6

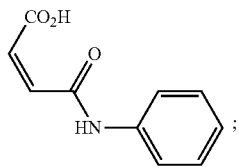

7

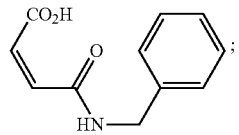

8

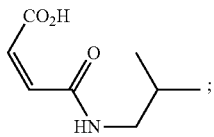

9

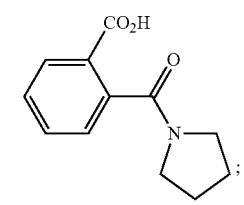

10

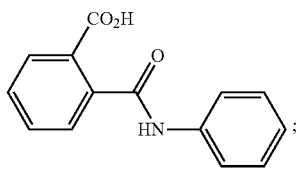

11

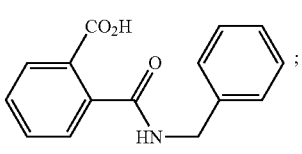

12

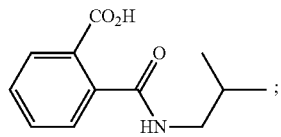

13

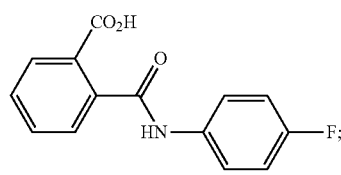

14

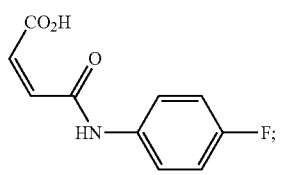
15
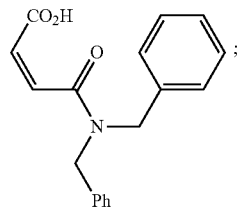
16
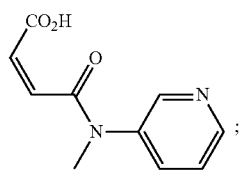
17
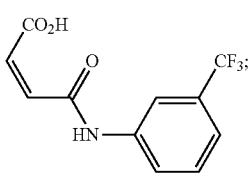
18
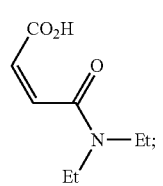
19
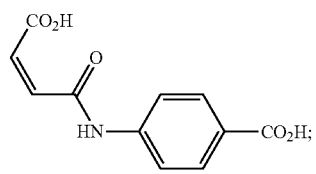
20
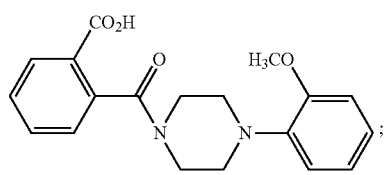
21
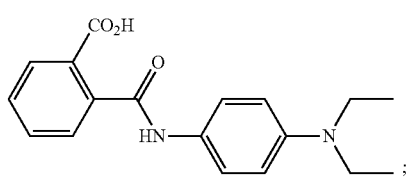
22
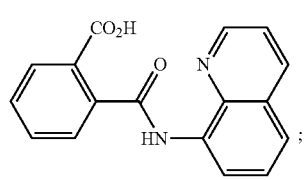
23
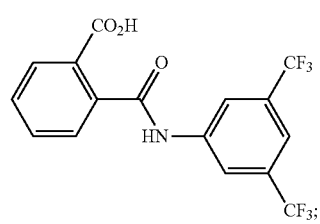
24
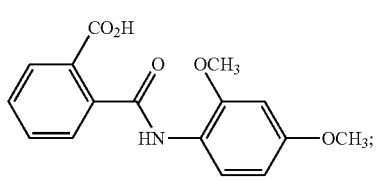
25
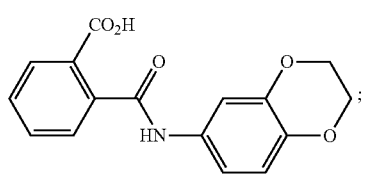
26
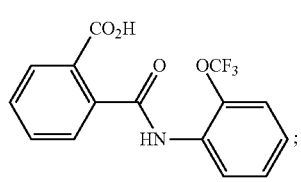
27
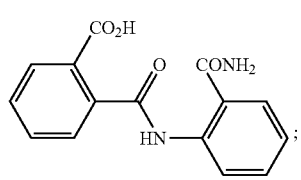
28
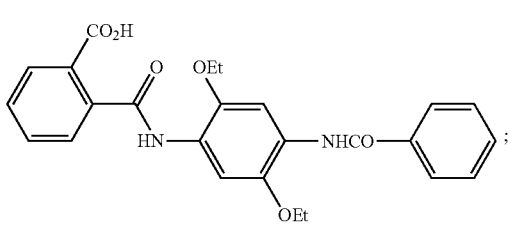
29
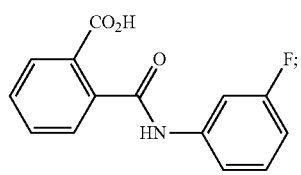
30
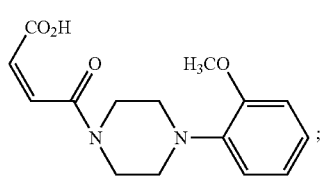
31

32
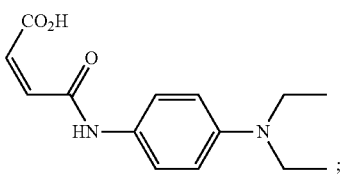
33
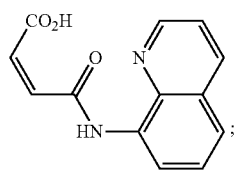
34
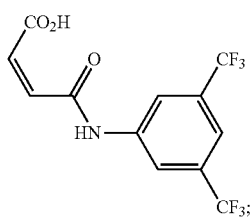
35
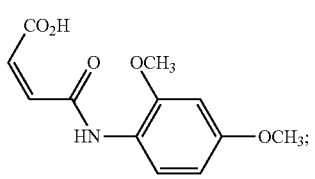
36
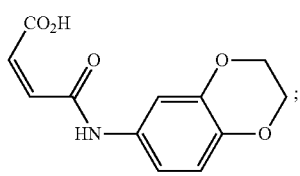
37
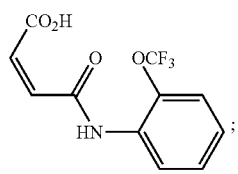
38
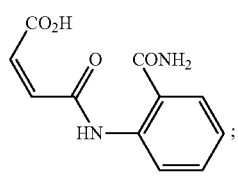
39
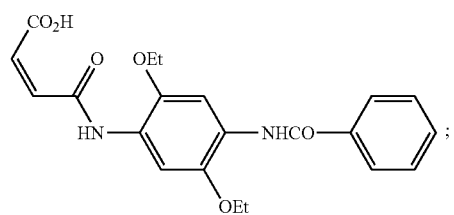
40
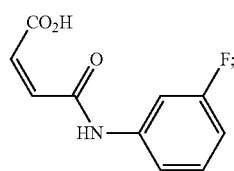
41
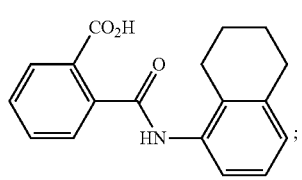
42
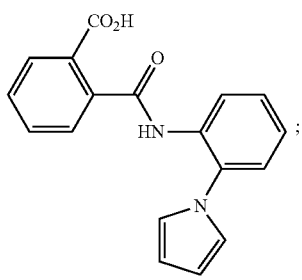
43
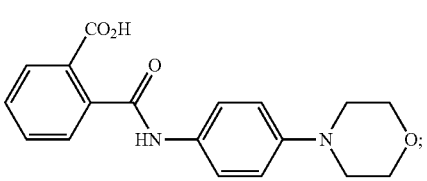
44
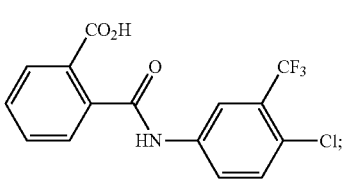
45
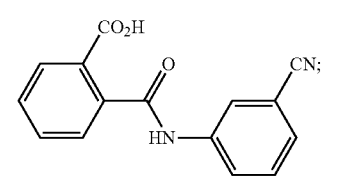
46
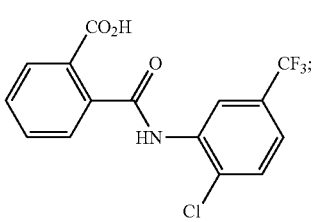
47
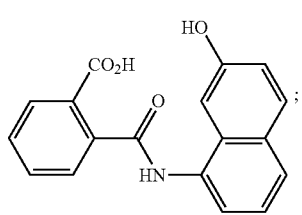

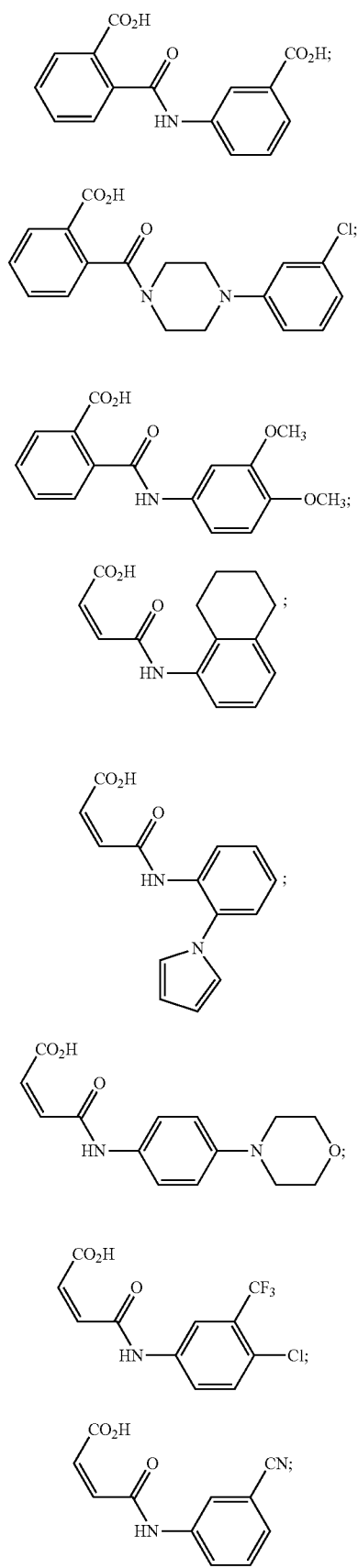
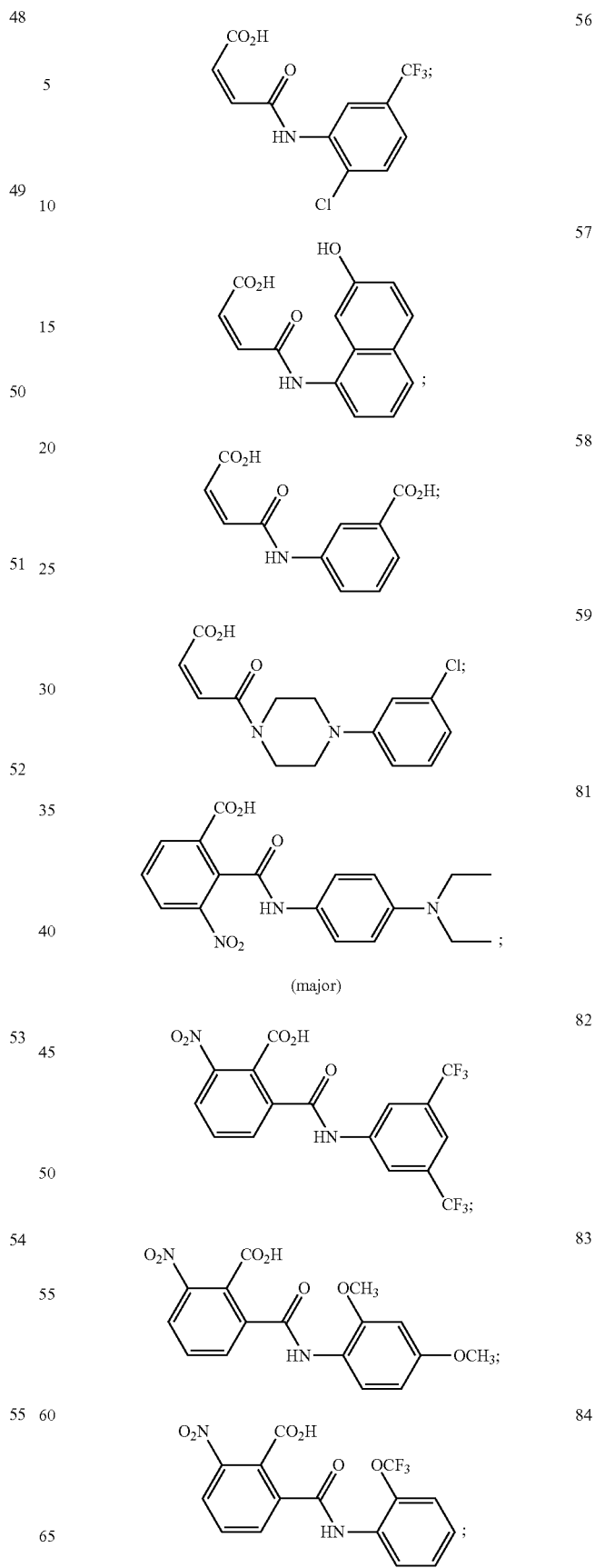

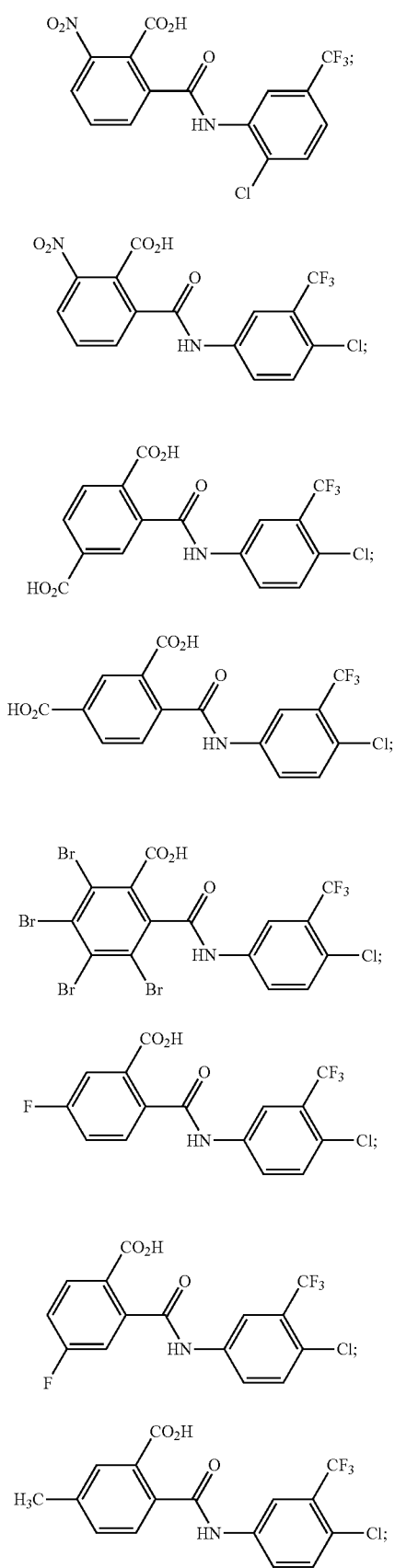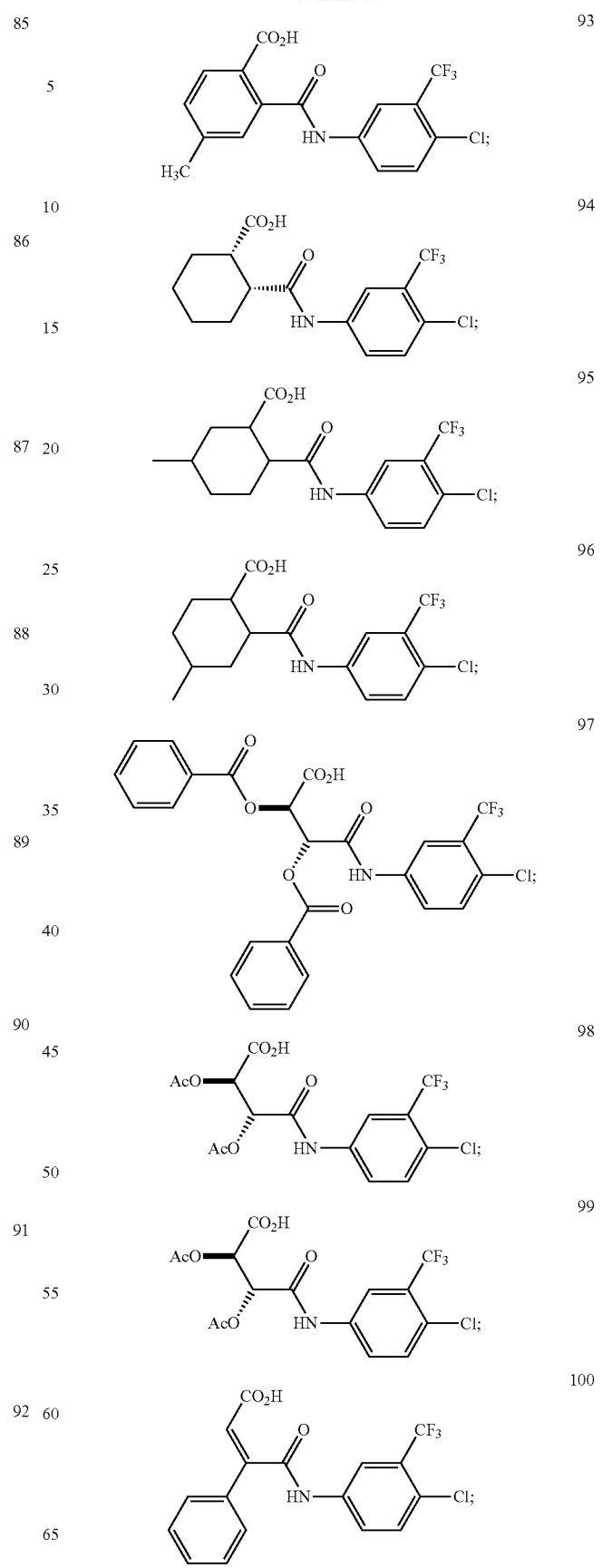

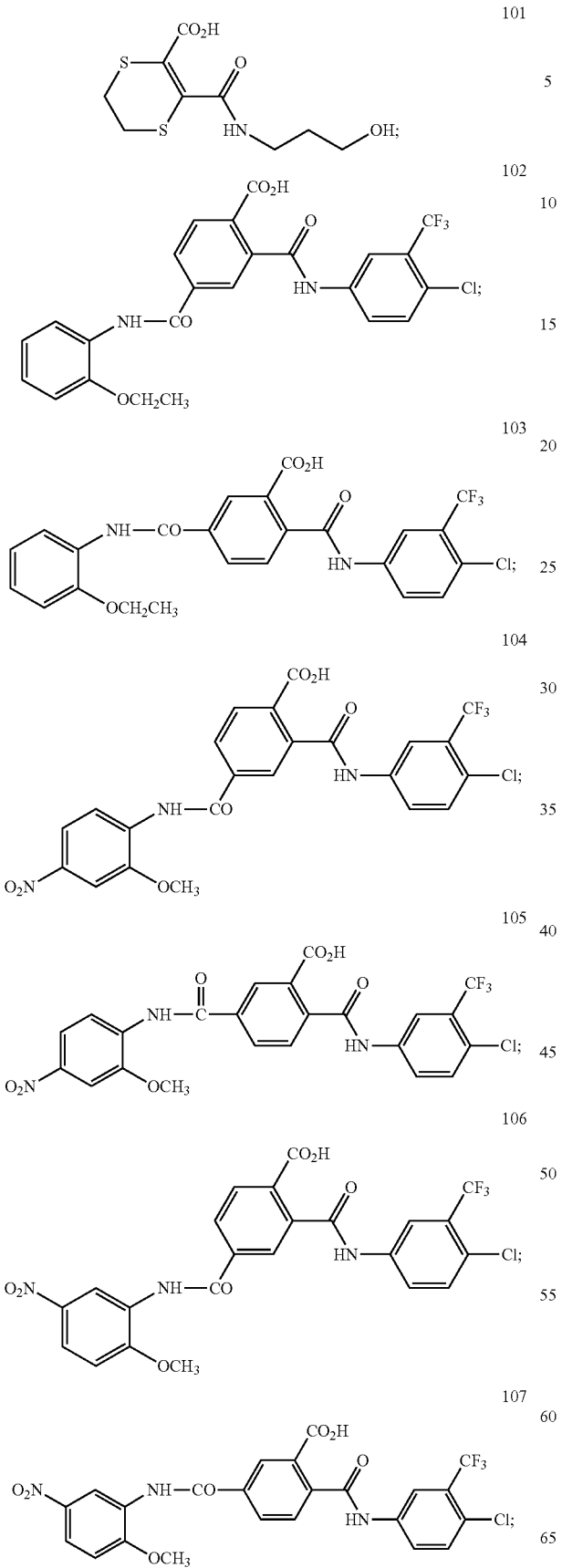
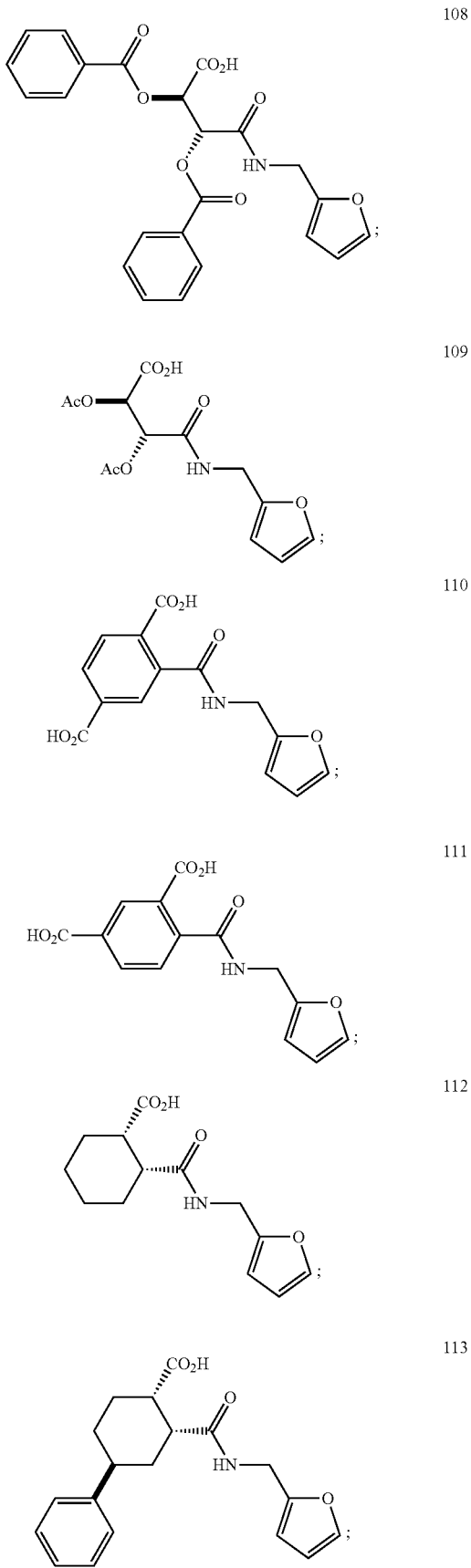

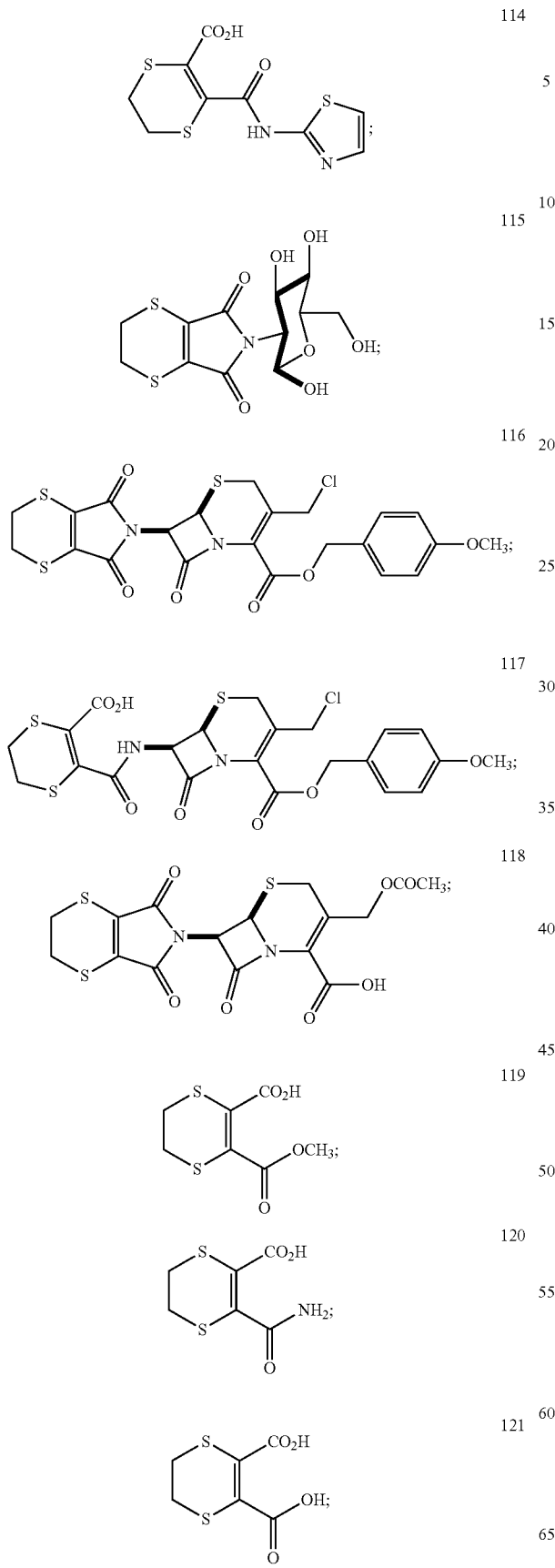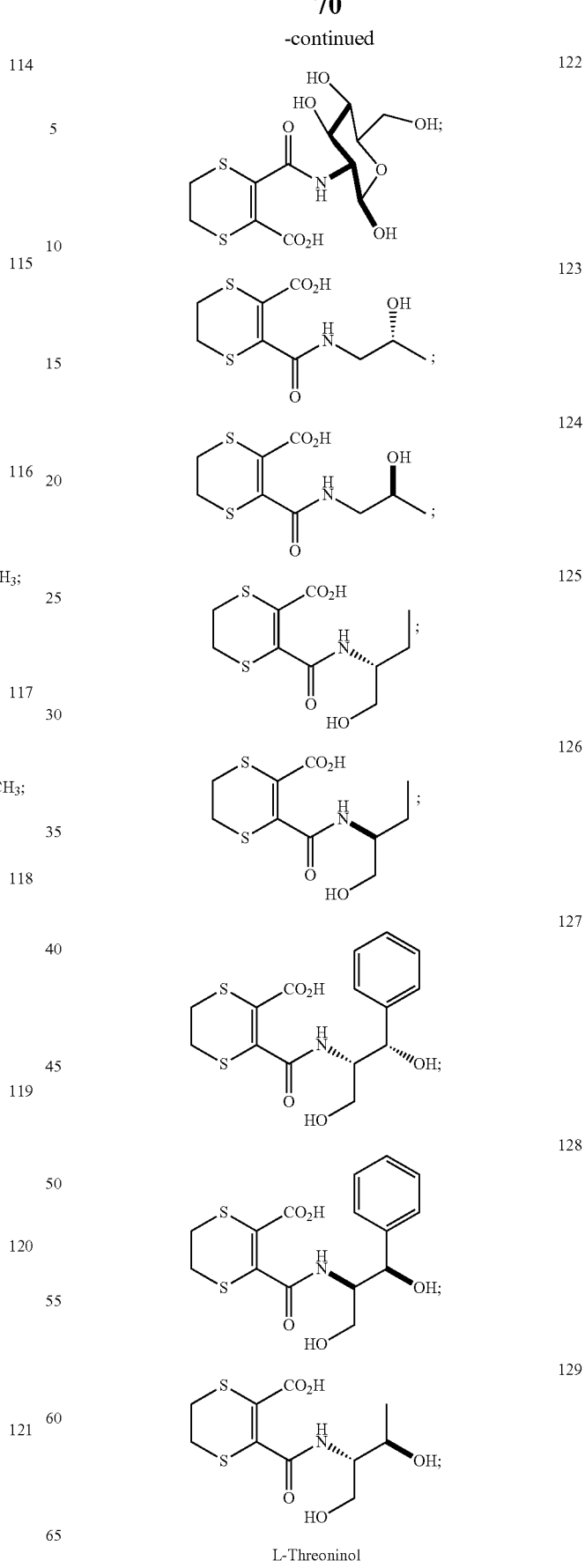
L-Threoninol

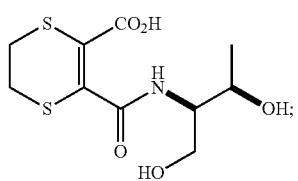
130
D-Threoninol
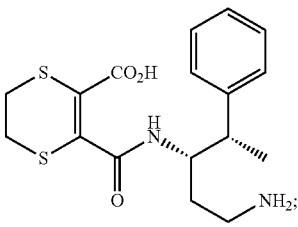
131
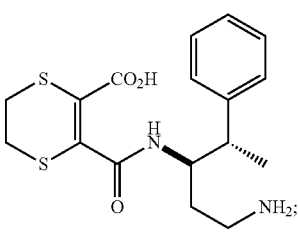
132
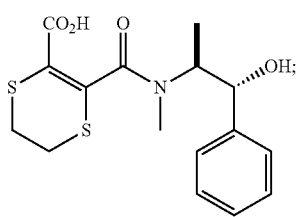
133
(1R, 2R)-(-)-Pseudoaphedrine
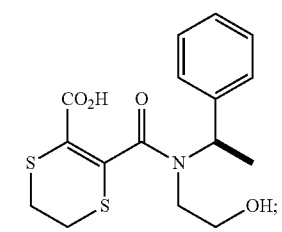
134
(R)-(+)-N-(2-Hydroxyethyl)
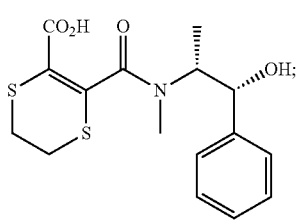
135
(1R,2S)(-)-Ephedrine
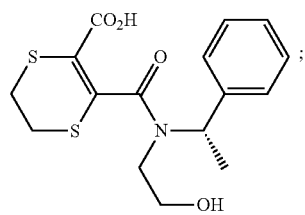
136
(S)-(-)-N-(2-Hydroxyethyl)-
alpha-phenylethylamine
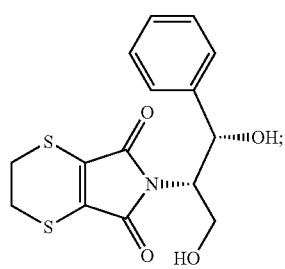
137
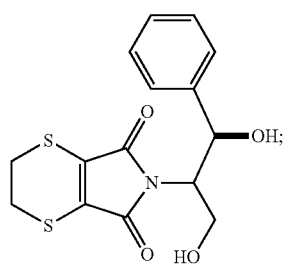
138
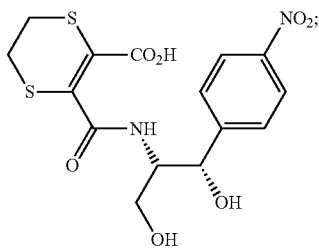
139
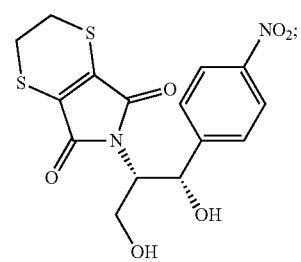
140
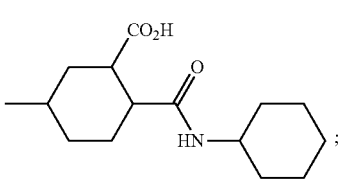
150

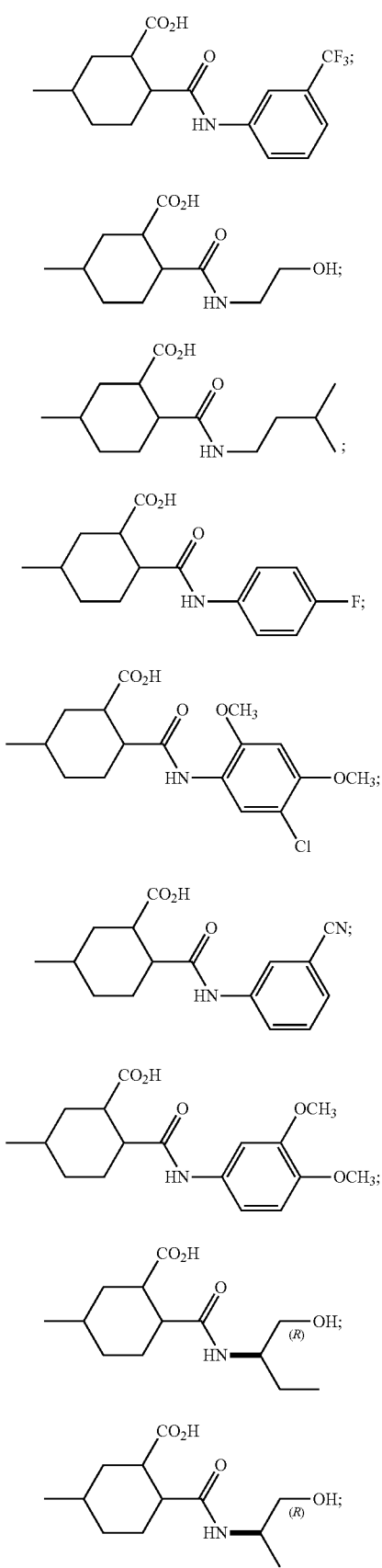
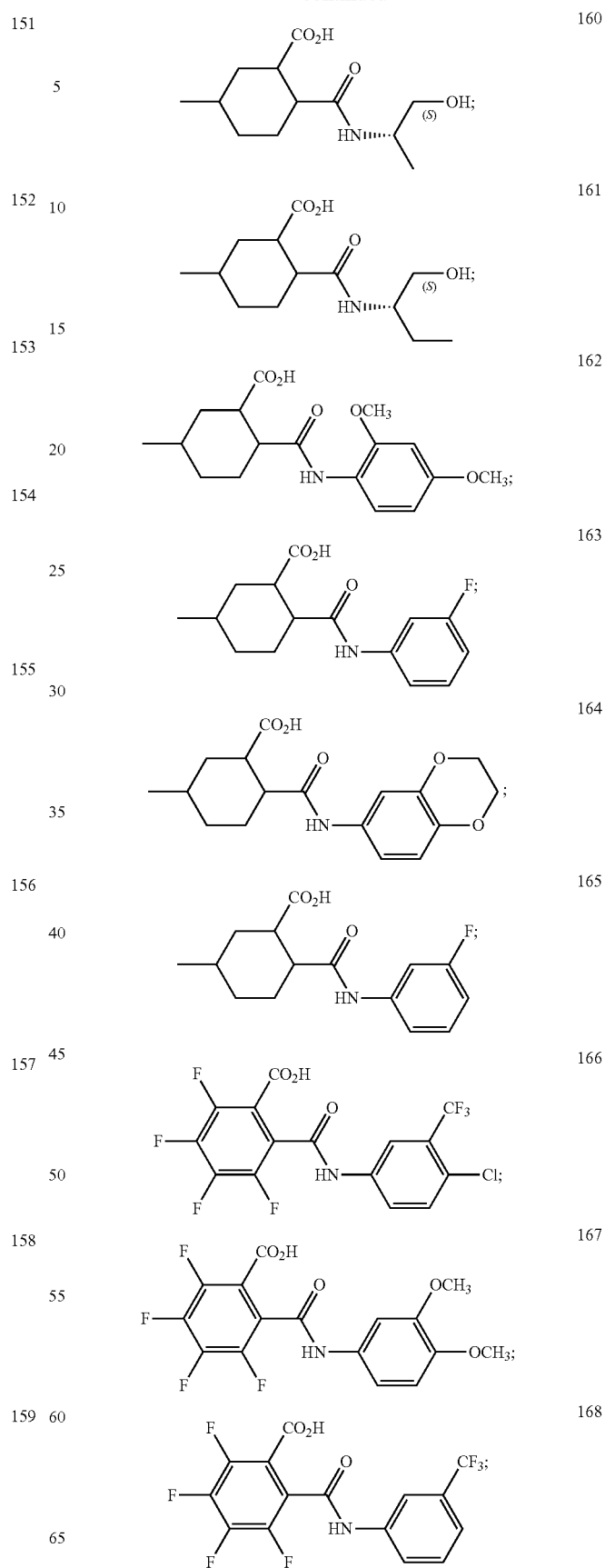

169 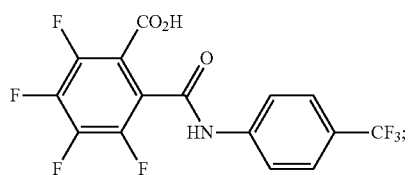
170 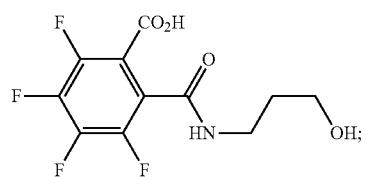
171 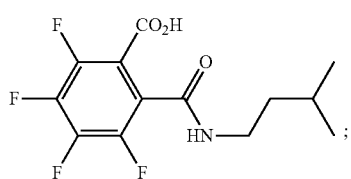
172 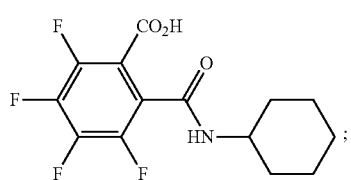
173 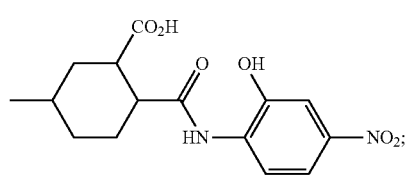
174 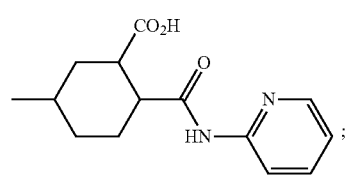
175 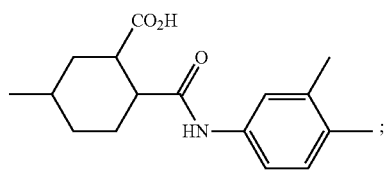
176 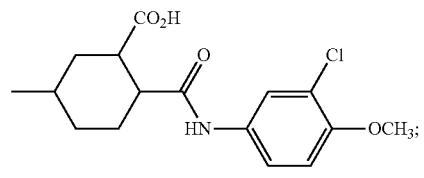
177 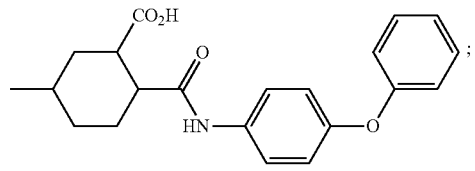
178 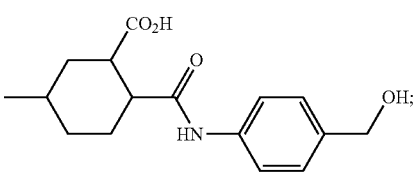
179 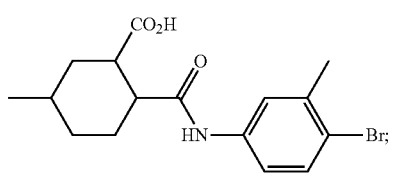
180 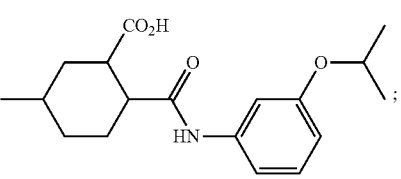
181 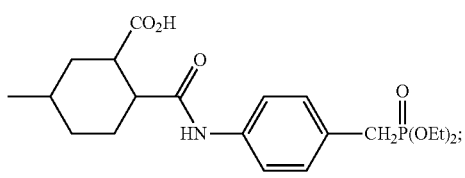
182 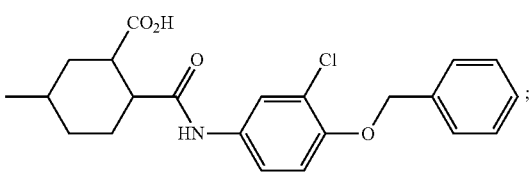
183 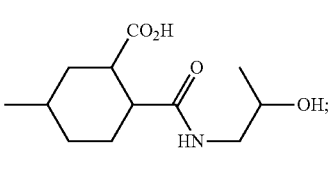
184 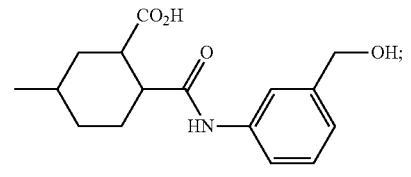
185
186 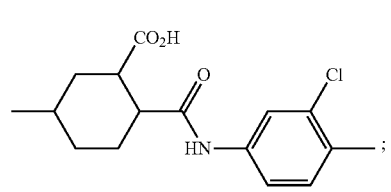

-continued

-continued

-continued

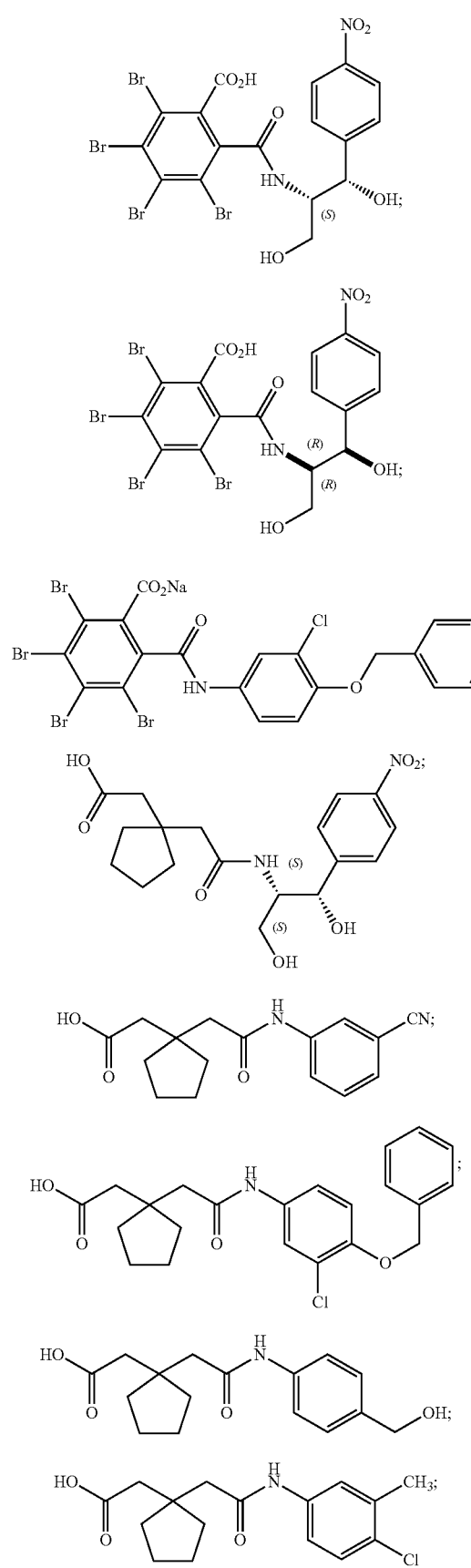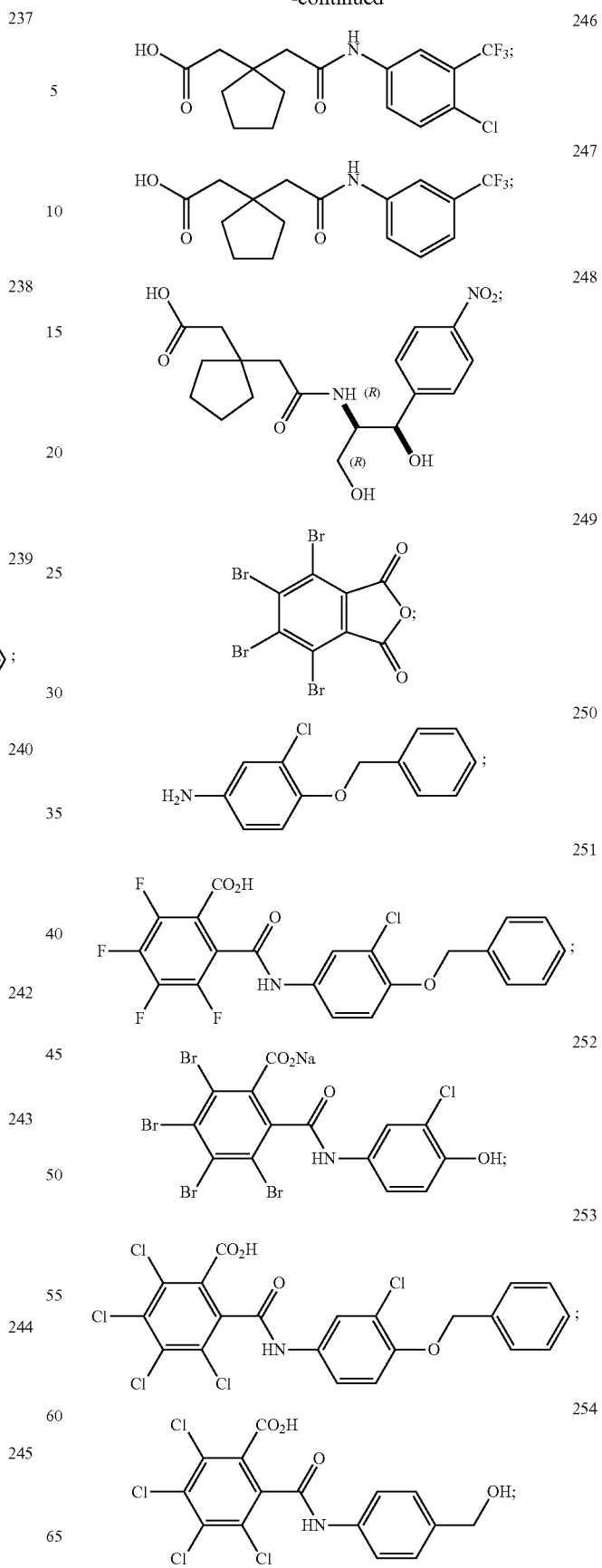

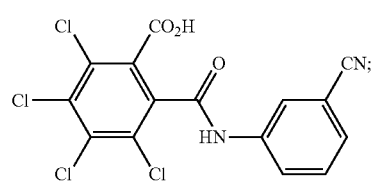
255
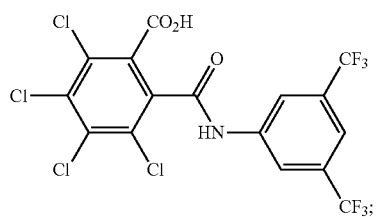
256
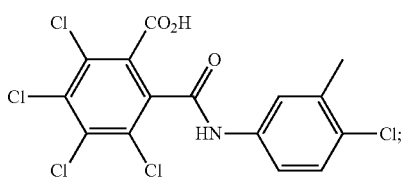
257
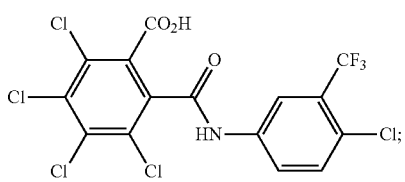
258
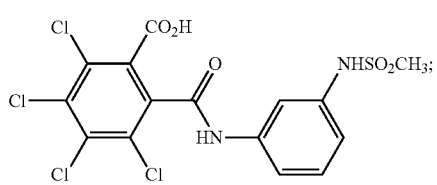
259
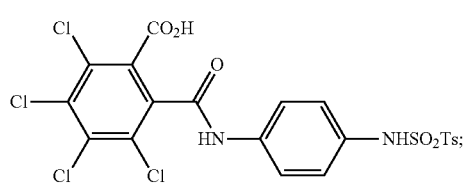
260
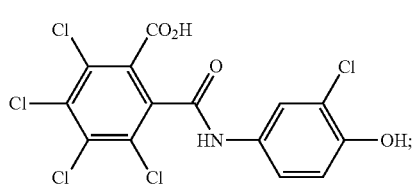
261
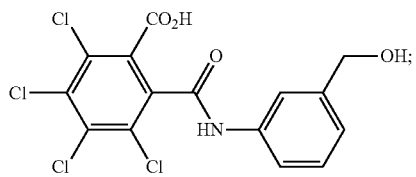
262
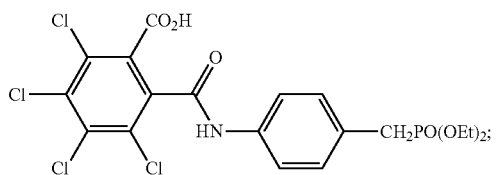
263
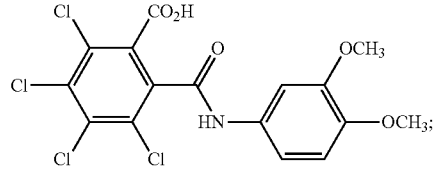
264
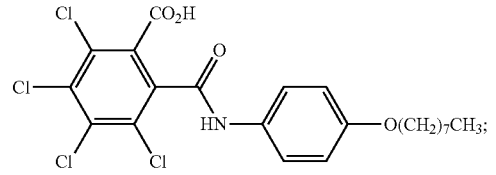
265
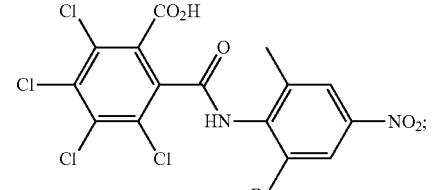
266
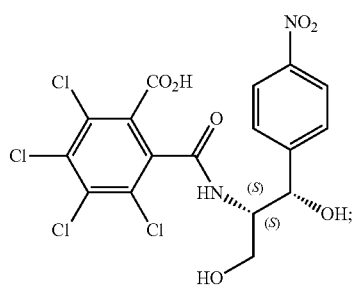
267
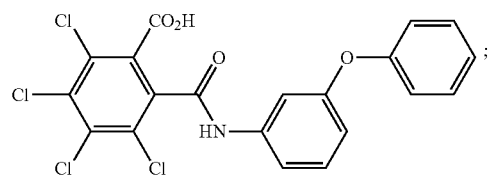
268
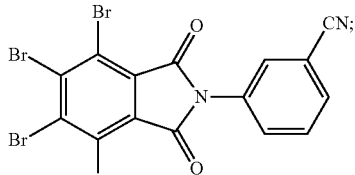
269
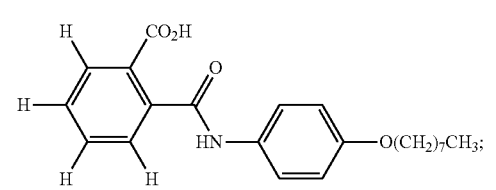
270

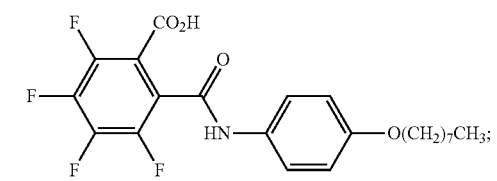
271
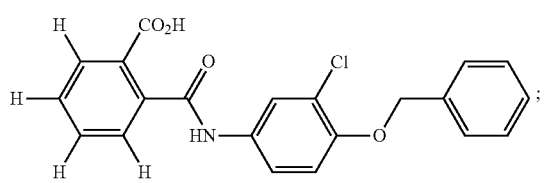
272
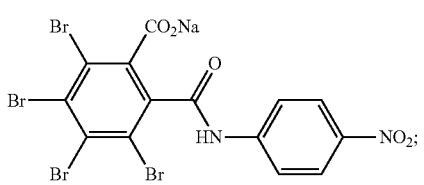
273
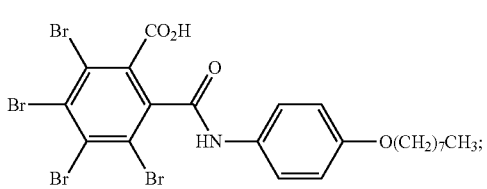
274
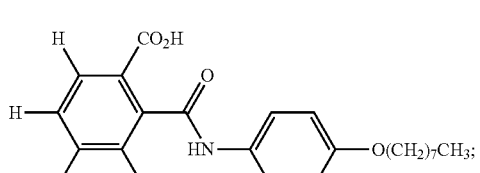
275
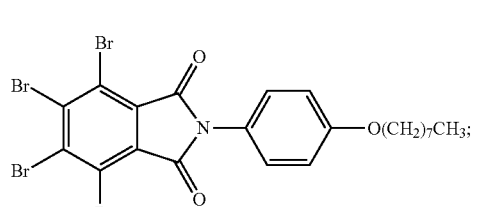
276
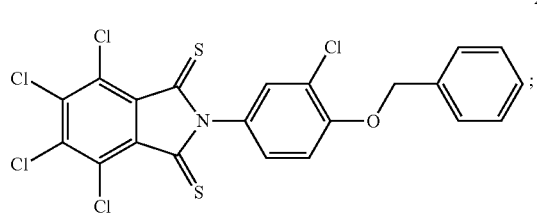
277
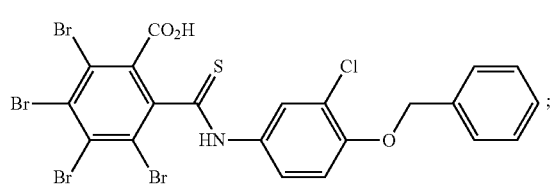
278
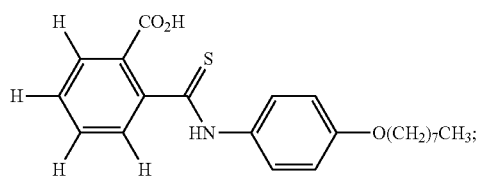
279
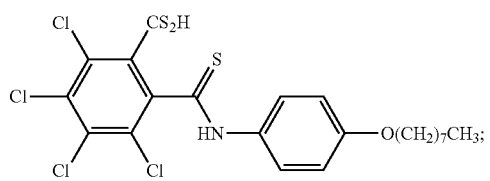
280
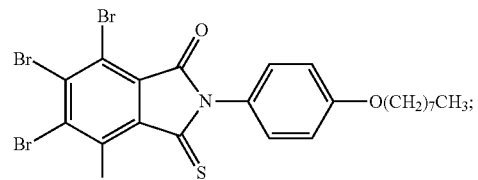
281
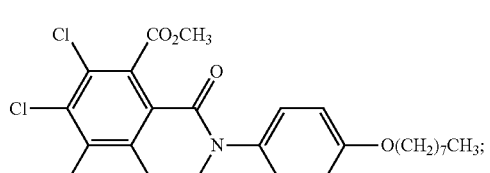
282
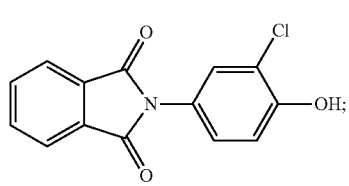
283
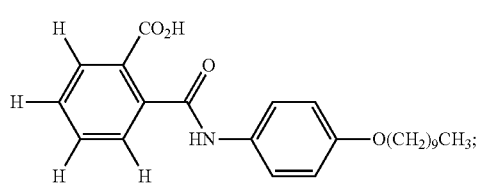
284
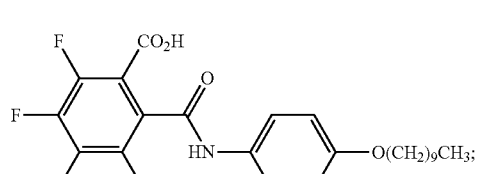
285
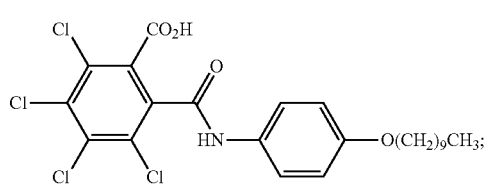
286

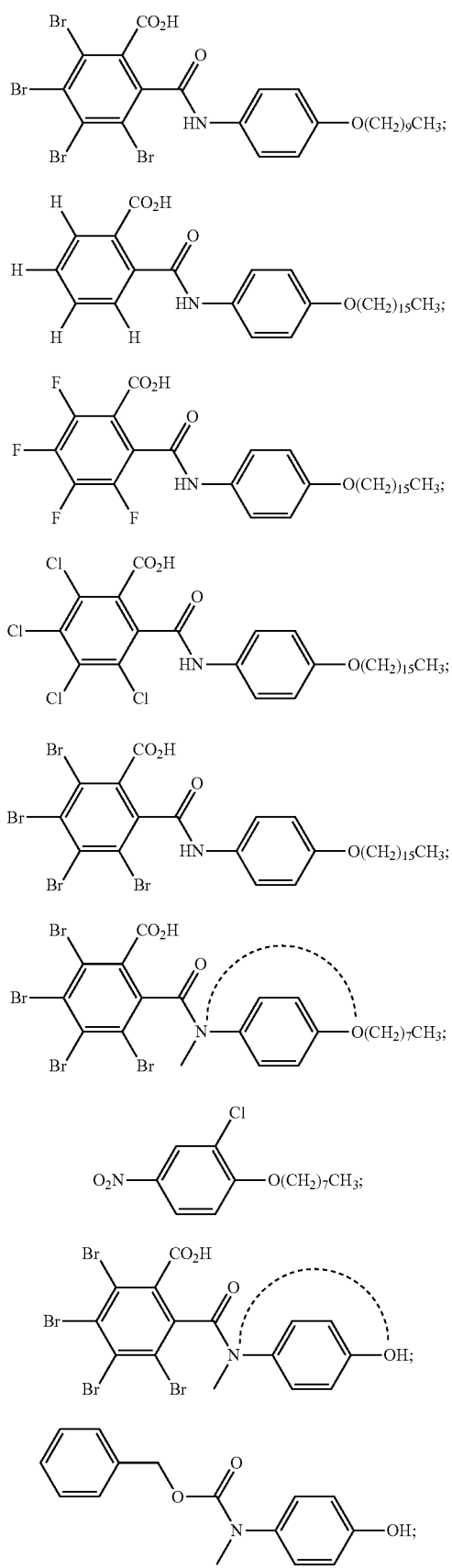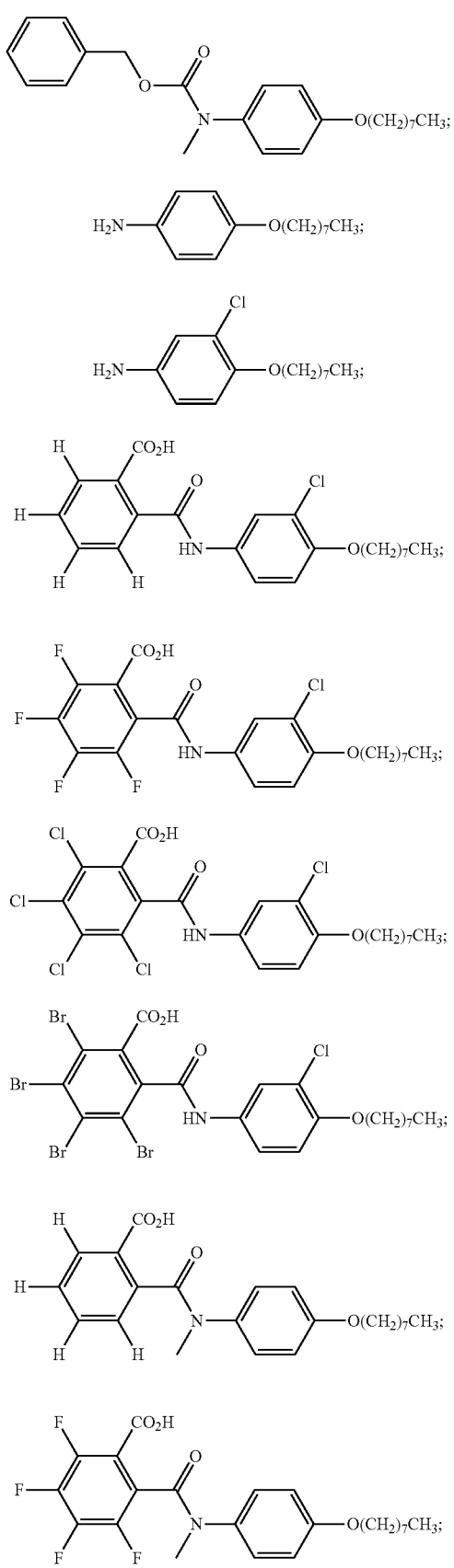

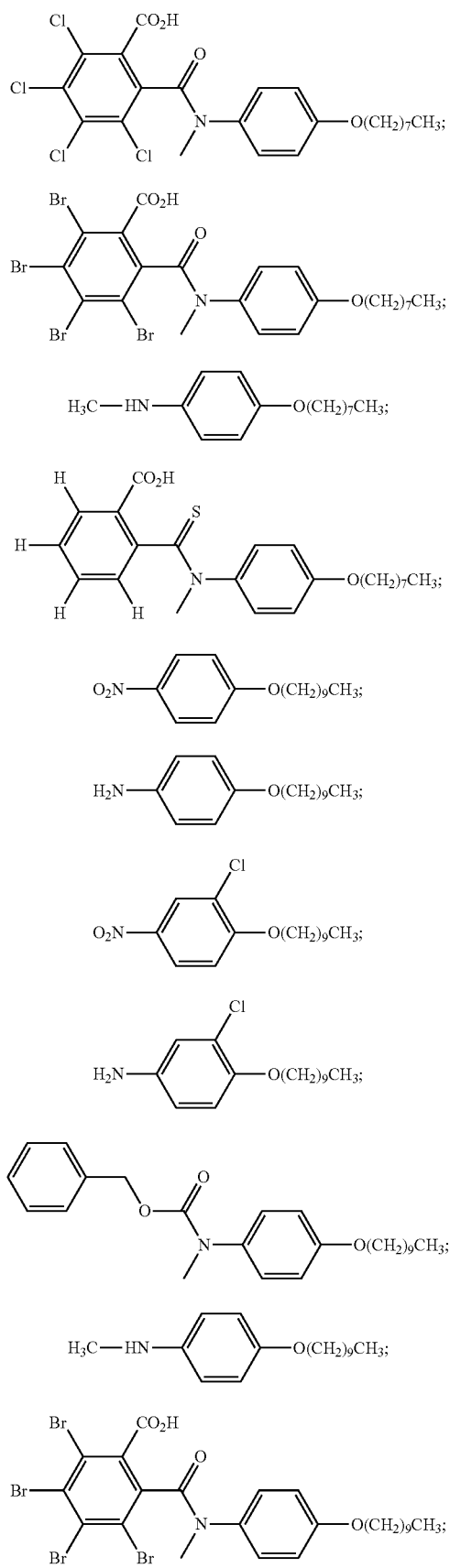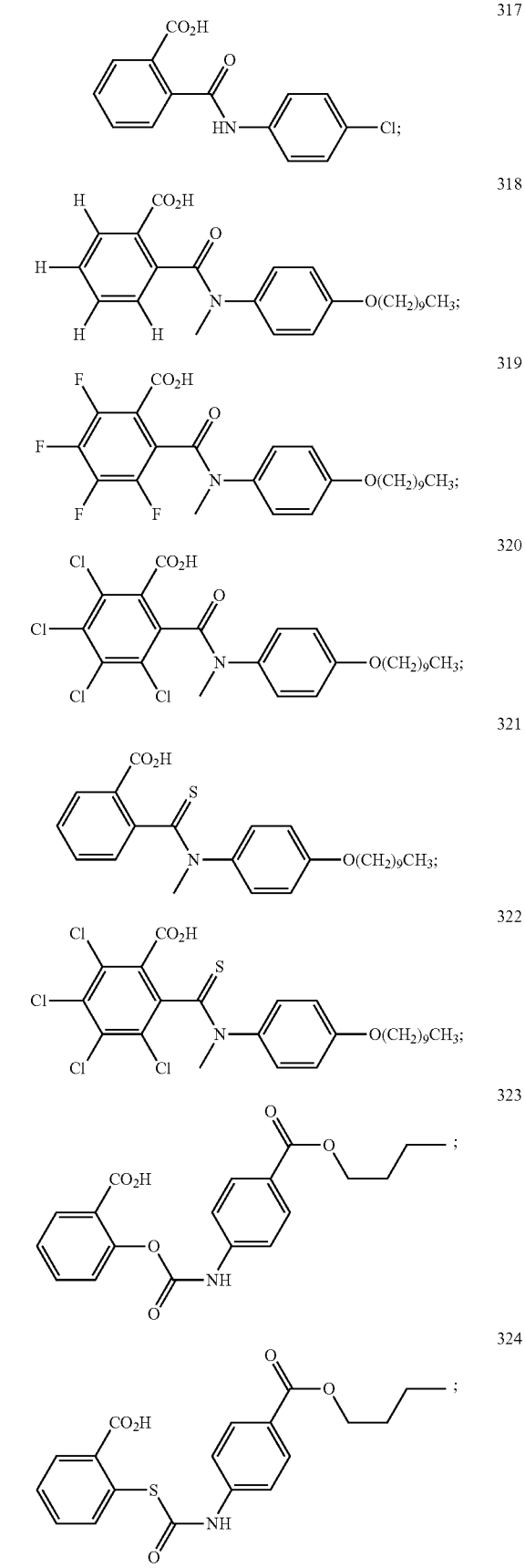

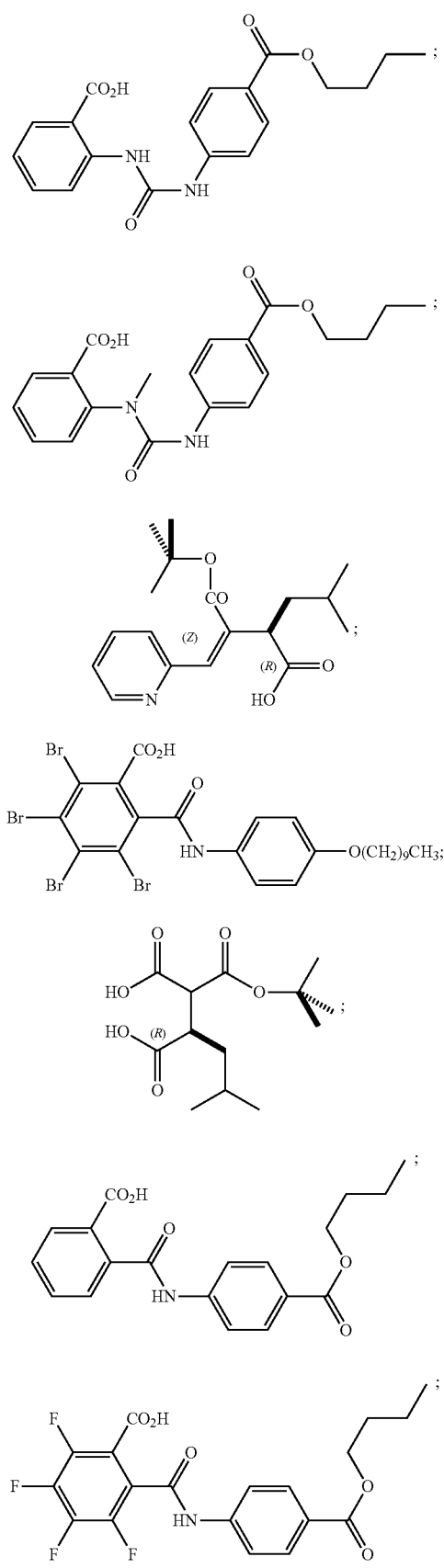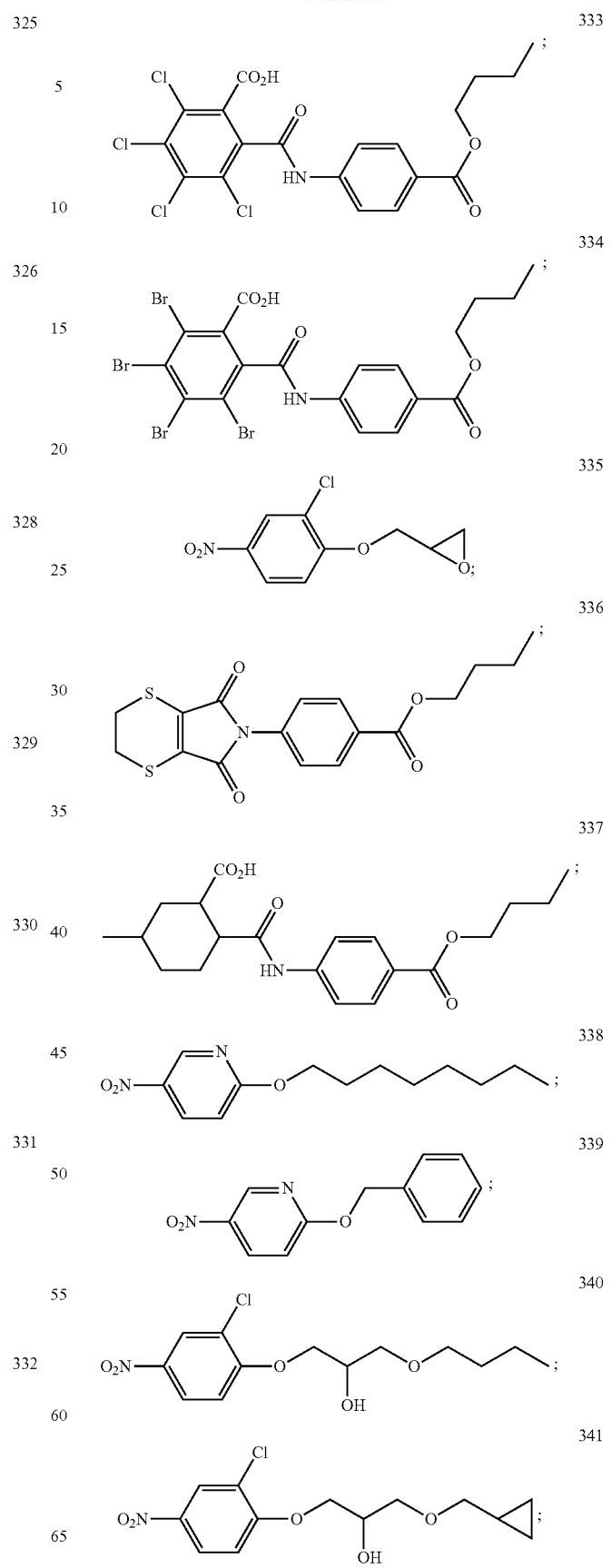

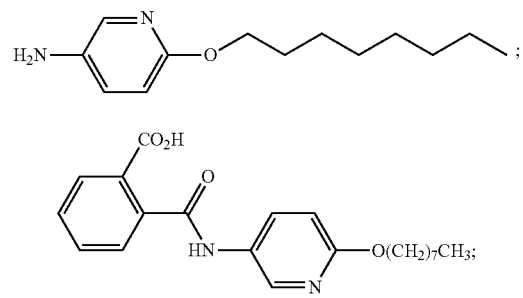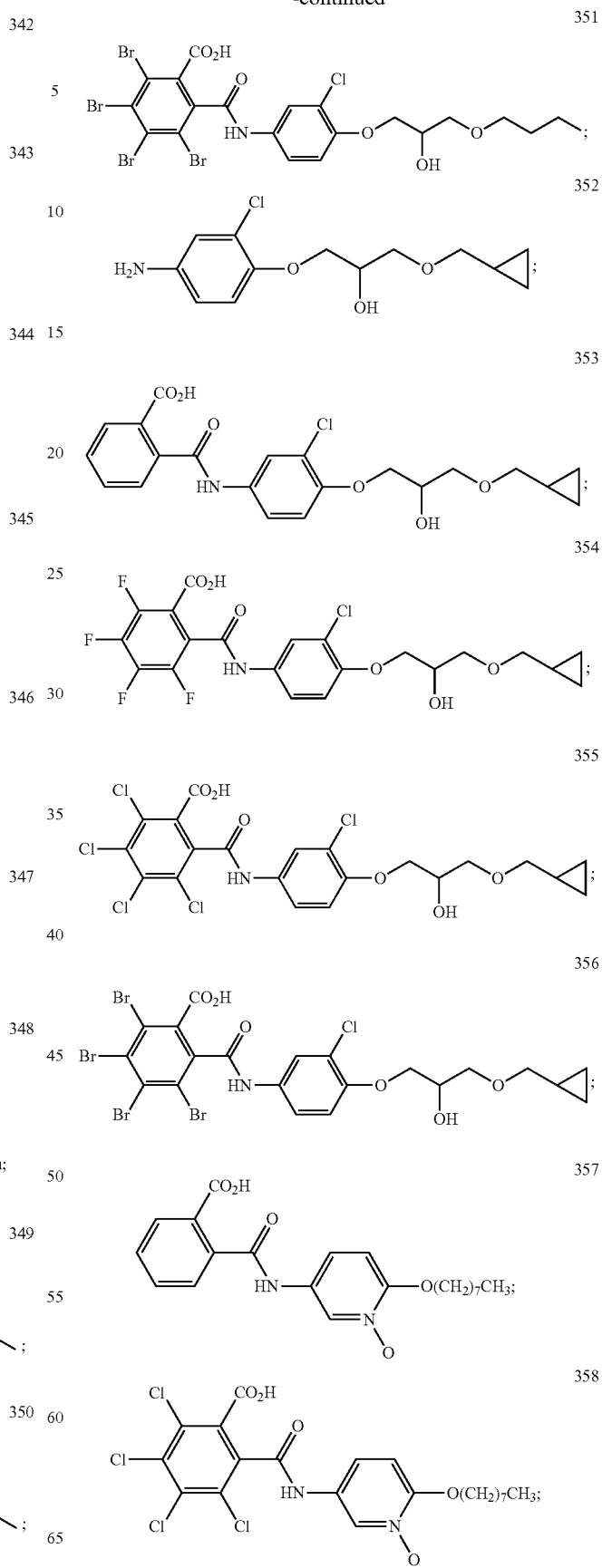

-continued

376 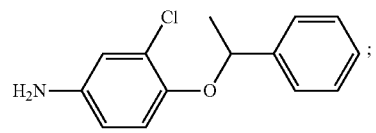
377 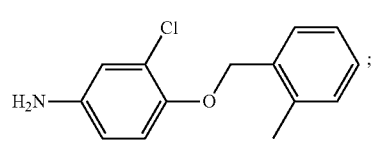
378 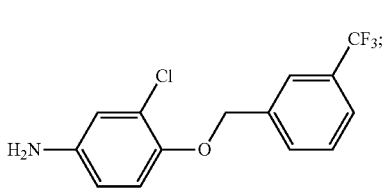
379 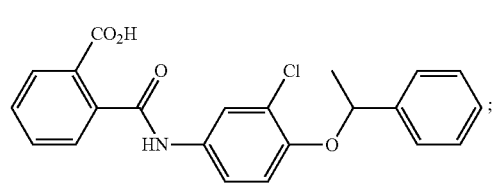
380 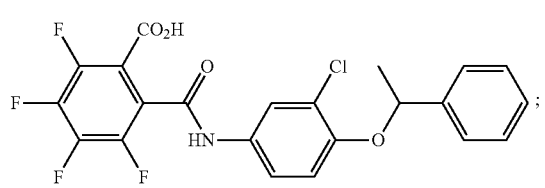
381 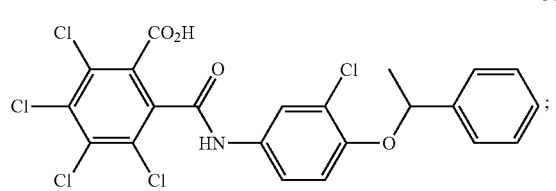
382 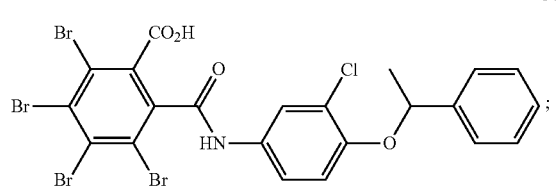
383 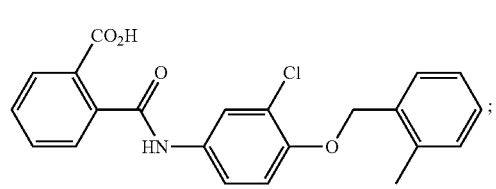
384 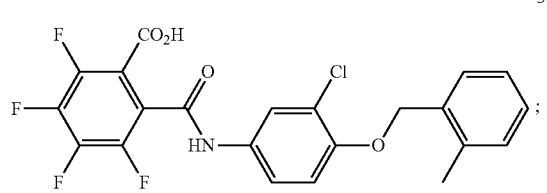
385 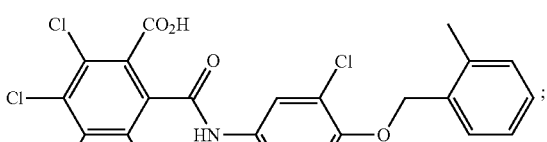
386 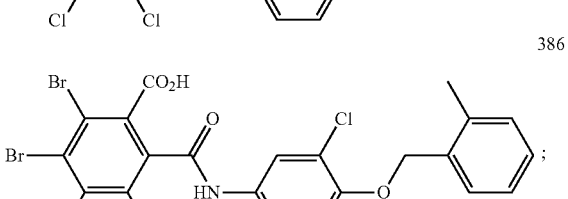
387 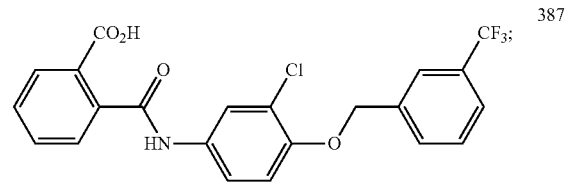
388 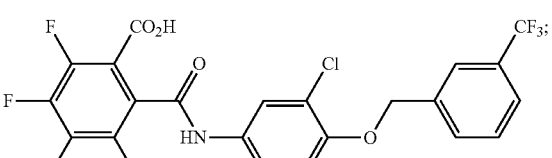
389 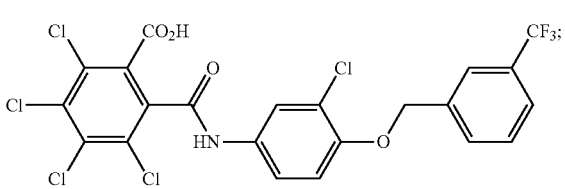
390 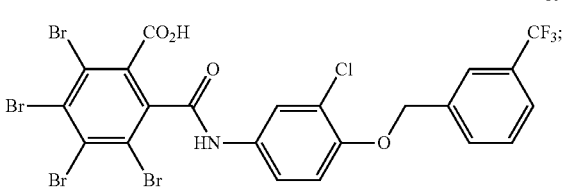
391 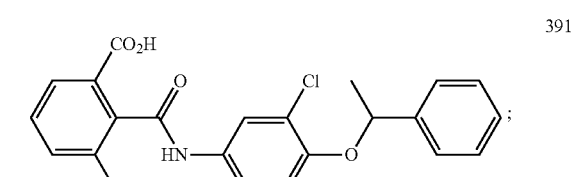
392 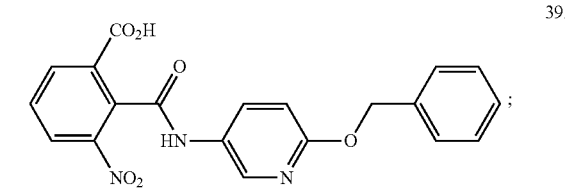

412 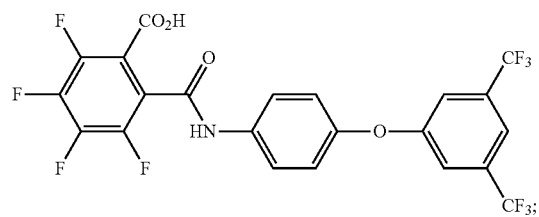
413 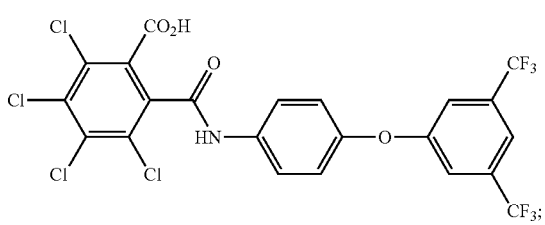
414 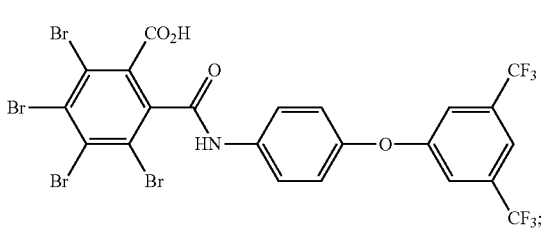
415 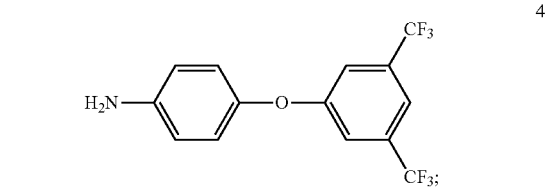
416 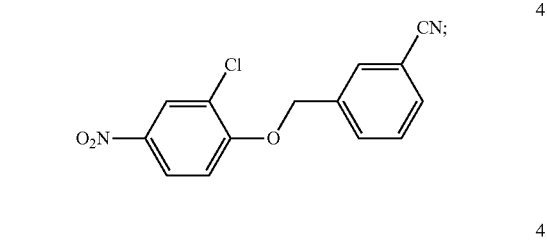
417 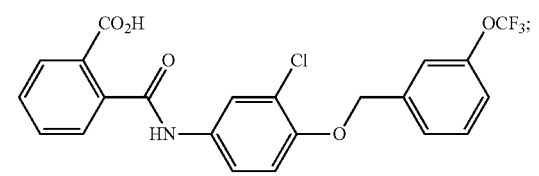
418 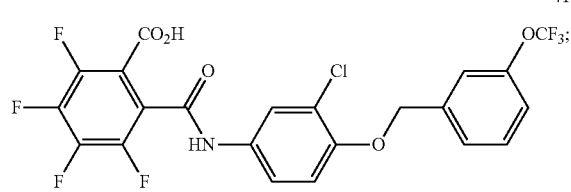
419 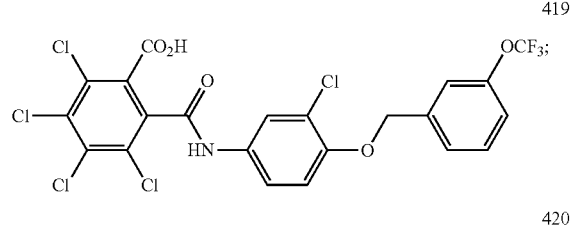
420 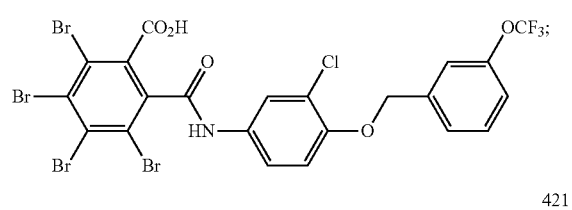
421 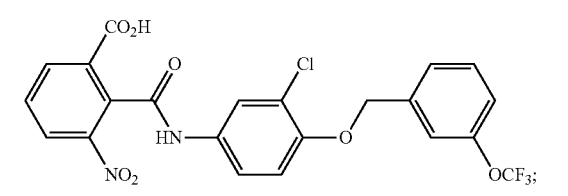
422 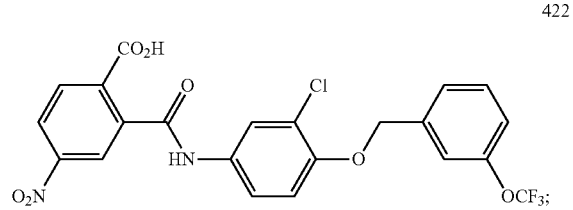
423 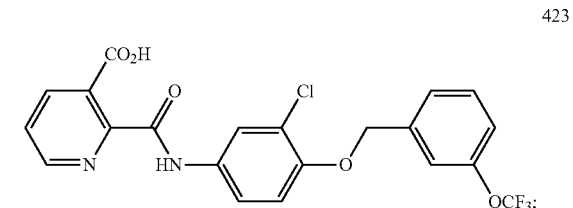
424 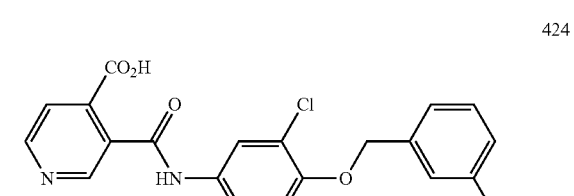
425 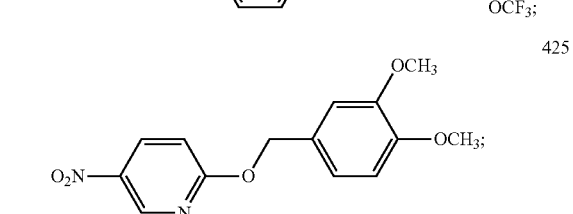
426 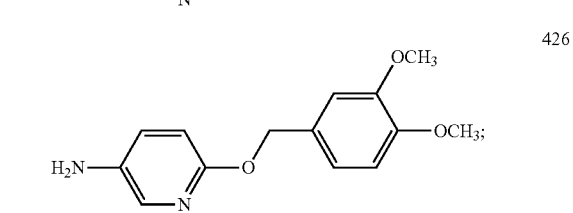

-continued

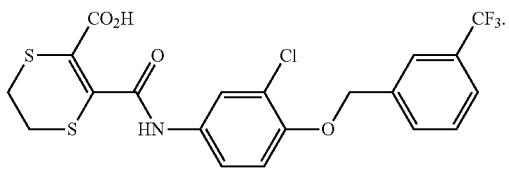
427

Example 2

This Example demonstrates screening methods for the identification and selection of compounds effective for treating, inhibiting, and/or killing bacteria, such as antibiotic resistant strains of bacteria. The screening methods include using TEM-1, P99, OXA-10, B1aR, and PBP2a assay protocols. TEM-1, P99, and OXA-10 are representative members of class A, class C, and class D β-lactamases. B1aR and PBP2a are penicillin-binding proteins. B1aR is a key β-lactam antibiotic sensor/signal transducer involved in manifestation of antibiotic resistance in certain Gram positive bacteria, including MRSA. In Table 10, for the results of the PBP2a assays, the term "X" refers to an inhibitory concentration of about 5 to about 1 mM, the term "XX" refers to an inhibitory concentration of about 1 to about 0.1 mM, and the term "XXX" refers to an inhibitory concentration of less than about 0.1 mM.

β-Lactamase Assays (TEM-1, P99, and OXA-10): The activity of the compounds of the invention (inhibitors) toward β-lactamases was evaluated using 96 well plates. The reaction mixture included 10 mM sodium phosphate, pH 7.0, 150 mM sodium chloride, 0.01% Triton X-100, 100 μM nitrocefin, 10 nM of β-lactamases (class A: TEM-1; class C: P99, or class D: OXA-10), and variable concentrations of the inhibitors in a total volume of 100 μL. β-Lactamases were pre-incubated with the compounds at room temperature for 5 minutes, and the assay was initiated by the addition of nitrocefin. The inhibition of the enzyme activity by the compounds was determined by monitoring color change (from yellow to red) of nitrocefin after 20 minutes. Stock solutions of the compounds were prepared in dimethyl sulfoxide (DMSO). No more than 5% DMSO was present in assays, unless noted otherwise.

B1aR Assay: The surface domain of B1aR (1 μM) was added to each inhibitor (at various concentrations) in 100 mM sodium phosphate, 50 mM sodium bicarbonate, at pH 7.0. The reaction mixtures were incubated at room temperature for 20 minutes. BOCILLIN FL, a fluorogenic ligand, was added to a concentration of 20 μM in a final volume of 20 μL. The mixtures were incubated at 37° C. for 5 minutes, at which point the reactions were quenched by the addition of 15 μL of the SDS sample buffer (125 mM Tris, 4% SDS, 20% glycerol, 2% 2-mercaptoethanol, pH 6.8), and were boiled for 4 minutes. The samples were loaded onto 15% SDS-PAGE, the gel was developed and scanned using a Storm 840® Fluorimager. The fluorescent bands of BOCILLIN FL-labeled B1aR$^S$ were analyzed by Image Quant 5.2 software.

PBP2 Assay: The PBP2 assay was performed according to the methods of Villegas-Esterada et al. (*J. Am. Chem. Soc.* 2008, 130, 9212-9213).

TABLE 10

| Cmpd DH-DOC | Mol. Wt. | DOC-mg DHD-mg | TEM-1 | P99 | OXA-10 | BlaR | PBP2a* |
|---|---|---|---|---|---|---|---|
| 0 | | | | | | | |
| 1 | | 600 | | | | | |
| 2 | C14H11NO3 M.w.: 241.07 | 1600 | | | | | |
| 3 | | 1800 | | | | | |
| 4 | | 1100 | | | | | |
| 5 | | 700 | | | | | |
| 6 | | 400 | | | | | |
| 7 | C14H12N2O3 M.w.: 256.08 | 200 | | | | | |
| 8 | C15H10F3NO3 M.w.: 309.06 | 800 | | | | | |
| 9 | | 400 | | | | | |
| 10 | | | | | | | |
| 11 | C8H11NO3 M.w.: 169.07 | 200 | | | | | |
| 12 | | 1700 | | | | | |
| 13 | | 1600 | | | | | |
| 14 | | 1100 | | | | | |
| 15 | | 1820 | | | | | |
| 16 | | 50 | | | | | |
| 17 | | 420 | | | | | |
| 18 | | 1200 | | | | | |
| 19 | C8H13NO3 M.w.: 171.09 | 510 | | | | | |
| 20 | C11H9NO5 M.w.: 235.05 | 1210 | | | | | |
| 21 | C19H20N2O4 M.w.: 340.14 | 710 | | | | | |
| 22 | C18H20N2O3 M.w.: 312.15 | 1010 | | | | | |
| 23 | | 1020 | | | | | |
| 24 | C16H9F6NO3 M.w.: 377.05 | 2025 | | | | | |
| 25 | C16H15NO5 M.w.: 301.10 | 1059 | | | | | |

TABLE 10-continued

| Cmpd DH-DOC | Mol. Wt. | DOC-mg DHD-mg | TEM-1 | P99 | OXA-10 | BlaR | PBP2a* |
|---|---|---|---|---|---|---|---|
| 26 | C16H13NO5 M.w.: 299.08 | 490 | | | | | |
| 27 | C15H10F3NO4 M.w.: 325.06 | 450 | | | | | |
| 28 | C15H12N2O4 M.w.: 284.08 | 880 | | | | | |
| 29 | C25H24N2O6 M.w.: 448.16 | 1120 | | | | | |
| 30 | C14H10FNO3 M.w.: 259.06 | 740 | | | | | |
| 31 | C15H18N2O4 M.w.: 290.13 | 1560 | | | | | |
| 32 | C14H18N2O3 M.w.: 262.13 | 2130 | | | | | |
| 33 | C13H10N2O3 M.w.: 242.07 | 1258 | | | | | |
| 34 | C12H7F6NO3 M.w.: 327.03 | 2240 | | | | | |
| 35 | C12H13NO5 M.w.: 251.08 | 2105 | | | | | |
| 36 | C12H11NO5 M.w.: 249.06 | 1750 | | | | | |
| 37 | C11H8F3NO4 M.w.: 275.04 | 2102 | | | | | |
| 38 | C11H10N2O4 M.w.: 234.06 | 1650 | | | | | |
| 39 | C21H22N2O6 M.w.: 398.15 | 1000 | | | | | |
| 40 | C10H8FNO3 M.w.: 209.05 | 1500 | | | | | |
| 41 | C18H17NO3 M.w.: 295.12 | 1020 | | | | | |
| 42 | C18H14N2O3 M.w.: 306.10 | 650 | | | | | |
| 43 | C18H18N2O4 M.w.: 326.13 | 750 | | | | | |
| 44 | C15H9ClF3NO3 M.w.: 343.02 | 220 | x | | | | |
| 45 | C15H10N2O3 M.w.: 266.07 | 540 | | | | | |
| 46 | C15H9ClF3NO3 M.w.: 343.02 | 1250 | | | | | |
| 47 | C18H13NO4 M.w.: 307.08 | 369 | x | | | | |
| 48 | C15H11NO5 M.w.: 285.06 | 250 | | | | | |
| 49 | C18H17ClN2O3 M.w.: 344.09 | 550 | | | | | |
| 50 | C16H15NO5 M.w.: 301.10 | 1150 | | | | | |
| 51 | C14H15NO3 M.w.: 245.11 | 1150 | | | | | |
| 52 | C14H12N2O3 M.w.: 256.08 | 2600 | | | | | |
| 53 | C14H16N2O4 M.w.: 276.11 | | | | | | x |
| 54 | C11H7ClF3NO3 M.w.: 293.01 | 1980 | | | | | |
| 55 | C11H8N2O3 M.w.: 216.05 | 1350 | | | | | |
| 56 | C11H7ClF3NO3 M.w.: 293.01 | | | | | | |
| 57 | C14H11NO4 M.w.: 257.07 | | | | | | |
| 58 | C11H9NO5 M.w.: 235.05 | | | | | | |
| 59 | C14H15ClN2O3 M.w.: 294.08 | | | | | | |
| 80 | | | | | | | |
| 81 | C18H19N3O5 M.w.: 357.13 | 300 | | | | | |
| 82 | C16H8F6N2O5 M.w.: 422.03 | 1820 | | | | | |
| 83 | C16H14N2O7 M.w.: 346.08 | 850 | | | | | |
| 84 | C15H9F3N2O6 M.w.: 370.04 | 1980 | | | | | |

TABLE 10-continued

| Cmpd DH-DOC | Mol. Wt. | DOC-mg DHD-mg | TEM-1 | P99 | OXA-10 | BlaR | PBP2a* |
|---|---|---|---|---|---|---|---|
| 85 | C15H8ClF3N2O5 M.w.: 388.01 | 2800 | | | | | x |
| 86 | C15H8ClF3N2O5 M.w.: 388.01 | 3200 | xx | | | | x |
| 87 | C16H9ClF3NO5 M.w.: 387.01 | 10 | | | | | |
| 88 | C16H9ClF3NO5 M.w.: 387.01 | 740 | | | | | |
| 89 | C15H5Br4ClF3NO3 M.w.: 659.27 | 1600 | xx | xxx | xxx | | |
| 90 | C15H8ClF4NO3 M.w.: 361.68 | 1200 | | | | | |
| 91 | C15H8ClF4NO3 M.w.: 361.68 | | | | | | |
| 92/93 | C16H11ClF3NO3 M.w.: 357.71 | 1500 | | | xx | | |
| 93/92 | C16H11ClF3NO3 M.w.: 357.71 | 1500 | | | xx | | |
| 94 | C15H15ClF3NO3 M.w.: 349.73 | 300 | | | | | x |
| 95/96 | C16H17ClF3NO3 M.w.: 363.76 | 600 | x | xxx | xx | | |
| 96/95 | C16H17ClF3NO3 M.w.: 363.76 | 600 | x | xxx | xx | | |
| 97 | C25H17ClF3NO7 M.w.: 535.06 | 100 | | x | x | | |
| 98 | C15H13ClF3NO7 M.w.: 411.03 | 1000 | | | | | |
| 99 | C17H11ClF3NO3 M.w.: 369.04 | 220 | | | | | |
| 100 | C17H11ClF3NO3 M.w.: 369.04 | 100 | | | | | x |
| 101 | C9H13NO4S2 M.w.: 263.03 | | | | | | |
| 102 | C24H18ClF3N2O5 M.w.: 506.09 | | | | | | |
| 103 | C24H18ClF3N2O5 M.w.: 506.09 | | | | | | |
| 104 | C23H15ClF3N3O7 M.w.: 537.06 | | | | | | |
| 105 | C23H15ClF3N3O7 M.w.: 537.06 | | | | | | |
| 106 | C23H15ClF3N3O7 M.w.: 537.06 | | | | | | |
| 107 | C23H15ClF3N3O7 M.w.: 537.06 | | | | | | |
| 108 | C23H19NO8 M.w.: 437.40 | 800 | | | | | x |
| 109 | C13H15NO8 M.w.: 313.26 | 1200 | | | | | x |
| 110 | C14H11NO6 M.w.: 289.24 | 100 | | | | | x |
| 111 | C14H11NO6 M.w.: 289.24 | 600 | | | | | x |
| 112 | C13H17NO4 M.w.: 251.28 | 1400 | | | | | |
| 113 | C19H21NO4 M.w.: 327.37 | 100 | | | | | |
| 114 | C9H8N2O3S3 M.w.: 288.37 | 1100 | | | | | |
| 115 | C12H15NO7S2 M.w.: 349.03 | 10 | | | | | |
| 116 | C22H19ClN2O6S3 M.w.: 538.01 | 400 | | | | | |
| 117 | C22H21ClN2O7S3 M.w.: 556.02 | 200 | | | | | |
| 118 | C16H14N2O7S3 M.w.: 442 | 350 | x | xxx | | | x |
| 119 | C7H8O4S2 M.w.: 219.99 | 980 | | | | | x |
| 120 | C6H7NO3S2 Mol. Wt.: 204.99 | 600 | | | xx | | x |
| 121 | C6H6O4S2 Mol. Wt.: 205.97 | 1800 | | | | | x |
| 122 | C12H17NO8S2 Mol. Wt.: 367.04 | 1700 | | | | | x |

TABLE 10-continued

| Cmpd DH-DOC | Mol. Wt. | DOC-mg DHD-mg | TEM-1 | P99 | OXA-10 | BlaR | PBP2a* |
|---|---|---|---|---|---|---|---|
| 123 | C9H13NO4S2 Mol. Wt.: 263 | 300 | | | | | |
| 124 | C9H13NO4S2 Mol. Wt.: 263 | 400 | | | | | |
| 125 | C10H15NO4S2 Mol. Wt.: 277 | 300 | | | | | |
| 126 | C10H15NO4S2 Mol. Wt.: 277 | | | | | | xx |
| 127 | C15H17NO5S2 Mol. Wt.: 355 | 200 | | | | | xx |
| 128 | C15H17NO5S2 Mol. Wt.: 355 | 200 | | | | | x |
| 129 | C10H15NO5S2 Mol. Wt.: 293.36 | 350 | | | | | x |
| 130 | C10H15NO5S2 Mol. Wt.: 293 | | | | | | |
| 131 | C17H22N2O3S2 Mol. Wt.: 366 | | | | | | |
| 132 | C17H22N2O3S2 Mol. Wt.: 366 | | | | | | |
| 133 | C16H19NO4S2 Mol. Wt.: 353 | 200 | | | | | x |
| 134 | C16H19NO4S2 Mol. Wt.: 353 | 10 | | | | | x |
| 135 | C16H19NO4S2 Mol. Wt.: 353.46 | 300 | | | | | x |
| 136 | C16H19NO4S2 Mol. Wt.: 353 | 650 | | | | | x |
| 137 | C15H15NO4S2 Mol. Wt.: 337.42 | 10 | | | | | |
| 138 | C15H15NO4S2 Mol. Wt.: 337.42 | 10 | xxx | xxx | | | x |
| 139 | C15H16N2O7S2 Mol. Wt.: 400.43 | 850 | | | | | x |
| 140 | C15H14N2O6S2 M.w.: 382.41 | 200 | xx | xx | xx | | x |
| 141 | C9H11NNa2O6S3 M.w.: 371.36 | 100 | | | | | x |
| 142 | C15H26N2O5S3 M.w.: 410.58 | 100 | | | | | x |
| 143 | C15H16N2O7S2 M.w.: 400.43 | 500 | | | | | x |
| 144 | C15H14N2O6S2 M.w.: 382.41 | 120 | | | | | x |
| 145 | C15H13NO5S2 M.w.: 351.02 | 300 | | | | | x |
| 146 | C15H13NNa2O6S2 M.w.: 413.00 | 650 | | | | | x |
| 147 | | | | | | | |
| 148 | | | | | | | |
| 149 | | | | | | | |
| 150 | C15H25NO3 M.w.: 267 | 1400 | | | | | |
| 151 | C16H18F3NO3 M.w.: 329 | 2200 | | | | | |
| 152 | C11H19NO4 M.w.: 229 | 100 | | | | | |
| 153 | C14H25NO3 M.w.: 255 | 850 | | | | | |
| 154 | C15H18FNO3 M.w.: 279 | 1100 | | | | | |
| 155 | C17H22ClNO5 M.w.: 356 | 2400 | | | | | |
| 156 | C16H18N2O3 M.w.: 286 | 1400 | | | | | |
| 157 | C17H23NO5 M.w.: 321 | 1700 | | | | | |
| 158 | C13H23NO4 M.w.: 257 | 100 | x | | | | |
| 159 | C12H21NO4 M.w.: 243 | 100 | | | | | |
| 160 | C12H21NO4 Mol. Wt.: 243 | 100 | | | | | |
| 161 | C13H23NO4 Mol. Wt.: 257 | 100 | | | | | |
| 162 | C17H23NO5 Mol. Wt.: 321 | 160 | | | | | |

TABLE 10-continued

| Cmpd DH-DOC | Mol. Wt. | DOC-mg DHD-mg | TEM-1 | P99 | OXA-10 | BlaR | PBP2a* |
|---|---|---|---|---|---|---|---|
| 163 | C15H18FNO3 Mol. Wt.: 279 | 420 | | | | | |
| 164 | C17H21NO5 Mol. Wt.: 319 | 1800 | | | | | |
| 165 | C15H18FNO3 Mol. Wt.: 279 | 250 | | | | | |
| 166 | C15H5ClF7NO3 Mol. Wt.: 416 | 450 | | | | | |
| 167 | C16H11F4NO5 Mol. Wt.: 373 | 100 | | | | | |
| 168 | C15H6F7NO3 Mol. Wt.: 381 | 120 | | | | | |
| 169 | C15H6F7NO3 Mol. Wt.: 381 | 210 | | | | | |
| 170 | C11H9F4NO4 Mol. Wt.: 295 | 100 | | | | | |
| 171 | C13H13F4NO3 Mol. Wt.: 307 | 200 | | | | | |
| 172 | C14H13F4NO3 Mol. Wt.: 319 | 200 | | | | | |
| 173 | C15H18N2O6 Mol. Wt: 322 | 200 | | | | | |
| 174 | C14H18N2O3 Mol. Wt.: 262 | 300 | | | | | |
| 175 | C17H23NO3 Mol. Wt.: 289 | 700 | | | | | |
| 176 | C16H20ClNO4 Mol. Wt.: 326 | 400 | | | | | |
| 177 | C21H23NO4 Mol. Wt.: 353 | 800 | | | | | |
| 178 | C16H21NO4 Mol. Wt.: 291 | 300 | | | | | |
| 179 | Mol. Wt.: 354 | 1100 | | | | | |
| 180 | C18H25NO4 Mol. Wt.: 319 | 700 | | | | | |
| 181 | C20H30NO6P Mol. Wt.: 411 | 1000 | | | | | |
| 182 | C22H24ClNO4 Mol. Wt.: 402 | 1000 | | | | | |
| 183 | C12H21NO4 Mol. Wt.: 243 | 300 | | | | | |
| 184 | C16H21NO4 Mol. Wt.: 291 | 150 | | | | | |
| 185 | C23H35NO4 Mol. Wt.: 390 | 40 | | | | | |
| 186 | C16H20ClNO3 Mol. Wt.: 310 | 100 | | | | | |
| 187 | C18H23Cl2NO4 Mol. Wt.: 388 | 150 | | | | | |
| 188 | C16H20ClNO3 Mol. Wt.: 310 | 200 | | | | | |
| 189 | C13H23NO5 Mol. Wt.: 273 | 100 | | | | | |
| 190 | C13H23NO5 Mol. Wt.: 273 | 130 | | | | | |
| 191 | C18H25NO5 Mol. Wt.: 335 | 650 | | | | | |
| 192 | C18H25NO4 Mol. Wt.: 319 | 400 | | | | | |
| 193 | C18H24N2O7 Mol. Wt.: 380 | 200 | | | | | |
| 194 | C18H24N2O7 Mol. Wt.: 380 | 1100 | | | | | |
| 195 | C14H13Br4NO3 Mol. Wt.: 563 | 300 | | | | | |
| 196 | C15H6Br4F3NO3 Mol. Wt.: 625 | 800 | xx | xx | | | |
| 197 | C11H9Br4NO4 Mol. Wt.: 539 | 400 | | | | | |
| 198 | C13H13Br4NO3 Mol. Wt.: 551 | | | | | | |
| 199 | C14H6Br4FNO3 Mol. Wt.: 575 | 300 | | | | | |
| 200 | C16H10Br4ClNO5 Mol. Wt.: 651 | 700 | | | | | |

TABLE 10-continued

| Cmpd DH-DOC | Mol. Wt. | DOC-mg DHD-mg | TEM-1 | P99 | OXA-10 | BlaR | PBP2a* |
|---|---|---|---|---|---|---|---|
| 201 | C15H5Br4N2NaO3 Exact Mass: 600 | 2700 | xx | xxx | xx | x | |
| 202 | C16H11Br4NO5 Mol. Wt.: 617 | 600 | | | | | |
| 203 | C12H11Br4NO4 Mol. Wt.: 553 | | | | | | |
| 204 | C11H9Br4NO4 Mol. Wt.: 539 | | | | | | |
| 205 | C11H9Br4NO4 Mol. Wt.: 539 | | | | | | |
| 206 | | | | | | | |
| 207 | C16H11Br4NO5 Mol. Wt.: 617 | | | | | | |
| 208 | C14H6Br4FNO3 Mol. Wt.: 575 | | | | | | |
| 209 | C16H9Br4NO5 Mol. Wt.: 615 | | | | | | |
| 210 | C14H6Br4FNO3 Mol. Wt.: 575 | 150 | | | | | |
| 211 | C17H11Br4Cl2NO4 Mol. Wt.: 684 | | | | | | |
| 212 | | | | | | | |
| 213 | | | | | | | |
| 214 | C15H6Br4F3NO3 Mol. Wt.: 625 | | | | | | |
| 215 | C11H9Br4NO4 Mol. Wt.: 539 | 300 | | | | | |
| 216 | C13H13Br4NO3 Mol. Wt.: 551 | 1000 | | | | | |
| 217 | C12H11Br4NO4 Mol. Wt.: 553 | 300 | | | | | xx |
| 218 | C14H6Br4N2O6 Mol. Wt.: 618 | 200 | | | | | |
| 219 | C13H6Br4N2O3 Mol. Wt.: 558 | 300 | | | | | |
| 220 | C16H11Br4NO3 Mol. Wt.: 585 | 500 | | | | | |
| 221 | C15H8Br4ClNO4 Mol. Wt.: 621 | 300 | | | | | |
| 222 | C20H11Br4NO4 Mol. Wt.: 649 | 900 | | | | | xx |
| 223 | C15H9Br4NO4 Exact Mass: 583 | 1400 | xxx | xxx | xxx | | |
| 224 | C15H8Br5NO3 Mol. Wt.: 650 | 200 | | | | | |
| 225 | C17H13Br4NO4 Mol. Wt.: 615 | | | | | | |
| 226 | C19H18Br4NO6P Mol. Wt.: 707 | 300 | | | | | |
| 227 | C21H10Br4ClNO3 Mol. Wt.: 579 | 100 | xxx | x | xxx | | |
| 228 | C11H9Br4NO4 Mol. Wt.: 539 | 100 | | | | | |
| 229 | C15H9Br4NO4 Mol. Wt.: 587 | 100 | | | | | |
| 230 | C22H21Br4NO3 Exact Mass: 662.8 | 200 | | | | | |
| 231 | C15H8Br4ClNO3 Mol. Wt.: 605 | 200 | | | | | |
| 232 | C15H8Br4ClNO3 Mol. Wt.: 605 | 400 | | x | x | | |
| 233 | C12H11Br4NO5 Mol. Wt.: 569 | | | | | | |
| 234 | C12H11Br4NO5 Mol. Wt.: 569 | | | | | | |
| 235 | C17H13Br4NO5 Mol. Wt.: 631 | | | | | | |
| 236 | C17H13Br4NO4 Mol. Wt.: 615 | 150 | | | | | |
| 237 | C17H12Br4N2O7 Mol. Wt.: 676 | 140 | | | | | |
| 238 | C17H12Br4N2O7 Mol. Wt.: 676 | 200 | | x | x | | |
| 239-Na | C21H11Br4ClNNaO4 M.w.: 719.38 | 1000 | xxx | xxx | xxx | xxx | |

TABLE 10-continued

| Cmpd DH-DOC | Mol. Wt. | DOC-mg DHD-mg | TEM-1 | P99 | OXA-10 | BlaR | PBP2a* |
|---|---|---|---|---|---|---|---|
| 240 | C18H24N2O7 Exact Mass: 380 | 400 | | | | | |
| 241 | | | | | | | |
| 242 | C16H18N2O3 Exact Mass: 286 | 200 | | | | | |
| 243 | C22H24ClNO4 Exact Mass: 401 | 700 | | | | | x |
| 244 | C16H21NO4 Exact Mass: 291 | 100 | | | | | |
| 245 | C16H20ClNO3 Exact Mass: 309 | 400 | | | | | |
| 246 | C16H17ClF3NO3 Exact Mass: 363 | 660 | | | xx | | |
| 247 | C16H18F3NO3 Exact Mass: 329 | 500 | | | | | |
| 248 | C18H24N2O7 Exact Mass: 380 | 700 | | | | | |
| 249 | C8Br4O3 Exact Mass: 460 | 10 | | | | | |
| 250 | C13H12ClNO Exact Mass: 233 | 100 | | | | | |
| 251 | C21H12ClF4NO4 Exact Mass: 453 | 100 | | | | | x |
| 252 | C14H5Br4ClNNaO4 Exact Mass: 624.7 | 300 5 g | | | | | |
| 253 | C21H12Cl5NO4 Exact Mass: 516.9 | 10 | xxx | xxx | xxx | xx | |
| 254 | C15H9Cl4NO4 Exact Mass: 406.9 | 400 | | | xx | | |
| 255 | C15H6Cl4N2O3 Exact Mass: 401.9 | 300 | | | | | |
| 256 | | | | | | | |
| 257 | C15H8Cl5NO3 Exact Mass: 424.9 | 1200 | | | | | x |
| 258 | C15H5Cl5F3NO3 Exact Mass: 478.9 | 1600 | xxx | xx | xx | | |
| 259 | C15H10Cl4N2O5S Exact Mass: 469.9 | 2100 | | | | | |
| 260 | | | | | | | |
| 261 | C14H6Cl5NO4 Exact Mass: 426.9 | 1400 | | | | | |
| 262 | C15H9Cl4NO4 Exact Mass: 406.9 | 1200 | | | | | x |
| 263 | C19H18Cl4NO6P Exact Mass: 527.0 | 2300 | | | | | |
| 264 | C16H11Cl4NO5 Exact Mass: 436.9 | 1800 | | | | | |
| 265 | C22H23Cl4NO4 Exact Mass: 505.0 | 700 | xxx | xxx | xxx | | |
| 266 | | | | | | | |
| 267 | C17H12Cl4N2O7 Exact Mass: 495.9 | 100 | | | | | x |
| 268 | C20H11Cl4NO4 Exact Mass: 468.9 | 1000 | xxx | xx | | | x |
| 269 | C15H4Br4N2O2 Exact Mass: 559.7 | 300 | | | | | |
| 270 | C22H27NO4 Exact Mass: 369.2 | 900 | xxx | xxx | xxx | xx | x |
| 271 | C22H23F4NO4 Exact Mass: 441.2 | 900 | xxx | xxx | xxx | xxx | x |
| 272 | C21H16ClNO4 Exact Mass: 381.1 | 800 | | | | | |
| 273 | C14H5Br4N2NaO5 Exact Mass: 619.7 | 100 | | | | | |
| 274 | C22H23Br4NO4 Exact Mass: 680.8 | 1700 5200 | xxx | xxx | xxx | | |
| 275 | C19H21NO4 Exact Mass: 327.1 | 700 | | | | | |
| 276 | | | | | | | |
| 277(1-4) | C21H10Cl5NOS2 Exact Mass: 530.9 | 100 100 | | xxx | | xxx | x |
| 278 | C21H12Br4ClNO3S Exact Mass: 708.7 | 500 | xxx | xxx | xxx | xxx | xxx |
| 279/2 | C22H27NO3S Exact Mass: 385.2 | 200 | xxx | xxx | | | |
| 280(1-2) | C22H23Cl4NOS3 Exact Mass: 553 | 200 100 | x | xxx | xxx | xxx | xx |

TABLE 10-continued

| Cmpd DH-DOC | Mol. Wt. | DOC-mg DHD-mg | TEM-1 | P99 | OXA-10 | BlaR | PBP2a* |
|---|---|---|---|---|---|---|---|
| 281 | C22H21Br4NOS2 | 120 | | | | xxx | |
| | Exact Mass: 694.8 | 100 | | | | | |
| 282 | C24H27Cl4NO4 | | x | x | xxx | | |
| | Exact Mass: 533.1 | | | | | | |
| 283 | C14H8ClNO3 | | | | | | |
| | Exact Mass: 273 | | | | | | |
| 284 | C24H31NO4 | 100 | | | | | |
| | Exact Mass: 397.2 | | | | | | |
| 285 | C24H27F4NO4 | 100 | | | | | |
| | Exact Mass: 469.2 | | | | | | |
| 286 | C24H27Cl4NO4 | | | | | | |
| | Exact Mass: 533.1 | | | | | | |
| 287 | C24H27Br4NO4 | 600 | | | | | |
| | Exact Mass: 708.9 | | | | | | |
| 288 | C30H43NO4 | 500 | | | x | x | |
| | Exact Mass: 481.3 | | | | | | |
| 289 | C30H39F4NO4 | 1200 | | xx | xxx | xxx | |
| | Exact Mass: 553.3 | | | | | | |
| 290 | C30H39Cl4NO4 | 500 | x | xxx | xxx | xxx | |
| | Exact Mass: 617.2 | | | | | | |
| 291 | C30H39Br4NO4 | 1000 | xxx | xxx | xxx | xx | |
| | Exact Mass: 793 | | | | | | |
| 292 | C23H25Br4NO4 | 200 | | | | | |
| | Exact Mass: 694.9 | | | | | | |
| 293 | C14H20ClNO3 | 200 | | | | | |
| | Exact Mass: 285.1 | | | | | | |
| 294 | C15H9Br4NO4 | 2500 | | | | | |
| | Mol. Wt.: 586.9 | | | | | | |
| 295 | C15H15NO3 | 20 g | | | | | |
| | Mol. Wt.: 257.3 | | | | | | |
| 296 | | 10 | | | | xx | |
| 297 | C23H31NO3 | 13 | | | | | |
| | Exact Mass: 369.2 | | | | | | |
| 298 | C14H22ClNO | 1100 | | | | | |
| | Exact Mass: 255.1 | | | | | | |
| 299 | C14H22ClNO | 5 | | | | | |
| | Exact Mass: 255.1 | | | | | | |
| 300 | C22H26ClNO4 | 700 | xxx | xx | xx | | xxx |
| | Mol. Wt: 403.9 | | | | | | |
| 301 | C22H22ClF4NO4 | 1000 | xx | xxx | xxx | xxx | xxx |
| | Mol. Wt.: 475.9 | | | | | | |
| 302-2 | C22H22Cl5NO4 | 300 | | | | xxx | xx |
| | Exact Mass: 539 | | | | | | |
| 303 | C22H22Br4ClNO4 | 1400 | | | | xx | |
| | Mol. Wt: 719.5 | | | | | | |
| 304 | C23H29NO4 | 100 | | | | | |
| | Mol. Wt: 383.5 | | | | | | |
| 305 | C23H25F4NO4 | 1200 | | xx | xx | | |
| | Mol. Wt: 455.4 | | | | | | |
| 306 | C23H25Cl4NO4 | 100 | | | | | |
| | Mol. Wt: 521.3 | | | | | | |
| 307 | C23H25Br4NO4 | 200 | | | | xxx | x |
| | Mol. Wt: 699.1 | | | | | | |
| 308 | C15H25NO- | | | | | | |
| | Exact Mass: 235.2 | | | | | | |
| 309 | C23H29NO3S | 100 | | | | | |
| | Mol. Wt: 399.5 | | | | | | |
| 310 | C16H25NO3 | 300 | | | | | |
| | Mol. Wt: 279.4 | | | | | | |
| 311 | C16H27NO | | | | | | |
| | Mol. Wt: 249.4 | | | | | | |
| 312 | C16H24ClNO3 | 10 g | | | | | |
| | Mol. Wt: 313.8 | | | | | | |
| 313 | C16H26ClNO | | | | | | |
| | Mol. Wt: 283.8 | | | | | | |
| 314 | C25H35NO3 | 100 | | | | | |
| | Mol. Wt: 397.6 | | | | | | |
| 315 | C17H29NO- | 2100 | | | | | |
| | Mol. Wt: 263.4 | | | | | | |
| 316 | C25H29Br4NO4 | 800 | | | | xx | |
| | Mol. Wt: 727.1 | | | | | | |
| 317 | C14H10ClNO3 | 1700 | | | | | |
| | Mol. Wt: 275.7 | | | | | | |
| 318 | C25H33NO4 | 1000 | | | | xxx | |
| | Exact Mass: 411.2 | | | | | | |

TABLE 10-continued

| Cmpd DH-DOC | Mol. Wt. | DOC-mg DHD-mg | TEM-1 | P99 | OXA-10 | BlaR | PBP2a* |
|---|---|---|---|---|---|---|---|
| 319 | C25H29F4NO4 Exact Mass: 483.2 | 500 600 | | | | xxx | |
| 320 | C25H29Cl4NO4 Exact Mass: 547.1 | | | | | | |
| 321 | C25H33NO3S Exact Mass: 427.2 | | | | | | |
| 322 | C25H29Cl4NO3S Exact Mass: 563.1 | | | | | | |
| 323 | C19H19NO6 Exact Mass: 357.1 | 1000 | | xxx | | | |
| 324 | C19H19NO5S Exact Mass: 373.1 | 200 | | xx | xx | | |
| 325 | C19H20N2O5 Exact Mass: 356.1 | 1200 | | | | | |
| 326 | C20H22N2O5 Exact Mass: 370.2 | 200 | | | | | |
| 327 | C20H28O7 Exact Mass: 380.2 | 100 | | | | | |
| 328 | C18H25NO4 Exact Mass: 319.2 | | | | | | |
| 329 | C24H27Br4NO4 713.09 | 1200 | | | | xxx | |
| 330 | C13H22O6 Mol. Wt: 274.3 | 10 | | | | | |
| 331 | C19H19NO5 Mol. Wt.: 341.36 | 1900 | | | | | |
| 332 | C19H15F4NO5 Mol. Wt.: 413.32 | 700 | | | | | |
| 333 | C19H15Cl4NO5 Mol. Wt.: 479.14 | 3000 | | | | x | |
| 334 | C19H15Br4NO5 Mol. Wt.: 656.94 | 600 | | | x | | |
| 335 | C9H8ClNO4 M.w. 229 | | | | | | |
| 336 | C17H17NO4S2 Mol. Wt.: 363.45 | 300 | | | | | |
| 337 | C20H27NO5 Mol. Wt.: 361.43 | 1400 | | | | | |
| 338 | | | | | | | |
| 339 | | 15 g | | | | | |
| 340 | | | | | | | |
| 341 | | | | | | | |
| 342 | | | | | | | |
| 343 | C21H26N2O4 Mol. Wt.: 370.44 | 1200 | x | | x | | |
| 344 | C21H22F4N2O4 Mol. Wt: 442.4 | 400 | | | x | | |
| 345 | C21H22Cl4N2O4 Mol. Wt.: 508.22 | 1800 | xxx | xxx | xxx | | |
| 346 | C21H22Br4N2O4 Mol. Wt.: 686.03 | 1800 | xxx | xxx | xxx | | x |
| 347 | | | | | | | |
| 348 | C21H24ClNO6 Mol. Wt.: 421.87 | 100 | | | | | |
| 349 | C21H20ClF4NO6 Mol. Wt.: 493.83 | 500 | | | | | |
| 350 | C21H20Cl5NO6 Mol. Wt.: 559.65 | 700 | | | x | | |
| 351 | C21H20Br4ClNO6 Mol. Wt.: 737.46 | 600 | | | | | |
| 352 | | | | | | | |
| 353 | C21H22ClNO6 Mol. Wt.: 419.86 | 100 | | | | | |
| 354 | C21H18ClF4NO6 | 100 | | | | | |
| 355 | C21H18Cl5NO6 Mol. Wt.: 557.64 Mol. | 100 | | | xxx | | |
| 356 | C21H18Br4ClNO6 Mol. Wt.: 735.44 | 100 | x | x | xx | | |
| 357 | C21H26N2O5 Mol. Wt.: 386.44 | 170 | | | | | |
| 358 | C21H22Cl4N2O5 Mol. Wt.: 524.22 | 300 | | | xxx | | |
| 359 | C21H22F4N2O5 Mol. Wt: 458.4 | 500 | | | | | |

TABLE 10-continued

| Cmpd DH-DOC | Mol. Wt. | DOC-mg DHD-mg | TEM-1 | P99 | OXA-10 | BlaR | PBP2a* |
|---|---|---|---|---|---|---|---|
| 360 | C21H22Br4N2O5 Mol. Wt.: 702.03 | 1100 | xx | x | xxx | | |
| 361 | C12H12N2O M.w.: 200.24 | | | | | | |
| 362 | C19H16N2O2 Mol. Wt.: 304.34 | 1000 | | | | | |
| 363 | C20H12F4N2O4 Mol. Wt.: 420.31 | 200 | | | | | |
| 364 | C20H12Cl4N2O4 Mol. Wt.: 486.13 | 1200 | | | x | | |
| 365 | C20H12Br4N2O4 Mol. Wt.: 663.94 | 1700 | | | xx | | |
| 366 | | | | | | | |
| 367 | | | | | | | |
| 368 | C20H12Cl4N2O5 Mol. Wt.: 502.13 | 300 | | | | | |
| 369 | C20H12Br4N2O5 Mol. Wt.: 679.94 | 300 | | | | | |
| 370 | C14H12ClNO3 M.w.: 277.7 | 7 g | | | | | |
| 371 | C14H12ClNO3 M.w.: 277.7 | | | | | | |
| 372 | C14H9ClF3NO3 M.w.: 331.67 | 10 g | | | | | |
| 373 | C14H12ClNO3 M.w.: 277.7 | | | | | | |
| 374 | C14H12ClNO3 M.w.: 277.7 | 12 g | | | | | |
| 375 | C14H9ClF3NO4 M.w.: 347.67 | | | | | | |
| 376 | C14H14ClNO M.w.: 247.72 | | | | | | |
| 377 | C14H14ClNO M.w.: 247.72 | 4500 | | | | | |
| 378 | C14H11ClF3NO2 M.w.: 317.69 | | | | | | |
| 379 | C22H18ClNO4 M.w.: 395.84 | 800 | | | | | |
| 380 | C22H14ClF4NO4 M.w.: 467.8 | 1200 | | | | | |
| 381 | C22H14Cl5NO4 M.w.: 533.62 | 100 | x | | xxx | | |
| 382 | C22H14Br4ClNO4 M.w.: 711.42 | 500 | xxx | xxx | xxx | | xxx |
| 383 | C22H18ClNO4 M.w.: 395.84 | 1200 | | | | | |
| 384 | C22H14ClF4NO4 M.w.: 467.8 | 1400 | | | | | |
| 385 | C22H14Cl5NO4 M.w.: 533.62 | 2900 | xx | xx | xxx | | xxx |
| 386 | C22H14Br4ClNO4 M.w.: 711.42 | 600 | xxx | xxx | xxx | xxx | xxx |
| 387 | C22H15ClF3NO4 Mol. Wt.: 449.81 | 200 | x | | x | xx | |
| 388 | C22H11ClF7NO4 Mol. Wt.: 521.77 | 400 | xx | | xx | | |
| 389 | C22H11Cl5F3NO4 Mol. Wt.: 587.59 | 900 | xxx | xxx | xxx | | |
| 390 | C22H11Br4ClF3NO4 Mol. Wt.: 765.39 | 2100 | xxx | xxx | xxx | | xxx |
| 391 | C22H17ClN2O6 M.w.: 440.83 | 400 | | | | | |
| 392 | C20H15N3O6 M.w.: 393.35 | 900 | | | | | |
| 393 | C10H14N2O5 M.w.: 242.23 | | x | | xxx | | |
| 394 | C10H14N2O5 M.w.: 242.23 | | | | | | |
| 395 | | | | | | | |
| 396 | | | | | | | |
| 397 | C10H16N2O3 M.w.: 212.25 | | | | | | |

TABLE 10-continued

| Cmpd DH-DOC | Mol. Wt. | DOC-mg DHD-mg | TEM-1 | P99 | OXA-10 | BlaR | PBP2a* |
|---|---|---|---|---|---|---|---|
| 398 | | | | | | | |
| 399 | | | | | | | |
| 400 | C18H20N2O6 M.w.: 360.36 | 700 | | | | | |
| 401 | C18H16F4N2O6 M.w.: 432.32 | 700 | | | | | |
| 402 | C18H16Cl4N2O6 M.w.: 498.14 | 1200 | | | | | |
| 403 | C18H16Br4N2O6 M.w.: 675.95 | 100 | | | | | |
| 404 | C18H16Br4N2O6 M.w.: 675.95 | 1100 | | | | | |
| 405 | C18H19N3O8 M.w.: 405.36 | 1200 | | | | | |
| 406 | C18H20N2O7 M.w.: 376.36 | 200 | | | | | |
| 407 | C18H16F4N2O7 M.w.: 448.32 | 300 | | | | | |
| 408 | C18H16Cl4N2O7 M.w.: 514.14 | 120 | | | | | |
| 409 | C18H16Cl4N2O7 M.w.: 514.14 | 20 | | | | | |
| 410 | C18H16Br4N2O7 M.w.: 691.94 | 190 | | | | | |
| 411 | C14H11ClF3NO2 M.w.: 317.69 | 200 | | | | | |
| 412 | C22H9F10NO4 M.w.: 541.3 | 250 | | | | xx | |
| 413 | C22H9Cl4F6NO4 M.w.: 607.11 | 1300 | xxx | xxx | xxx | x | xxx |
| 414 | C22H9Br4F6NO4 M.w.: 784.92 | 1300 5200 | xxx | xxx | xxx | xxx | xxx |
| 415 | C22H9Cl4F6NO4 M.w.: 607.11 | | | | | | |
| 416 | C14H9ClN2O3 M.w.: 288.69 | 500 | | | | | |
| 417 | C22H15ClF3NO5 M.w.: 465.81 | 500 | | | | xx | |
| 418 | C22H11ClF7NO5 M.w.: 537.77 | 1000 | | | xx | xxx | x |
| 419 | C22H11Cl5F3NO5 M.w.: 603.59 | 1200 | xxx | xx | xxx | xxx | xxx |
| 420 | C22H11Br4ClF3NO5 M.w.: 781.39 | 900 | xxx | xx | xxx | xxx | xxx |
| 421 | C22H14ClF3N2O7 M.w.: 510.8 | 500 | | | | | |
| 422 | C22H14ClF3N2O7 M.w.: 510.8 | 900 | xx | xx | xx | xxx | xxx |
| 423 | C21H14ClF3N2O5 M.w.: 466.79 | 500 | | | | | |
| 424 | C21H14ClF3N2O5 M.w.: 466.79 | 700 | | | | | |
| 425 | C14H14N2O5 M.w.: 290.27 | | | | | | |
| 426 | C14H16N2O3 M.w.: 260.29 | | | | | | |
| 427 | C20H15ClF3NO4S2 M.w.: 489.92 | 700 | | | | | |

Example 3

This example identifies if inhibitory activity was detected at a 25 µg/mL dose of a compound (selected examples of Compounds 1-414, illustrated above after Table 10) against the bacteria examined. The symbol "+" indicates activity against the bacterial while the term "-" indicates there was no observed inhibitory activity. The minimum inhibitory concentrations (MICs) of antibiotics were determined by the micro dilution procedure in Mueller Hinton II Broth (BBL) in accordance with recommendations of the Clinical and Laboratory Standards Institute (see, Bou et al, *Methicillin-Resistant Staphylococcus aureus (MRSA) Protocols* in *Method in Molecular Biology*, 2007, 391, 29-49, Springer Protocols, Springer Science+Business Media, LLC, Secaucus, N.J., USA). Final bacterial inoculum was $5 \times 10^5$ CFU/mL. Inoculated micro titer plates were incubated at 35° C. for 24 hours prior to results being recorded.

Table 11 illustrates data showing that minimal inhibitory concentrations were generally observed at 25 mg/mL. On top of each cell is the corresponding compound #. The sign below the number indicates growth (+) or no growth (−) at 25 µg/mL. The compounds were dissolved in 100% DMSO to a concentration of 2,000 µf/mL and transferred to Mueller Hinton broth (200 µL) to a final concentration of 25 µg/mL (final DMSO in this case is 1.25%). The compounds that were not readily soluble at concentration of 2,000 µg/mL were diluted in DMSO to 1,000 µf/mL and transferred (5 µL instead of 2.5 µL) to Mueller Hinton broth for a final concentration in DMSO of 2.5%.

In another test, the compounds were dissolved in 80% DMSO plus 20% of buffer (100 mM sodium Phosphate, 0.5% $Na_2CO_3$) to 2,000 µg/mL and the minimal inhibitory concentrations were determined by diluting the compounds to 40 µg/mL or lower. However, the resulting minimal inhibitory concentrations were the same as from DMSO when the minimal inhibitory concentrations were in Mueller Hinton broth or Mueller Hinton broth supplemented with one fifth of buffer (100 mM sodium Phosphate, 0.5% $Na_2CO_3$). The minimal inhibitory concentrations were also determined under the above conditions but compounds were first transferred from 2,000 µg/mL of DMSO to buffer (100 mM sodium Phosphate, 0.5% $Na_2CO_3$) to make a final concentration of 800 µg/mL. However, because some compounds separated from the buffer solution, they were transferred to Mueller Hinton to arrive at 40 µg/mL and lower. The resulting minimal inhibitory concentrations were higher in comparison to two conditions described above.

Minimum inhibitory concentrations were also determined for the compounds against NRS11 ($Mec^S$) or NRS100 ($Mec^R$) (data not shown). $Mec^S$ refers to methicillin sensitive *Staphylococcus aureus* and $Mec^R$ refers to the resistant variant of *Staphylococcus aureus*. In determining the minimum inhibitory concentrations (MICs) against NRS11 ($Mec^S$) or NRS100 ($Mec^R$), the compounds were dissolved in 100% DMSO to a concentration of 1,000 µg/mL and diluted directly into Mueller Hinton II Broth to final 16 µg/mL for MIC testing.

Example 4

This example demonstrates the inhibition of various bacterial strains by selected compounds of the invention. Table 12 illustrates the results and the minimal inhibitory concentration (MIC) for *S. aureus, Enterococcus faecalis, Pseudomonas aeruginosa, Klebsiella pneumonia*, and *Proteus mirabilis*. The inoculum is about $1.5 \times 10^5$ CFU/mL. The minimal inhibitory concentrations (MIC) were done in Muller-Hinton II Broth with the exception of *Enterococcus faecalis* ATCC 29212, which was done in Brain Heart Infusion Broth. The concentration of DMSO at 200 µg/mL was 10%.

TABLE 11

Bacterial Inhibition by Compounds Described Herein

| 1 | 2 | 3 | 4 | 5 | 6 | 7 | 8 | 9 | 10 | 11 | 12 |
|---|---|---|---|---|---|---|---|---|----|----|----|
| + | + | + | + | + | + | + | + | + | +  | +  | +  |
| 13 | 14 | 15 | 16 | 17 | 18 | 19 | 20 | 21 | 22 | 23 | 24 |
| + | + | + | + | + | + | + | + | + | + | + | + |
| 25 | 26 | 27 | 28 | 29 | 30 | 31 | 32 | 33 | 34 | 35 | 36 |
| + | + | + | + | + | + | + | + | + | + | + | + |
| 37 | 38 | 39 | 39a | 40 | 41 | 42 | 43 | 44 | 45 | 46 | 47 |
| + | + | + | + | + | + | + | + | + | + | + | + |
| 48 | 49 | 50 | 51 | 52 | 53 | 54 | 55 | 56 | 57 | 58 | 59 |
| + | + | + | + | + | + | + | + | + | + | + | + |
| 60 | 72 | 81a | 81b | 81m | 82 | 83 | 84 | 85 | 86 | 87 | 88 |
| + | + | + | + | + | + | + | + | + | + | + | + |
| 89 | 90/91 | 92/93 | 94 | 95/96 | 97 | 98 | 99 | 100 | 101 | 108 | 109 |
| + | + | + | + | + | + | + | + | + | + | + | + |
| 110 | 111 | 112 | 113 | 114 | 115 | 116 | 117 | 118 | 119 | 120 | 121 |
| + | + | + | + | + | + | + | + | + | + | + | + |
| 122 | 123 | 124 | 125 | 127 | 128 | 129 | 133 | 134 | 135 | 136 | 137 |
| + | + | + | + | + | + | + | + | + | + | + | + |
| 138 | 139 | 140 | 141 | 142 | 143 | 144 | 145 | 146 | 150 | 151 | 152 |
| + | + | + | + | + | + | + | + | + | + | + | + |
| 153 | 154 | 155 | 156 | 157 | 158 | 159 | 160 | 161 | 162 | 163 | 164 |
| + | + | + | + | + | + | + | + | + | + | + | + |
| 165 | 166 | 167 | 168 | 169 | 170 | 171 | 172 | 173 | 174 | 175 | 176 |
| + | + | + | + | + | + | + | + | + | + | + | + |
| 177 | 178 | 179 | 180 | 181 | 182 | 183 | 184 | 185 | 186 | 187 | 188 |
| + | + | + | + | + | + | + | + | + | + | + | + |
| 189 | 190 | 191 | 192 | 193 | 194 | 195 | 196 | 197 | 199 | 200 | 201 |
| + | + | + | + | + | + | + | + | + | + | + | + |
| 202 | 210 | 215 | 216 | 217 | 218 | 219 | 220 | 221 | 222 | 223H | 223Na |
| + | + | + | + | + | + | + | + | + | + | + | + |
| 224 | 2226 | 227 | 228 | 229 | 230- | 231 | 232 | 236 | 237 | 240 | 242 |
| + | + | + | + | + | -+ | + | + | + | + | + | + |
| 243 | 244 | 245 | 246 | 247 | 248 | 249 | 250 | 255 | 251 | 251b | 252 |
| + | + | + | + | + | + | + | + | + | + | + | + |
| 253 | 254 | 255 | 257 | 258 | 259 | 261 | 262 | 263 | 264 | 267 | 268 |
| − | + | + | + | + | + | + | + | + | + | + | + |
| 269 | 272 | 273 | 275 | 277-1 | 277-2 | 277-3 | 277-4 | 278 | 279-2 | 280-1 | 280-2 |
| + | + | + | + | + | + | + | + | − | + | + | − |
| 281 | 281-1 | 288 | 289 | 290 | 291 | 292 | 294-1 | 294-2 | 295 | 296 | 298 |
| − | + | − | + | − | − | + | + | + | + | + | + |
| 299 | 300 | 301 | 302 | 302-2 | 303 | 304 | 305 | 306 | 307 | 309 | 310 |
| − | − | − | − | − | − | + | − | + | + | + | + |
| 312 | 314 | 316 | 317 | 323 | 327 | 333 | 336 | 349 | 451 | 353 | 356 |
| + | + | − | + | + | + | + | + | + | + | + | − |
| 358 | 359 | 360 | 362 | 363 | 364 | 366 | 366-2 | 369 | 380 | 381 | 384 |
| + | + | + | + | + | + | + | + | + | + | + | + |
| 386 | 387 | 400 | 402 | 406 | 407 | 412 | 413 | 414 | | | |
| − | + | + | + | + | + | + | − | − | | | |

TABLE 12

| Strain | Vancomycin | Oxaxillian | MIC (μg/mL) of Compound # | | | |
|---|---|---|---|---|---|---|
| | | | 239 | 253 | 265 | 274 |
| Enterococcus faecalis ATCC 29212 | 4 | 8 | 200 | 200 | 6 | 100 |
| Staphylococcus aureus NRS100 (COL) | 1 | 500 | 100 | 50 | 6 | 3 |
| Staphylococcus aureus (COLVA) | 1000 | 500 | 25 | 50 | 6 | 3 |
| Staphylococcus aureus NRS1 (Mec$^r$. Vani) | 4 | 500 | 50 | 50 | 6 | 3 |
| Staphylococcus aureus ATCC 29213 | 1 | <0.5 | 25 | 50 | 6 | 3 |
| Escherichia coli ATCC 29194 | | | 400 | 400 | 200 | 400 |
| Pseudomonas aeruginosa ATCC 27853 | | | 200 | 200 | 200 | 200 |
| Klebsiella pneumonia ATCC 33495 | | | 200 | 200 | 200 | 200 |
| Proteus mirabilis ATCC 35659 | | | 400 | 400 | 200 | 400 |

Example 5

This example demonstrates the inhibition of methicillin-resistant strains of S. aureus NRS11 (Mec$^S$) with selected compounds of the invention. All recited compounds were dissolved in DMSO or in 1% sodium carbonate and transferred to micro titer plates to final concentrations of 1000 μg/mL. The compounds 345, 346, 355, 365, 381, 389, and 385 demonstrated significant inhibitory properties, as indicated in Table 13.

TABLE 13

| Compound # | MIC (μg/mL) |
|---|---|
| 324 | 2,000 |
| 325 | 256 |
| 326 | 2,000 |
| 330 | 2,000 |
| 331 | 2,000 |
| 332 | 2,000 |
| 334 | 128 |
| 337 | 2,000 |
| 343 | 256 |
| 344 | 256 |
| 345 | 16 |
| 346 | <8 |
| 348 | >2,000 |
| 350 | 500 |
| 354 | 500 |
| 355 | 128 |
| 357 | >2,000 |
| 359 | 1,000 |
| 363 | >2,000 |
| 365 | 8 |
| 368 | 500 |
| 379 | >2,000 |
| 381 | 16 |
| 382 | <8 |
| 389 | <8 |
| 385 | 16 |
| 388 | 128 |
| 390 | <8 |
| 391 | 500 |
| 390-1 | <8 |
| 392 | 500 |

TABLE 13-continued

| Compound # | MIC (μg/mL) |
|---|---|
| 390-2 | <8 |
| 383 | 128 |
| 401 | >2,000 |
| 403 | >2,000 |
| 404 | >2,000 |
| 405 | >2,000 |
| 408 | >2,000 |
| 409 | 1,000 |
| 410 | 500 |

Example 6

This Example demonstrates the inhibition of methicillin-resistant strains of S. aureus NRS100 (Mec$^R$) with selected compounds of the invention. The recited compounds were dissolved in DMSO or in 1% sodium carbonate and transferred into micro titer plate to final concentration of 1000 μg/mL. The compounds 345, 346, 355, 365, 381, 382, 385, 389, 390, 390-1, and 390-2 demonstrated significant inhibitory activity as indicated below in Table 14.

TABLE 14

| Compound | MIC (μg/mL) | Compound | MIC (μg/mL) | Compound | MIC (μg/mL) |
|---|---|---|---|---|---|
| 324 | 2,000 | 389 | <8 | 230 | >16 |
| 325 | 256 | 385 | 16 | 253 | >16 |
| 326 | 2,000 | 388 | 128 | 277-4 | >16 |
| 330 | 2,000 | 390 | <8 | 278 | 16 |
| 331 | 2,000 | 391 | 500 | 279-2 | >16 |
| 332 | 2,000 | 390-1 | <8 | 280-2 | 8 |
| 334 | 128 | 392 | 500 | 281 | 4 |
| 337 | 2,000 | 390-2 | 4 | 282 | 16C |
| 343 | 256 | 383 | 128 | 289 | 16C |
| 344 | 256 | 401 | >2,000 | 290 | 16C |
| 345 | 16 | 403 | >2,000 | 291 | 16-C |
| 346 | <8 | 404 | >2,000 | 299 | 16 |
| 348 | >2,000 | 405 | >2,000 | 300 | 8 |
| 350 | 500 | 408 | >2,000 | 301 | 16 |
| 354 | 500 | 409 | 1,000 | 302 | 4 |
| 355 | 32 | 410 | 500 | 302-2 | 4 |
| 357 | >2,000 | 417 | 250 | 303 | 4 |
| 359 | 1,000 | 418 | 125 | 305 | 16 |
| 363 | >2,000 | 419 | 8 | 316 | 16C |
| 365 | 16 | 420 | 8 | 323 | >16 |
| 368 | 500 | 421 | 250 | 356 | >16 |
| 379 | >2,000 | 422 | 125 | 386 | 8 |
| 381 | 32 | 423 | 250 | 413 | 8 |
| 382 | <8 | 424 | >250 | 414 | 4 |

Table 15 illustrates the inhibition of methicillin-resistant strains of S. aureus by selected compounds of the invention. The compounds were dissolved in 100% DMSO to 1,000 μg/mL and diluted directly into Mueller Hinton II Broth to final 16 μg/mL for MIC testing.

TABLE 15

| Compound | MIC (μg/mL) | Compound | MIC (μg/mL) |
|---|---|---|---|
| 345 | 16 | 302 | 4 |
| 346 | 8 | 312-2 | 4 |
| 390 | 8 | 303 | 4 |
| 390-1 | 8 | 386 | 16 |
| 390-2 | 4 | 413 | 16 |
| 280-2 | 8 | 414 | 4 |
| 281 | 4 | 419 | 8 |
| 300 | 16 | 420 | 4 |

Example 7

This Example illustrates the $IC_{50}$ values of selected compounds for inhibition of β-lactamases. The β-lactamase assays were performed according to the methods described in Example 2. These compounds display inhibitory properties against β-lactamases. Results of the β-lactamase assays are shown in Table 16.

TABLE 16

| DH-DOC | IC50s (μM) | | |
|---|---|---|---|
| | TEM-1 | P99 | OXA-10 |
| 253 | 32.3 ± 5.9 | 104.8 ± 8.7 | 222.0 ± 17.0 |
| 265 | 3.6 ± 0.5 | 10.3 ± 0.3 | 9.9 ± 0.8 |
| 274 | 2.4 ± 0.1 | 3.1 ± 0.5 | 5.5 ± 0.5 |
| 289 | 23.1 ± 2.4 | 1.2 ± 0.1 | 0.7 ± 0.15 |
| 290 | 0.6 ± 0.06 | 0.4 ± 0.06 | 0.5 ± 0.05 |
| 291 | 0.2 ± 0.04 | 0.2 ± 0.02 | 0.3 ± 0.06 |
| 300 | 0.7 ± 0.08 | 10.3 ± 0.4 | 30.7 ± 2.8 |
| 301 | 5.1 ± 1.0 | 9.9 ± 1.7 | 23.0 ± 2.0 |
| 345 | 4.9 ± 0.2 | 27.8 ± 2.9 | 37.9 ± 6.0 |
| 346 | 2.8 ± 0.3 | 7.8 ± 1.2 | 13.1 ± 0.8 |
| 382 | 5.3 ± 1.1 | 24.4 ± 1.9 | 26.6 ± 1.6 |
| 386 | 7.4 ± 1.2 | 15.3 ± 1.6 | 31.6 ± 3.5 |
| 389 | 4.5 ± 0.4 | 20.2 ± 3.0 | 44.2 ± 3.4 |
| 390 | 1.9 ± 0.1 | 6.0 ± 0.8 | 14.2 ± 1.1 |
| 413 | 27.0 ± 2.9 | 31.2 ± 6.4 | 80.8 ± 7.0 |
| 414 | 4.5 ± 0.4 | 12.0 ± 0.5 | 19.5 ± 2.0 |
| 419 | 2.3 ± 0.1 | 13.0 ± 2.0 | 10.8 ± 0.7 |
| 420 | 1.6 ± 0.1 | 6.9 ± 1.5 | 8.4 ± 1.1 |

It should be understood that various changes and modifications to the embodiments described herein will be apparent to those skilled in the art. Such changes and modifications can be made without departing from the spirit and scope of the claimed subject matter and without diminishing its intended advantages. It is therefore intended that such changes and modifications be covered by the appended claims.

All patents, patent applications, publications, scientific articles, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, applications, publications, scientific articles, electronically available information, and other referenced materials or documents.

What is claimed is:

1. A compound of Formula II:

(II)

wherein
X is absent or $(C_1-C_{24})$alkyene;
Y is oxygen or sulfur;
Z is carbon or nitrogen, provided that when Z is nitrogen, $R_8$ is absent;
$R_2$ is hydrogen or halo;
$R_3$ is hydrogen, halo, or —CONH$(C_6-C_{20})$alkyl;
$R_4$ and $R_5$ are each independently hydrogen, halo, or nitro;
$R_6$, $R_7$, and $R_{11}$ are each independently hydrogen or $(C_1-C_4)$alkyl;
$R_8$ is absent or hydrogen;
$R_9$ is hydrogen, $(C_1-C_4)$alkyl, trifluoromethyl, or trifluoromethoxy;
$R_{10}$ is hydrogen, halo, or —O$(C_6-C_{20})$aryl;
any $(C_1-C_{24})$alkylene or $(C_6-C_{20})$aryl is optionally substituted on carbon with one or more oxo, hydroxyl, halo, $(C_6-C_{20})$aryl, nitro, cyano, $(C_1-C_6)$alkoxy, or trifluoromethyl groups or any combination thereof, and optionally exchanged on carbon with one or more oxo, imino, or thio groups;
at least one of $R_2$-$R_{11}$ is not hydrogen;
a is 0, 1, or 2; and
n is 0 or 1;

or a pharmaceutically acceptable salt, as prodrug, or to metabolite thereof.

2. The compound of claim 1 wherein $R_2$, $R_3$, $R^4$, and $R_5$ are each halo.

3. The compound of claim 1 wherein $R_2$, $R_3$, $R_4$, and $R_5$ are each flouro, chloro, or bromo.

4. The compound of claim 1 wherein $R_3$ is hydrogen or —CONH$(C^6)$aryl wherein the $(C_6)$aryl is optionally substituted with one or more hydroxyl, halo, $(C_6-C_{20})$aryl, nitro, cyano, $(C_1-C_6)$alkoxy, or trifluoromethyl groups, or any combination thereof.

5. The compound of claim 1 wherein $R_4$ and $R_5$ are each independently hydrogen or nitro.

6. The compound of claim 1 wherein X is absent.

7. The compound of claim 1 wherein X is —$CH_2$— or —$CH(CH_3)$—.

8. The compound of claim 1 wherein Y is oxygen.

9. The compound of claim 1 wherein Y is sulfur.

10. The compound of claim 1 wherein $R_9$ is methyl, trifluoromethyl, or trifluoromethoxy, and a is 1 or 2.

11. The compound of claim 1 wherein $R_{10}$ is hydrogen or halo.

12. The compound of claim 1 wherein $R_{10}$ is chloro.

13. The compound of claim 1 wherein
X is absent, —$CH_2$—, or —$CH(CH_3)$—;
Y is oxygen or sulfur;
Z is carbon or nitrogen;
$R_2$ is hydrogen, fluorine, chlorine, or bromine;
$R_3$ is hydrogen, fluorine, chlorine, bromine, or —CONH (2-methoxy-4-nitro)phenyl;
$R_4$ and $R_5$ are each independently hydrogen, fluorine, chlorine, bromine, or nitro;
$R_6$, $R_7$, and $R_{11}$ are each hydrogen:
$R_8$ is absent or hydrogen;
$R_9$ is hydrogen, $(C_1-C_4)$alkyl, trifluoromethyl, or trifluoromethoxy;
$R_{10}$ is hydrogen, chlorine, or —O-phenyl;
a is 0, 1, or 2; and
n is 0 or 1.

14. The compound of claim 1 wherein the compound is:
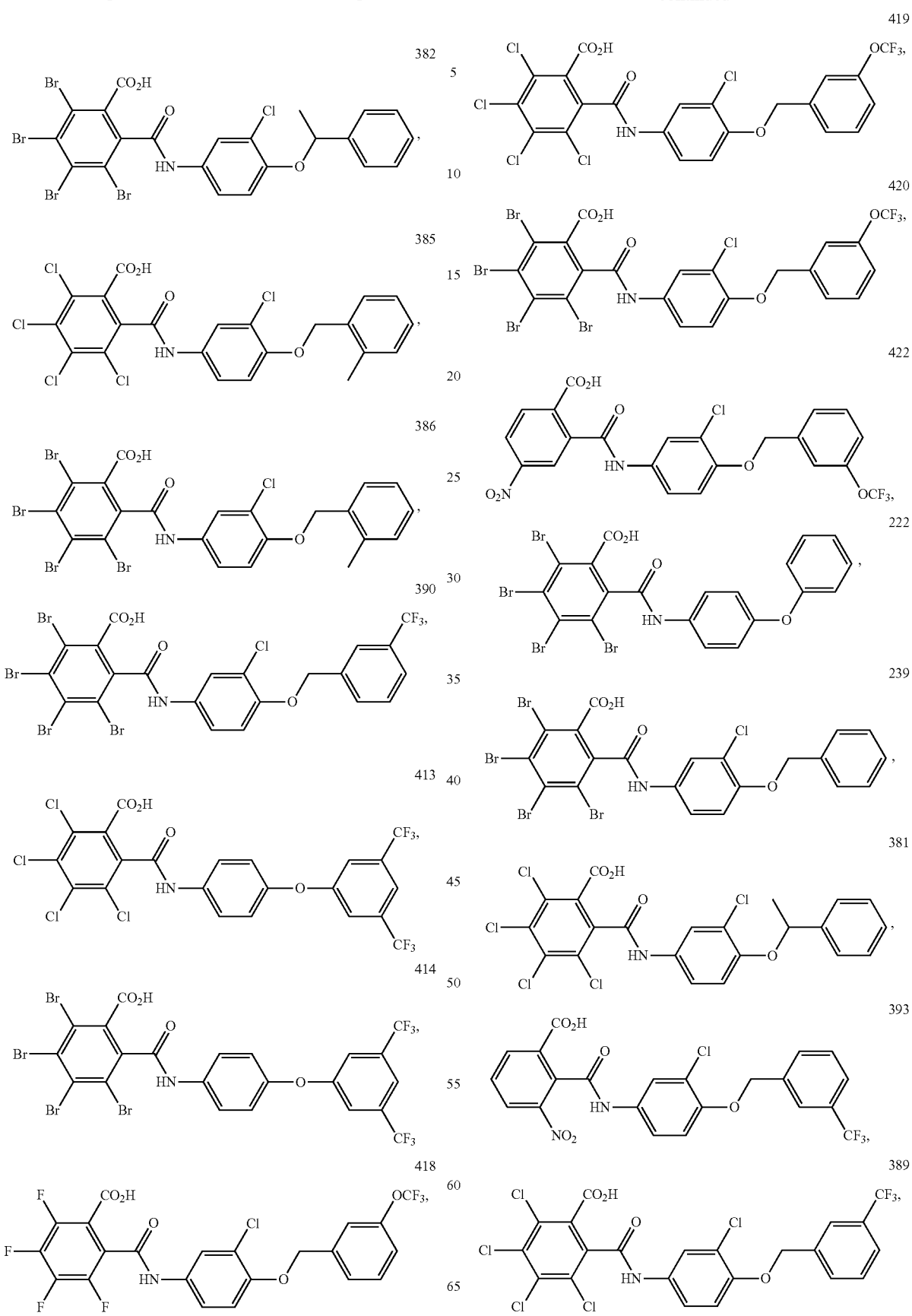

-continued

DHD-251, 253, 387, 412, 296, 417, 388 [chemical structures]

15. The compound of claim 9 wherein the compound is:

277-3 [chemical structure] or 278-2 [chemical structure].

16. The compound of claim 1 wherein the compound is:

364 [chemical structure] or

365 [chemical structure].

17. A pharmaceutical composition comprising a compound of claim 1 and a pharmaceutically acceptable carrier.

18. A method of treating an animal afflicted with a bacterial infection comprising administering to an animal in need of such treatment an effective antibacterial amount of a compound of claim 1.

19. A method of killing or inhibiting the growth of a bacteria comprising contacting the bacteria with an effective amount of a compound of claim 1.

20. A pharmaceutical composition comprising an anti-vancomycin-resistant methicillin-resistant *Staphylococcus aureus* compound of claim 1, and a pharmaceutically acceptable diluent or carrier.

21. The compound:

382 [chemical structure],

-continued

-continued
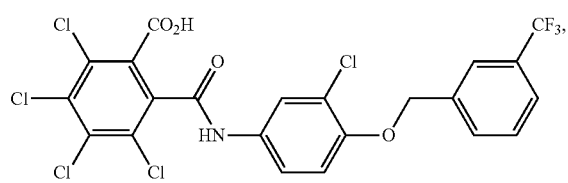
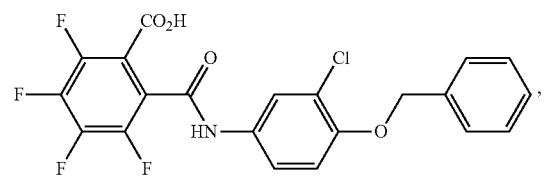
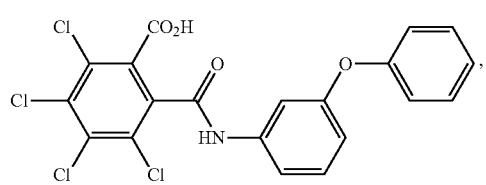
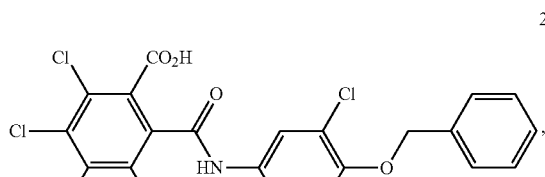
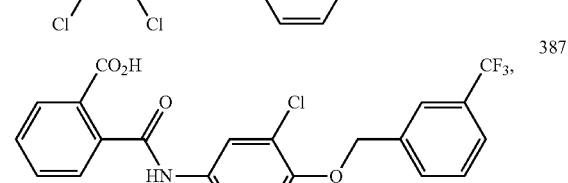
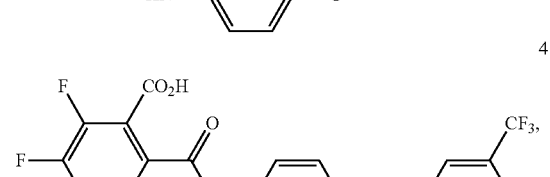
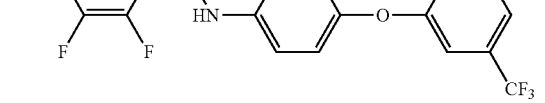
-continued
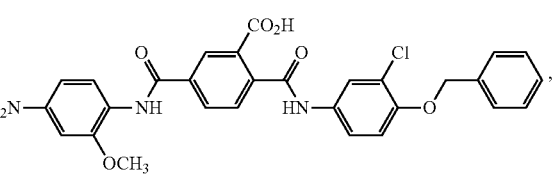
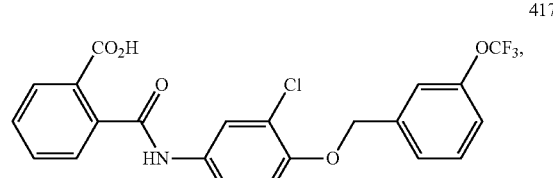
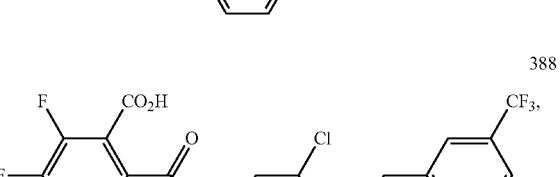
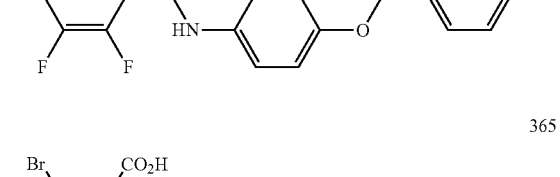
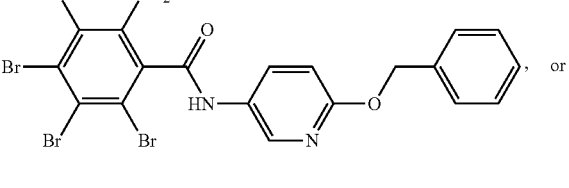
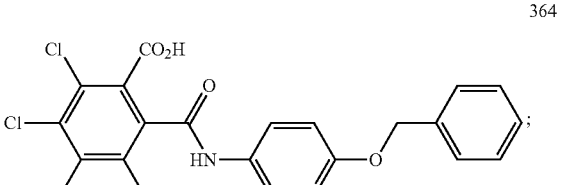
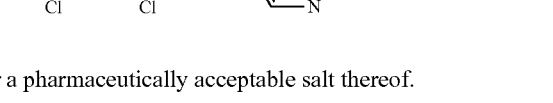
or a pharmaceutically acceptable salt thereof.
* * * * *